US011482682B2

(12) United States Patent
Shin et al.

(10) Patent No.: US 11,482,682 B2
(45) Date of Patent: Oct. 25, 2022

(54) COMPOUND FOR ORGANIC OPTOELECTRONIC DIODE, ORGANIC OPTOELECTRONIC DIODE, AND DISPLAY DEVICE

(71) Applicant: SAMSUNG SDI CO., LTD., Yongin-si (KR)

(72) Inventors: Chang Ju Shin, Suwon-si (KR); Changwoo Kim, Suwon-si (KR); Hyung Sun Kim, Suwon-si (KR); Dong Wan Ryu, Suwon-si (KR); Seungjae Lee, Suwon-si (KR); Yuna Jang, Suwon-si (KR); Dong Min Kang, Suwon-si (KR); Eun Sun Yu, Suwon-si (KR); Hanill Lee, Suwon-si (KR); Sung-Hyun Jung, Suwon-si (KR); Juyeon Jung, Suwon-si (KR); Ho Kuk Jung, Suwon-si (KR)

(73) Assignee: SAMSUNG SDI CO., LTD., Yongin-si (KR)

( * ) Notice: Subject to any disclaimer, the term of this patent is extended or adjusted under 35 U.S.C. 154(b) by 336 days.

(21) Appl. No.: 16/635,209

(22) PCT Filed: Jul. 30, 2018

(86) PCT No.: PCT/KR2018/008648

§ 371 (c)(1),
(2) Date: Jan. 30, 2020

(87) PCT Pub. No.: WO2019/027212

PCT Pub. Date: Feb. 7, 2019

(65) Prior Publication Data

US 2021/0091314 A1 Mar. 25, 2021

(30) Foreign Application Priority Data

Aug. 1, 2017 (KR) ........................ 10-2017-0097839

(51) Int. Cl.
*H01L 51/00* (2006.01)
*C07D 405/04* (2006.01)
(Continued)

(52) U.S. Cl.
CPC ........ *H01L 51/0073* (2013.01); *C07D 405/04* (2013.01); *C07D 405/10* (2013.01);
(Continued)

(58) Field of Classification Search
CPC ............ H01L 51/0073; H01L 51/0067; C09K 2211/1018
See application file for complete search history.

(56) References Cited

U.S. PATENT DOCUMENTS 7,651,791 B2 1/2010 Nakano et al.
7,846,560 B2 12/2010 Nakano et al.
(Continued)

FOREIGN PATENT DOCUMENTS

JP 2011-29220 A 2/2011
JP 2014-127687 A 7/2014
(Continued)

OTHER PUBLICATIONS

European Search Report dated Mar. 26, 2021.
International Search Report dated Nov. 1, 2018 for PCT/KR2018/008648.

*Primary Examiner* — Anthony Ho
(74) *Attorney, Agent, or Firm* — Lee IP Law, P.C.

(57) ABSTRACT

Disclosed are a compound for an organic optoelectronic diode, a composition for an organic optoelectronic diode, including the compound for the organic optoelectronic diode, an organic optoelectronic diode including the same, and a display device.

20 Claims, 1 Drawing Sheet

100

(51) Int. Cl.

| | |
|---|---|
| ***C07D 405/10*** | (2006.01) |
| ***C07D 405/14*** | (2006.01) |
| ***C09K 11/06*** | (2006.01) |
| *H01L 51/50* | (2006.01) |

(52) U.S. Cl.

CPC ............ *C07D 405/14* (2013.01); *C09K 11/06* (2013.01); *H01L 51/0067* (2013.01); *C09K 2211/1018* (2013.01); *H01L 51/5012* (2013.01); *H01L 51/5016* (2013.01); *H01L 51/5072* (2013.01); *H01L 51/5092* (2013.01); *H01L 51/5096* (2013.01); *H01L 2251/5384* (2013.01)

(56) References Cited

U.S. PATENT DOCUMENTS

| | | | |
|---|---|---|---|
| 9,209,406 | B2 | 12/2015 | Mizutani et al. |
| 2015/0155498 | A1 | 6/2015 | Ahn et al. |
| 2016/0133851 | A1 | 5/2016 | Jo et al. |
| 2016/0260905 | A1 | 9/2016 | Lee et al. |
| 2016/0351817 | A1 | 12/2016 | Kim et al. |
| 2020/0251659 | A1 | 8/2020 | Lee et al. |

FOREIGN PATENT DOCUMENTS

| | | | |
|---|---|---|---|
| JP | 2015-131806 | A | 7/2015 |
| JP | 2015-520772 | A | 7/2015 |
| JP | 2016-534555 | A | 11/2016 |
| JP | 2020/525509 | A | 8/2020 |
| KR | 10-2012-0096383 | A | 8/2012 |
| KR | 10-2012-0104067 | A | 9/2012 |
| KR | 10-2013-0025190 | A | 3/2013 |
| KR | 10-2013-0134202 | A | 12/2013 |
| KR | 10-2014-0003500 | A | 1/2014 |
| KR | 10-2014-0120090 | A | 10/2014 |
| KR | 10-2015-0079646 | A | 7/2015 |
| KR | 10-2015-0126555 | A | 11/2015 |
| KR | 10-2016-0041822 | A | 4/2016 |
| KR | 10-2016-0078251 | A | 7/2016 |
| KR | 10-2016-0141361 | A | 12/2016 |
| KR | 10-2017-0013152 | A | 2/2017 |
| WO | WO 2013/077352 | A1 | 5/2013 |
| WO | WO 2013-180478 | A1 | 12/2013 |
| WO | WO 2019/004599 | A1 | 1/2019 |

【Figure 1】
100
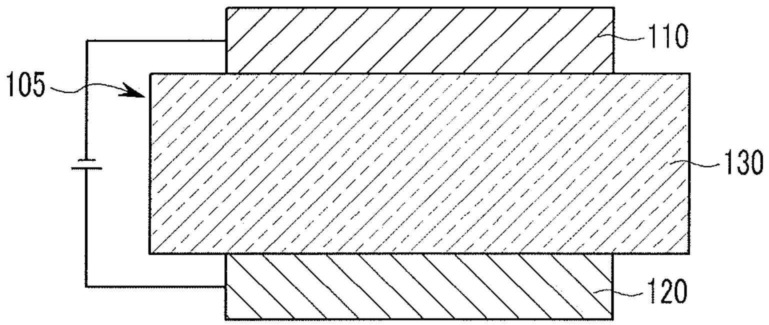
【Figure 2】
200
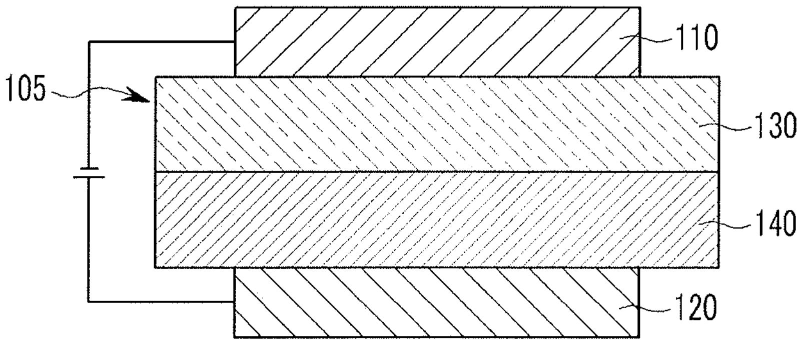

COMPOUND FOR ORGANIC OPTOELECTRONIC DIODE, ORGANIC OPTOELECTRONIC DIODE, AND DISPLAY DEVICE

CROSS REFERENCE TO RELATED APPLICATIONS

This is the U.S. national phase application based on PCT/KR2018/008648, filed Jul. 30, 2018, which is based on Korean Patent Application No. 10-2017-0097839, filed Aug. 1, 2017, the entire contents of all of which are hereby incorporated by reference.

TECHNICAL FIELD

A compound for an organic optoelectronic diode, an organic optoelectronic diode, and a display device are disclosed.

BACKGROUND ART

An organic optoelectronic diode is a device that converts electrical energy into photoenergy, and vice versa.

An organic optoelectronic diode may be classified as follows in accordance with its driving principles. One is a photoelectric device where excitons are generated by photoenergy, separated into electrons and holes, and are transferred to different electrodes to generate electrical energy, and the other is a light emitting device where a voltage or a current is supplied to an electrode to generate photoenergy from electrical energy.

Examples of the organic optoelectronic diode may be an organic photoelectric device, an organic light emitting diode, an organic solar cell, and an organic photo conductor drum.

Of these, an organic light emitting diode (OLED) has recently drawn attention due to an increase in demand for flat panel displays. The organic light emitting diode is a device converting electrical energy into light by applying current to an organic light emitting material, and has a structure in which an organic layer is disposed between an anode and a cathode. Herein, the organic layer may include a light emitting layer and optionally an auxiliary layer, and the auxiliary layer may include at least one layer selected from, for example a hole injection layer, a hole transport layer, an electron blocking layer, an electron transport layer, an electron injection layer, and a hole blocking layer in order to improve efficiency and stability of an organic light emitting diode.

Performance of an organic light emitting diode may be affected by characteristics of the organic layer, and among them, may be mainly affected by characteristics of an organic material of the organic layer.

Particularly, development for an organic material being capable of increasing hole and electron mobility and simultaneously increasing electrochemical stability is needed so that the organic light emitting diode may be applied to a large-size flat panel display.

DISCLOSURE

An embodiment provides a compound for an organic optoelectronic diode capable of realizing an organic optoelectronic diode having high efficiency, a long life-span, and the like.

Another embodiment provides an organic optoelectronic diode including the compound.

Another embodiment provides a display device including the organic optoelectronic diode.

According to an embodiment of the present invention, a compound for an organic optoelectronic diode represented by Chemical Formula 1A is provided.

[Chemical Formula 1A]

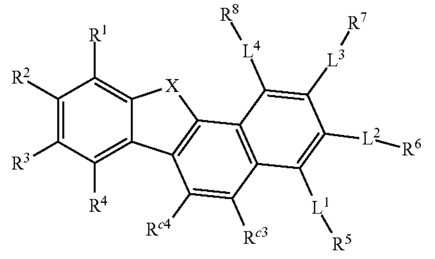

In Chemical Formula 1A,

X is O, S, or $CR^aR^b$, $R^1$ to $R^4$, $R^a$, $R^b$, $R^{c3}$, and $R^{c4}$ are independently hydrogen, deuterium, a cyano group, a substituted or unsubstituted C1 to C30 silyl group, a substituted or unsubstituted C1 to C30 alkyl group, or a substituted or unsubstituted C6 to C30 aryl group, $L^1$ to $L^4$ are independently a single bond, or a substituted or unsubstituted C6 to C30 arylene group, $R^5$ to $R^8$ are independently hydrogen, deuterium, a cyano group, a substituted or unsubstituted C1 to C30 silyl group, a substituted or unsubstituted C1 to C30 alkyl group, a substituted or unsubstituted C6 to C30 aryl group, or a substituted or unsubstituted C2 to C30 heterocyclic group, at least one of $R^5$ to $R^8$ is a substituted or unsubstituted pyridinyl group, a substituted or unsubstituted pyrimidinyl group, or a substituted or unsubstituted triazinyl group, and the "substituted" refers to replacement of at least one hydrogen by deuterium, a C1 to C10 alkyl group, a C6 to C30 aryl group, or a C2 to C20 heterocyclic group.

According to another embodiment, an organic optoelectronic diode includes an anode and a cathode facing each other and at least one organic layer disposed between the anode and the cathode, wherein the organic layer includes the aforementioned compound for the organic optoelectronic diode.

According to another embodiment, a display device including the organic optoelectronic diode is provided.

An organic optoelectronic diode having high efficiency and a long life-span may be realized.

DESCRIPTION OF THE DRAWINGS

FIGS. 1 and 2 are cross-sectional views showing organic light emitting diodes according to embodiments.

MODE FOR INVENTION

Hereinafter, embodiments of the present invention are described in detail. However, these embodiments are exemplary, the present invention is not limited thereto and the present invention is defined by the scope of claims.

In the present specification, when a definition is not otherwise provided, "substituted" refers to replacement of at least one hydrogen of a substituent or a compound by deuterium, a halogen, a hydroxyl group, an amino group, a substituted or unsubstituted C1 to C30 amine group, a nitro group, a substituted or unsubstituted C1 to C40 silyl group, a C1 to C30 alkyl group, a C1 to C10 alkylsilyl group, a C6 to C30 arylsilyl group, a C3 to C30 cycloalkyl group, a C3 to C30 heterocycloalkyl group, a C6 to C30 aryl group, a C2 to C30 heteroaryl group, a C1 to C20 alkoxy group, a C1 to C10 trifluoroalkyl group, a cyano group, or a combination thereof.

In the chemical formulae of the present specification, unless a specific definition is otherwise provided, hydrogen is boned at the position when a chemical bond is not drawn where supposed to be given.

In one example of the present invention, the "substituted" refers to replacement of at least one hydrogen of a substituent or a compound by deuterium, a C1 to C30 alkyl group, a C1 to C10 alkylsilyl group, a C6 to C30 arylsilyl group, a C3 to C30 cycloalkyl group, a C3 to C30 heterocycloalkyl group, a C6 to C30 aryl group, or a C2 to C30 heteroaryl group. In one example of the present invention, the "substituted" refers to replacement of at least one hydrogen of a substituent or a compound by deuterium, a C1 to C30 alkyl group, a C1 to C10 alkylsilyl group, a C6 to C30 arylsilyl group, a C3 to C30 cycloalkyl group, a C3 to C30 heterocycloalkyl group, a C6 to C30 aryl group, or a C2 to C30 heteroaryl group. In addition, in specific examples of the present invention, the "substituted" refers to replacement of at least one hydrogen of a substituent or a compound by deuterium, a C1 to C5 alkyl group, a phenyl group, a biphenyl group, a terphenyl group, a naphthyl group, a triphenyl group, a fluorenyl group, a fused fluorenyl group, a pyridinyl group, a pyrimidinyl group, a triazinyl group, quinolinyl group, an isoquinolinyl group, a quinazolinyl group, a quinoxalinyl group, a naphthyridinyl group, a benzofuranpyrimidinyl group, a benzothiophenepyrimidinyl group, a dibenzofuranyl group, a dibenzothiophenyl group, or a carbazolyl group. In addition, in specific examples of the present invention, the "substituted" refers to replacement of at least one hydrogen of a substituent or a compound by deuterium, a methyl group, an ethyl group, a propanyl group, a butyl group, a phenyl group, a naphthyl group, a para-biphenyl group, a meta-biphenyl group, an ortho-biphenyl group, a terphenyl group, a fluorenyl group (fluorenephenyl group, 9-methylfluoren-9-yl group, 9-phenylfluorene-9-phenylene group, etc.), a fused fluorenyl group (9,9'-spirofluorenyl group, etc.), a pyrimidinyl group, a triazinyl group, a quinazolinyl group, a quinoxalinyl group, a naphthyridinyl group, a benzonaphthofuranyl group, a benzonaphthothiophenyl group, a benzofuranpyrimidinyl group, a benzothiophenepyrimidinyl group, a carbazolyl group, a dibenzofuranyl group, or a dibenzothiophenyl group.

In the present specification, when a definition is not otherwise provided, "hetero" refers to one including one to three heteroatoms selected from N, O, S, P, and Si, and remaining carbons in one functional group.

In the present specification, when a definition is not otherwise provided, "alkyl group" refers to an aliphatic hydrocarbon group. The alkyl group may be "a saturated alkyl group" without any double bond or triple bond.

The alkyl group may be a C1 to C30 alkyl group. More specifically, the alkyl group may be a C1 to C20 alkyl group or a C1 to C10 alkyl group. For example, a C1 to C4 alkyl group may have one to four carbon atoms in the alkyl chain, and may be selected from methyl, ethyl, propyl, iso-propyl, n-butyl, iso-butyl, sec-butyl, and t-butyl.

Specific examples of the alkyl group may be a methyl group, an ethyl group, a propyl group, an isopropyl group, a butyl group, an isobutyl group, a t-butyl group, a pentyl group, a hexyl group, a cyclopropyl group, a cyclobutyl group, a cyclopentyl group, a cyclohexyl group, and the like.

In the present specification, "aryl group" refers to a group including at least one hydrocarbon aromatic moiety, and all the elements of the hydrocarbon aromatic moiety have p-orbitals which form conjugation, for example a phenyl group, a naphthyl group, and the like, two or more hydrocarbon aromatic moieties may be linked by a sigma bond and may be, for example a biphenyl group, a terphenyl group, a quarterphenyl group, and the like, or two or more hydrocarbon aromatic moieties are fused directly or indirectly to provide a non-aromatic fused ring. For example, a fluorenyl group may be included.

The aryl group may include a monocyclic, polycyclic or fused ring polycyclic (i.e., rings sharing adjacent pairs of carbon atoms) functional group.

In the present specification, "heterocyclic group" is a generic concept of a heteroaryl group, and may include at least one hetero atom selected from N, O, S, P, and Si instead of carbon (C) in a cyclic compound such as aryl group, a cycloalkyl group, a fused ring thereof, or a combination thereof. When the heterocyclic group is a fused ring, the entire ring or each ring of the heterocyclic group may include one or more heteroatoms.

For example, "heteroaryl group" may refer to an aryl group including at least one hetero atom selected from N, O, S, P, and Si instead of carbon (C). Two or more heteroaryl groups are linked by a sigma bond directly, or when the C2 to C60 heteroaryl group includes two or more rings, the two or more rings may be fused. When the heteroaryl group is a fused ring, each ring may include 1 to 3 hetero atoms.

Specific examples of the heterocyclic group may be a pyridinyl group, a pyrimidinyl group, a pyrazinyl group, a pyridazinyl group, a triazinyl group, a quinolinyl group, an isoquinolinyl group, a quinazolinyl group, a quinoxalinyl group, a benzofuranpyrimidinyl group, a benzothiophenepyrimidinyl group, and the like.

More specifically, the substituted or unsubstituted C6 to C30 aryl group may be a substituted or unsubstituted phenyl group, a substituted or unsubstituted naphthyl group, a substituted or unsubstituted anthracenyl group, a substituted or unsubstituted phenanthrenyl group, a substituted or unsubstituted naphthacenyl group, a substituted or unsubstituted pyrenyl group, a substituted or unsubstituted biphenyl group, a substituted or unsubstituted p-terphenyl group, a substituted or unsubstituted m-terphenyl group, a substituted or unsubstituted o-terphenyl group, a substituted or unsubstituted chrysenyl group, a substituted or unsubstituted triphenylene group, a substituted or unsubstituted perylenyl group, a substituted or unsubstituted fluorenyl group, a substituted or unsubstituted indenyl group, a substituted or unsubstituted furanyl group, a substituted or unsubstituted thiophenyl group, or a combination thereof, but is not limited thereto.

More specifically, the substituted or unsubstituted C2 to C30 heterocyclic group may be a substituted or unsubstituted pyrrolyl group, a substituted or unsubstituted pyrazolyl group, a substituted or unsubstituted imidazolyl group, a substituted or unsubstituted triazolyl group, a substituted or unsubstituted oxazolyl group, a substituted or unsubstituted thiazolyl group, a substituted or unsubstituted oxadiazolyl group, a substituted or unsubstituted thiadiazolyl group, a substituted or unsubstituted pyridyl group, a substituted or unsubstituted pyrimidinyl group, a substituted or unsubstituted pyrazinyl group, a substituted or unsubstituted triazinyl group, a substituted or unsubstituted benzofuranyl group, a substituted or unsubstituted benzothiophenyl group, a substituted or unsubstituted benzimidazolyl group, a substituted or unsubstituted indolyl group, a substituted or unsubstituted quinolinyl group, a substituted or unsubstituted isoquinolinyl group, a substituted or unsubstituted quinazolinyl group, a substituted or unsubstituted quinoxalinyl group, a substituted or unsubstituted naphthyridinyl group, a substituted or unsubstituted azatriphenylenyl group, a substituted or unsubstituted benzofuranpyrimidinyl group, a substituted or unsubstituted benzothiophenepyrimidinyl group, a substituted or unsubstituted benzoxazinyl group, a substituted or unsubstituted benzthiazinyl group, a substituted or unsubstituted acridinyl group, a substituted or unsubstituted phenazinyl group, a substituted or unsubstituted phenothiazinyl group, a substituted or unsubstituted phenoxazinyl group, a substituted or unsubstituted dibenzofuranyl group, or a substituted or unsubstituted dibenzothiophenyl group, or a combination thereof, but is not limited thereto.

In the present specification, hole characteristics refer to an ability to donate an electron to form a hole when an electric field is applied, and that a hole formed in the anode may be easily injected into a light emitting layer, and a hole formed in a light emitting layer may be easily transported into an anode and transported in the light emitting layer due to conductive characteristics according to a highest occupied molecular orbital (HOMO) level.

In addition, electron characteristics refer to an ability to accept an electron when an electric field is applied, and that an electron formed in a cathode may be easily injected into a light emitting layer, and an electron formed in a light emitting layer may be easily transported into a cathode and transported in the light emitting layer due to conductive characteristics according to a lowest unoccupied molecular orbital (LUMO) level.

Hereinafter, a compound for an organic optoelectronic diode is described.

The compound for the organic optoelectronic diode is represented by a combination of Chemical Formula 1 and Chemical Formula 2.

[Chemical Formula 1]

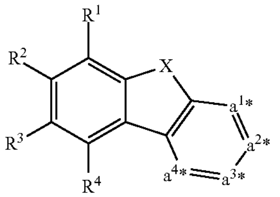

[Chemical Formula 2]

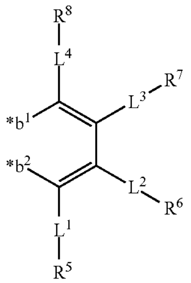

In Chemical Formula 1 and Chemical Formula 2,

X is O, S, or $CR^aR^b$, adjacent two of $a^1$*, $a^2$*, $a^3$*, and $a^4$* are C and linking portions with *$b^1$ and *$b^2$, two of $a^1$*, $a^2$*, $a^3$*, and $a^4$* that are not linked with *$b^1$ and *$b^2$ are independently $CR^c$, $R^1$ to $R^4$, $R^a$, $R^b$, and $R^c$ are independently hydrogen, deuterium, a cyano group, a substituted or unsubstituted C1 to C30 silyl group, a substituted or unsubstituted C1 to C30 alkyl group, or a substituted or unsubstituted C6 to C30 aryl group, $L^1$ to $L^4$ are independently a single bond or a substituted or unsubstituted C6 to C30 arylene group, $R^5$ to $R^8$ are independently hydrogen, deuterium, a cyano group, a substituted or unsubstituted C1 to C30 silyl group, a substituted or unsubstituted C1 to C30 alkyl group, a substituted or unsubstituted C6 to C30 aryl group, or a substituted or unsubstituted C2 to C30 heterocyclic group, at least one of $R^5$ to $R^8$ is a substituted or unsubstituted pyridinyl group, a substituted or unsubstituted pyrimidinyl group, or a substituted or unsubstituted triazinyl group, and the "substituted" refers to replacement of at least one hydrogen by deuterium, a C1 to C10 alkyl group, a C6 to C30 aryl group, or a C2 to C20 heterocyclic group. In an embodiment of the present invention, the compound represented by the combination of Chemical Formula 1 and Chemical Formula 2 according to the fusion point of the additional benzo ring may be for example represented by Chemical Formula 1A. The compound represented by Chemical Formula 1A may be a first compound for an organic optoelectronic diode described later.

[Chemical Formula 1A]

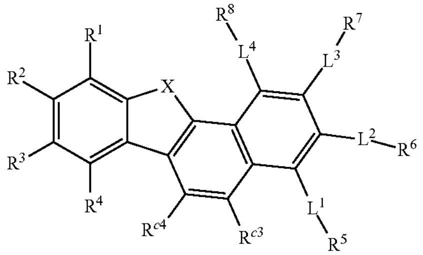

Considering that the T1 energy level of Chemical Formula 1A is about 0.11 eV or higher than that of Chemical Formula 1B, and the T1 energy level is further lowered when the mother body is further substituted, Chemical Formula 1B may exhibit a lower efficiency than Chemical Formula 1A due to the low T1 energy level when the green device is applied.

[Chemical Formula 1B]

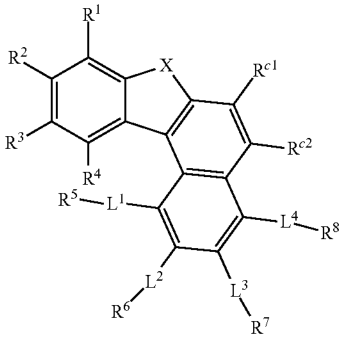

Chemical Formula 1A T1 energy level: 2.700 eV

Chemical Formula 1B T1 energy level: 2.589 eV

In Chemical Formula 1A and Chemical Formula 1B, the definitions of X, $R^1$ to $R^4$, $L^1$ to $L^4$ and $R^5$ to $R^8$ are the same as described above, and $R^{c1}$, $R^{c2}$, $R^{c3}$, and $R^{c4}$ are the same as the definitions of $R^c$ described above.

In specific example of the present invention, the "substituted" refers to replacement of at least one hydrogen by deuterium, a C1 to C4 alkyl group, or a C6 to C18 aryl group, more specifically replacement of at least one hydrogen by deuterium, a C1 to C4 alkyl group, a phenyl group, a naphthyl group, a para-biphenyl group, a meta-biphenyl group, an ortho-biphenyl group, a terphenyl group, a fluorenyl group (fluorenephenyl group, 9-methylfluoren-9-yl group, a 9-phenylfluorene-9-phenylene group, etc.), a fused fluorenyl group (9,9'-spirofluorenyl group, etc.), a pyrimidinyl group, a triazinyl group, a quinazolinyl group, a quinoxalinyl group, a naphthyridinyl group, a benzonaphthofuranyl group, a benzonaphthothiophenyl group, a benzofuranpyrimidinyl group, a benzothiophenepyrimidinyl group, a carbazolyl group, a dibenzofuranyl group, or a dibenzothiophenyl group.

The compound for the organic optoelectronic diode according to the present invention is a material in which a heterocycle including at least two N's in fused dibenzofuran, fused dibenzothiophene, or fused fluorenyl core is introduced, and the fused benzo ring is substituted with the heterocycle including at least two N's, thereby controlling the relatively T1 energy level, and thus allowing the energy level to be particularly suitable for the phosphorescence Red, which in turn lowers the driving voltage and realizes long life-span and high efficiency of a device.

In a specific embodiment of the present invention, $R^5$ to $R^8$ may independently be hydrogen, deuterium, a substituted or unsubstituted C1 to C30 alkyl group, a substituted or unsubstituted C6 to C30 aryl group, or a substituted or unsubstituted C2 to C30 heterocyclic group, and at least one of $R^5$ to $R^8$ may be a substituted or unsubstituted C2 to C30 heterocyclic group.

In a more specific embodiment, one of $R^5$ to $R^8$ may be a substituted or unsubstituted pyridinyl group, a substituted or unsubstituted pyrimidinyl group, or a substituted or unsubstituted triazinyl group, and the rest may be hydrogen, deuterium, a cyano group, a substituted or unsubstituted C1 to C30 silyl group, a substituted or unsubstituted C1 to C30 alkyl group, or a substituted or unsubstituted C6 to C30 aryl group.

In the most specific embodiment, $R^5$ may be a substituted or unsubstituted pyridinyl group, a substituted or unsubstituted pyrimidinyl group, or a substituted or unsubstituted triazinyl group and $R^6$ to $R^8$ may independently be hydrogen, deuterium, a substituted or unsubstituted C1 to C30 alkyl group, or a substituted or unsubstituted C6 to C30 aryl group, $R^6$ may be a substituted or unsubstituted pyridinyl group, a substituted or unsubstituted pyrimidinyl group, or a substituted or unsubstituted triazinyl group and $R^5$, $R^7$, and $R^8$ may independently be hydrogen, deuterium, a substituted or unsubstituted C1 to C30 alkyl group, or a substituted or unsubstituted C6 to C30 aryl group, $R^7$ may be a substituted or unsubstituted pyridinyl group, a substituted or unsubstituted pyrimidinyl group, or a substituted or unsubstituted triazinyl group, and $R^5$, $R^6$, and $R^8$ may independently be hydrogen, deuterium, a substituted or unsubstituted C1 to C30 alkyl group, or a substituted or unsubstituted C6 to C30 aryl group, or $R^8$ may be substituted or unsubstituted pyridinyl group, a substituted or unsubstituted pyrimidinyl group, or a substituted or unsubstituted triazinyl group and $R^5$ to $R^7$ may independently be hydrogen, deuterium, a substituted or unsubstituted C1 to C30 alkyl group, or a substituted or unsubstituted C6 to C30 aryl group.

For example, Chemical Formula 1A may be represented by one of Chemical Formula 1A-a, Chemical Formula 1A-b, Chemical Formula 1A-c, and Chemical Formula 1A-d.

[Chemical Formula 1A-a]

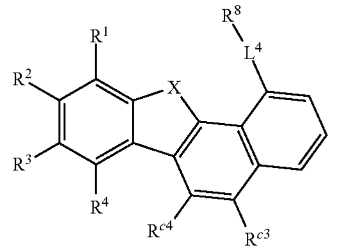

[Chemical Formula 1A-b]

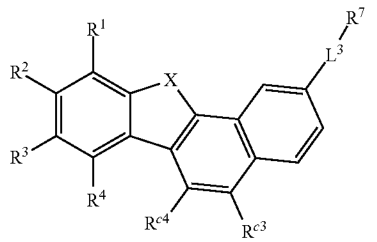

[Chemical Formula 1A-c]

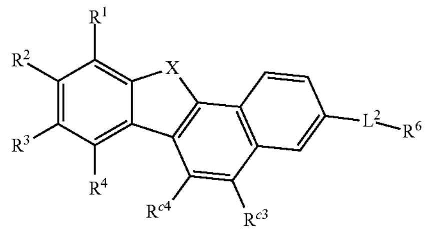

[Chemical Formula 1A-d]

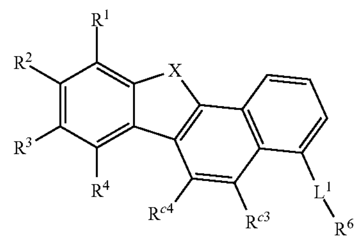

In Chemical Formula 1A-a, Chemical Formula 1A-b, Chemical Formula 1A-c, and Chemical Formula A-d, X, $R^1$ to $R^4$, $L^1$ to $L^4$, and $R^5$ to $R^8$ are the same as described above and $R^{c3}$ and $R^{c4}$ are the same as the definition of $R^c$.

In a specific embodiment of the present invention, when one of $R^5$ to $R^8$ is a substituted or unsubstituted C2 to C30 heterocyclic group, the substituted or unsubstituted C2 to C30 heterocyclic group may be a substituted or unsubstituted pyridinyl group, a substituted or unsubstituted pyrimidinyl group, a substituted or unsubstituted triazinyl group, a substituted or unsubstituted benzofuranpyrimidinyl group, a substituted or unsubstituted benzothiophenepyrimidinyl group, a substituted or unsubstituted naphthyridinyl group, or a substituted or unsubstituted azatriphenylenyl group, and in a specific embodiment, the substituted or unsubstituted C2 to C30 heterocyclic group may be a substituted or unsubstituted pyridinyl group, a substituted or unsubstituted pyrimidinyl group or a substituted or unsubstituted triazinyl group.

For example, the substituted or unsubstituted C2 to C30 heterocyclic group may be a substituted or unsubstituted triazinyl group.

For example, when any one of $R^5$ to $R^8$ is a substituted or unsubstituted C2 to C30 heterocyclic group, it may be selected from the substituents of Group I.

[Group I]

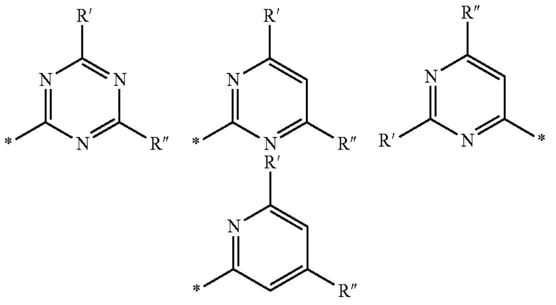

In Group I, R' and R" are independently a substituted or unsubstituted C6 to C30 aryl group or a substituted or unsubstituted C2 to C30 heterocyclic group. In Group I, R' and R" may independently be a substituted or unsubstituted C6 to C30 aryl group, a phenyl group, a naphthyl group, a biphenyl group, a terphenyl group, an anthracenyl group, a phenanthrenyl group, a fluorenyl group, or a triphenylene group, or more desirably a phenyl group, a naphthyl group, a biphenyl group, a fluorenyl group, or a terphenyl group. In Group I, when R' and R" are independently a substituted or unsubstituted C2 to C30 heterocyclic group, they may be desirably a dibenzofuranyl group or a dibenzothiophenyl group. In a specific embodiment of the present invention, $R^1$ to $R^4$ may independently be hydrogen, deuterium, or a substituted or unsubstituted C1 to C30 alkyl group, in a more embodiment, $R^1$ may be hydrogen and $R^2$ to $R^4$ may independently be hydrogen, deuterium, or a substituted or unsubstituted C1 to C20 alkyl group, or For example, $R^1$ to $R^4$ may be all hydrogen.

In a specific embodiment of the present invention, $R^a$, $R^b$, and $R^c$ may independently be hydrogen, deuterium, a substituted or unsubstituted C1 to C30 alkyl group, or a substituted or unsubstituted C6 to C30 aryl group, in a more specific embodiment, $R^a$ and $R^b$ may independently be a substituted or unsubstituted C1 to C20 alkyl group, or a substituted or unsubstituted C6 to C20 aryl group and $R^c$ may be hydrogen, deuterium, or a substituted or unsubstituted C1 to C20 alkyl group, or for example, $R^a$ and $R^b$ may independently be a substituted or unsubstituted methyl group, a substituted or unsubstituted ethyl group, a substituted or unsubstituted propyl group, a substituted or unsubstituted isopropyl group, a substituted or unsubstituted phenyl group, a substituted or unsubstituted biphenyl group, or a substituted or unsubstituted naphthyl group, and $R^c$ may be hydrogen.

On the other hand, $R^{c1}$ to $R^{c4}$ are the same as the definition of $R^c$ described above.

In a specific embodiment of the present invention, $L^1$ to $L^4$ may independently be a single bond or a substituted or unsubstituted C6 to C20 arylene group, for example a single bond, a substituted or unsubstituted phenylene group, or a substituted or unsubstituted biphenylene group, or in a more specific embodiment, $L^1$ to $L^4$ may independently be a single bond, a substituted or unsubstituted phenylene group, or a substituted or unsubstituted biphenylene group.

For example, the phenylene group or biphenylene group may be selected from the linking groups of Group II.

[Group II]

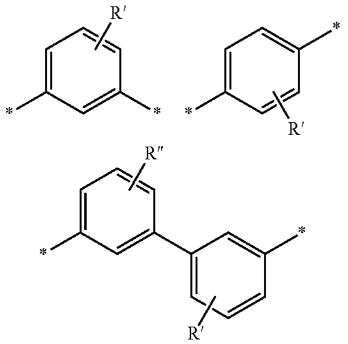

In Group II, R' and R" are independently a hydrogen atom, a substituted or unsubstituted C6 to C30 aryl group, or a substituted or unsubstituted C2 to C30 heterocyclic group.

In the most specific embodiment of the present invention, the compound for the organic optoelectronic diode may be represented by Chemical Formula 1A-b or Chemical Formula 1A-c, X may be O or S, $R^1$ to $R^4$ may independently be hydrogen, $L^2$ and $L^3$ may independently be a single bond or a substituted or unsubstituted C6 to C30 arylene group, and $R^6$ and $R^7$ may independently be a substituted or unsubstituted pyridinyl group, a substituted or unsubstituted pyrimidinyl group, or a substituted or unsubstituted triazinyl group.

The compound for the organic optoelectronic diode (first compound for the organic optoelectronic diode) represented by a combination of Chemical Formula 1 and Chemical Formula 2 may be for example selected from compounds of Group 1, but is not limited thereto.

[Group 1]
Inv-001
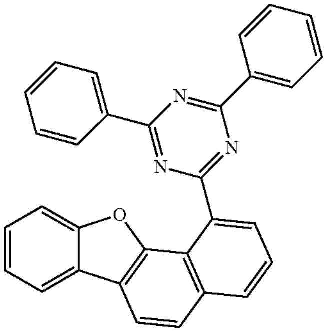
Inv-002
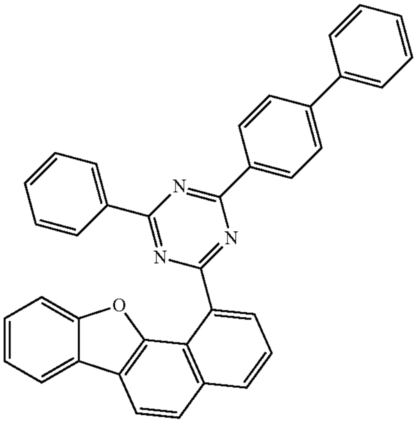
Inv-003
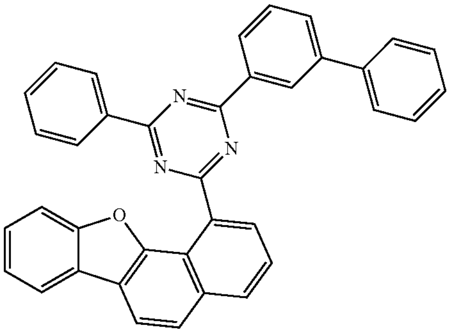
Inv-004
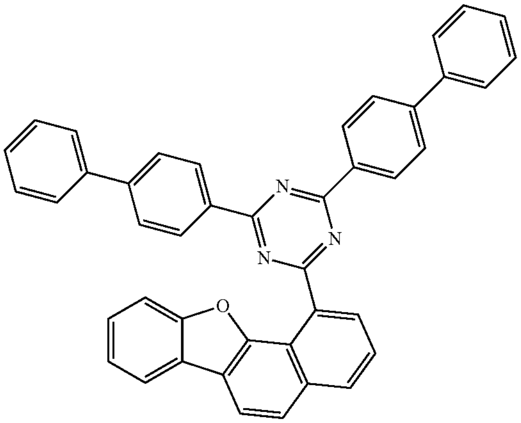
Inv-005
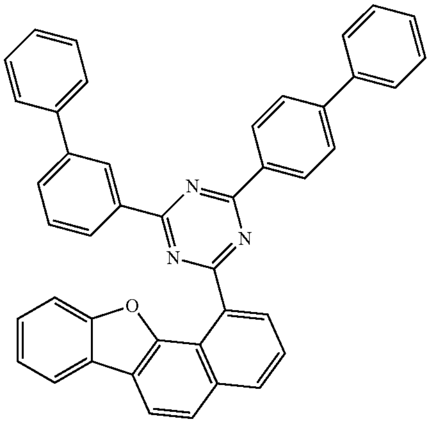
Inv-006
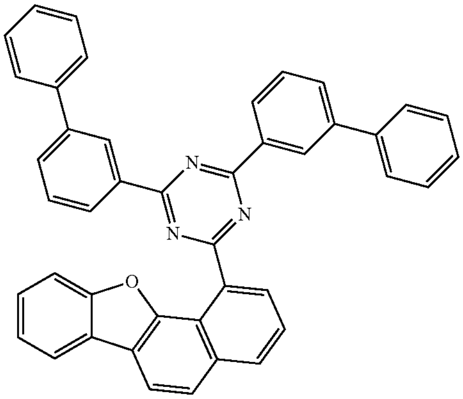

-continued
Inv-007
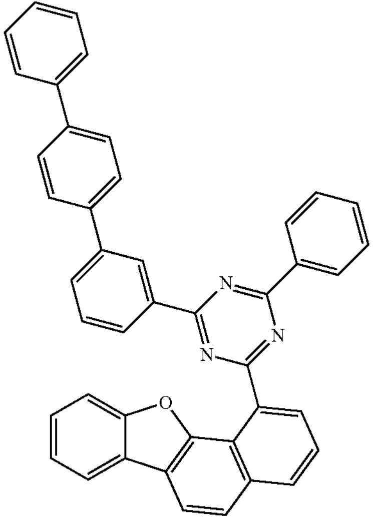
Inv-008
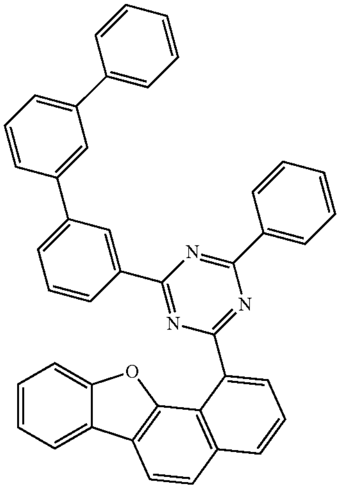
Inv-009
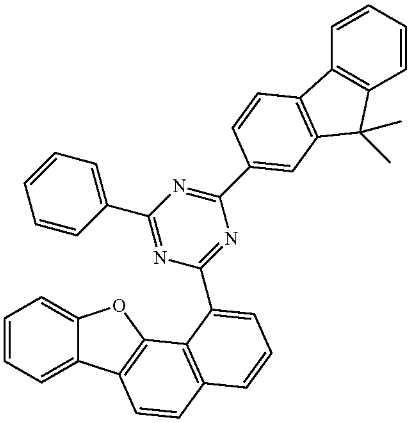
Inv-010
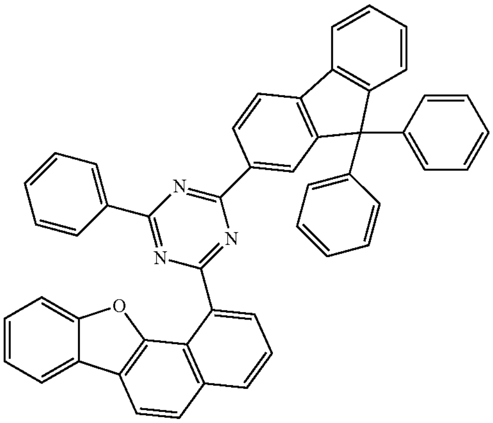
Inv-011
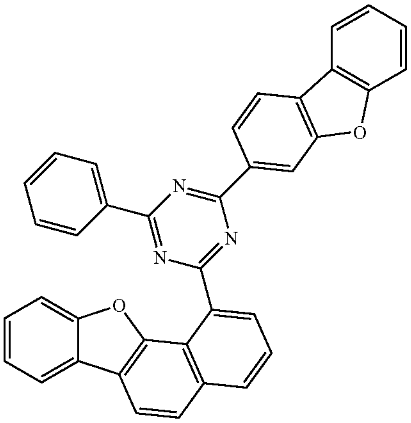
Inv-012
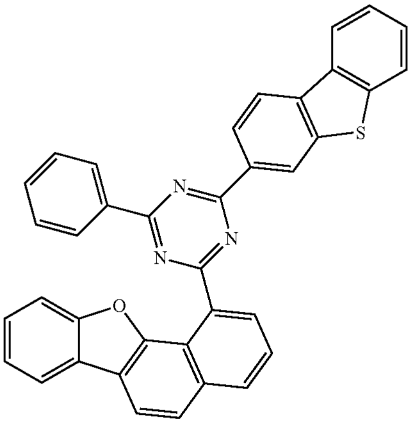

-continued
Inv-013
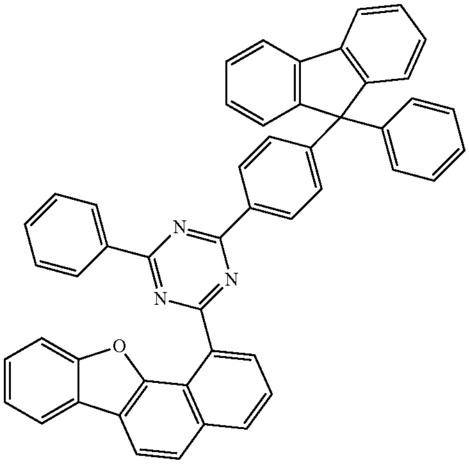
Inv-014
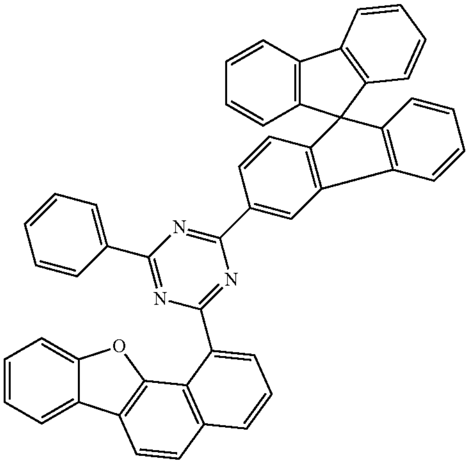
Inv-015
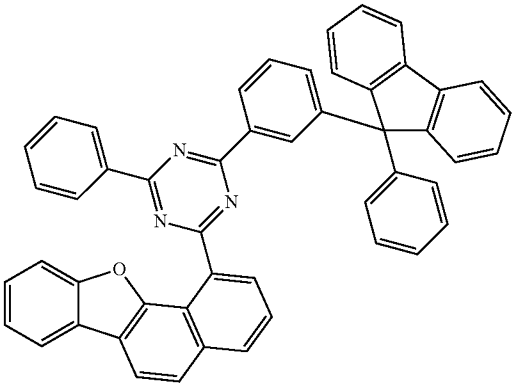
Inv-016
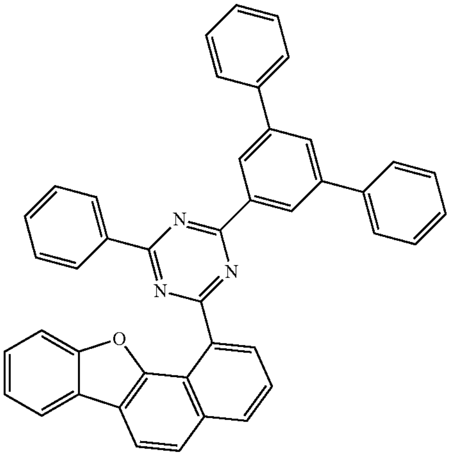
Inv-017
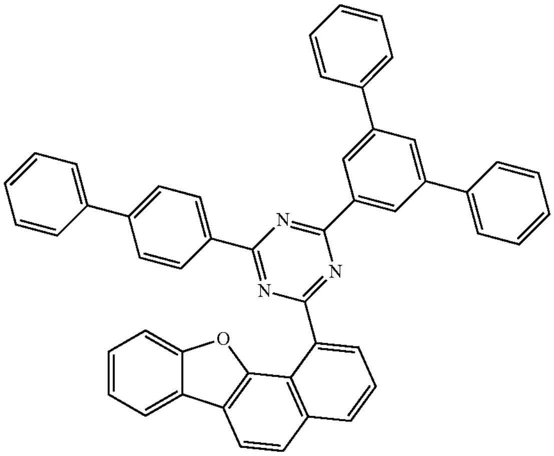
Inv-018
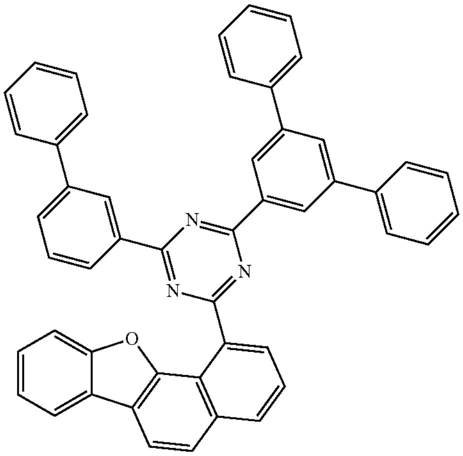

-continued
Inv-019
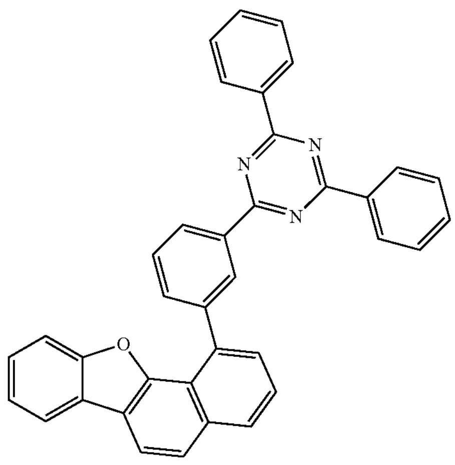
Inv-020
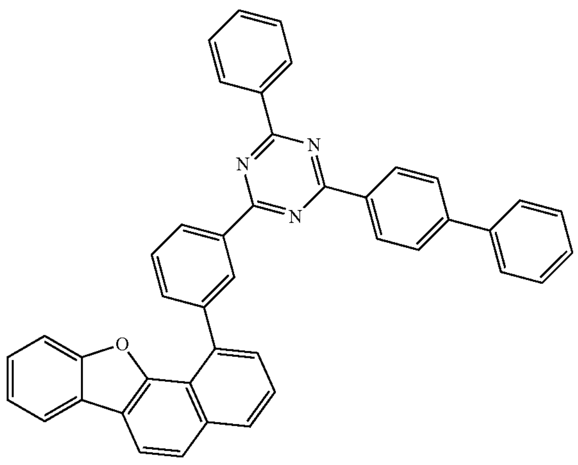
Inv-021
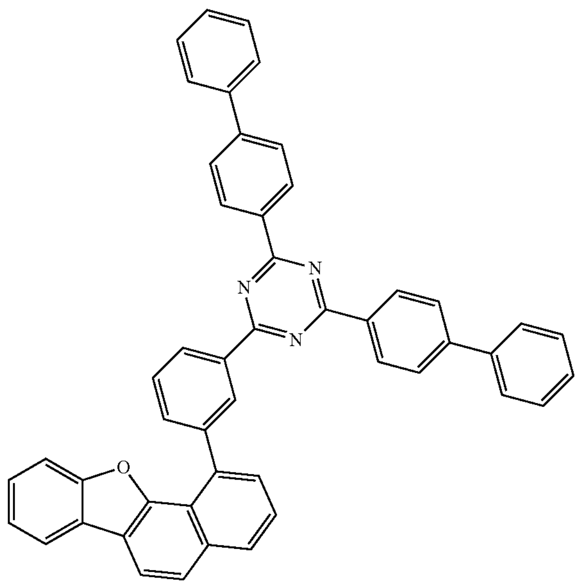
Inv-022
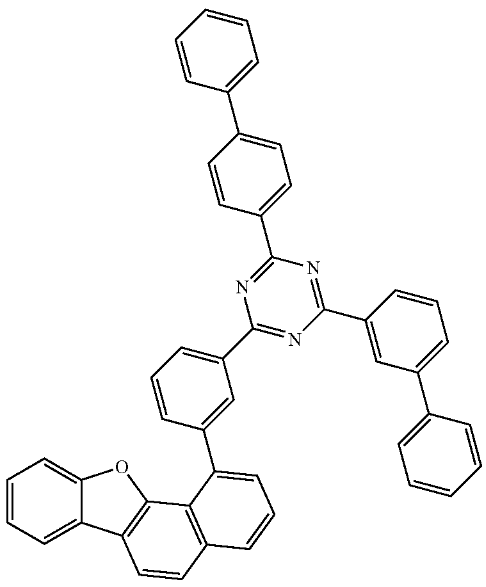
Inv-023
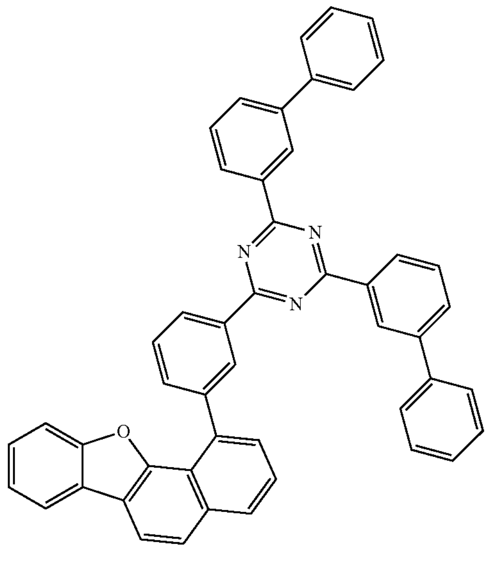
Inv-024
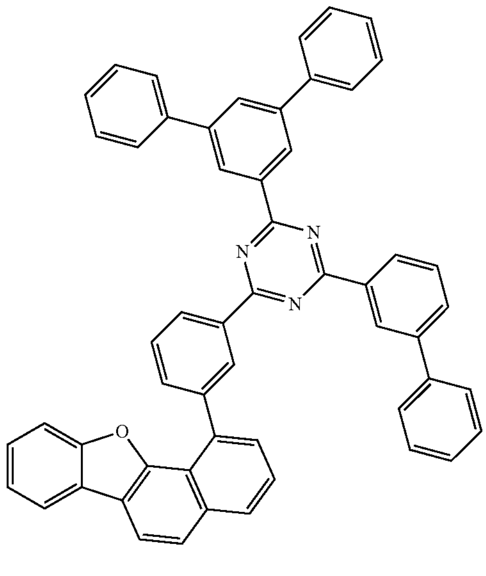

-continued
Inv-025
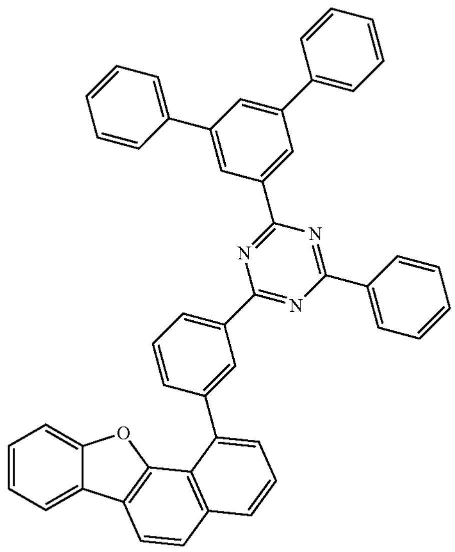
Inv-026
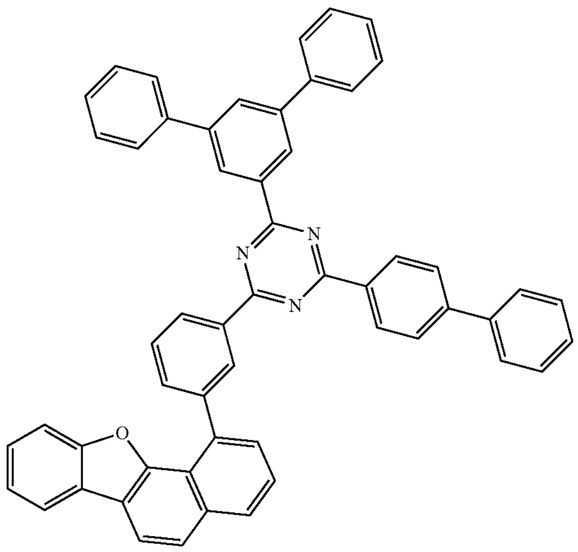
Inv-027
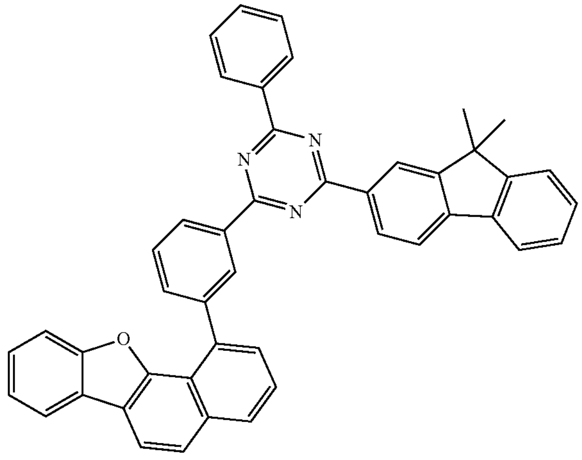
Inv-028
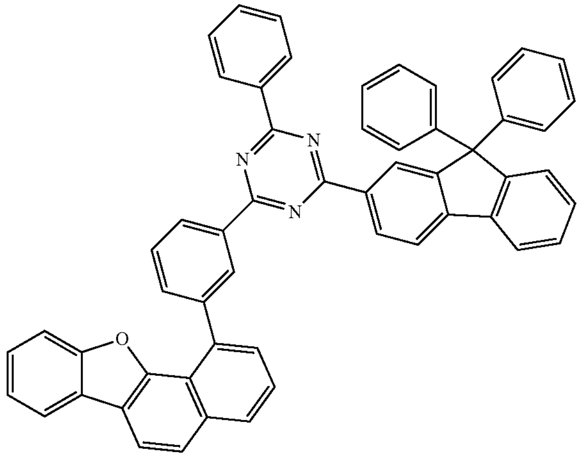
Inv-029
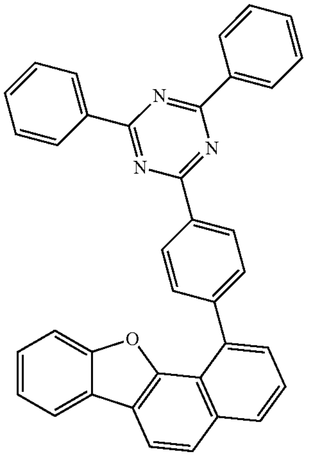
Inv-030
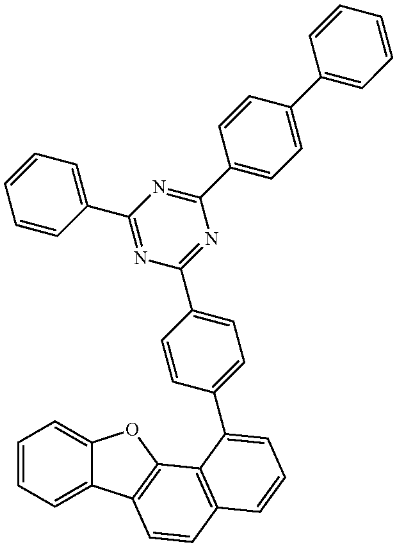

-continued
Inv-031
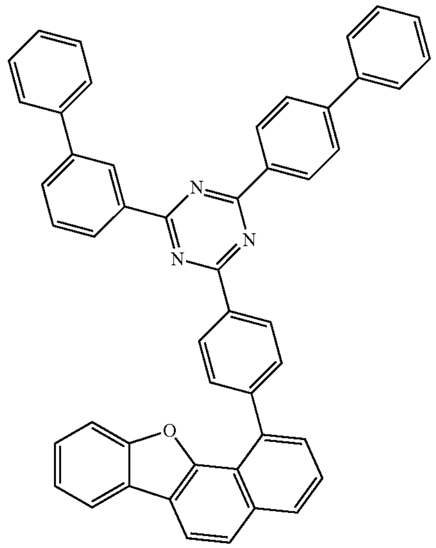
Inv-032
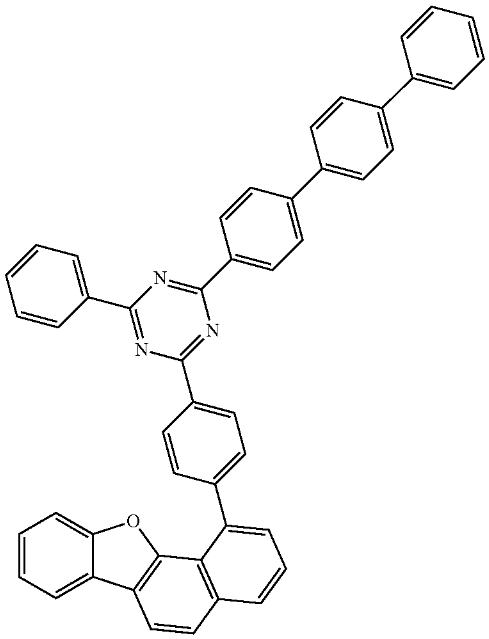
Inv-033
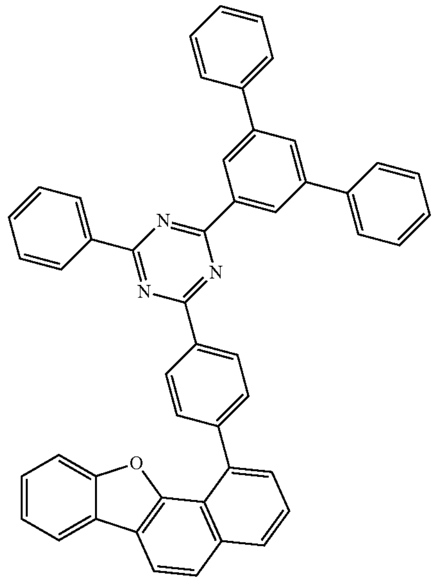
Inv-034
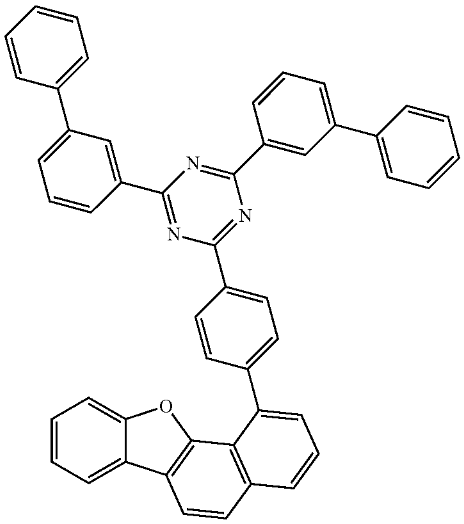

-continued
Inv-035
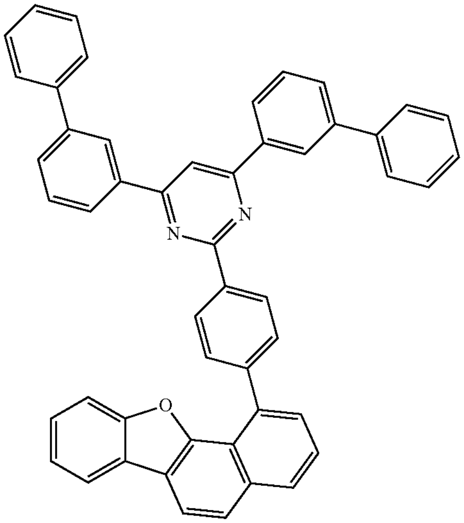
Inv-036
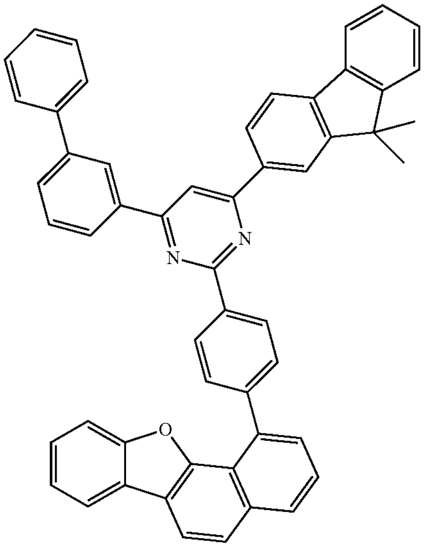
Inv-037
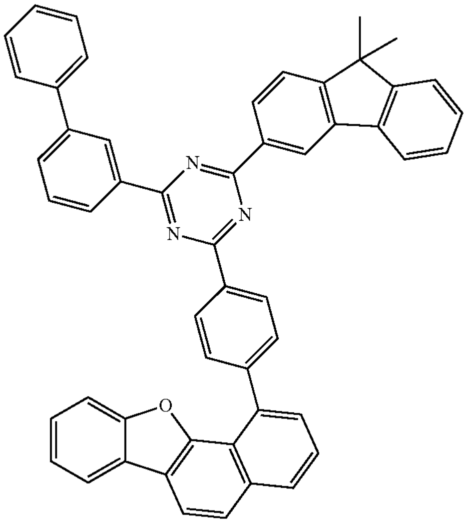
Inv-038
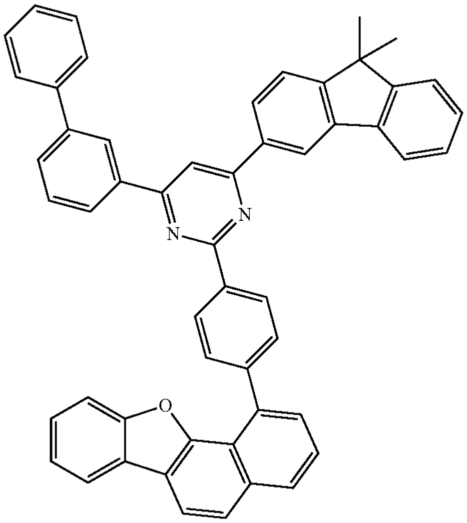
Inv-039
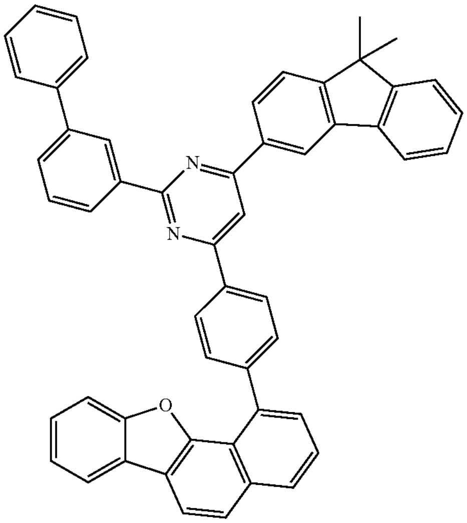
Inv-040
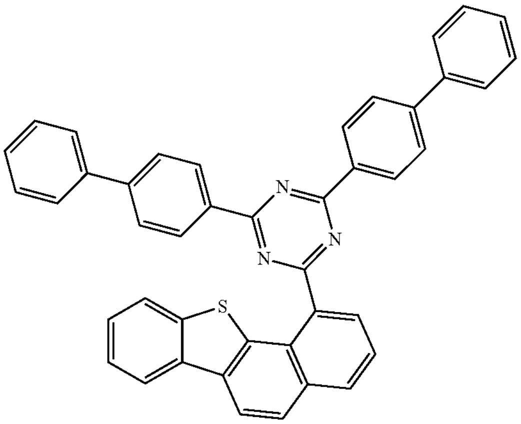

-continued
Inv-041
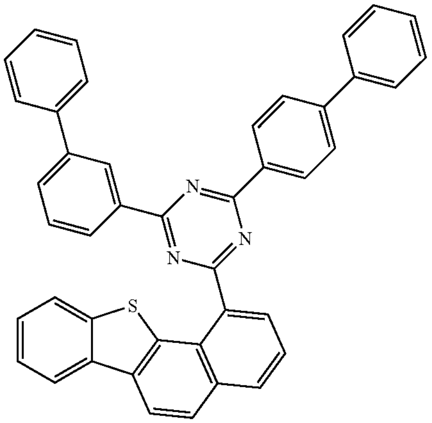
Inv-042
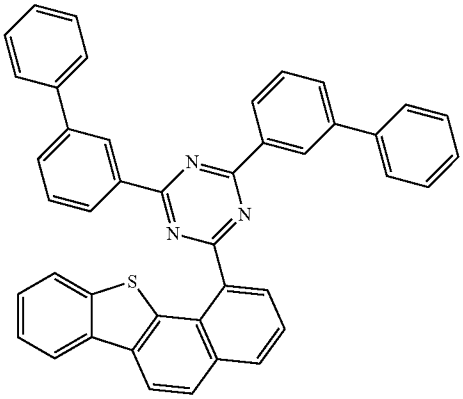
Inv-043
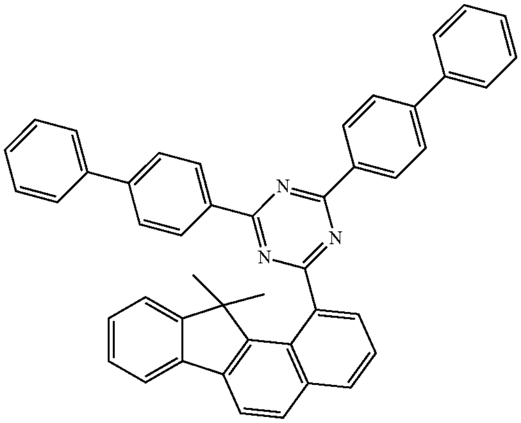
Inv-044
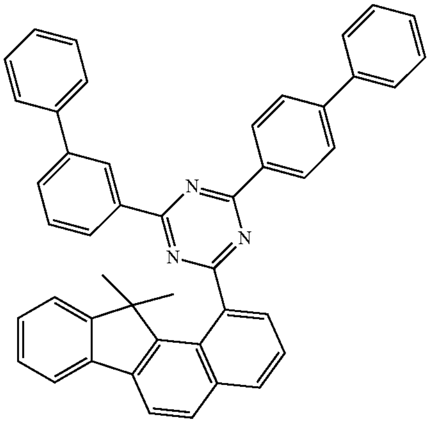
Inv-045
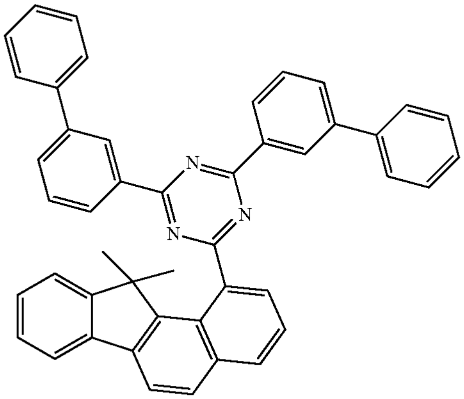
Inv-046
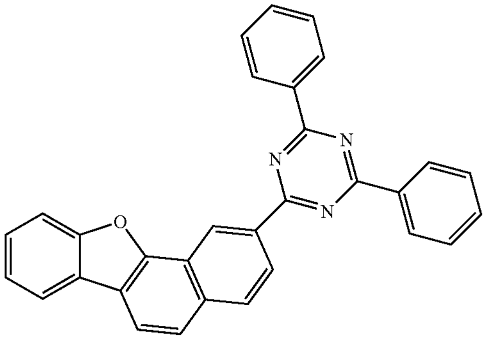

-continued
Inv-047
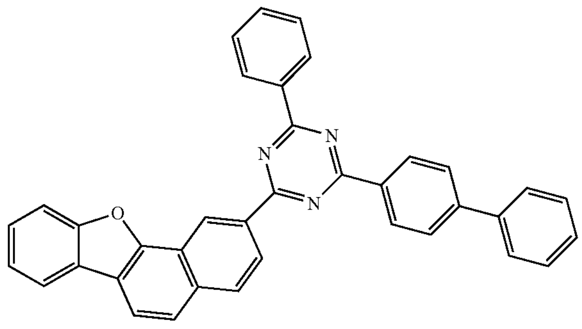
Inv-048
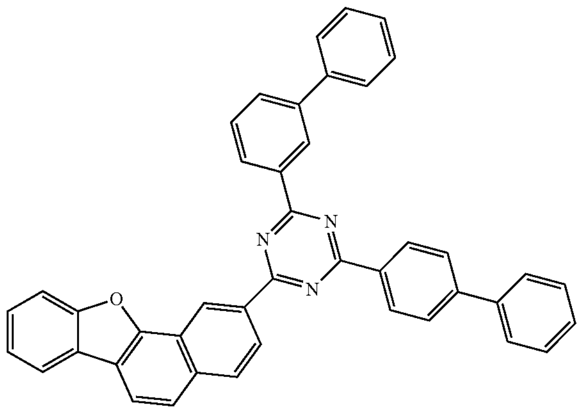
Inv-049
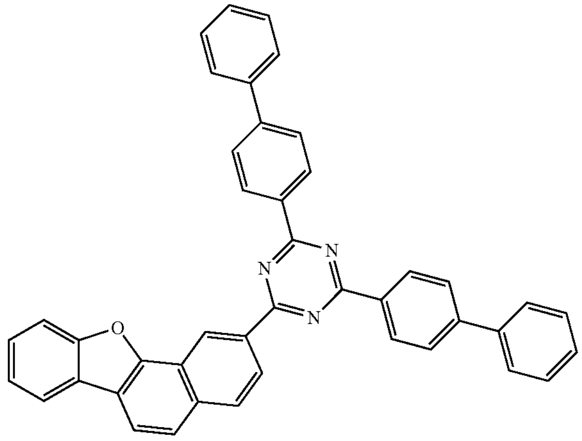
Inv-050
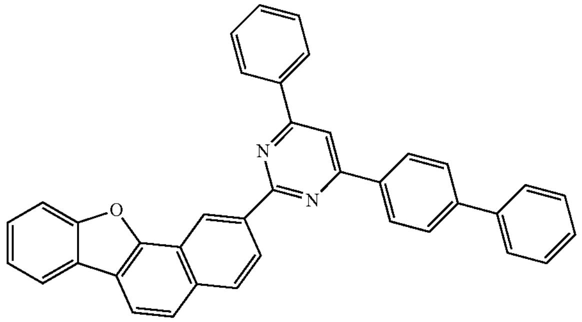
Inv-051
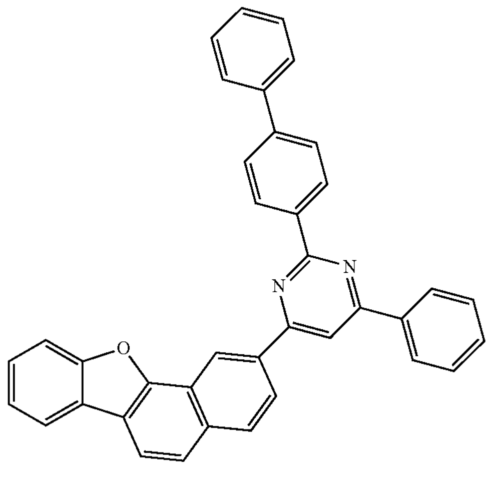
Inv-052
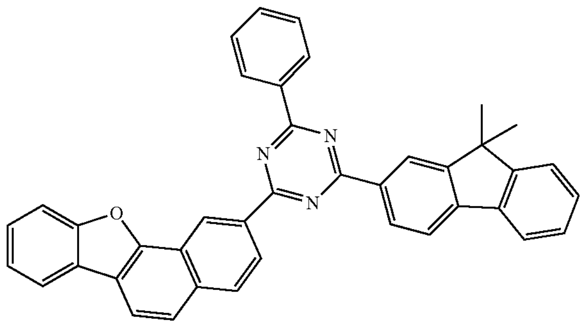

-continued
Inv-053
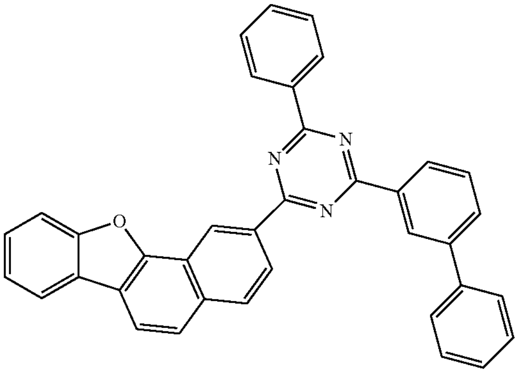
Inv-054
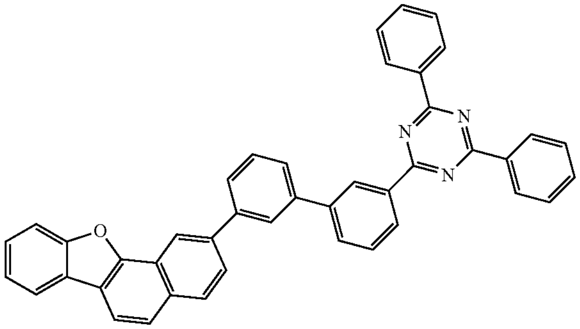
Inv-055
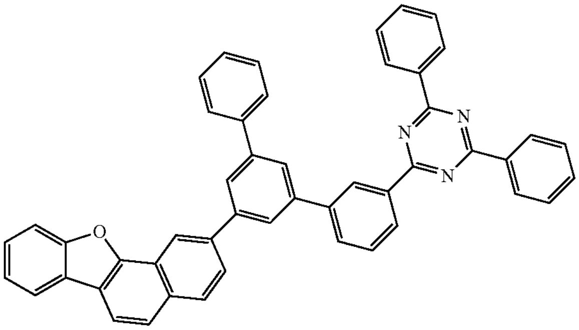
Inv-056
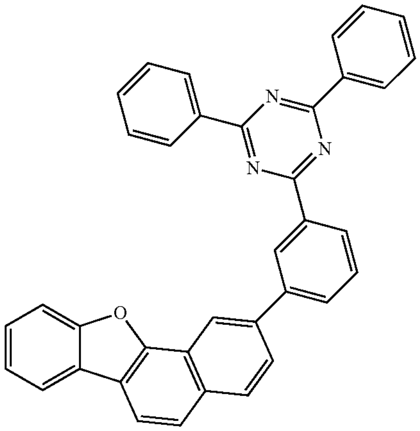
Inv-057
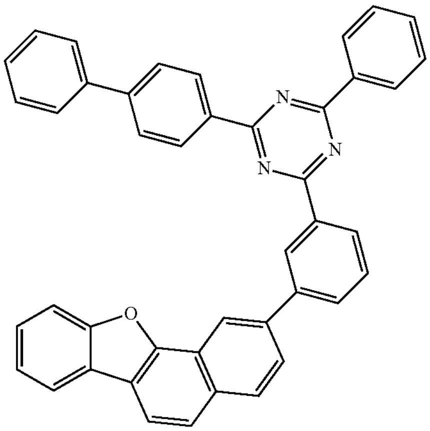
Inv-058
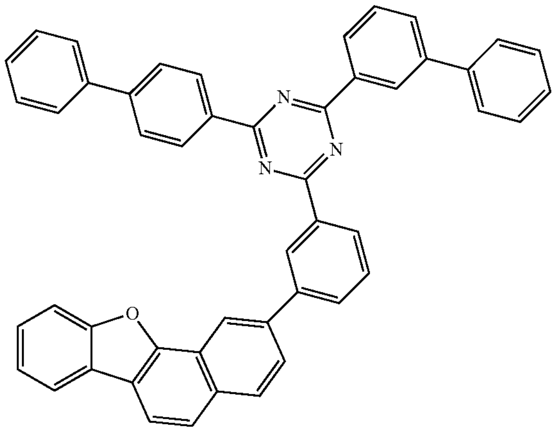

-continued
Inv-059
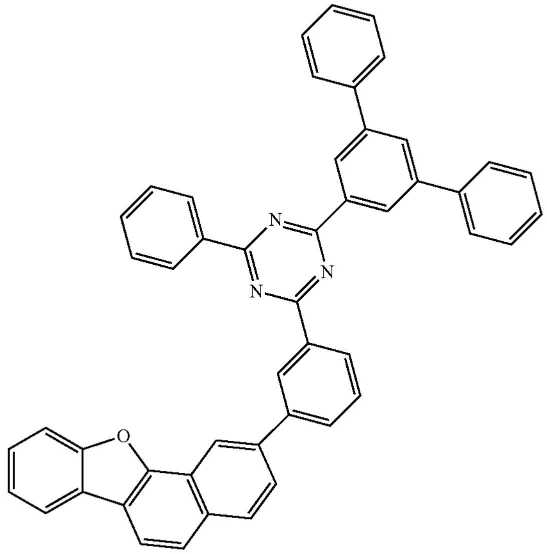
Inv-060
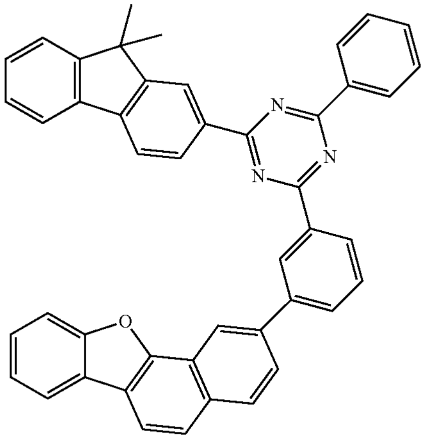
Inv-061
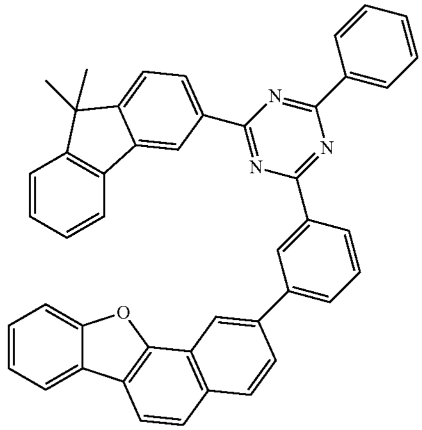
Inv-062
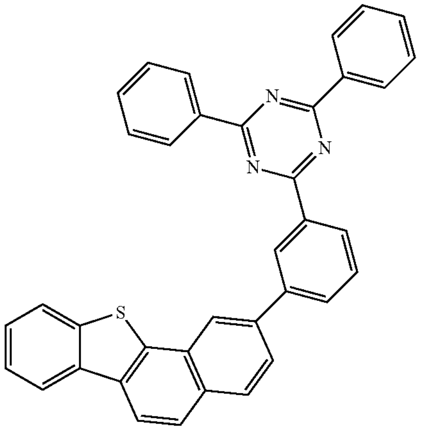
Inv-063
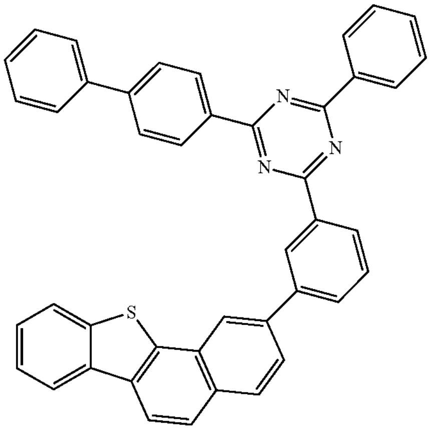
Inv-064
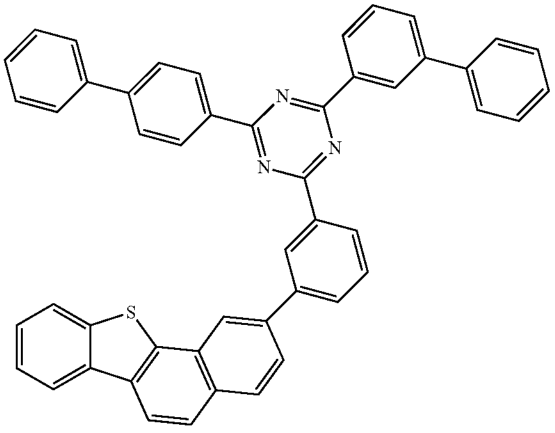

-continued
Inv-065
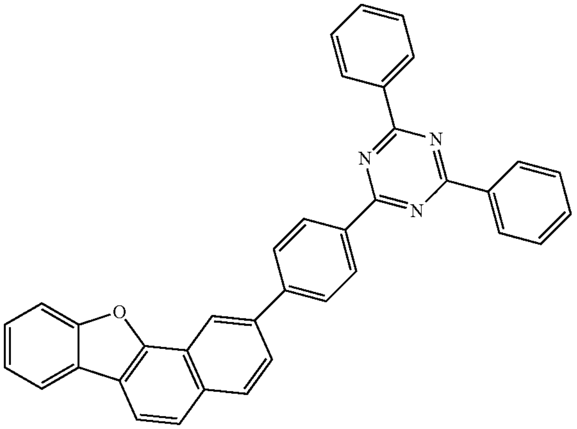
Inv-066
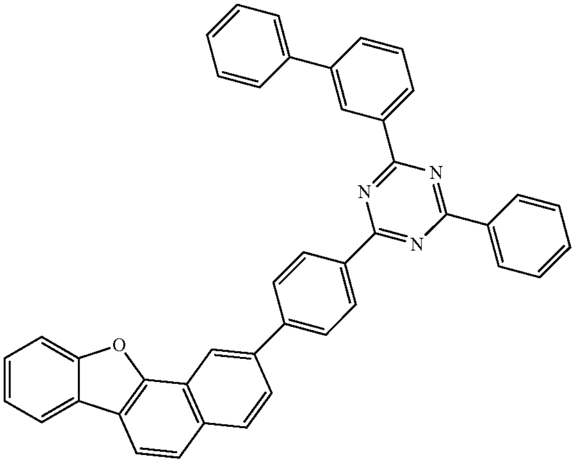
Inv-067
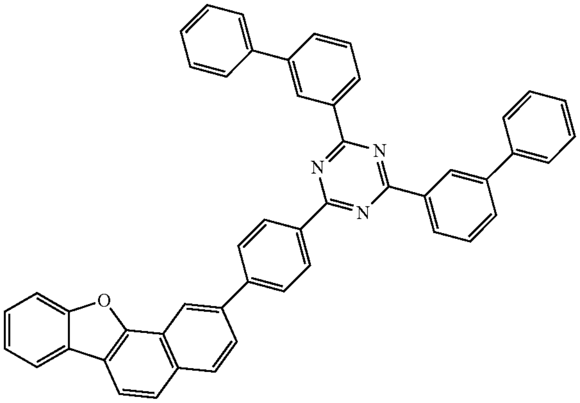
Inv-068
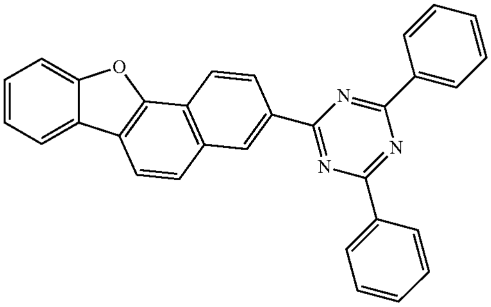
Inv-069
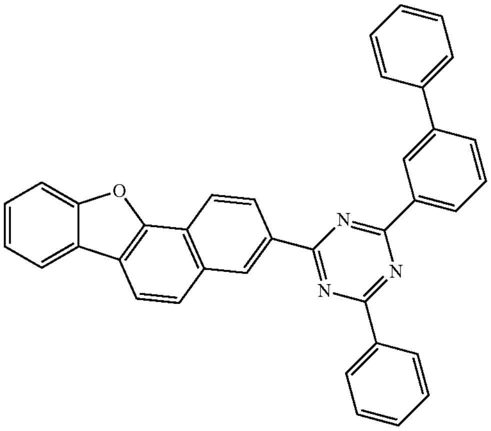
Inv-070
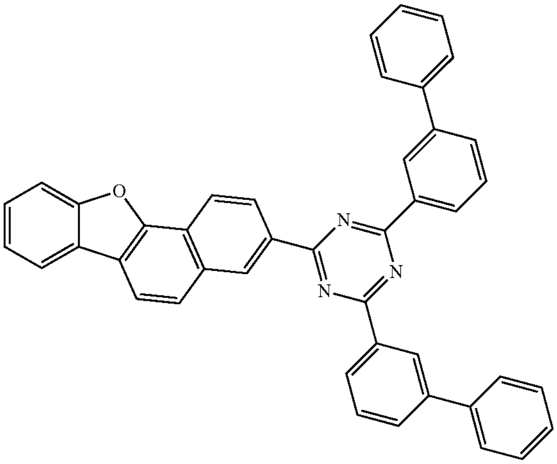

-continued
Inv-071
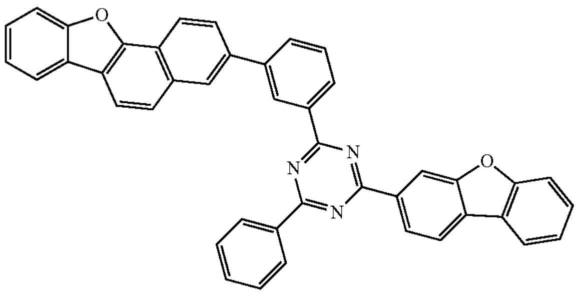
Inv-072
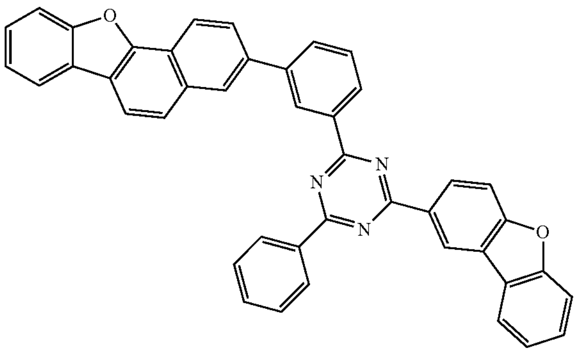
Inv-073
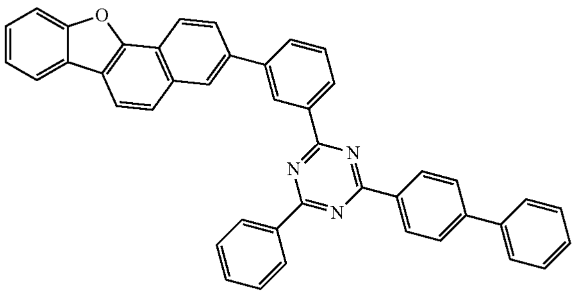
Inv-074
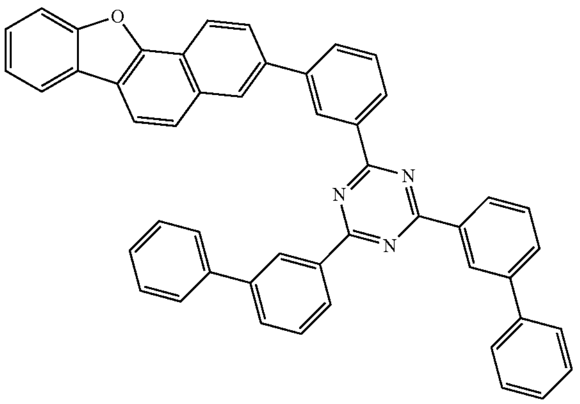
Inv-075
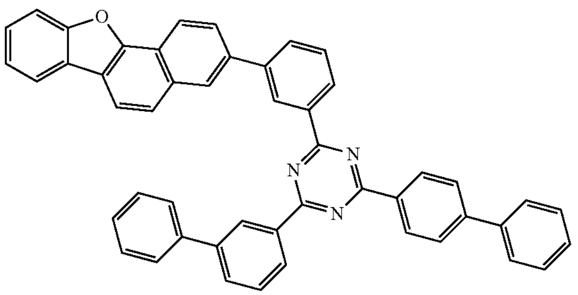
Inv-076
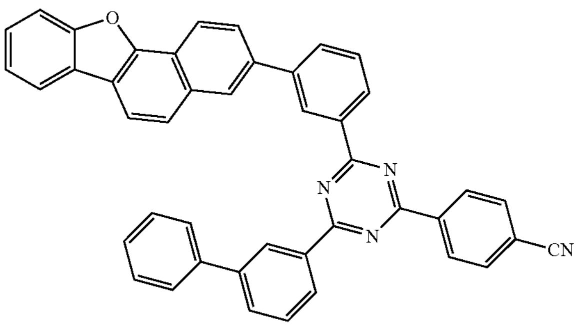
Inv-077
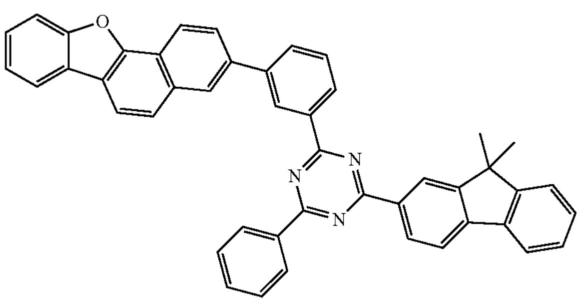
Inv-078
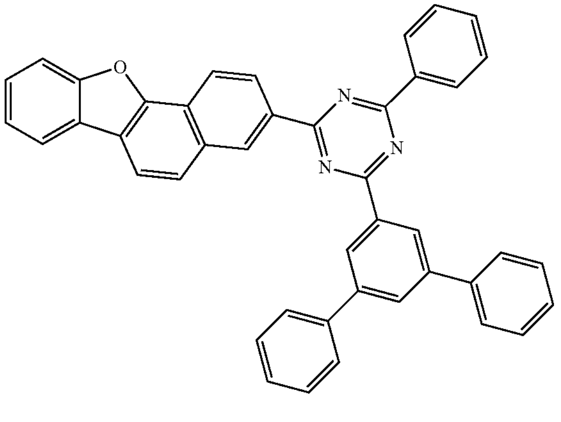

-continued
Inv-079
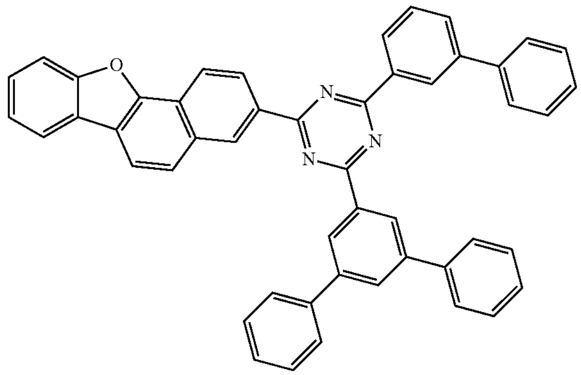
Inv-080
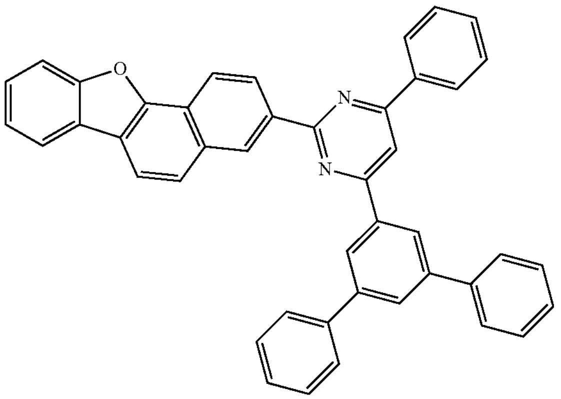
Inv-081
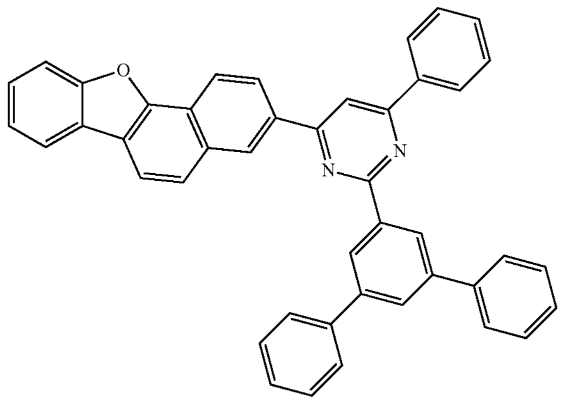
Inv-082
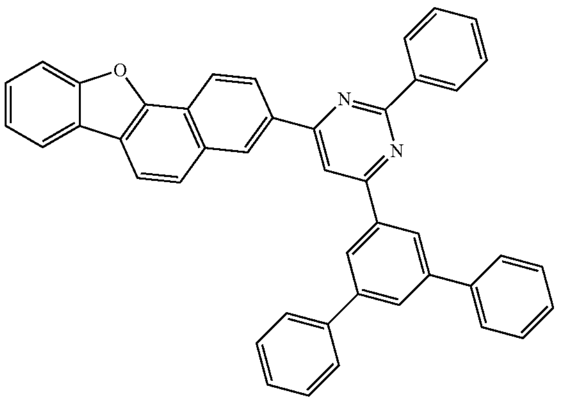
Inv-083
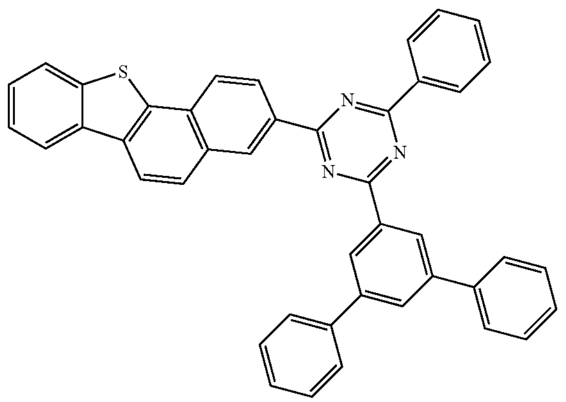
Inv-084
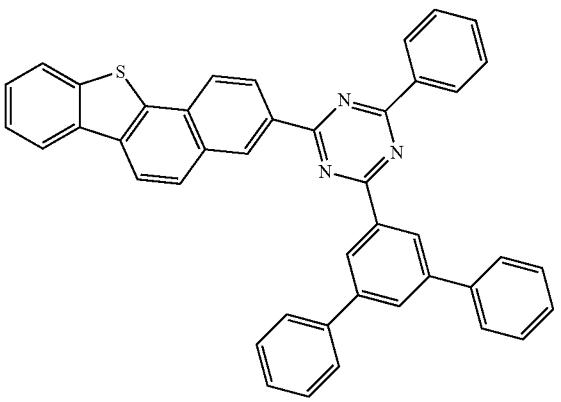
Inv-085
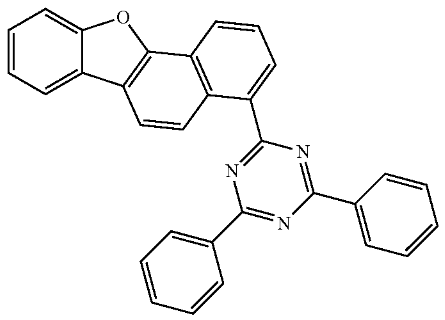
Inv-086
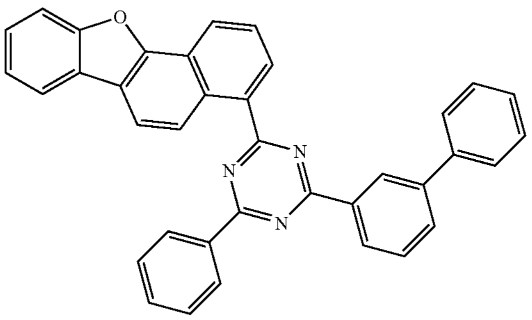

-continued
Inv-087
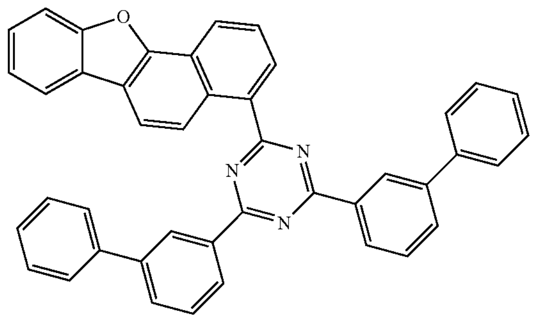
Inv-088
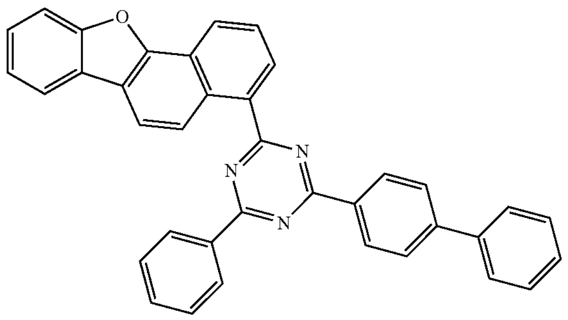
Inv-089
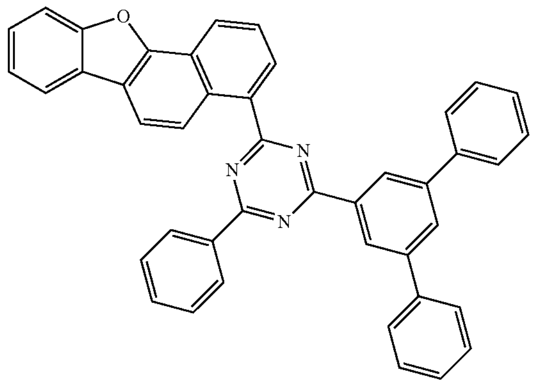
Inv-090
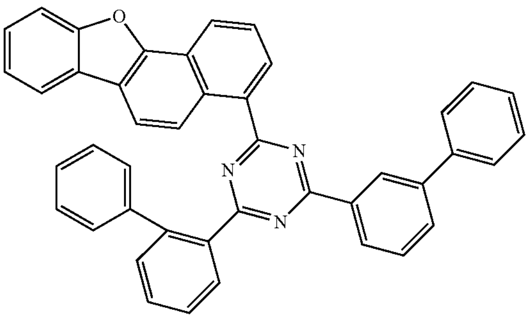
Inv-091
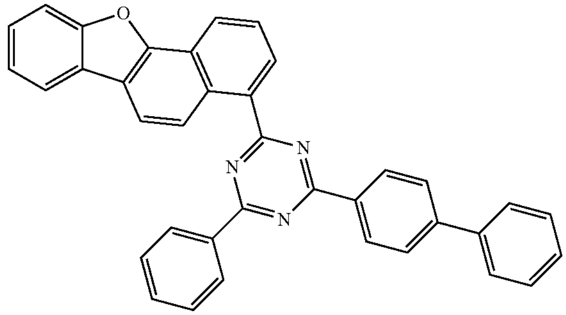
Inv-092
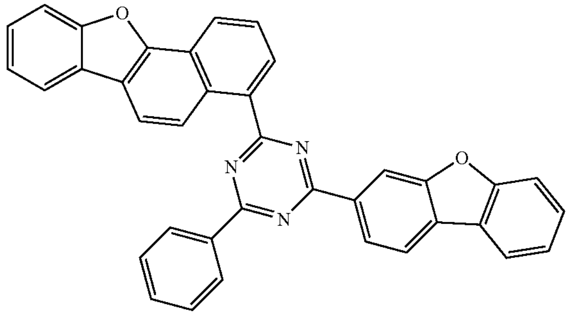
Inv-093
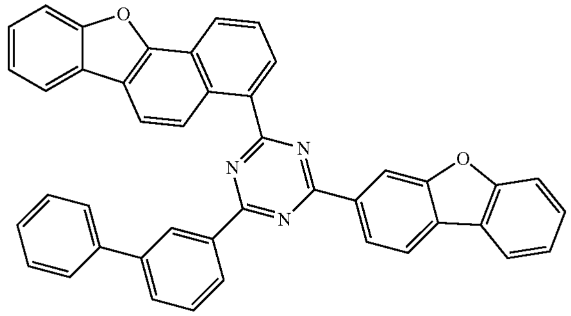
Inv-094
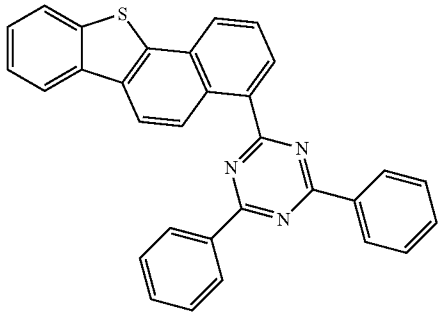

-continued
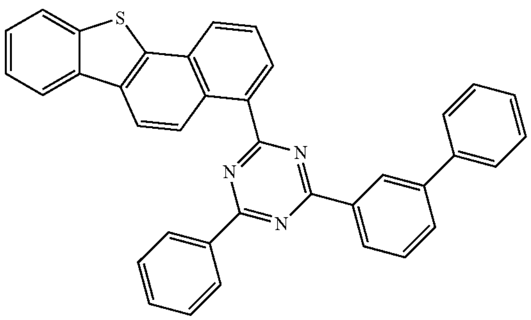
Inv-095
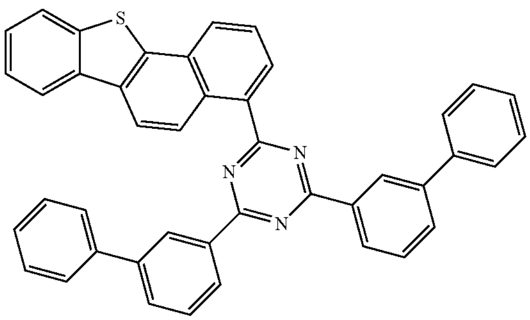
Inv-096
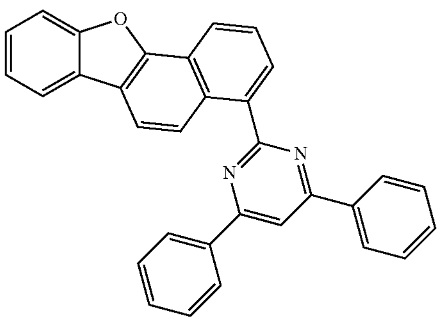
Inv-097
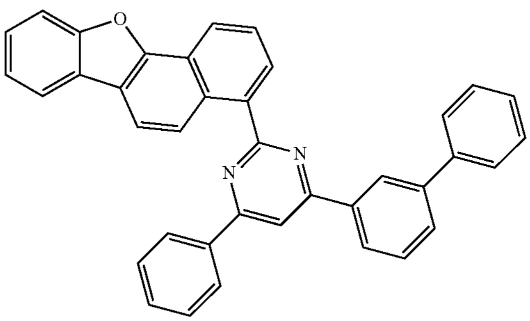
Inv-098
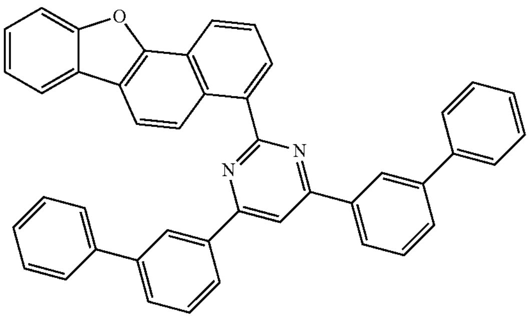
Inv-099
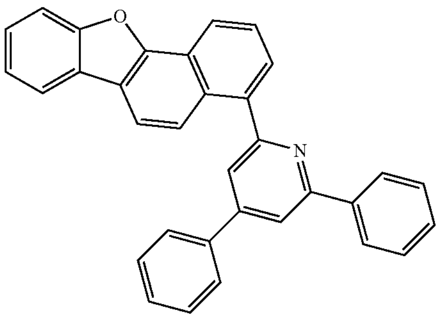
Inv-100
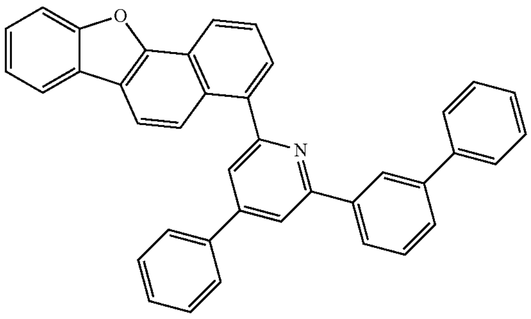
Inv-101
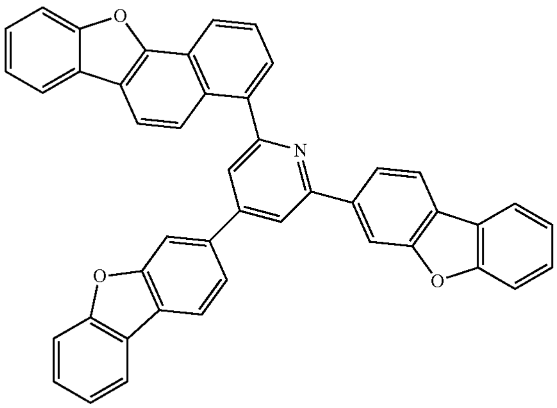
Inv-102

-continued
Inv-103
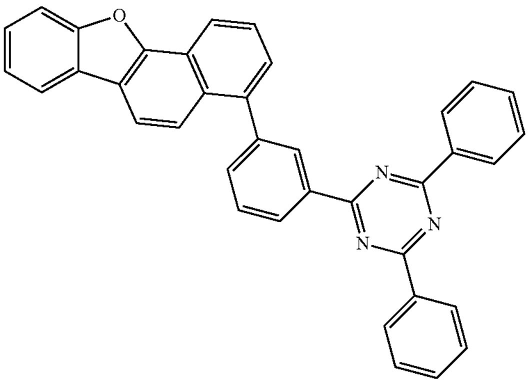
Inv-104
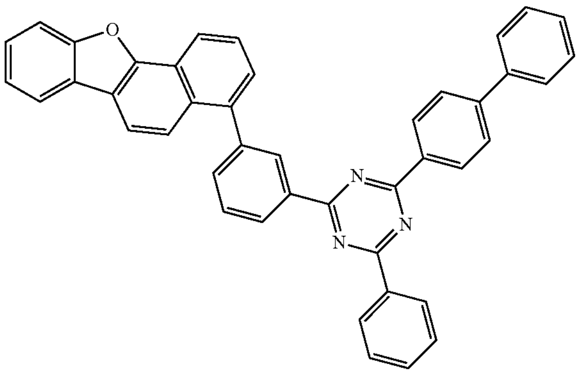
Inv-105
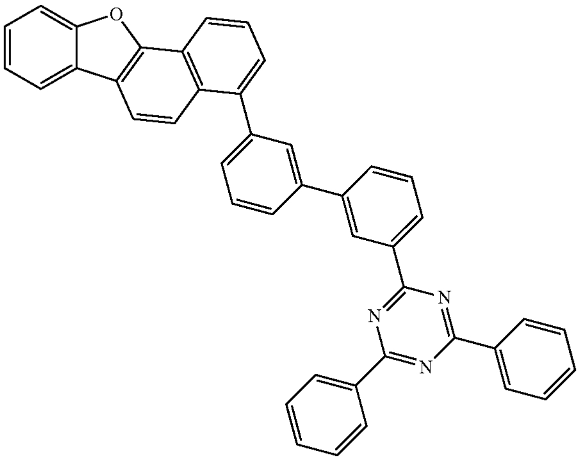
Inv-106
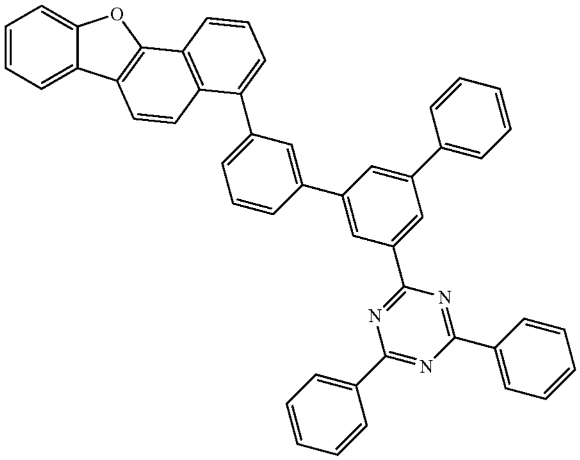
Inv-107
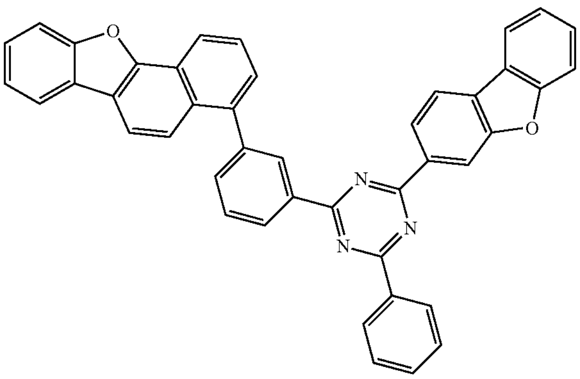
Inv-108
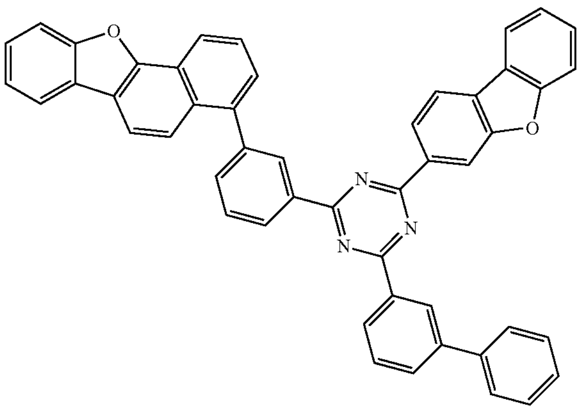

-continued
Inv-109
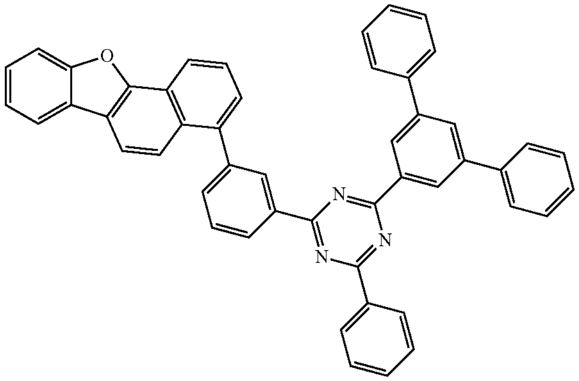
Inv-110
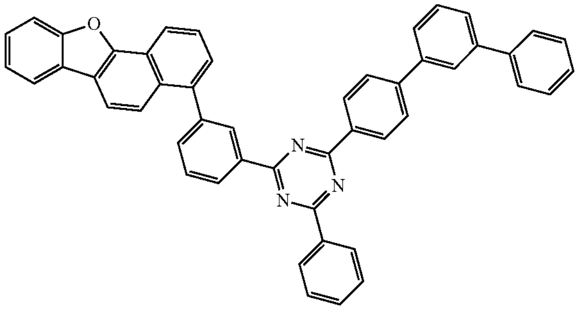
Inv-111
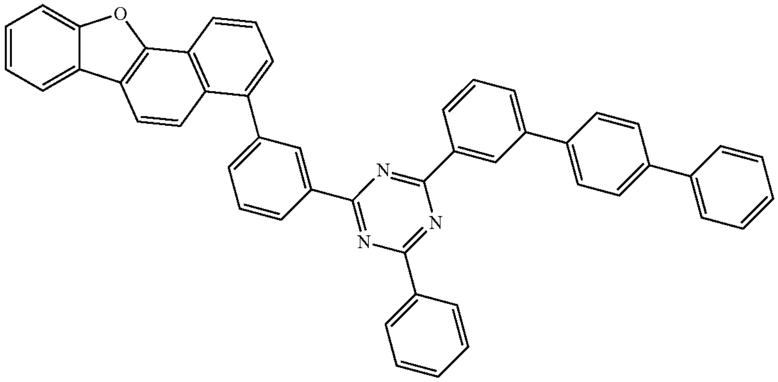
Inv-112
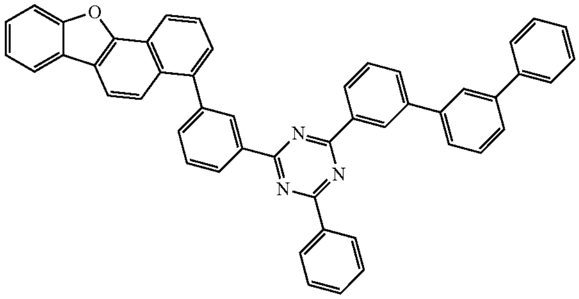
Inv-113
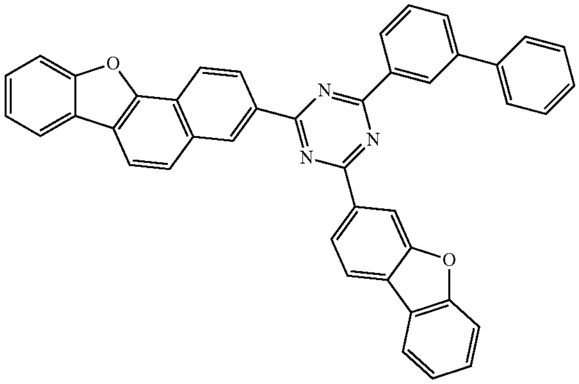
Inv-114
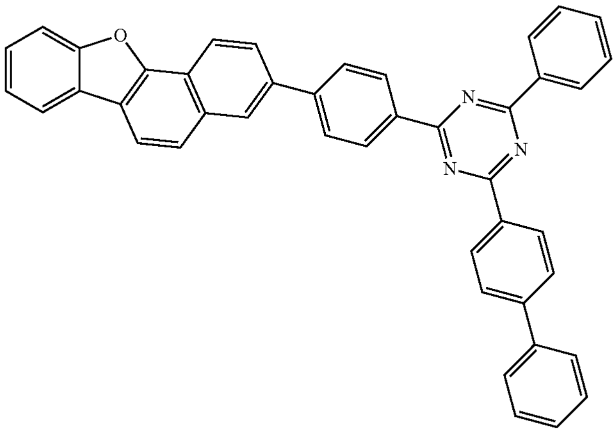

-continued
Inv-115
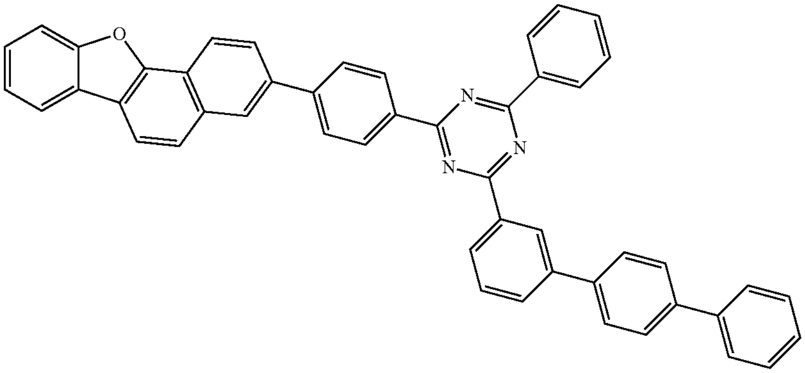
Inv-116
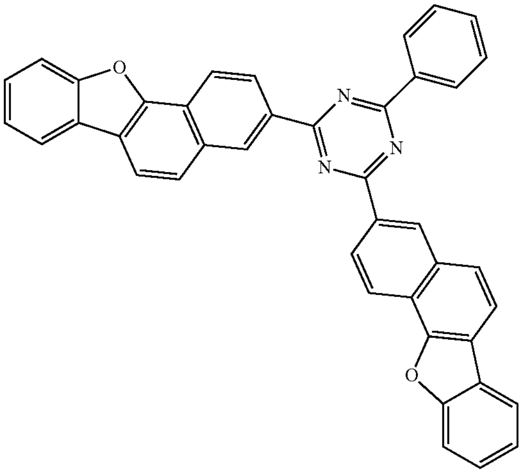
Inv-117
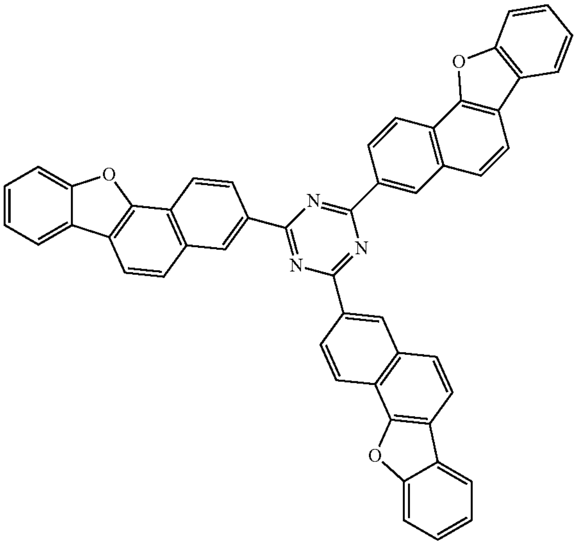
Inv-118
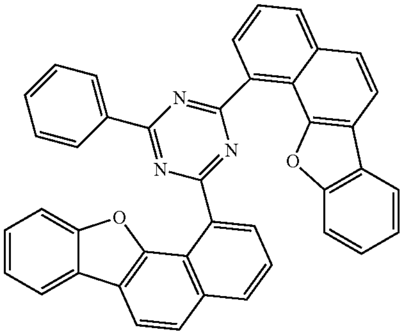
Inv-119
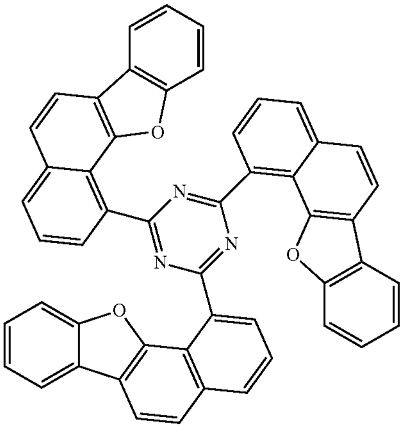

-continued
Inv-120
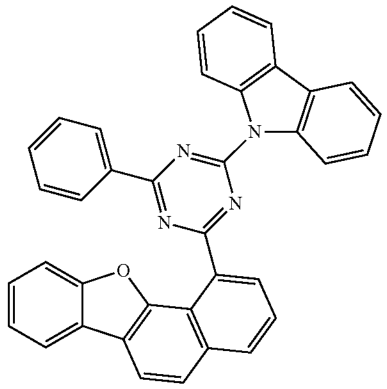
Inv-121
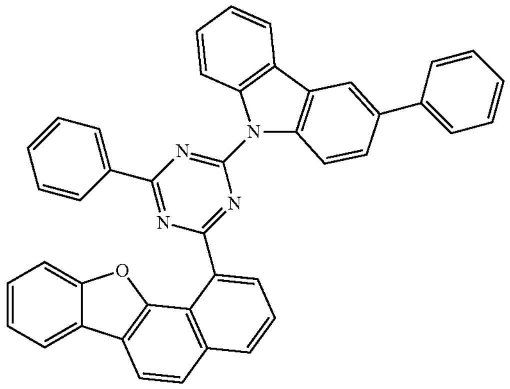
Inv-122
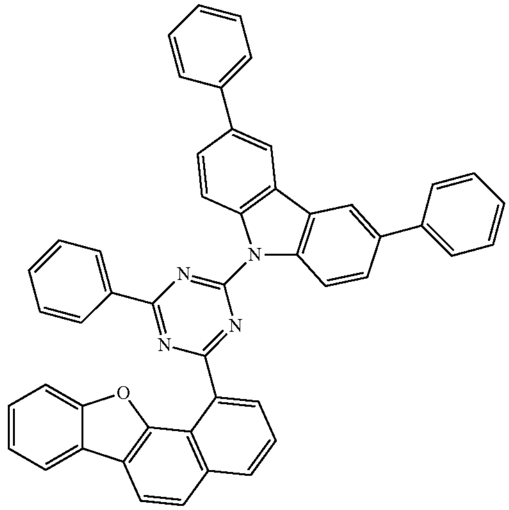
Inv-123
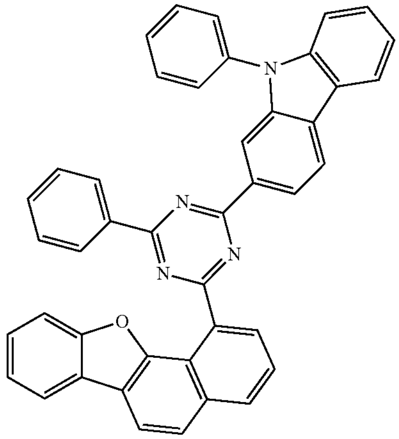
Inv-124
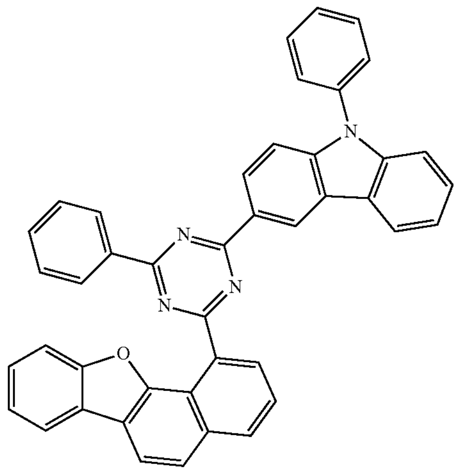
Inv-125
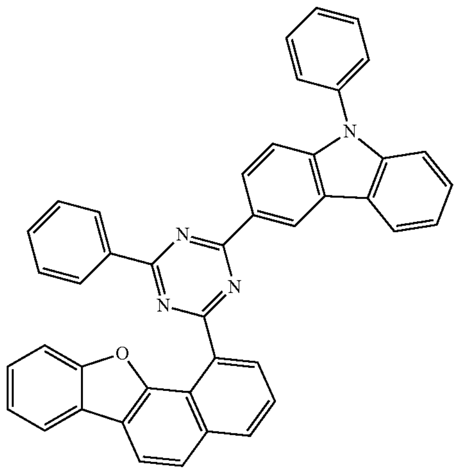

-continued
Inv-126
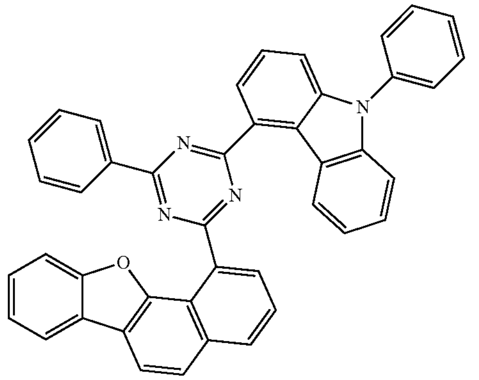
Inv-127
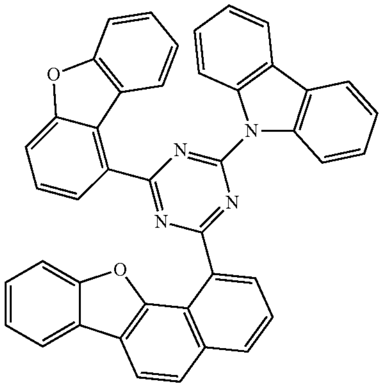
Inv-128
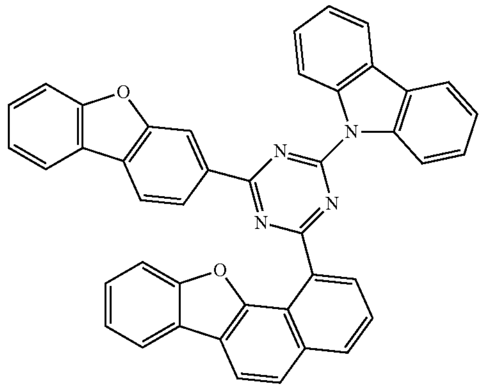
Inv-129
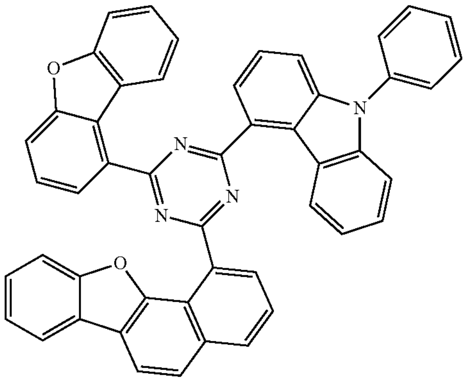
Inv-130
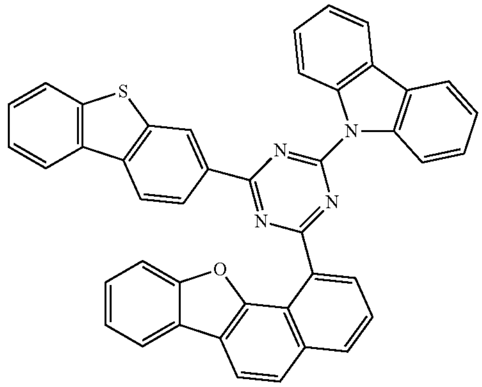
Inv-131
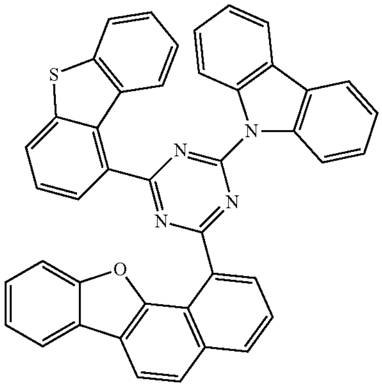
Inv-132
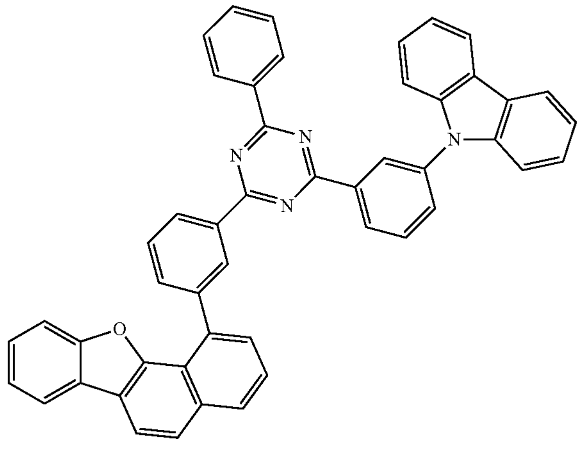
Inv-133
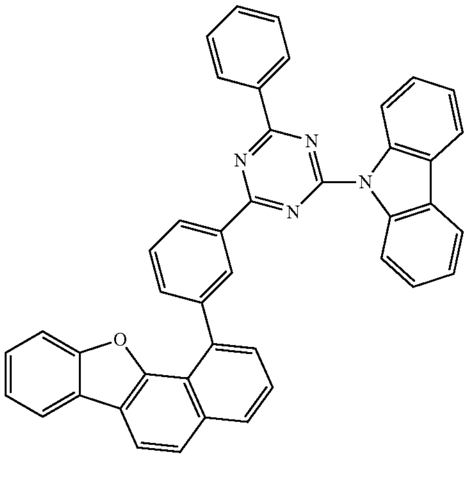

-continued
Inv-134
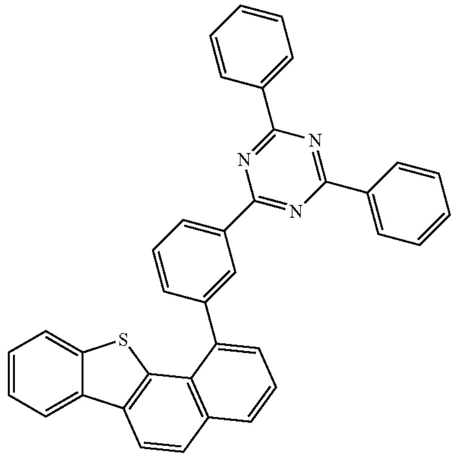
Inv-135
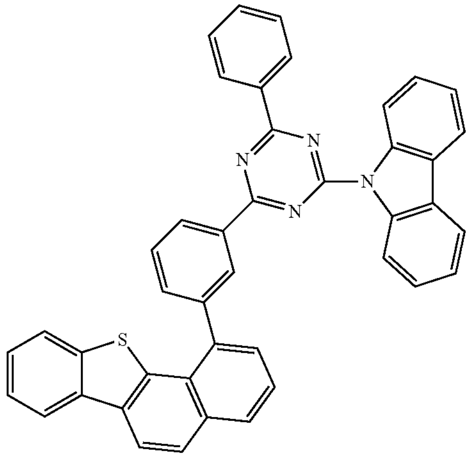
Inv-136
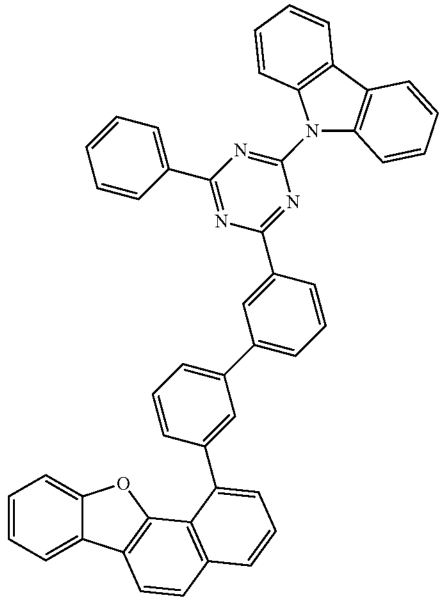
Inv-137
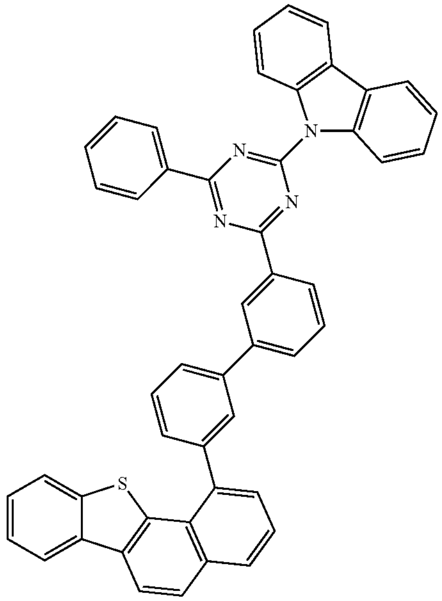
Inv-138
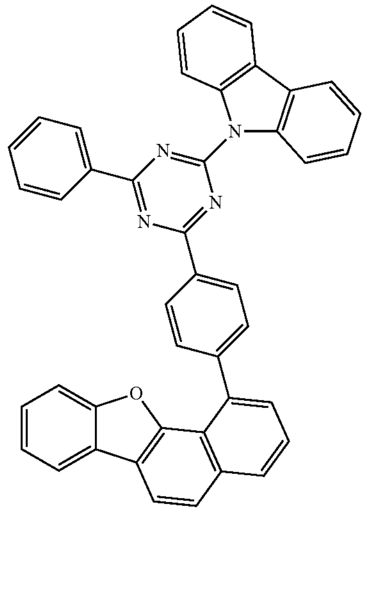
Inv-139
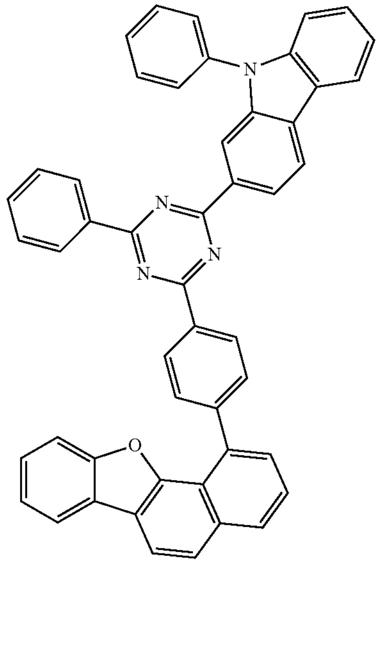

-continued
Inv-140
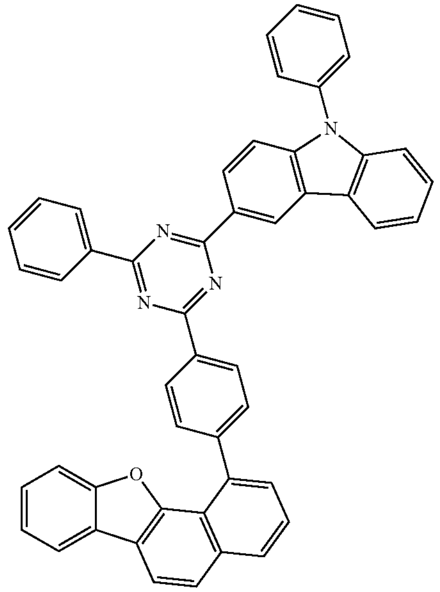
Inv-141
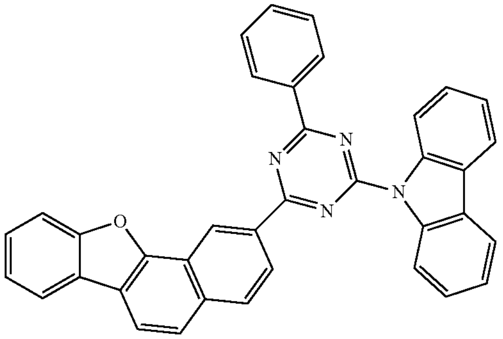
Inv-142
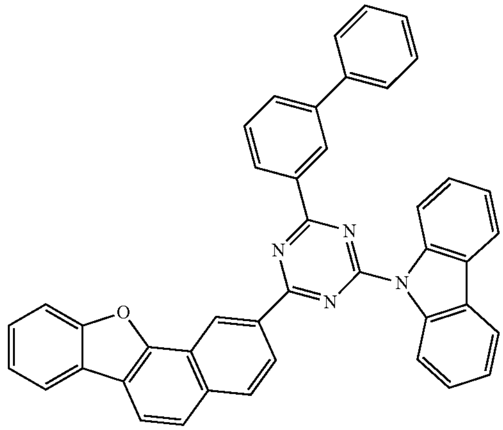
Inv-143
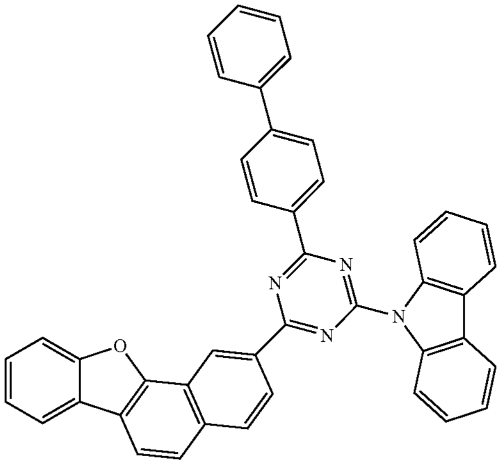
Inv-144
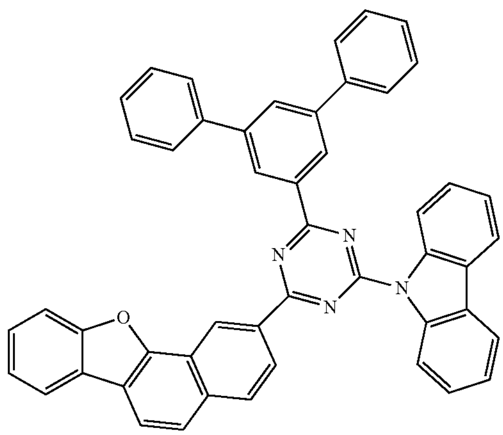
Inv-145
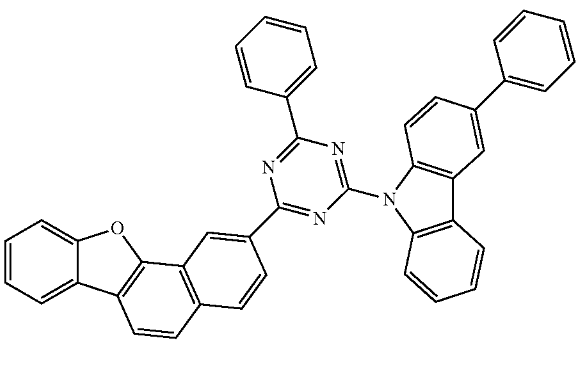

-continued
Inv-146
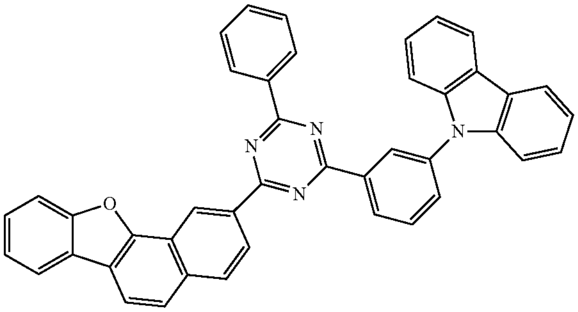
Inv-147
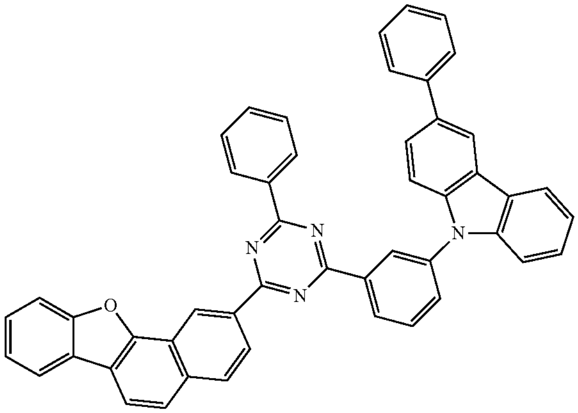
Inv-148
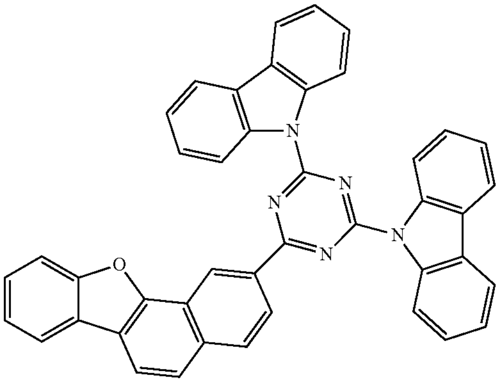
Inv-149
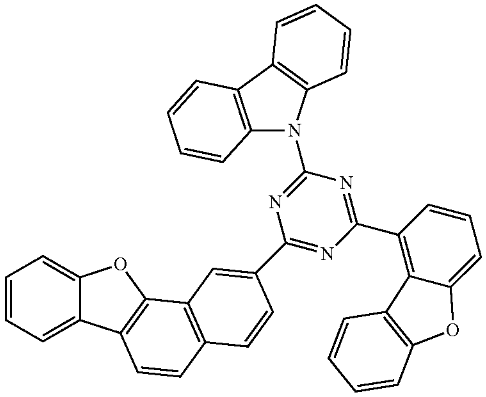
Inv-150
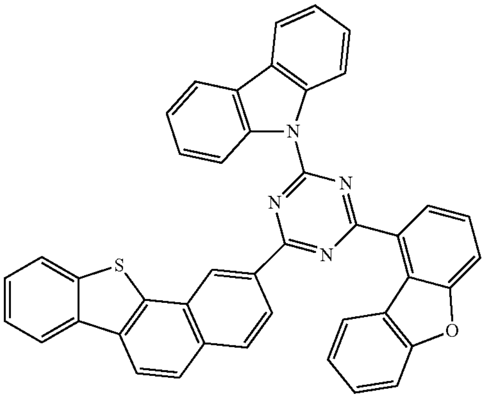
Inv-151
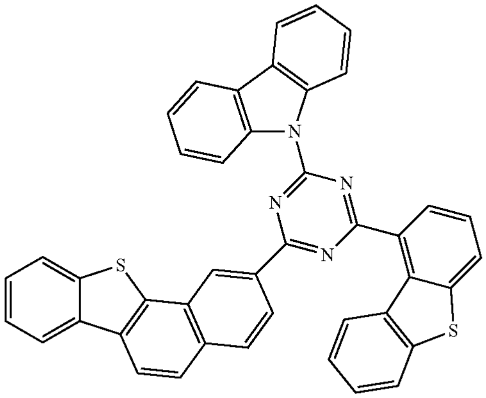

-continued
Inv-152
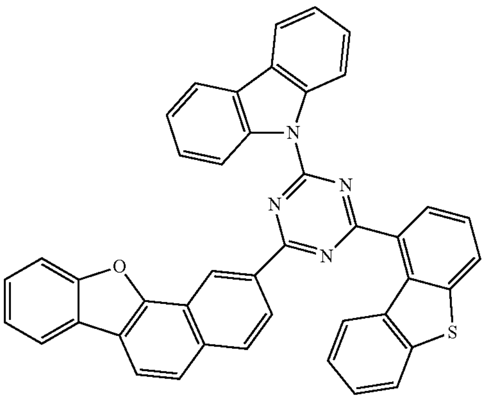
Inv-153
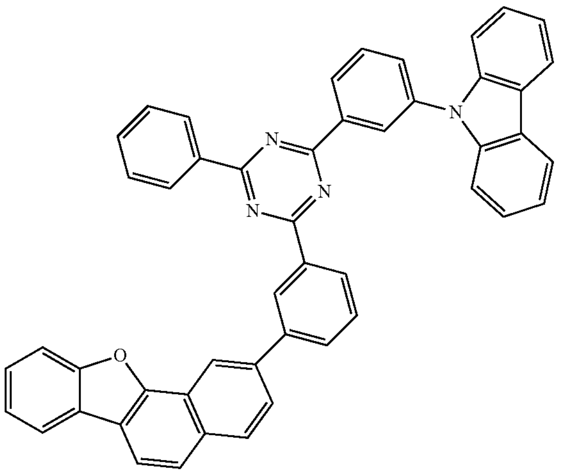
Inv-154
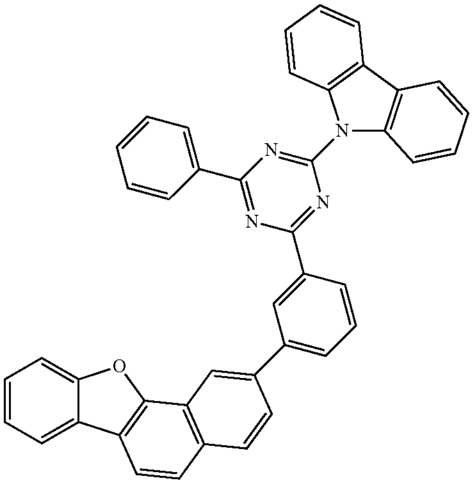
Inv-155
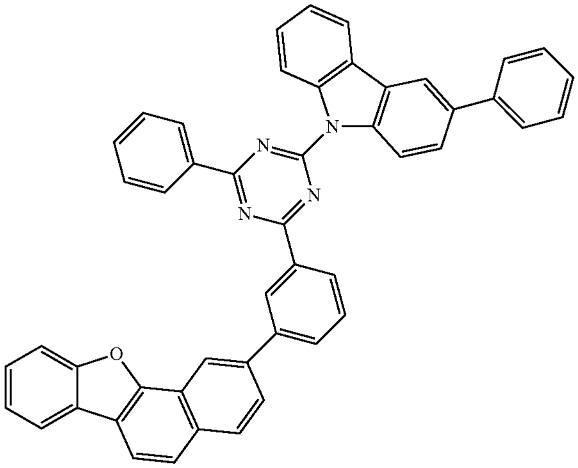
Inv-156
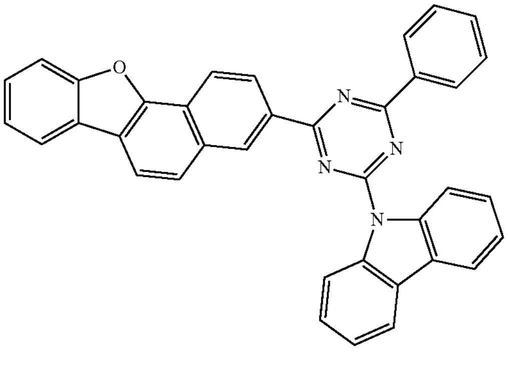
Inv-157
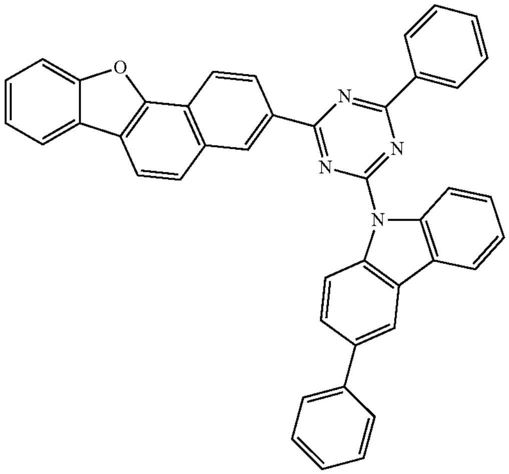

-continued
Inv-158
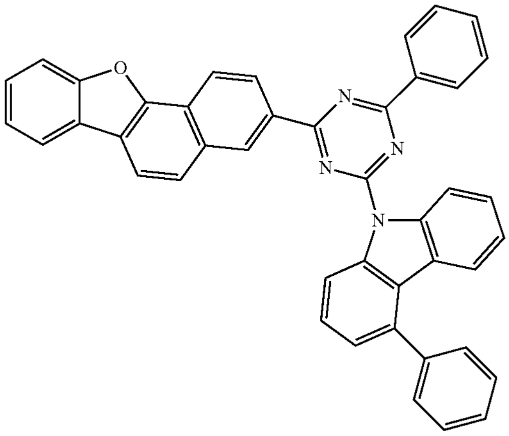
Inv-159
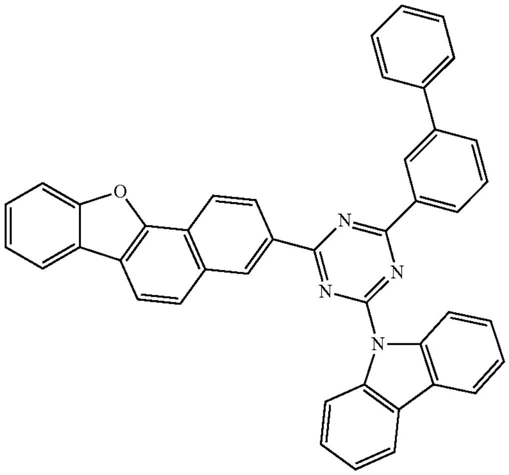
Inv-160
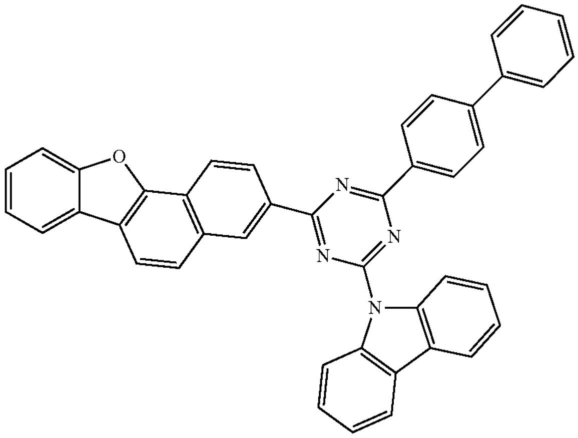
Inv-161
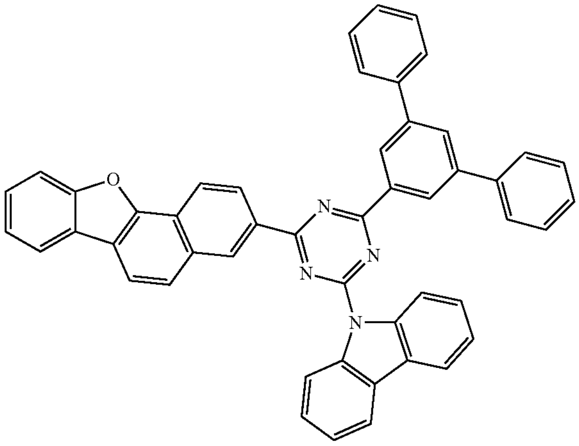
Inv-162
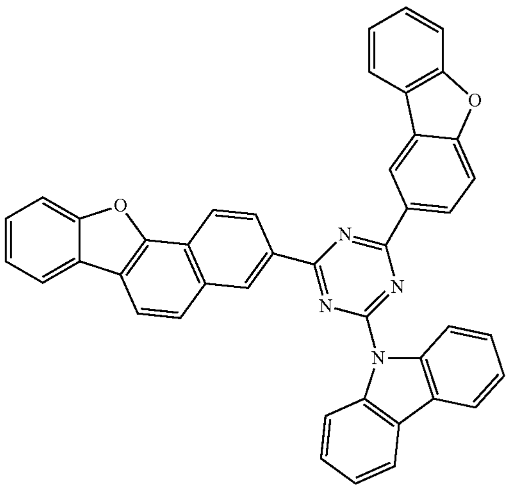
Inv-163
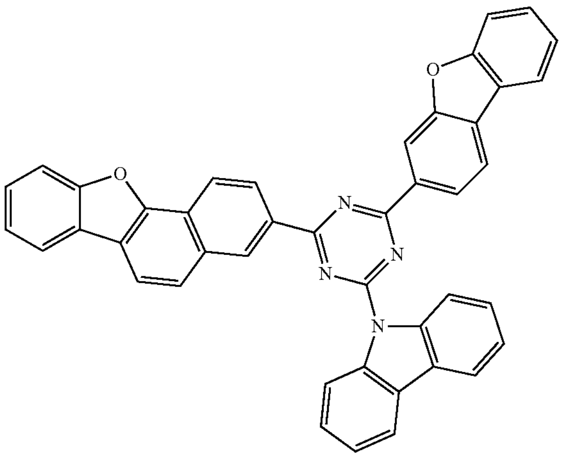

-continued
Inv-164
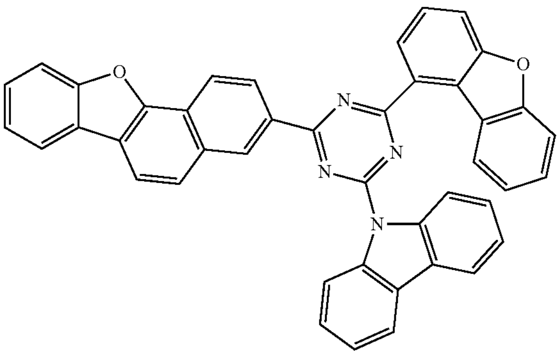
Inv-165
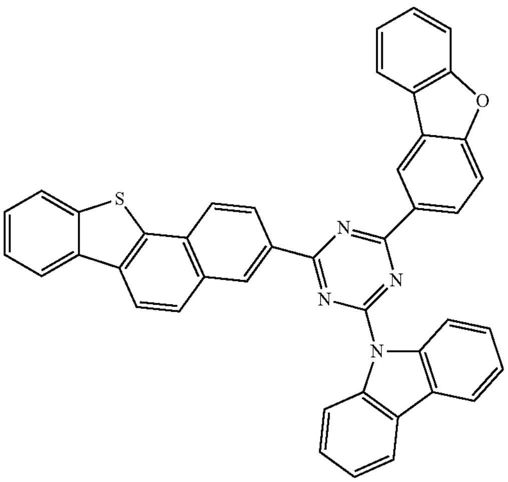
Inv-166
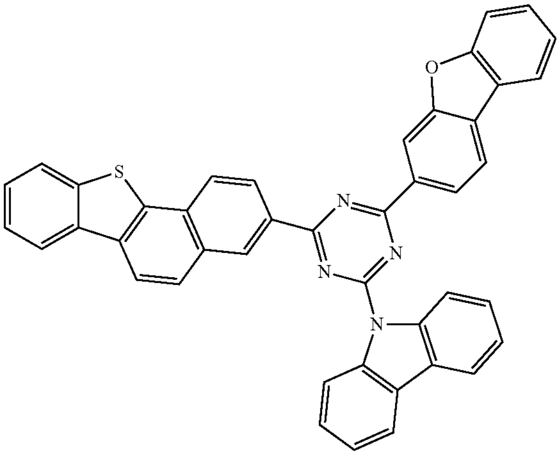
Inv-167
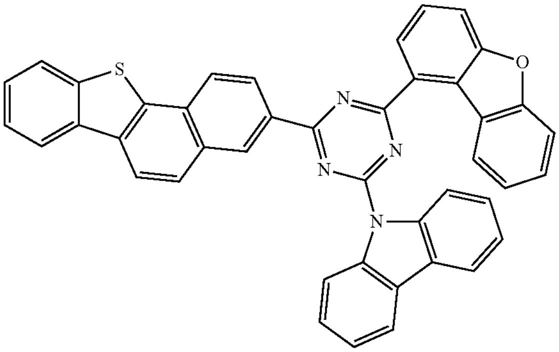
Inv-168
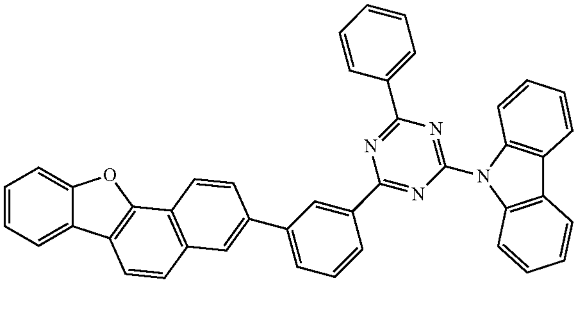
Inv-169
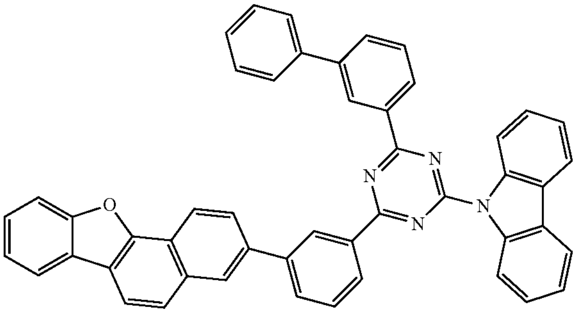

-continued
Inv-170
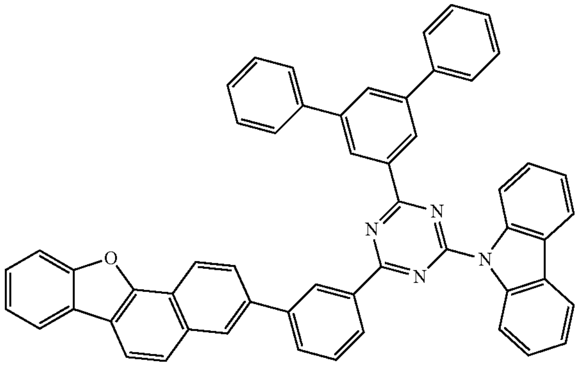
Inv-171
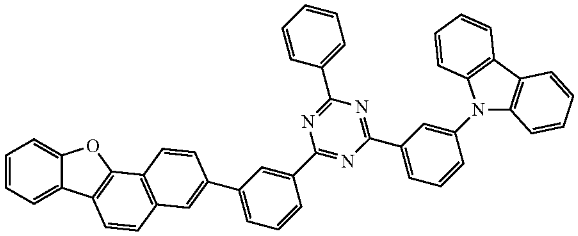
Inv-172
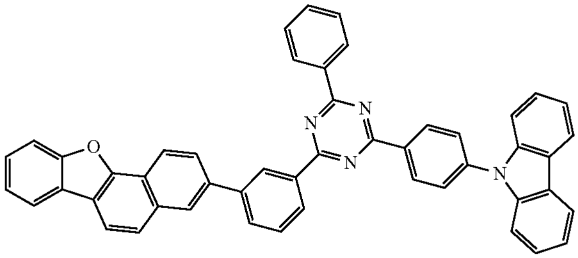
Inv-173
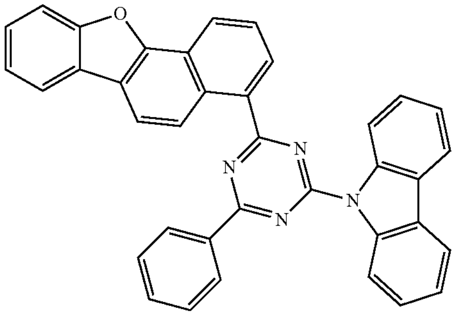
Inv-174
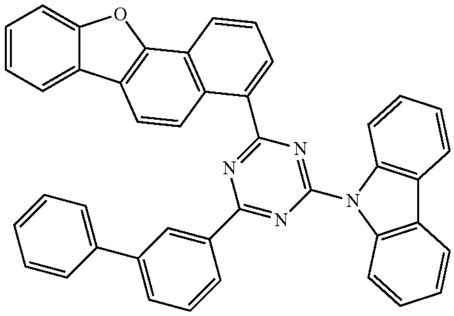
Inv-175
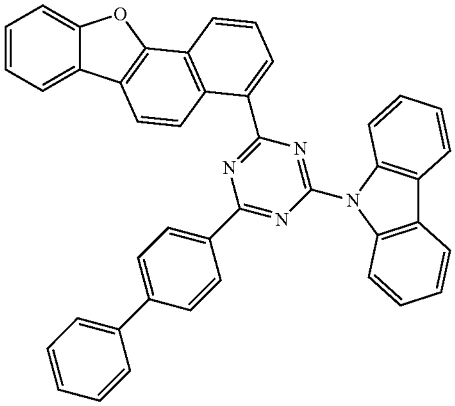
Inv-176
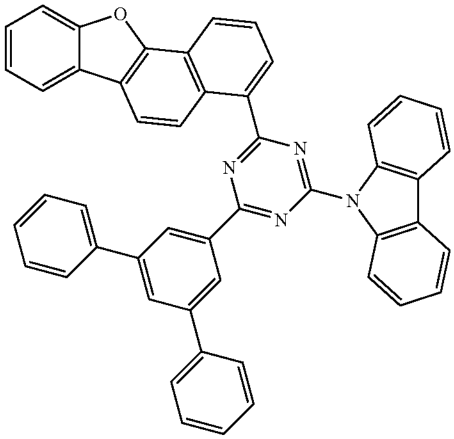
Inv-177
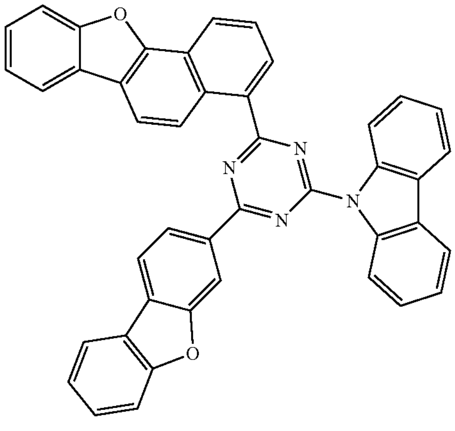

-continued
Inv-178
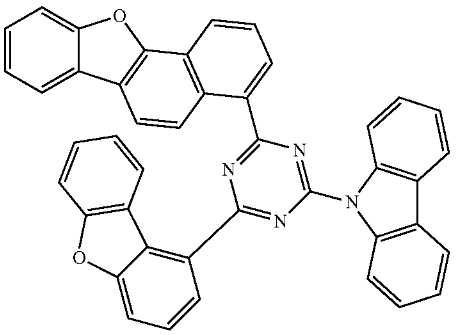
Inv-179
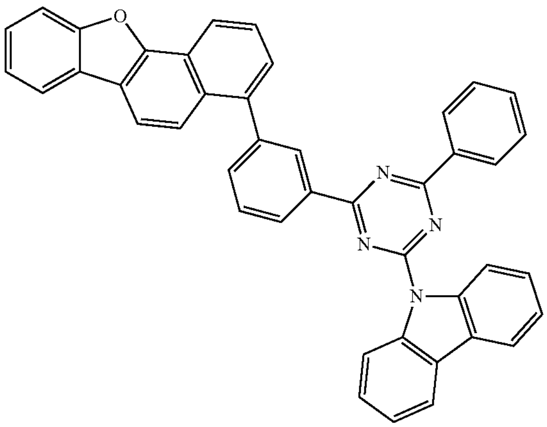
Inv-180
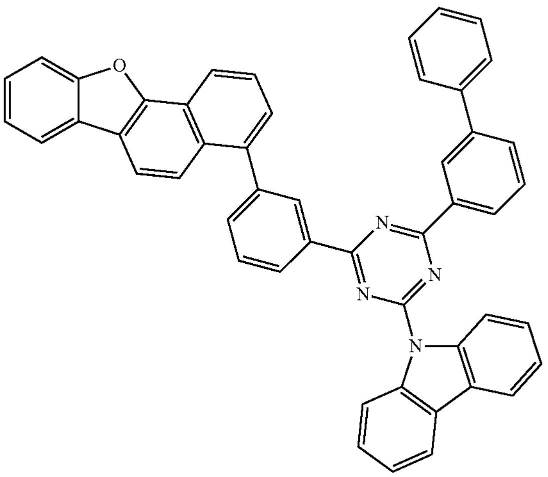
Inv-181
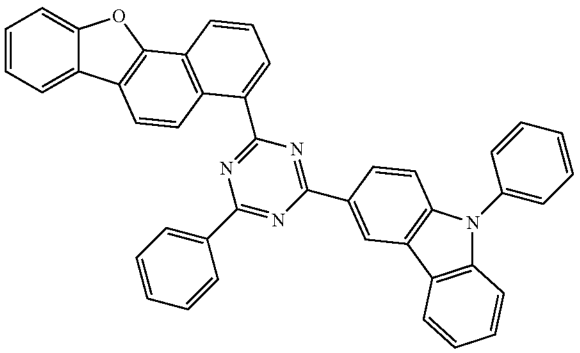
Inv-182
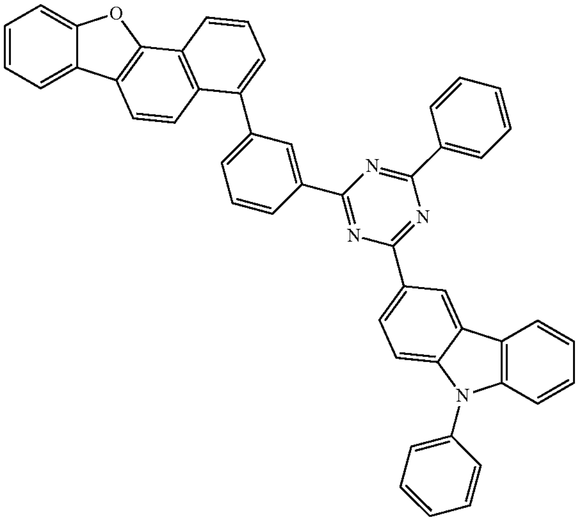
Inv-183
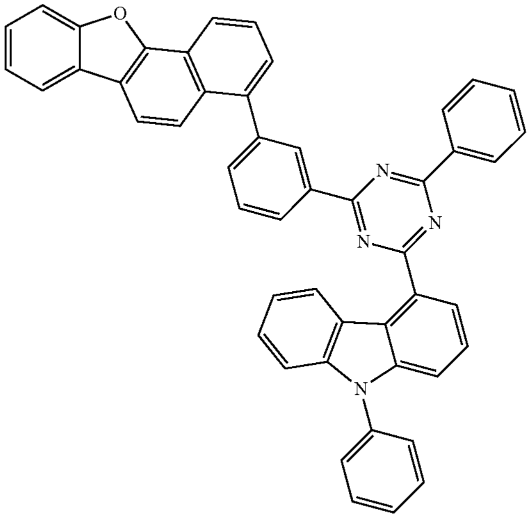

-continued

Inv-184

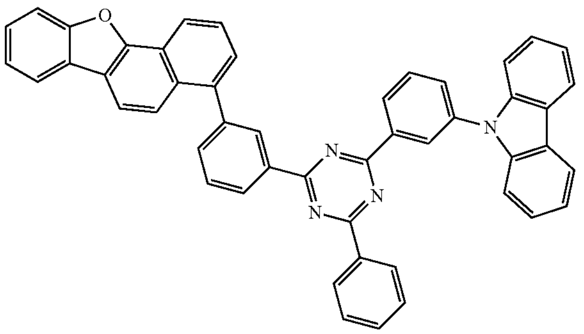

Inv-185

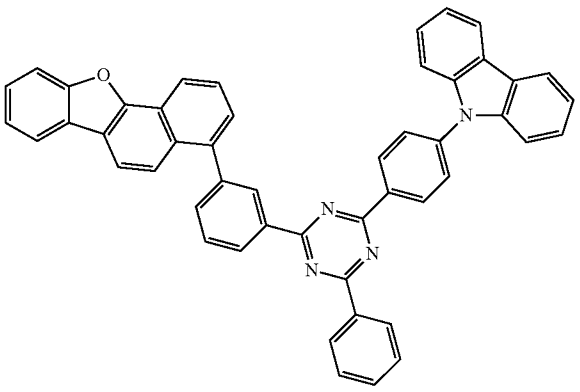

The aforementioned compound for the organic optoelectronic diode may be applied to an organic optoelectronic diode alone or in combination with another compound for an organic optoelectronic diode. When the aforementioned compound for the organic optoelectronic diode is used with other compounds for an organic optoelectronic diode, they may be applied in a form of a composition.

In addition, the present invention provides a composition for an organic optoelectronic diode including the first compound represented by Chemical Formula 1A described above (first compound for an organic optoelectronic diode) and "at least one compound of a compound represented by Chemical Formula 2] and a compound composed of a moiety represented by [Chemical Formula 3] and a moiety represented by [Chemical Formula 4]" as a second compound (second compound for an organic optoelectronic diode).

[Chemical Formula 2]

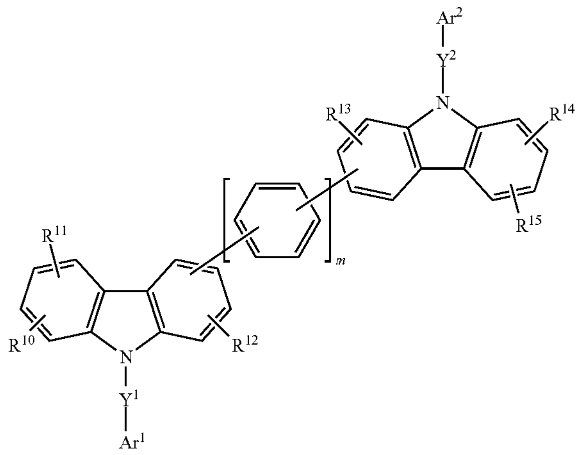

In Chemical Formula 2, $Y^1$ and $Y^2$ are independently a single bond, a substituted or unsubstituted C6 to C30 arylene group, a substituted or unsubstituted C2 to C30 heteroarylene group, or a combination thereof, $Ar^1$ and $Ar^2$ are independently a substituted or unsubstituted C6 to C30 aryl group, a substituted or unsubstituted C2 to C30 heterocyclic group, or a combination thereof, $R^{10}$ to $R^{15}$ are independently hydrogen, deuterium, a substituted or unsubstituted C1 to C20 alkyl group, a substituted or unsubstituted C6 to C30 aryl group, a substituted or unsubstituted C2 to C50 heterocyclic group, or a combination thereof, and m is one of integers of 0 to 2;

[Chemical Formula 3]

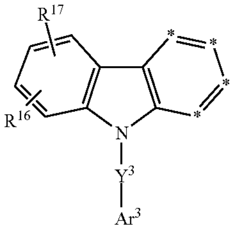

[Chemical Formula 4]

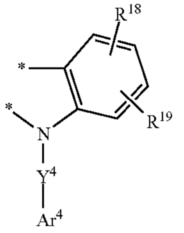

wherein, in Chemical Formulae 3 and 4, $Y^3$ and $Y^4$ are independently a single bond, a substituted or unsubstituted C6 to C30 arylene group, a substituted or unsubstituted C2 to C30 heteroarylene group, or a combination thereof, $Ar^3$ and $Ar^4$ are independently a substituted or unsubstituted C6 to C30 aryl group, a substituted or unsubstituted C2 to C30 heterocyclic group, or a combination thereof, $R^{16}$ to $R^{19}$ are independently hydrogen, deuterium, a substituted or unsubstituted C1 to C20 alkyl group, a substituted or unsubstituted C6 to C50 aryl group, a substituted or unsubstituted C2 to C50 heterocyclic group, or a combination thereof, adjacent two *'s of Chemical Formula 3 are linked with two *'s of Chemical Formula 4 to form a fused ring and *'s which do not form a fused ring in Chemical Formula 3 are independently $CR^a$, and R' is hydrogen, deuterium, a substituted or unsubstituted C1 to C10 alkyl group, a substituted or unsubstituted C6 to C12 aryl group, a substituted or unsubstituted C2 to C12 heterocyclic group, or a combination thereof;

wherein the "substituted" refers to replacement of at least one hydrogen by deuterium, a C1 to C4 alkyl group, a C6 to C18 aryl group, or a C2 to C18 heteroaryl group.

In an embodiment of the present invention, $Y^1$ and $Y^2$ of Chemical Formula 2 may independently be a single bond, or a substituted or unsubstituted C6 to C18 arylene group.

In an embodiment of the present invention, $Ar^1$ and $Ar^2$ of Chemical Formula 2 may independently be a substituted or unsubstituted phenyl group, a substituted or unsubstituted biphenyl group, a substituted or unsubstituted terphenyl group, a substituted or unsubstituted naphthyl group, a substituted or unsubstituted anthracenyl group, a substituted or unsubstituted triphenylenyl group, a substituted or unsubstituted pyridinyl group, a substituted or unsubstituted pyrimidinyl group, a substituted or unsubstituted quinazolyl group, a substituted or unsubstituted isoquinazolyl group, a substituted or unsubstituted dibenzothiophenyl group, a substituted or unsubstituted dibenzofuranyl group, a substituted or unsubstituted carbazolyl group, a substituted or unsubstituted fluorenyl group, or a combination thereof.

In an embodiment of the present invention, $R^{10}$ to $R^{15}$ of Chemical Formula 2 may independently be hydrogen, deuterium, or a substituted or unsubstituted C6 to C12 aryl group.

In an embodiment of the present invention, m of Chemical Formula 2 may be 0 or 1.

In a specific embodiment of the present invention, Chemical Formula 2 may be one of the structures of Group III, and $*-Y^1-Ar^1$ and $*-Y^2-Ar^2$ may be one of the substituents of Group IV.

[Group III]

C-1

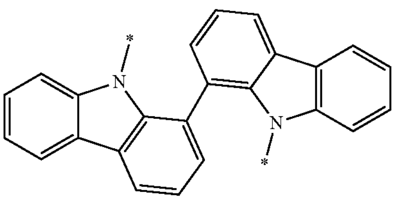

C-2

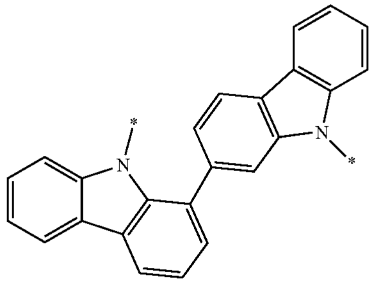

-continued

C-3

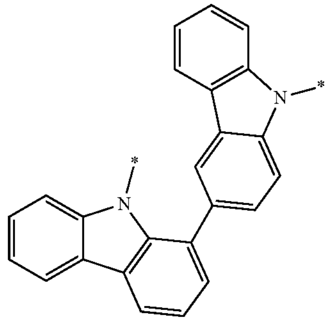

C-4

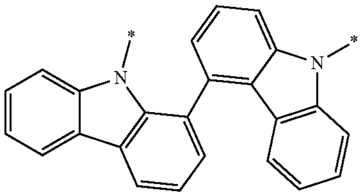

C-5

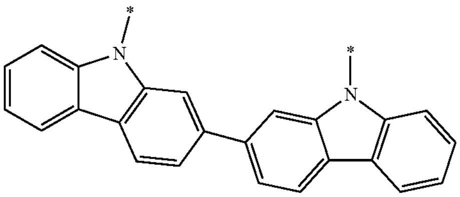

C-6

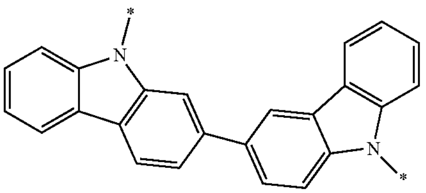

C-7

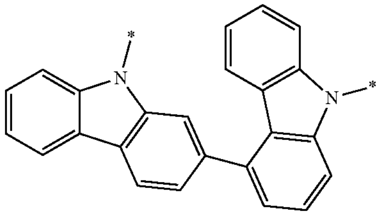

C-8

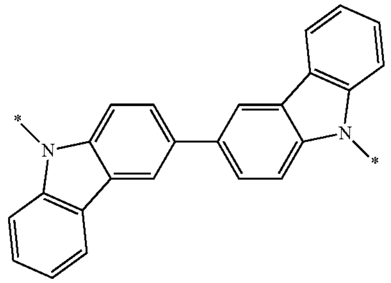

-continued
C-9
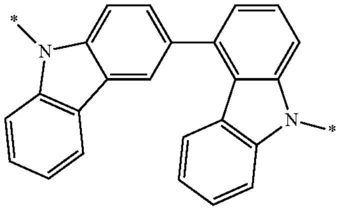
C-10
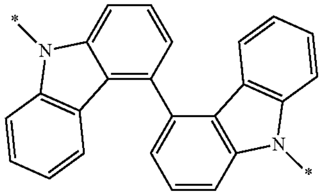
C-11
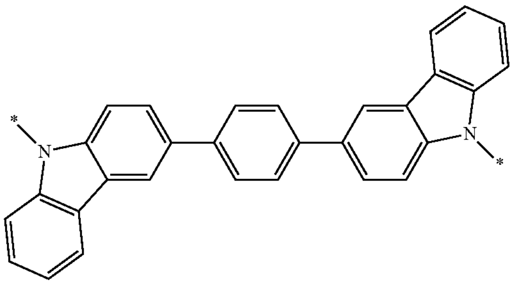
C-12
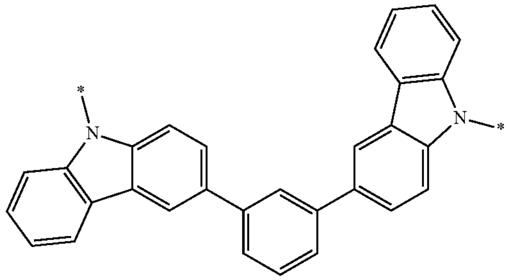
C-13
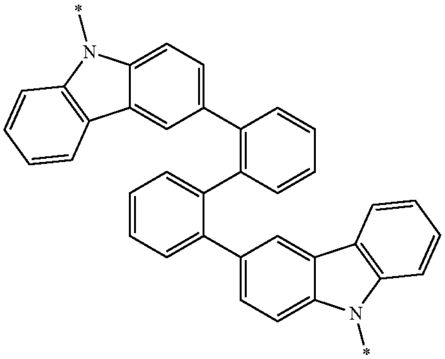
-continued
C-14
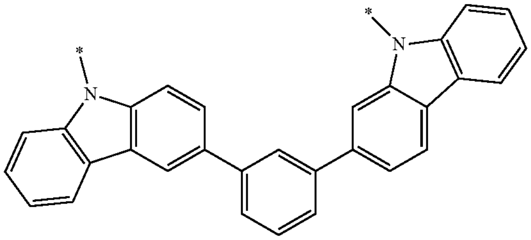
C-15
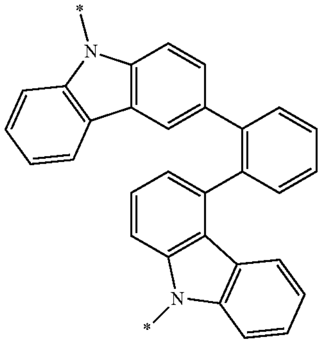
C-16
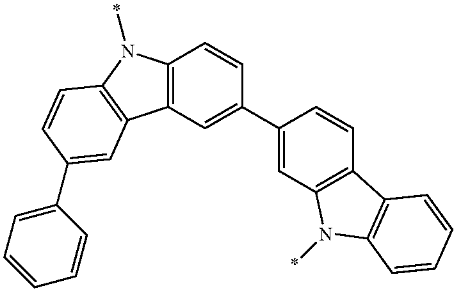
C-17
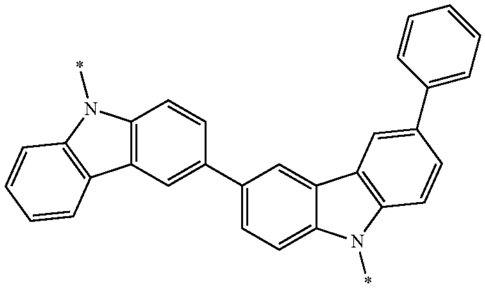
C-18
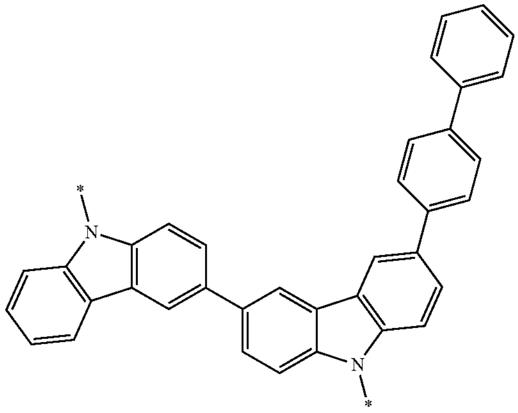

[Group IV]
B-1
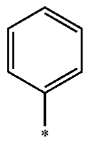
B-2
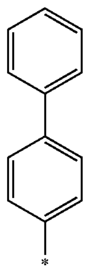
B-3
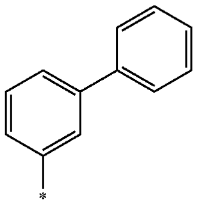
B-4
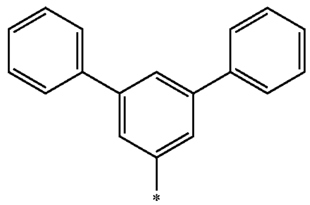
B-5
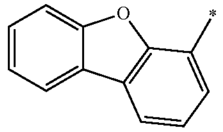
B-6
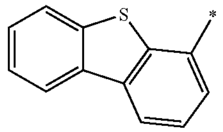
B-7
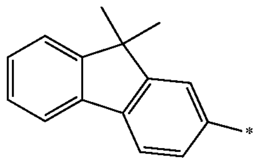
B-8
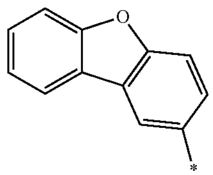
B-9
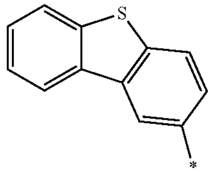
B-10
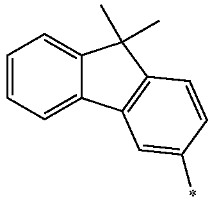
B-11
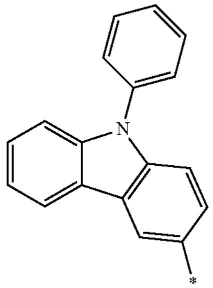
B-12
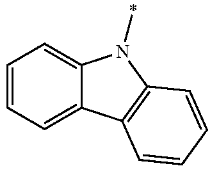
B-13
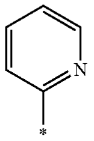
B-14
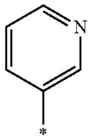
B-15
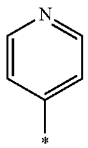
B-16
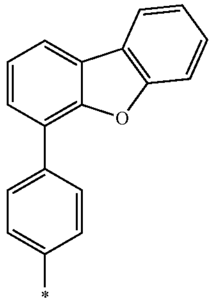

-continued

B-17

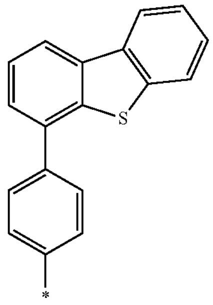

B-18

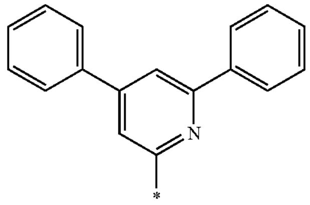

B-19

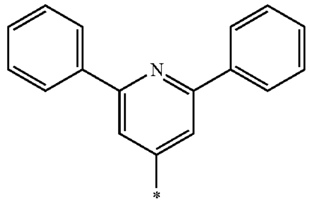

B-20

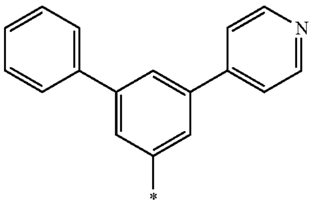

B-21

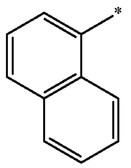

B-22

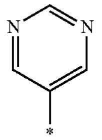

B-23

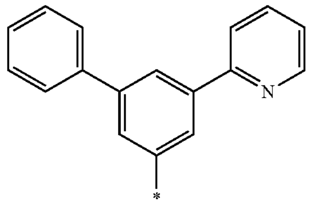

-continued

B-24

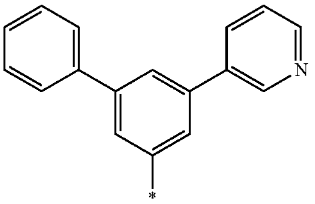

B_25

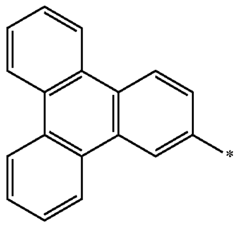

B-26

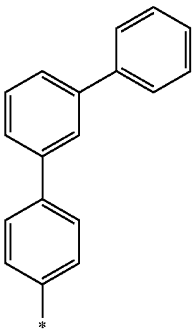

B-27

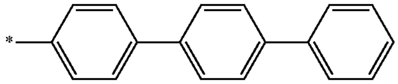

B-28

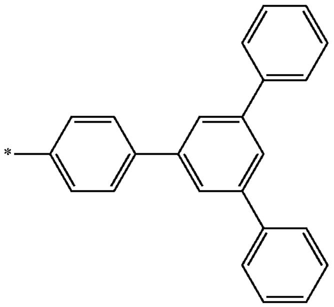

In Group III and Group IV, * is a linking point.

Specifically, Chemical Formula 2 may be represented by C-8 of Group III, and *—$Y^1$—$Ar^1$ and *—$Y^2$—$Ar^2$ may be represented by one of B-1 to B-4 of Group IV.

More specifically, *—$Y^1$—$Ar^1$ and *—$Y^2$—$Ar^2$ may be selected from B-2, B-3, and a combination of Group IV.

The second compound for the organic optoelectronic diode, represented by Chemical Formula 2, may be compounds of Group 2, but is not limited thereto.

[Group 2]
[B-1]
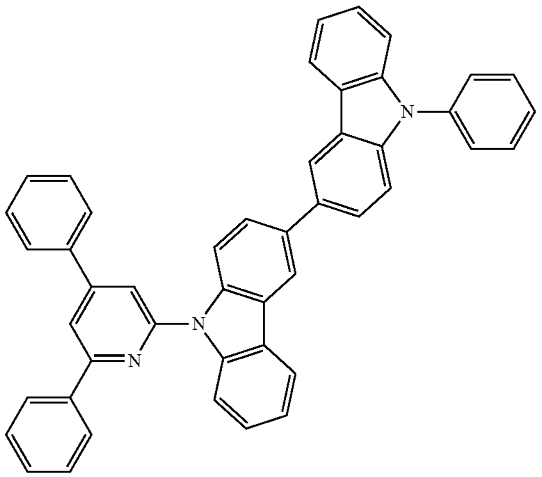
[B-2]
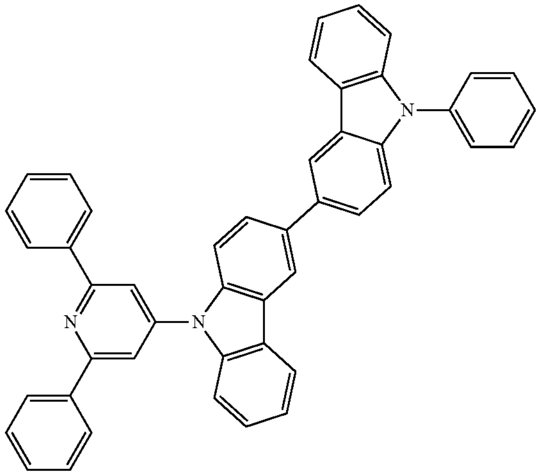
[B-3]
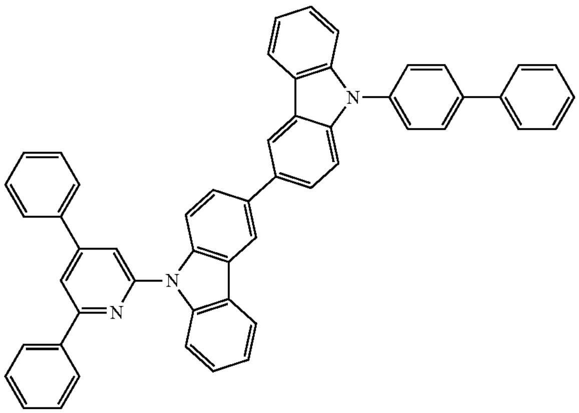
-continued
[B-4]
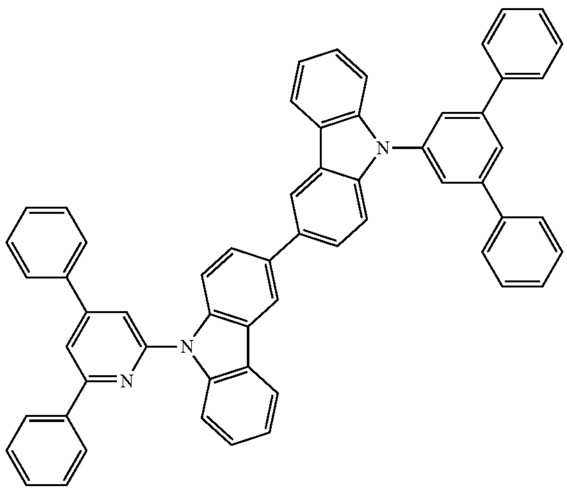
[B-5]
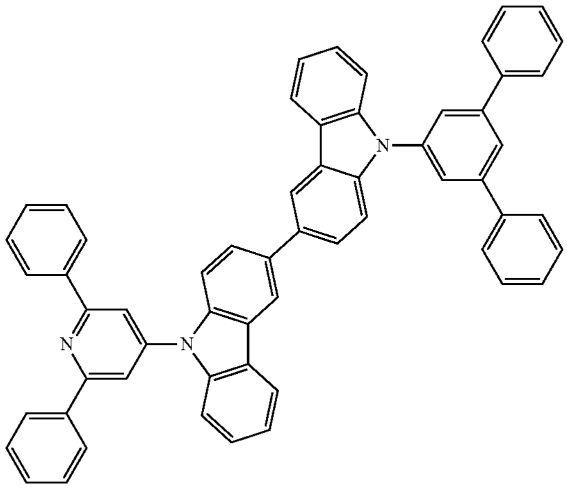
[B-6]
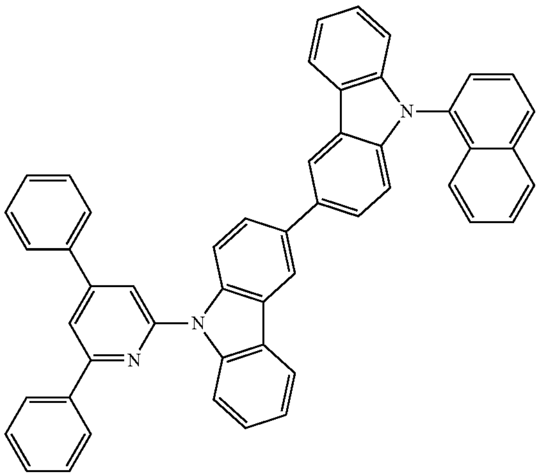

-continued
[B-7]
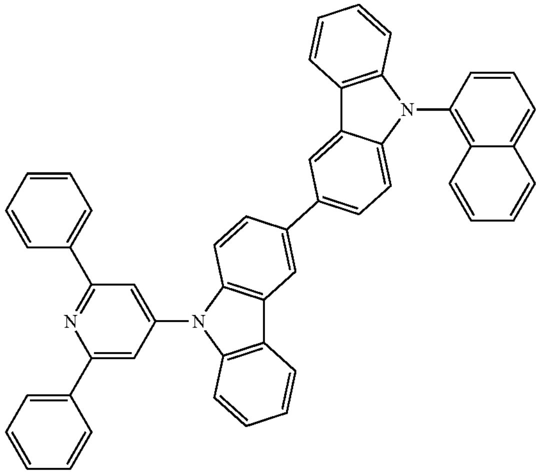
[B-8]
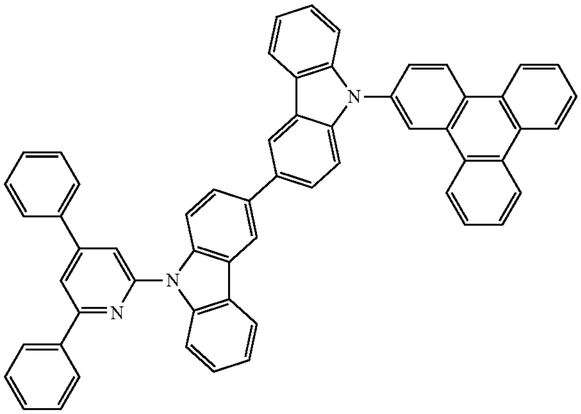
[B-9]
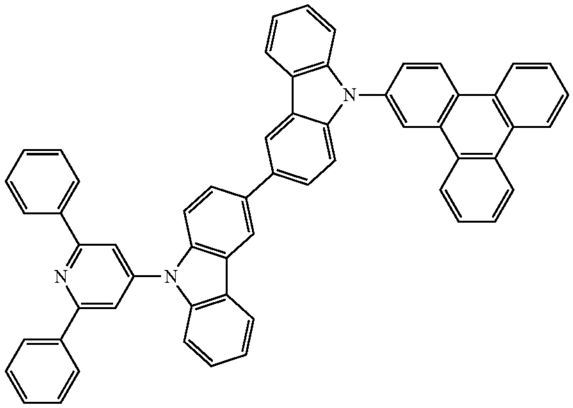
-continued
[B-10]
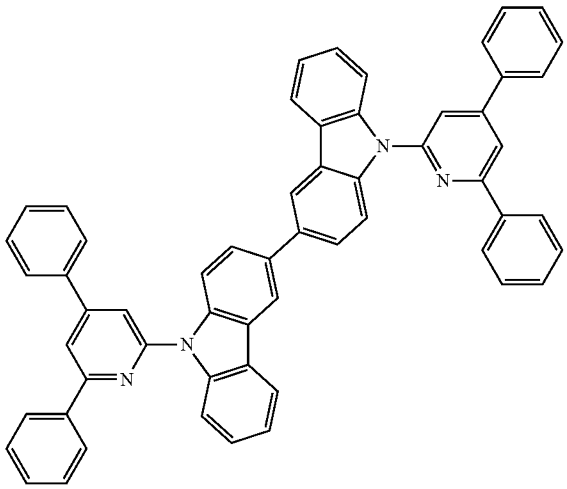
[B-11]
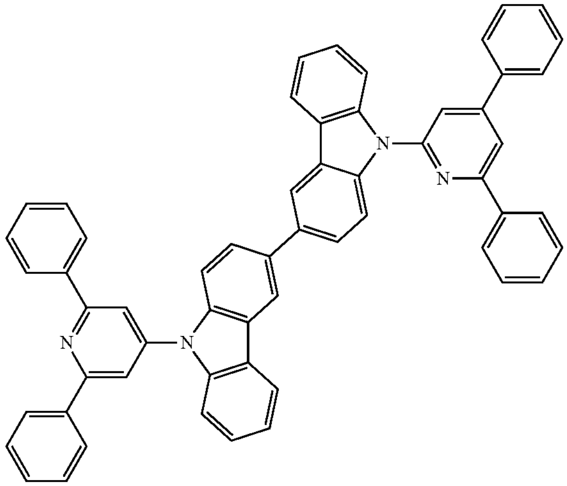
[B-12]
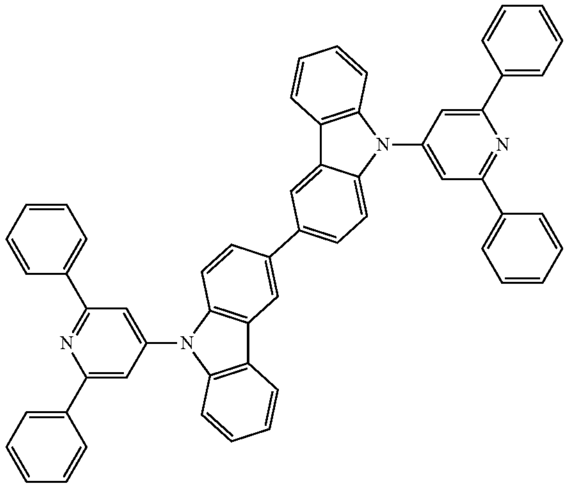

-continued
[B-13]
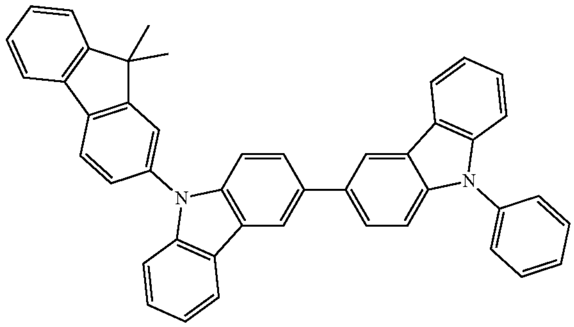
[B-14]
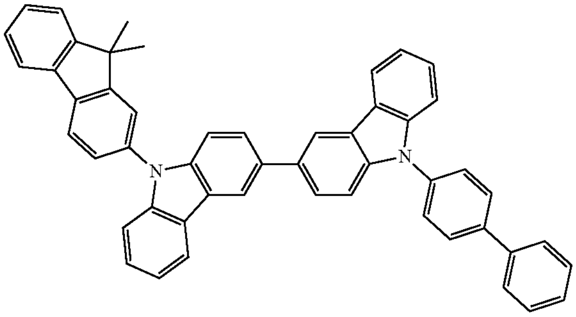
[B-15]
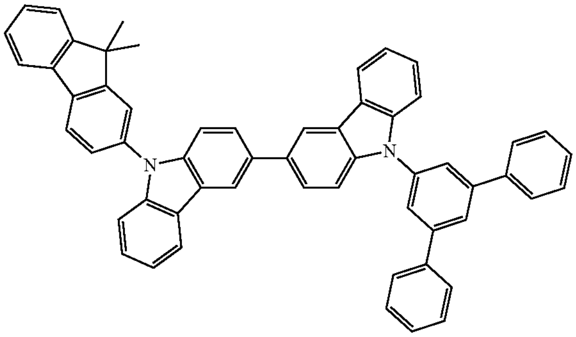
[B-16]
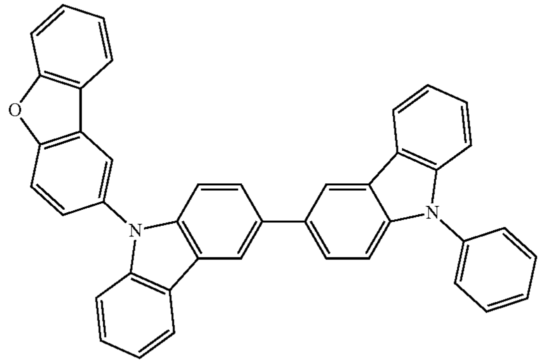
-continued
[B-17]
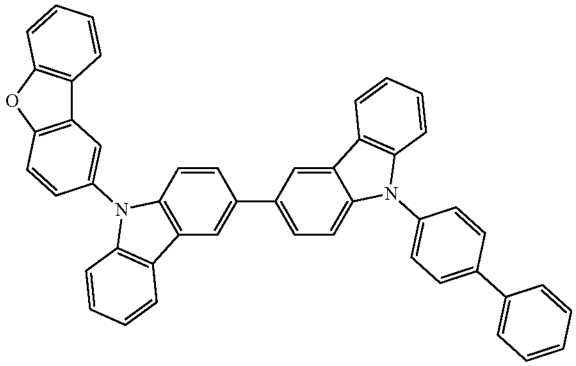
[B-18]
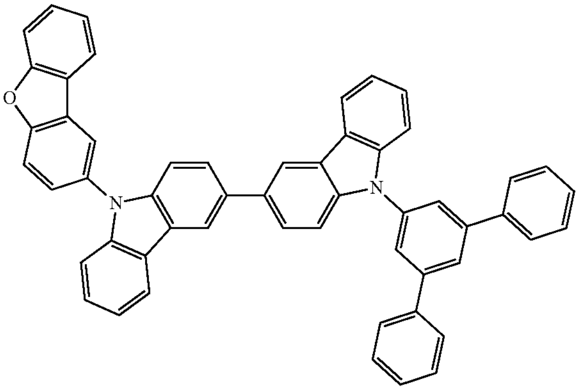
[B-19]
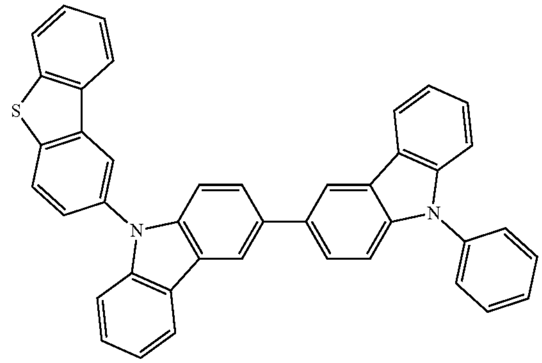
[B-20]
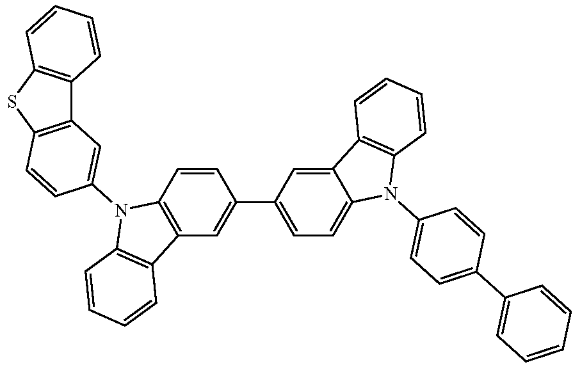

-continued
[B-21]
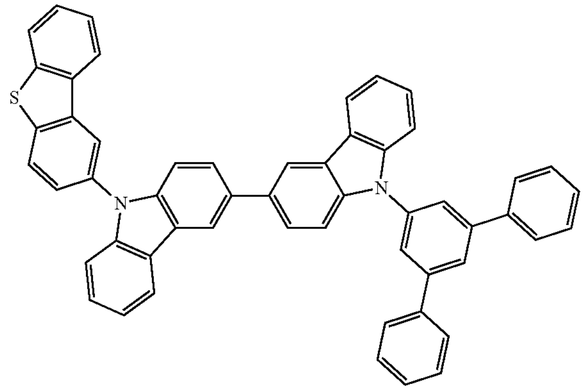
[B-22]
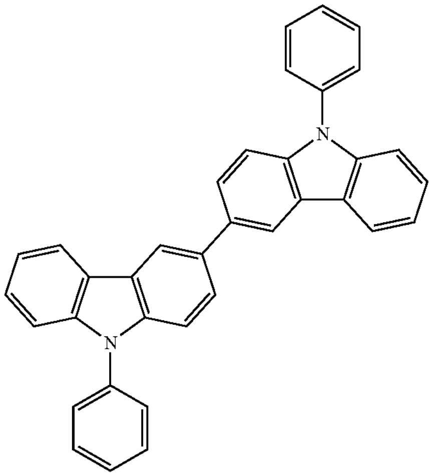
[B-23]
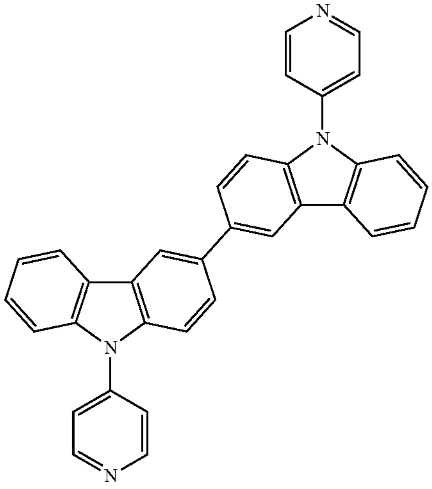
-continued
[B-24]
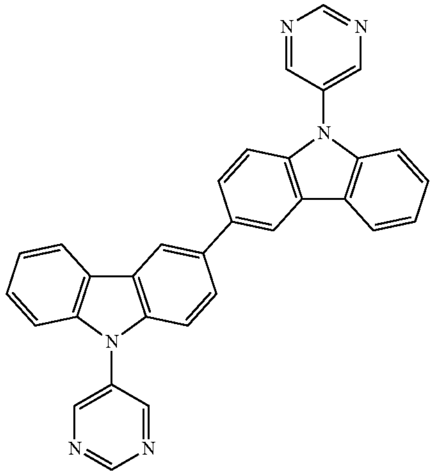
[B-25]
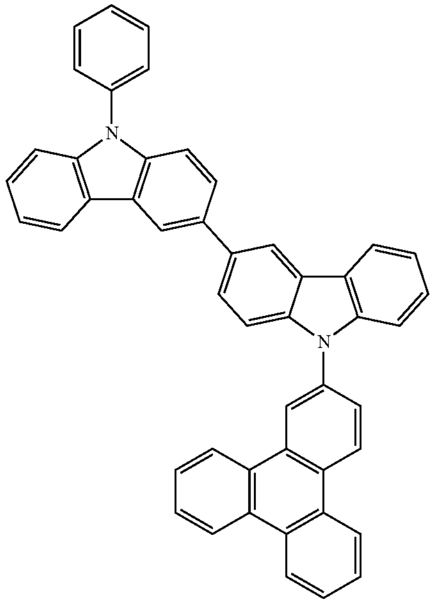

-continued
[B-26]
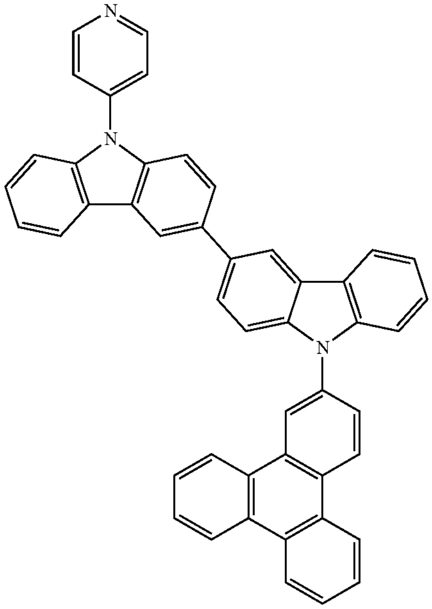
[B-27]
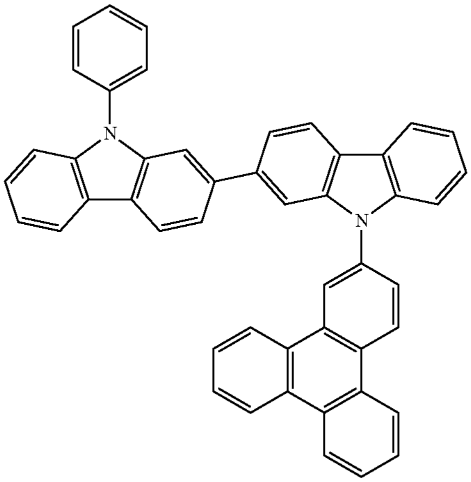
[B-28]
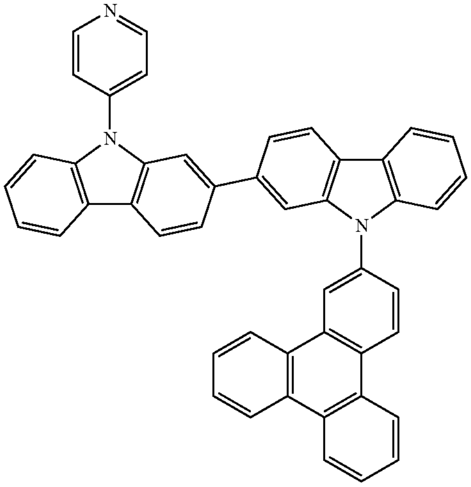
-continued
[B-29]
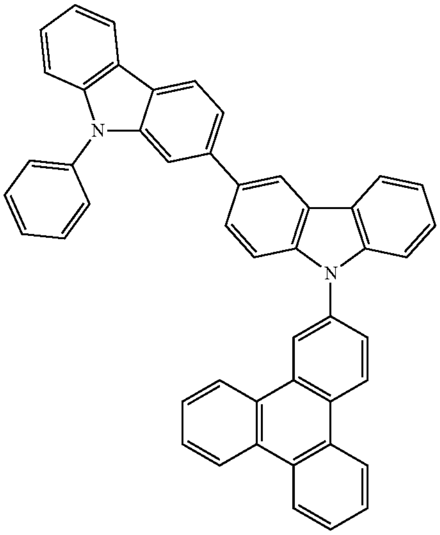
[B-30]
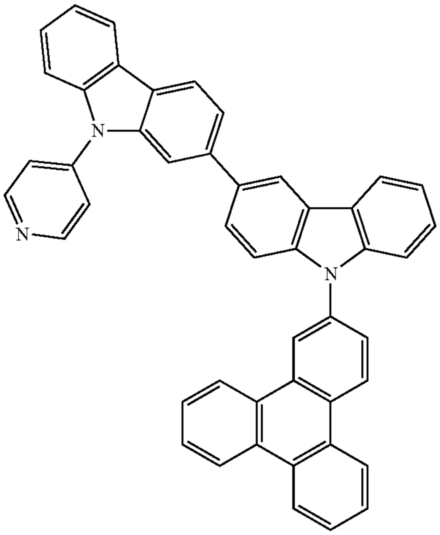

-continued
[B-31]
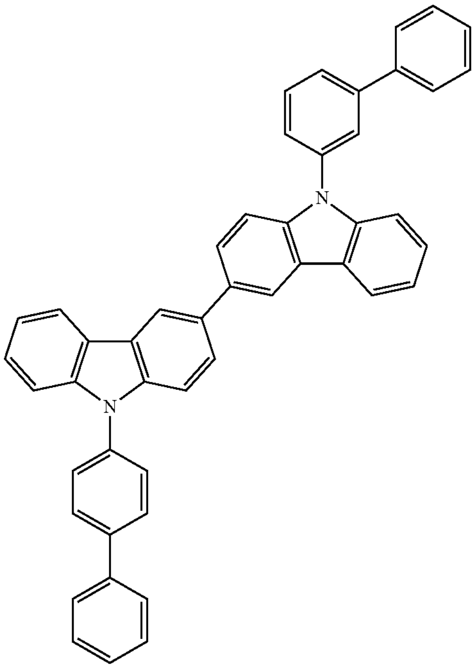
[B-32]
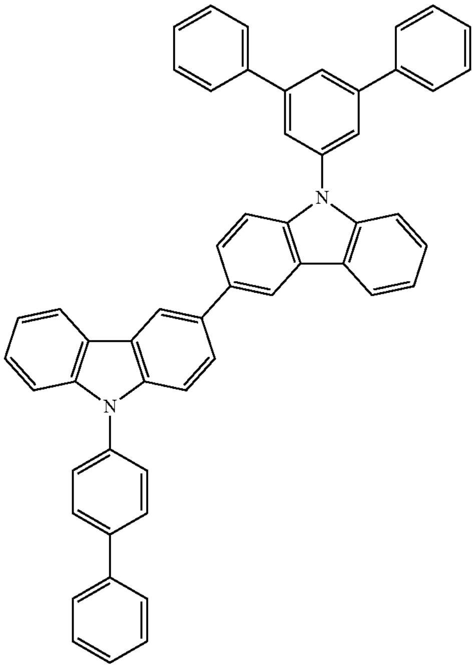
-continued
[B-33]
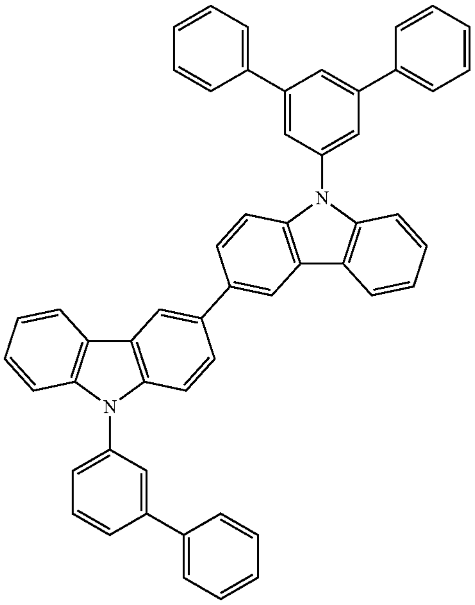
[B-34]
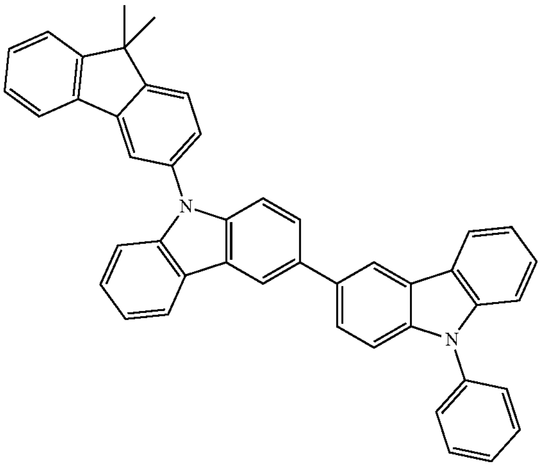

-continued
[B-35]
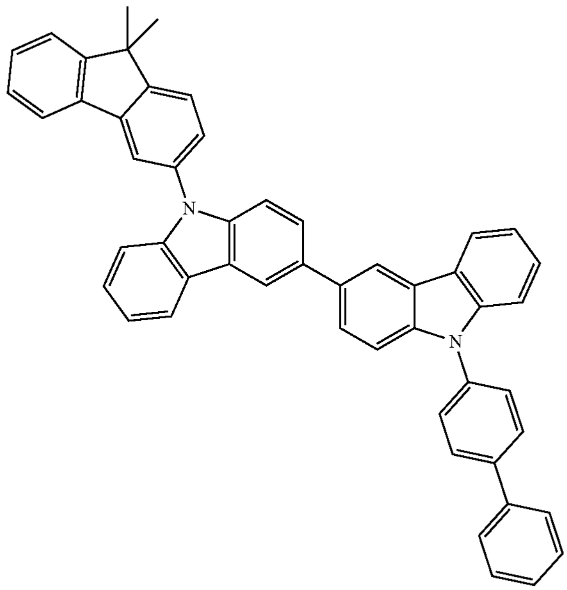
[B-36]
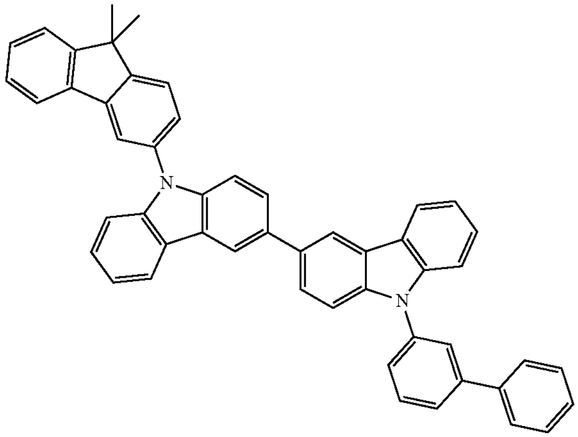
[B-37]
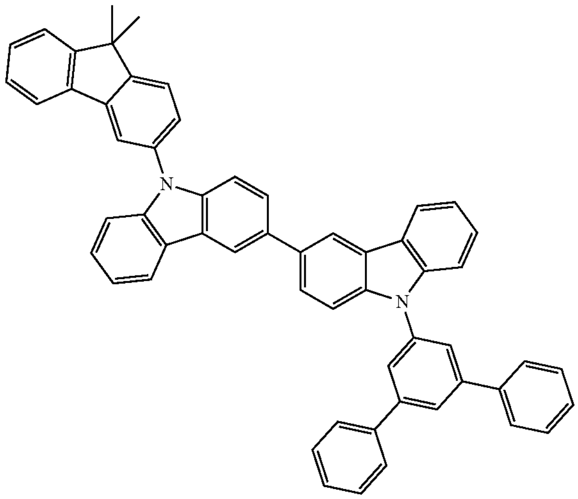
-continued
[B-38]
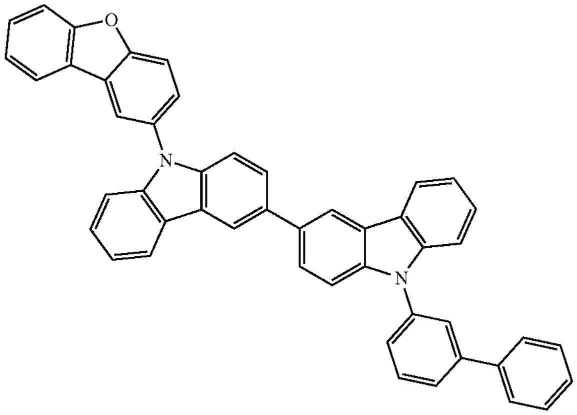
[B-39]
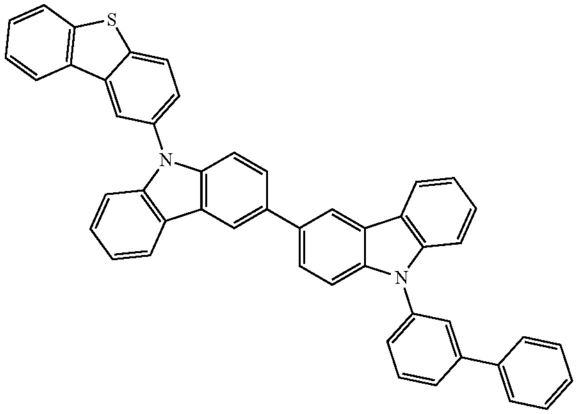
[B-40]
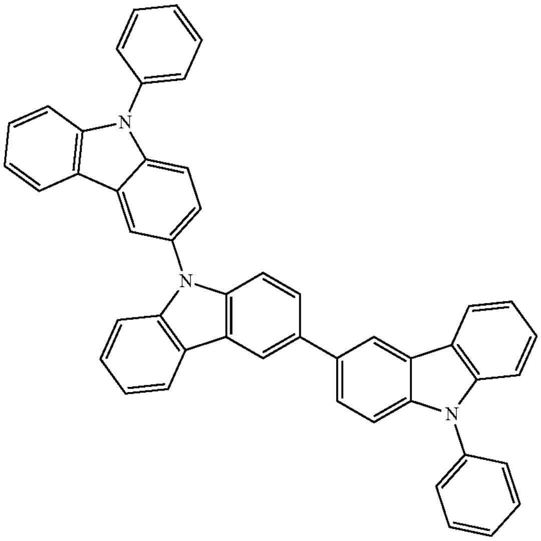

-continued
[B-41]
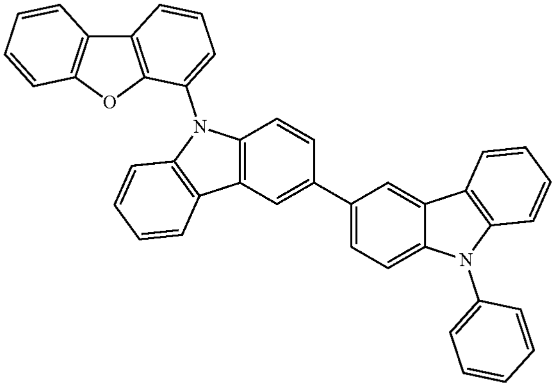
[B-42]
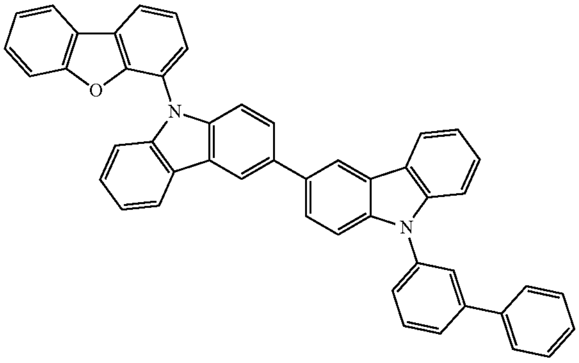
[B-43]
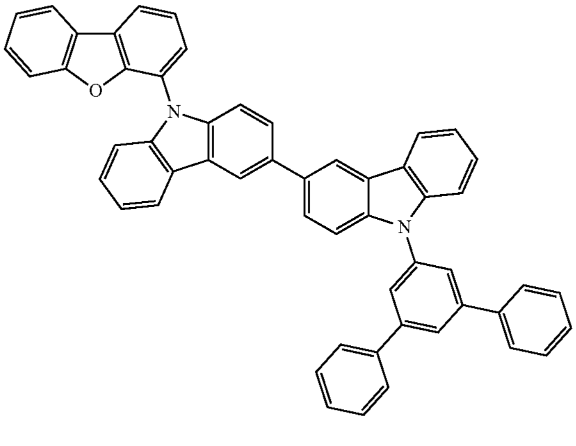
-continued
[B-44]
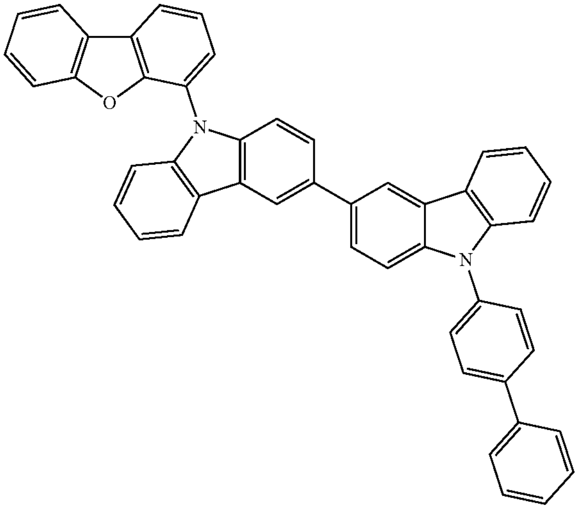
[B-45]
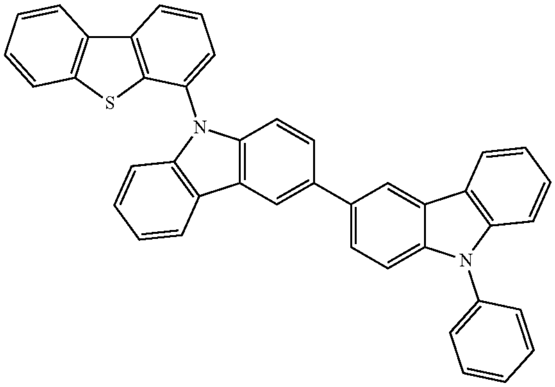
[B-46]
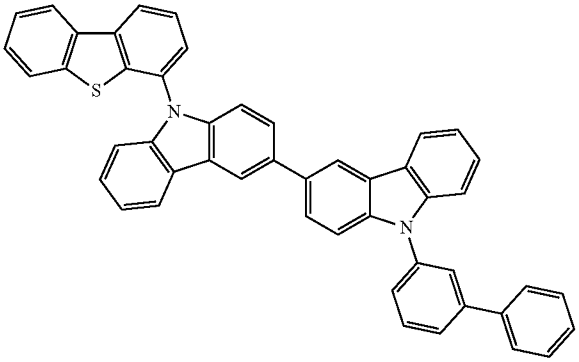

-continued
[B-47]
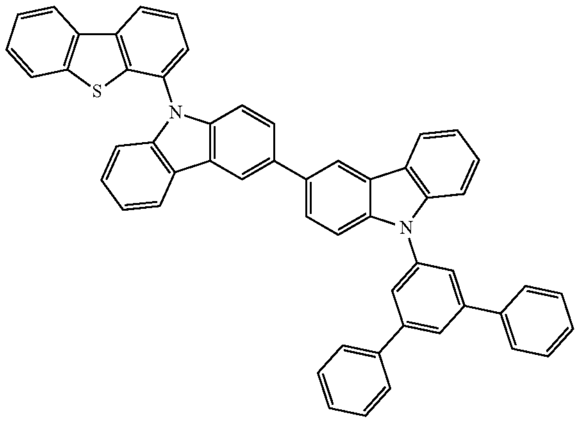
[B-48]
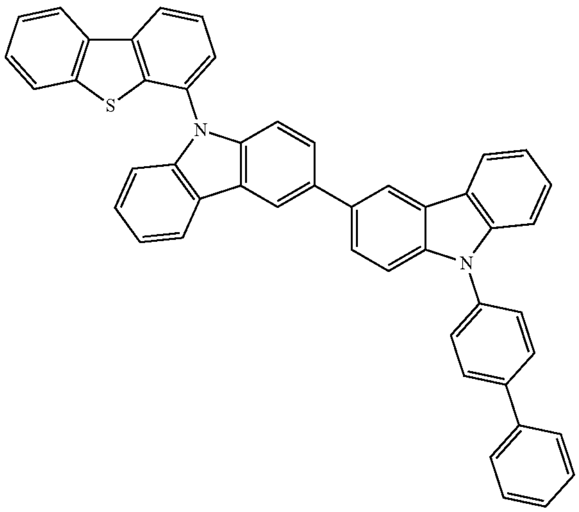
[B-49]
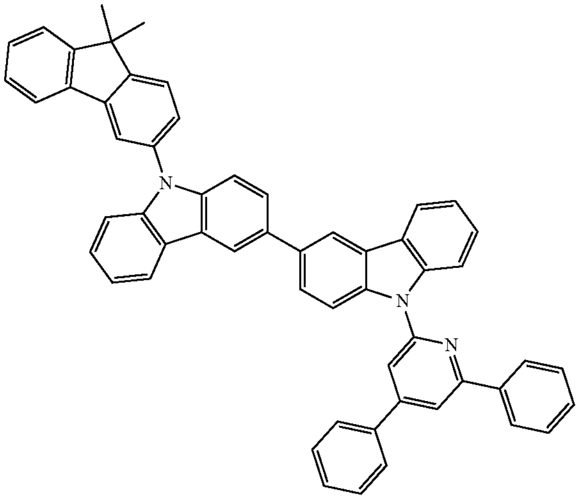
-continued
[B-50]
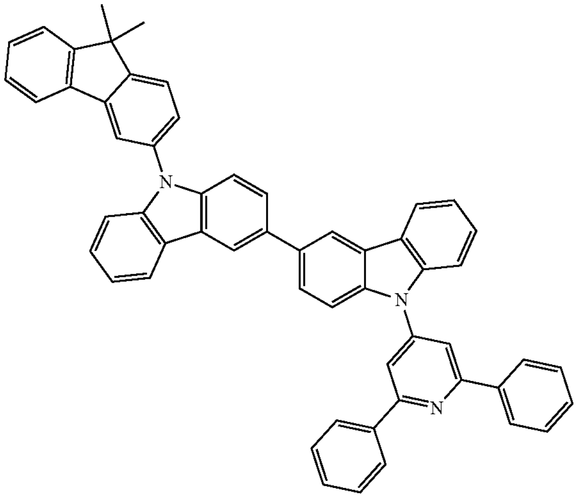
[B-51]
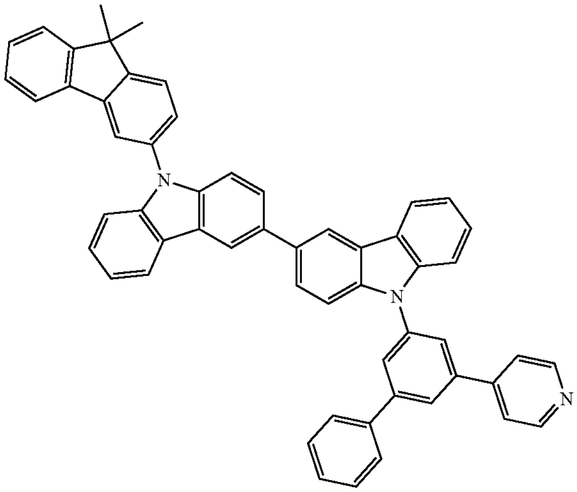
[B-52]
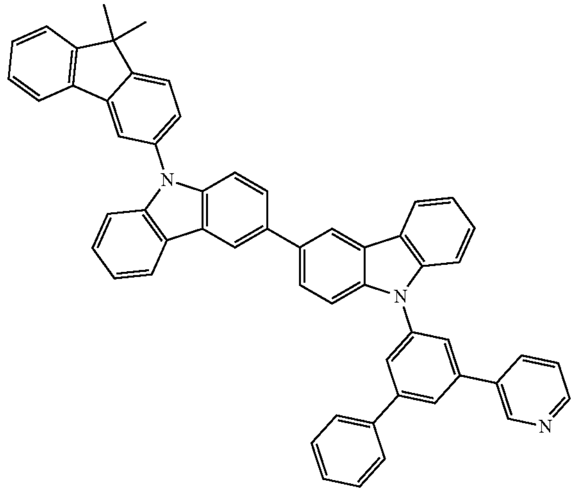

-continued
[B-53]
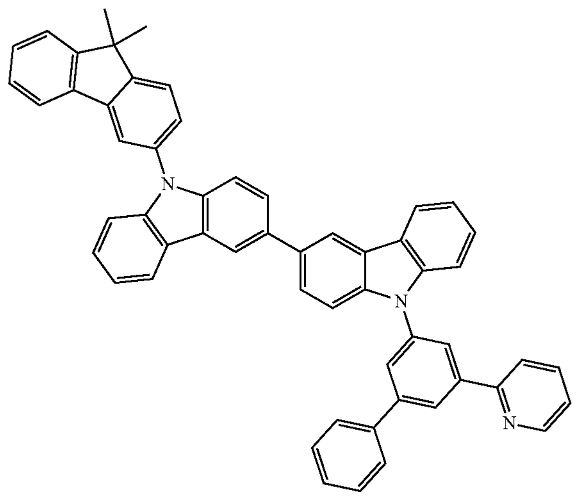
[B-54]
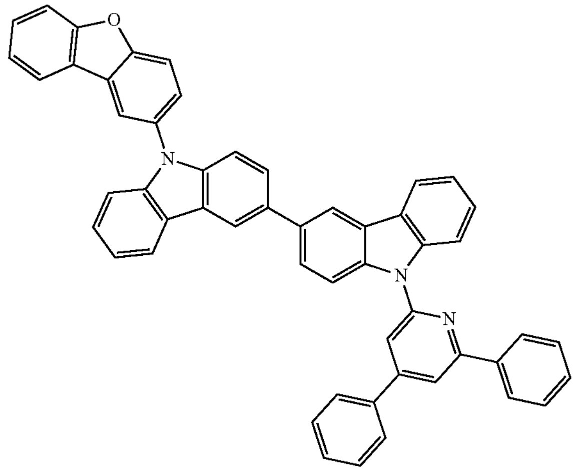
[B-55]
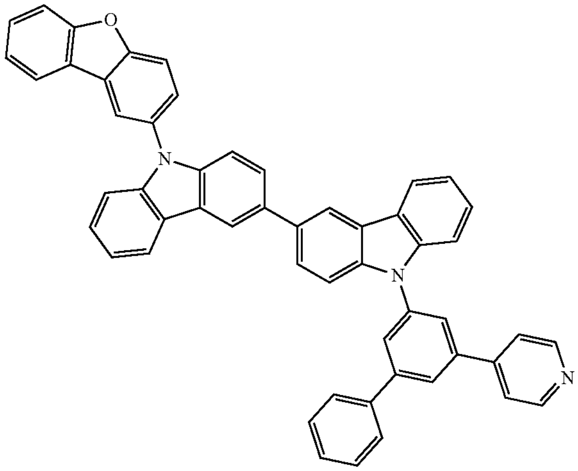
-continued
[B-56]
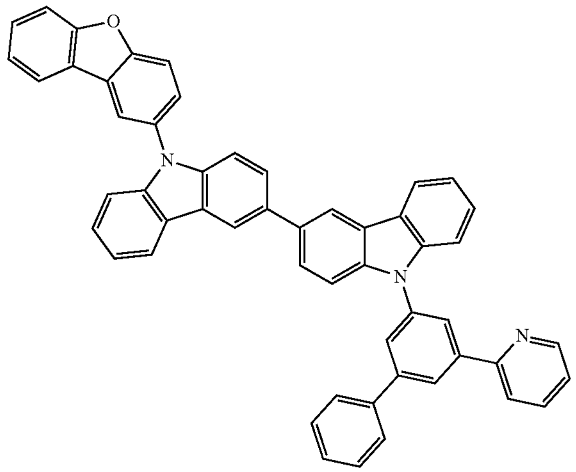
[B-57]
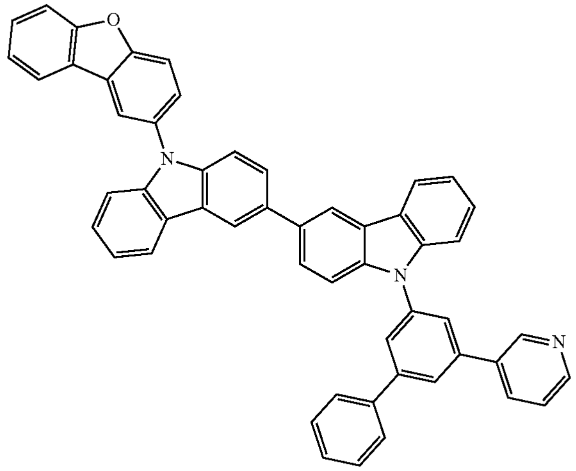
[B-58]
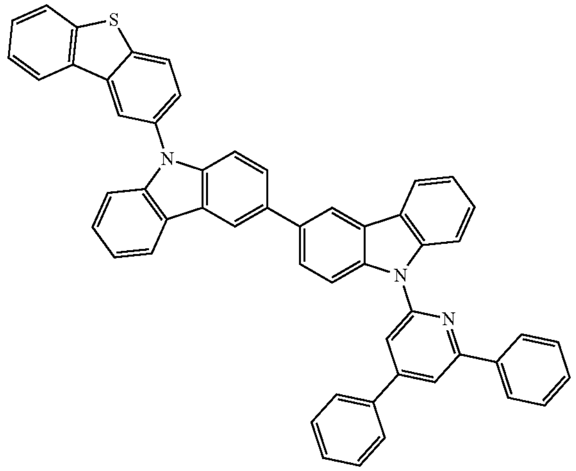

-continued
[B-59]
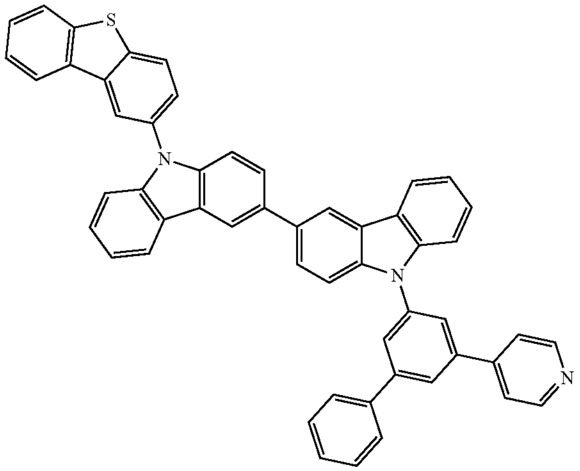
[B-60]
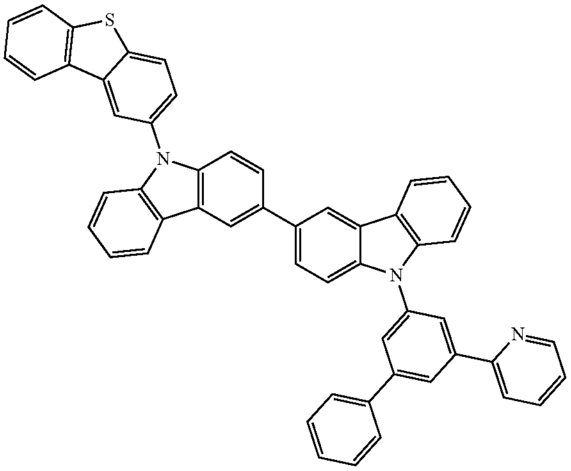
[B-61]
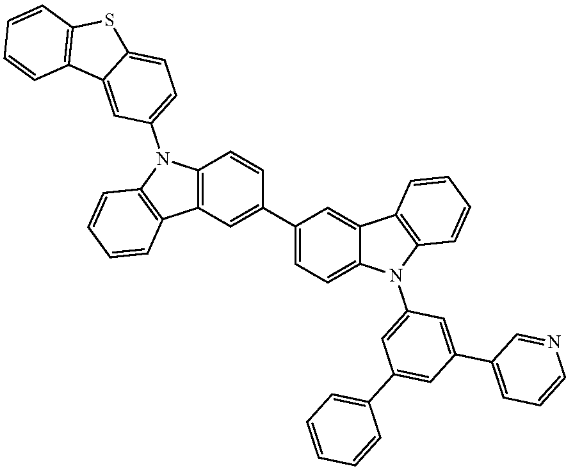
-continued
[B-62]
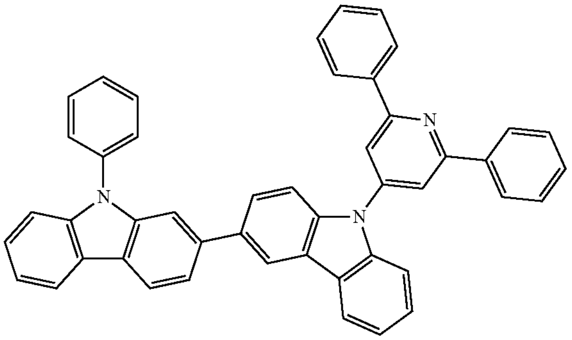
[B-63]
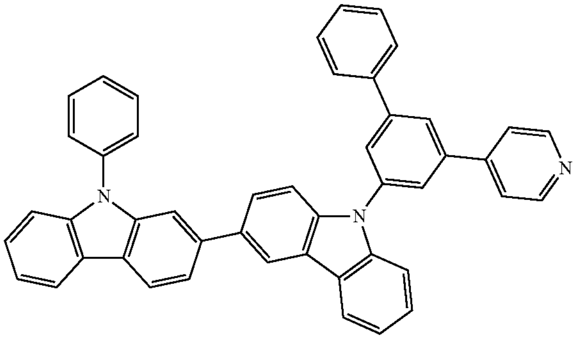
[B-64]
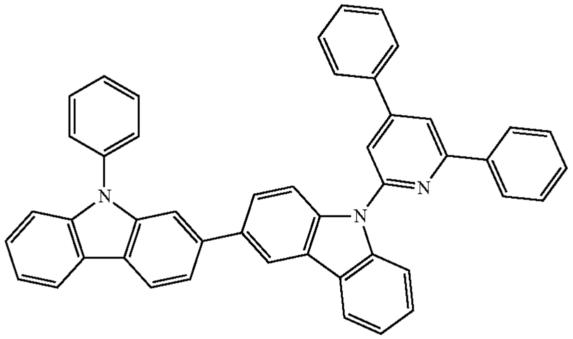
[B-65]
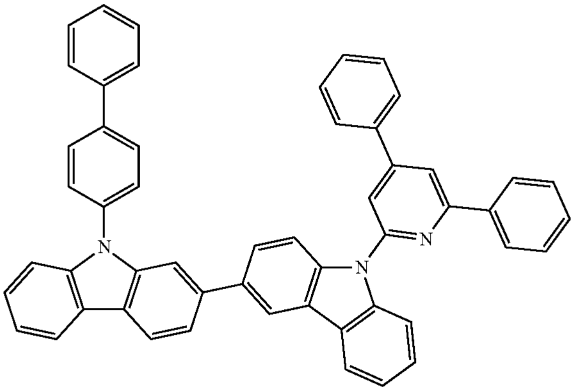

-continued
[B-66]
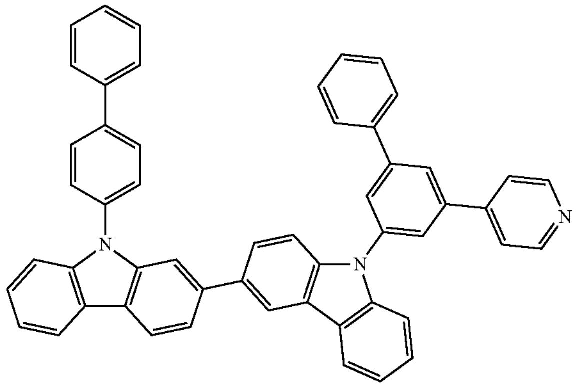
[B-67]
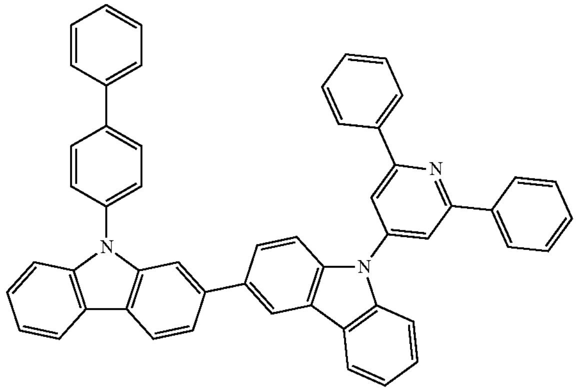
[B-68]
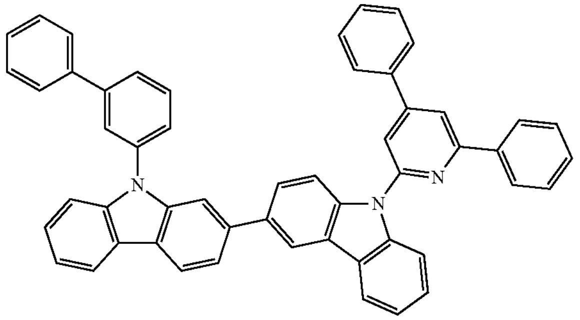
[B-69]
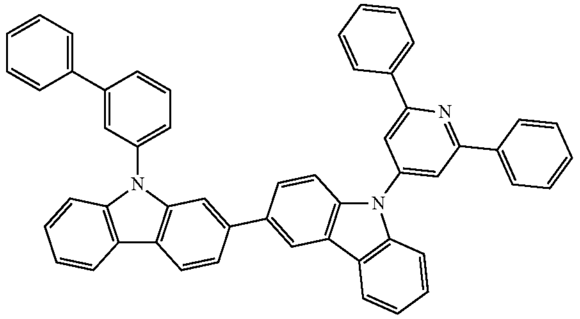
-continued
[B-70]
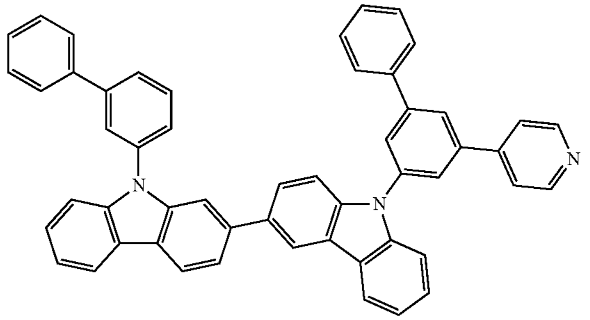
[B-71]
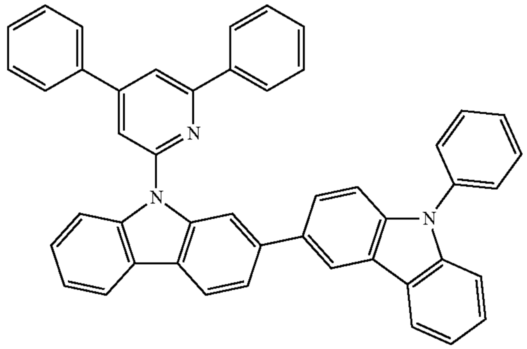
[B-72]
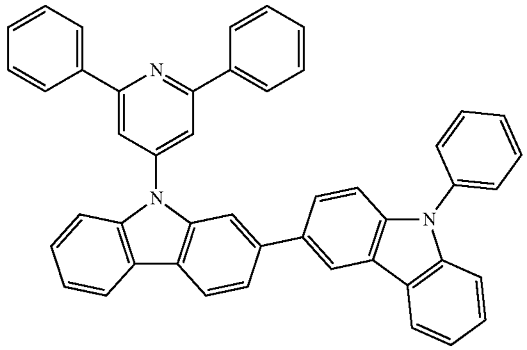
[B-73]
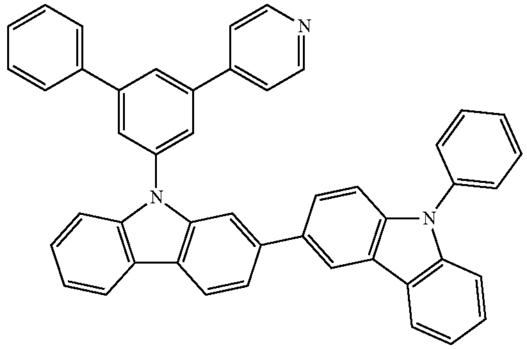

-continued
[B-74]
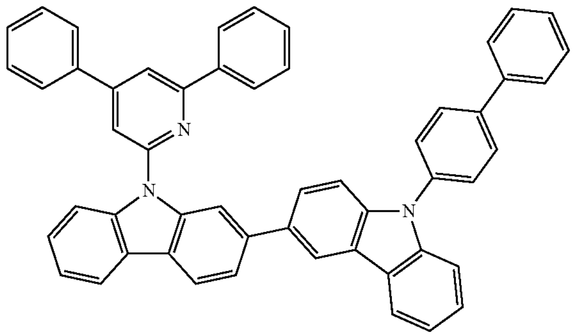
[B-75]
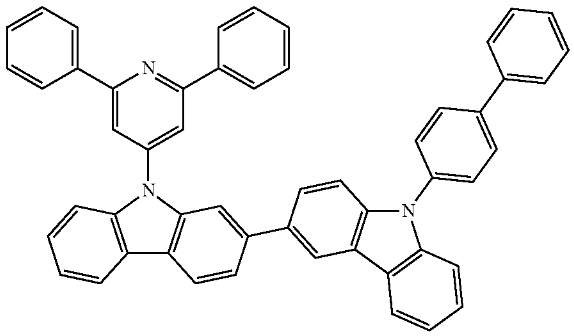
[B-76]
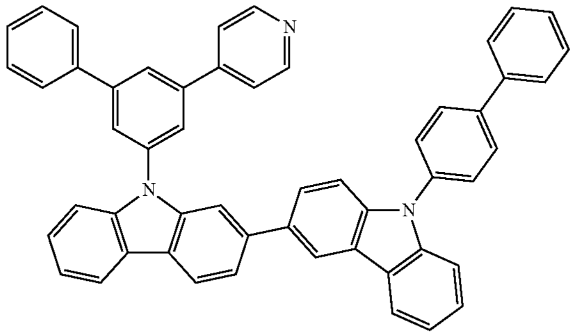
[B-77]
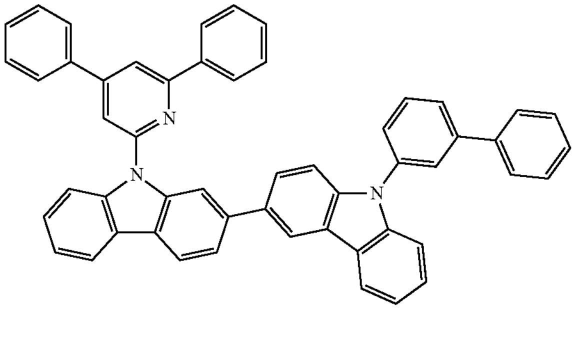
-continued
[B-78]
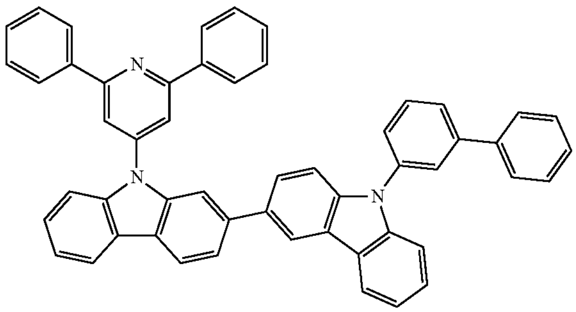
[B-79]
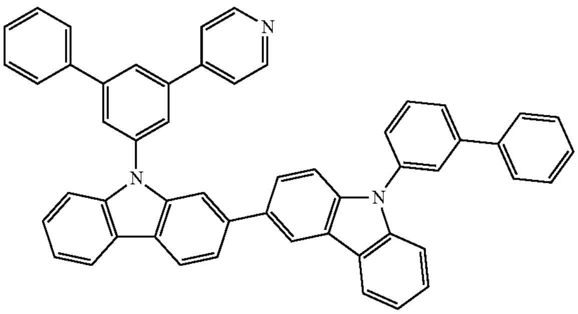
[B-80]
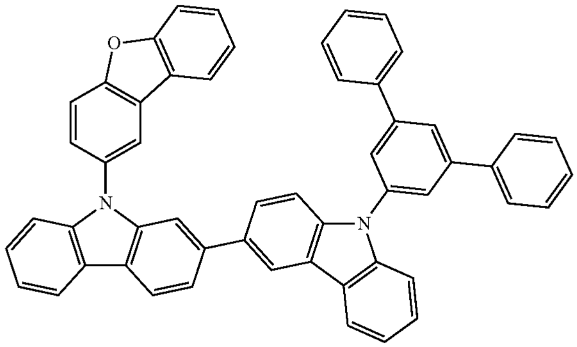
[B-81]
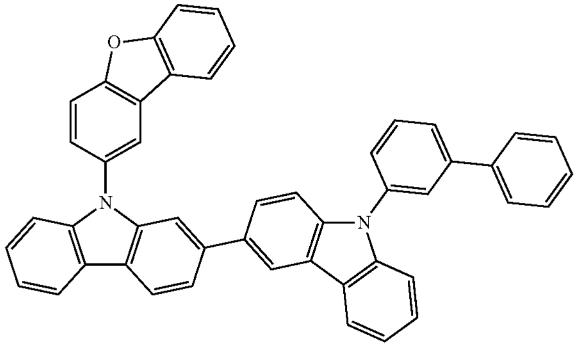

[B-82]
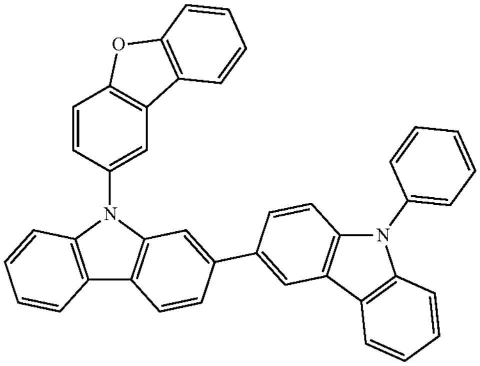
[B-83]
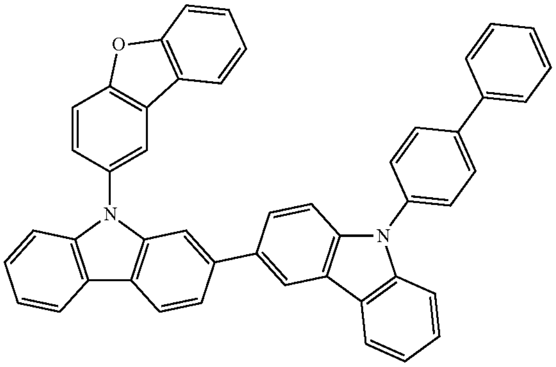
[B-84]
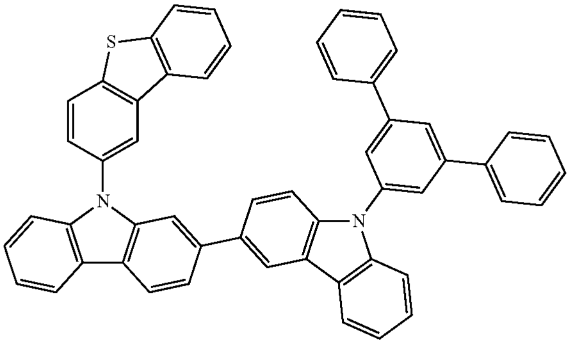
[B-85]
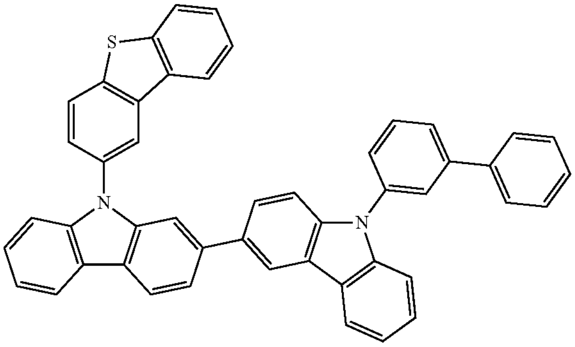
[B-86]
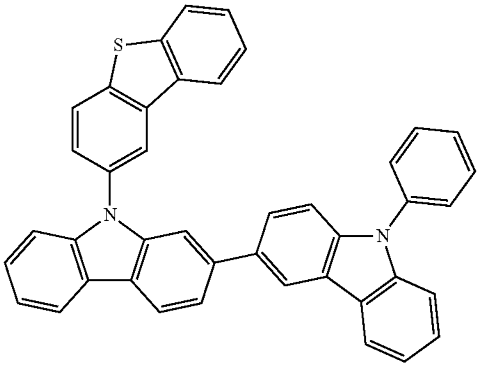
[B-87]
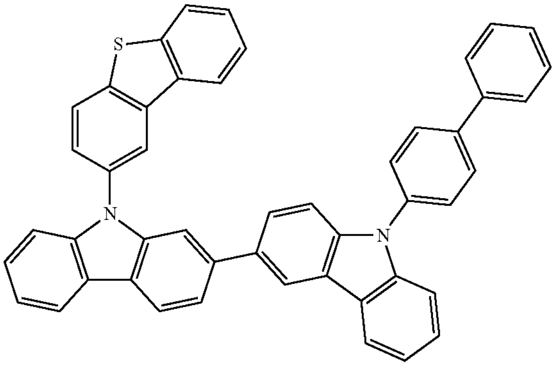
[B-88]
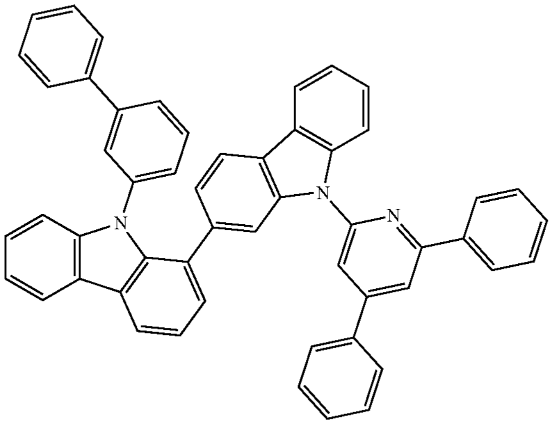
[B-89]
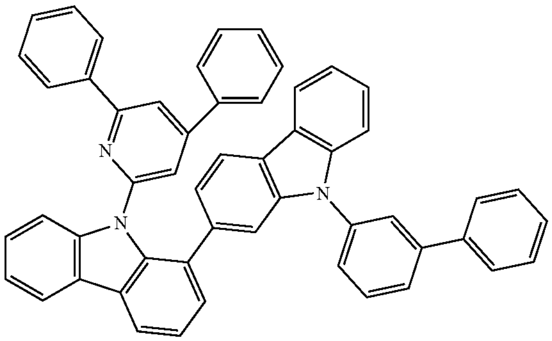

-continued
[B-90]
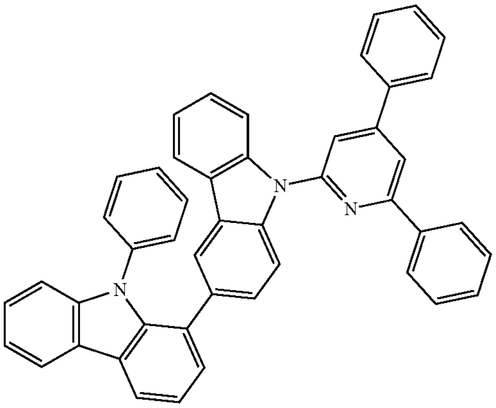
[B-91]
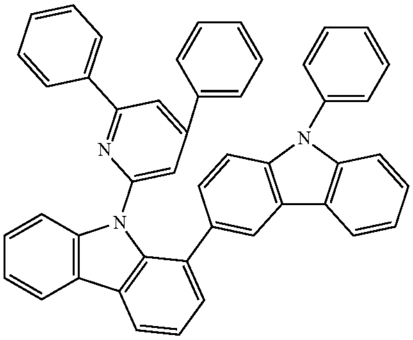
[B-92]
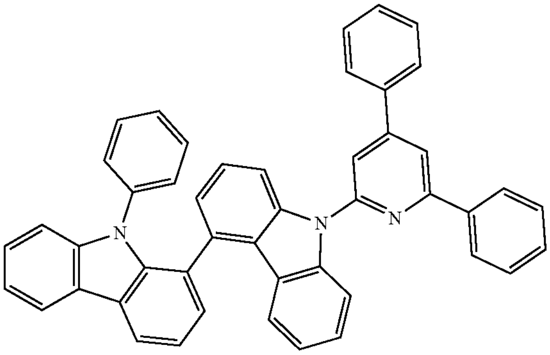
[B-93]
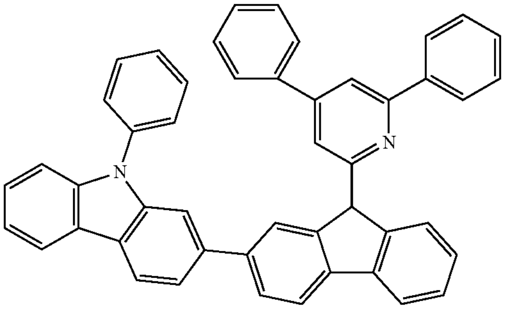
-continued
[B-94]
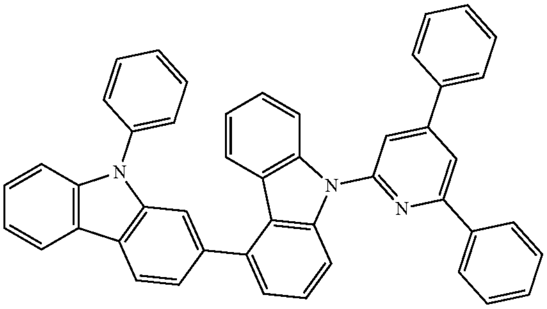
[B-95]
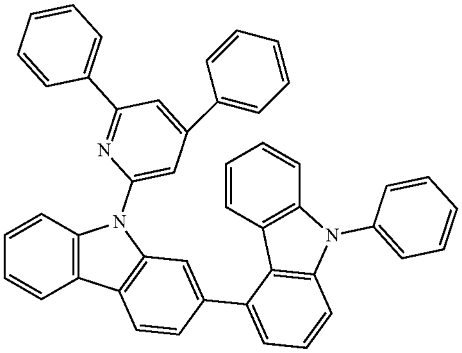
[B-96]
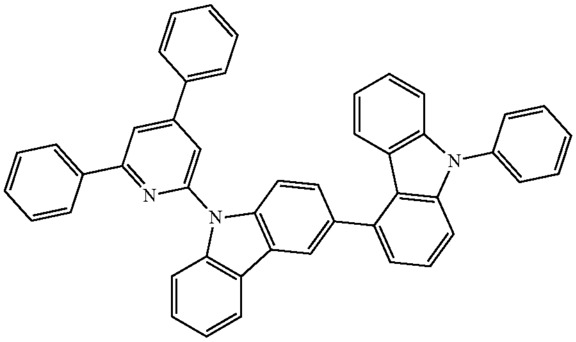
[B-97]
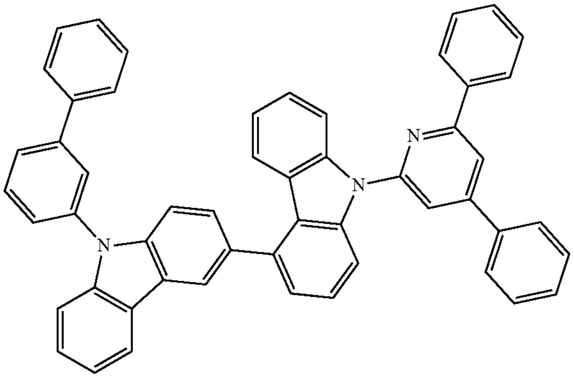

-continued
[B-98]
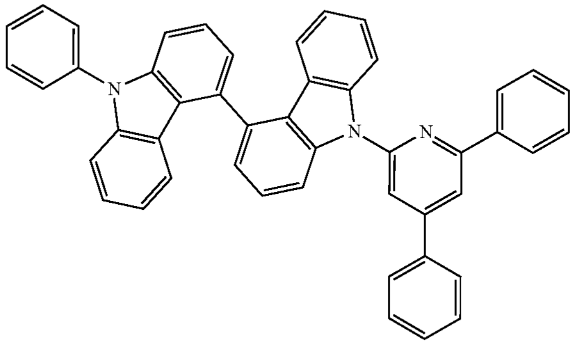
[B-99]
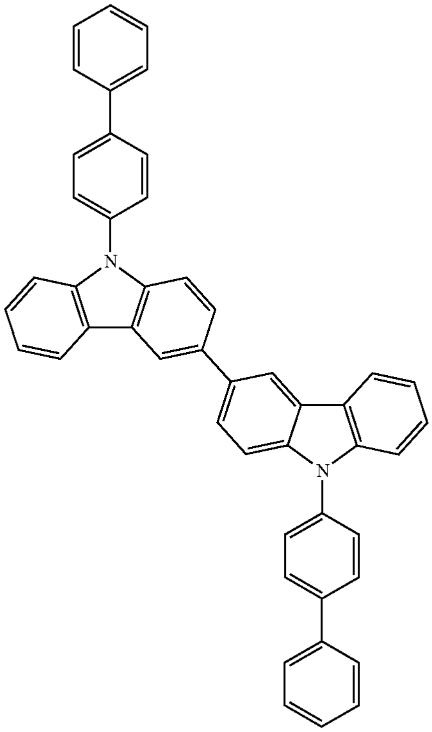
-continued
[B-100]
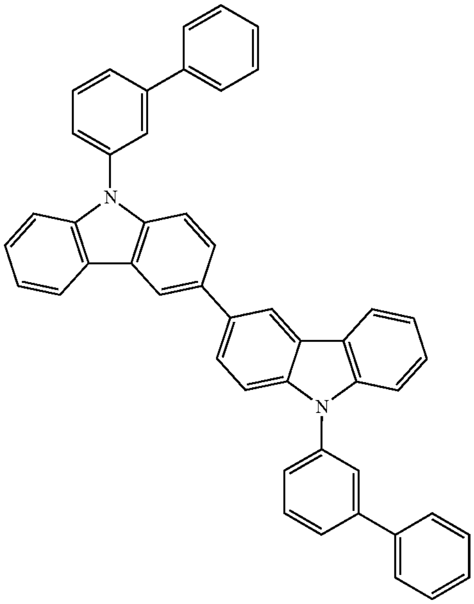
[B-101]
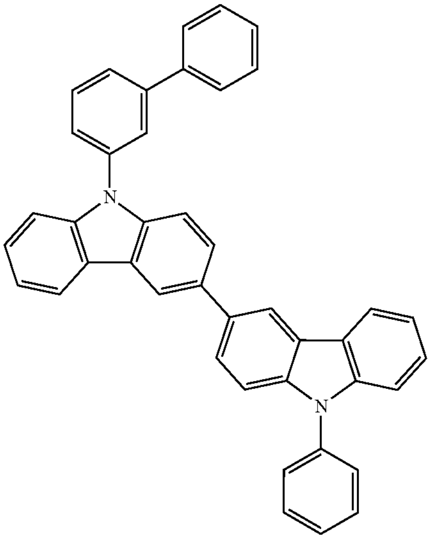
[B-102]
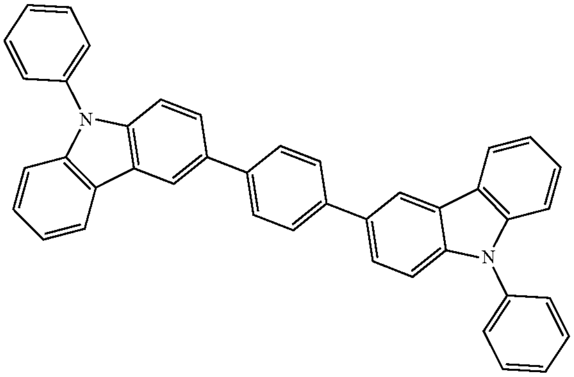

-continued
[B-103]
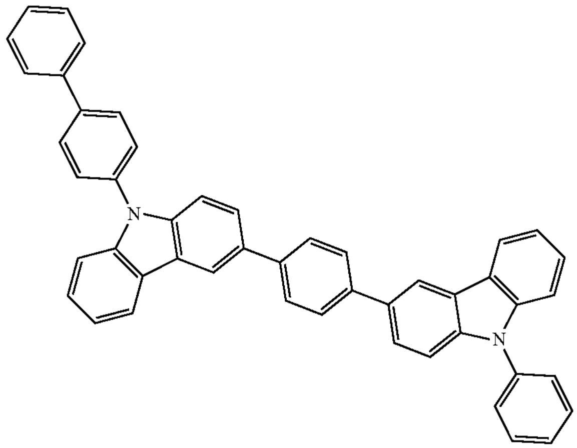
[B-104]
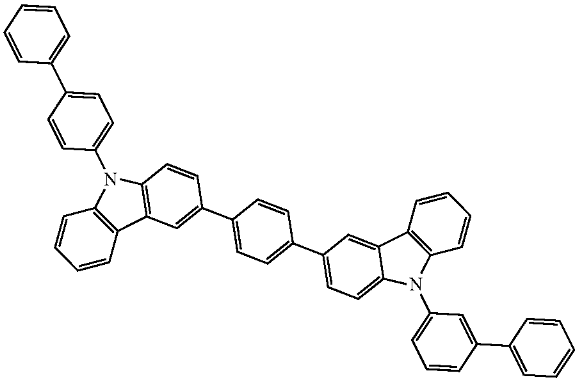
[B-105]
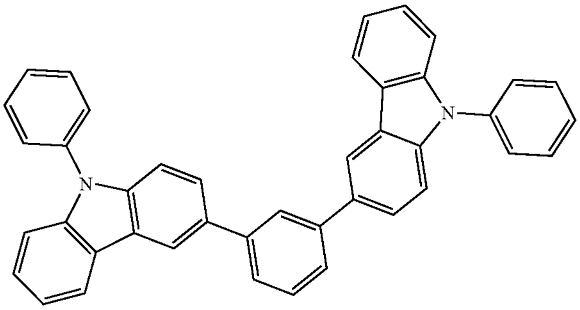
[B-106]
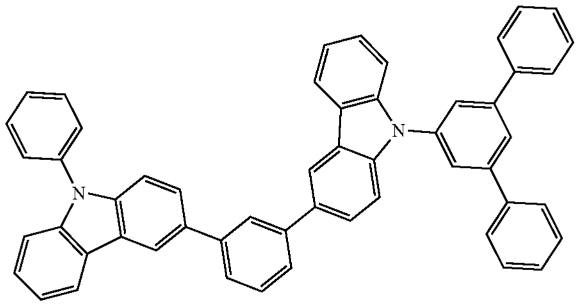
-continued
[B-107]
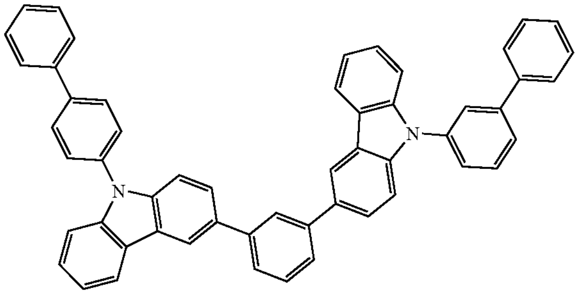
[B-108]
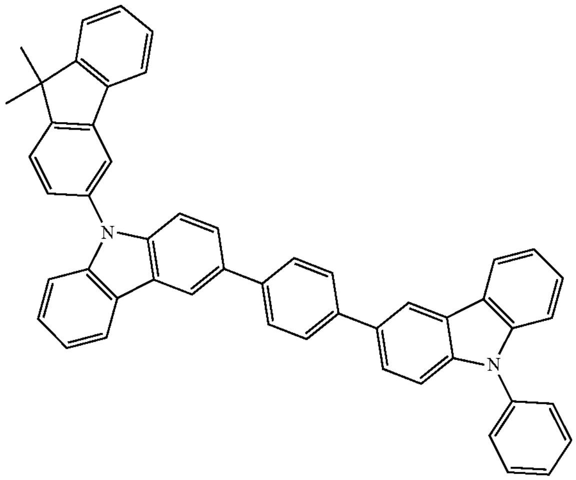
[B-109]
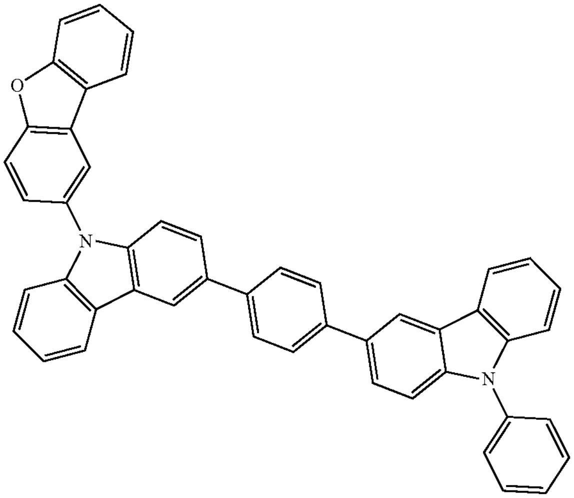

-continued
[B-110]
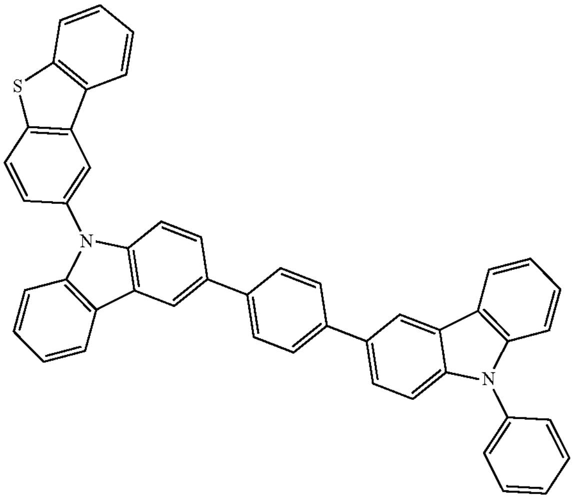
[B-111]
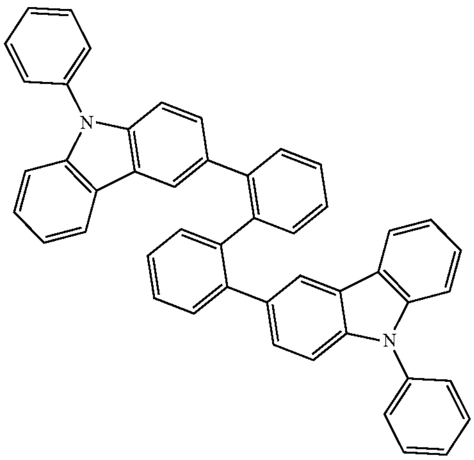
[B-112]
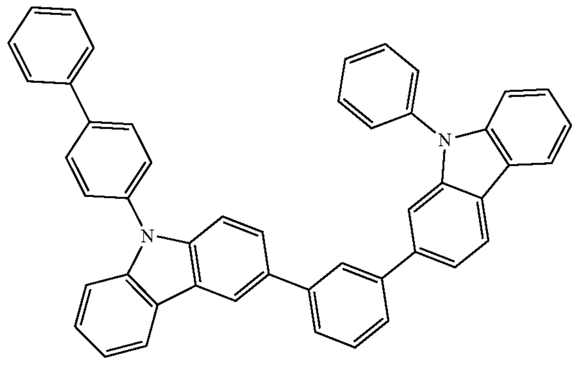
-continued
[B-113]
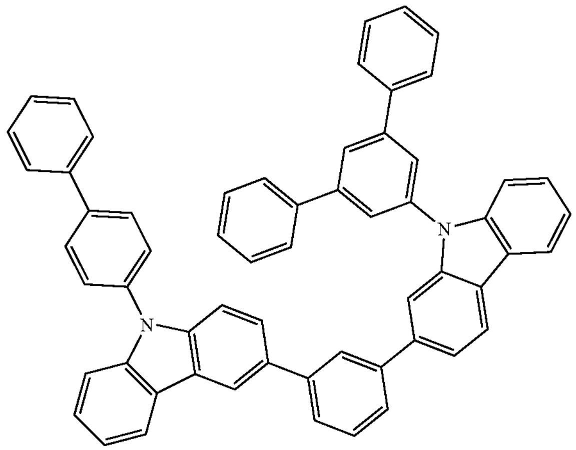
[B-114]
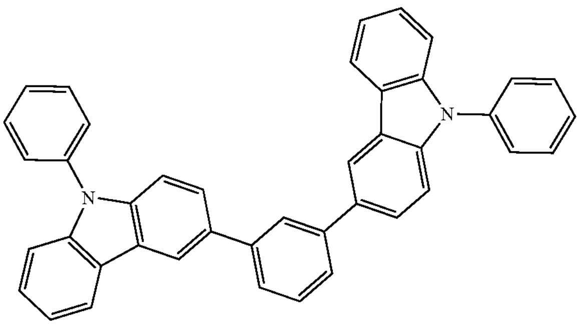
[B-115]
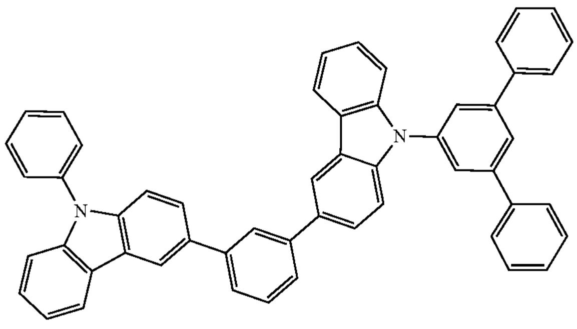
[B-116]
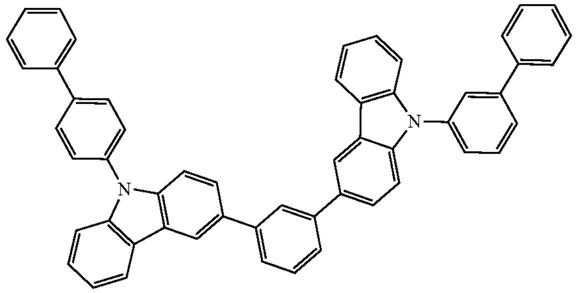

-continued
[B-117]
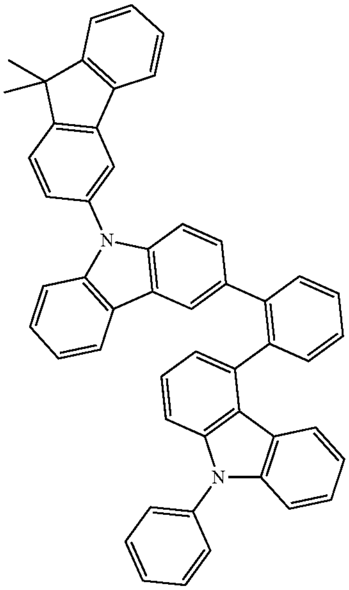
[B-118]
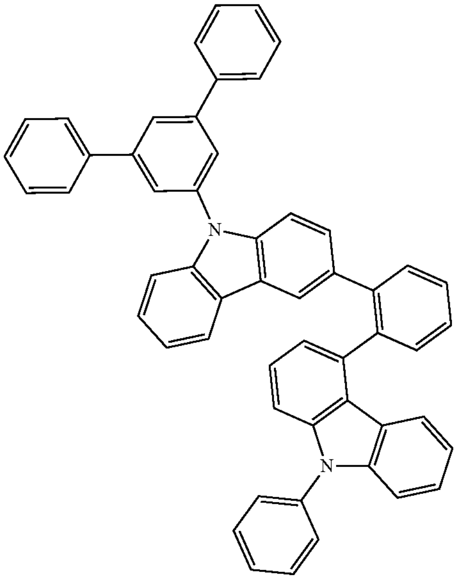
-continued
[B-119]
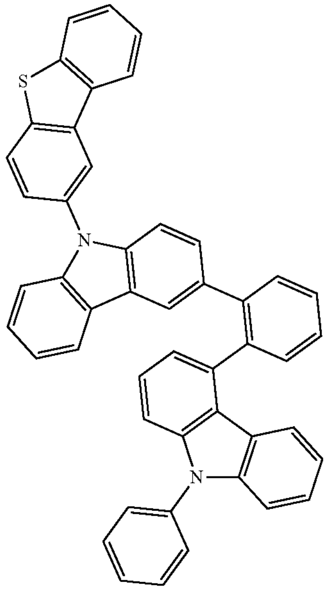
[B-120]
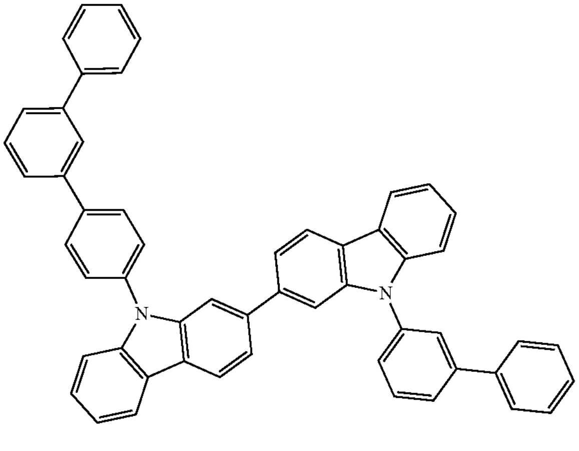
[B-121]
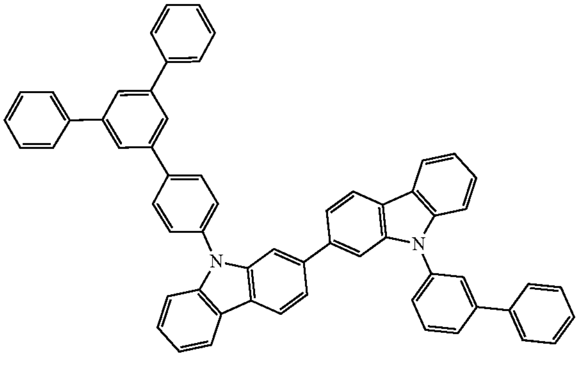

-continued
[B-122]
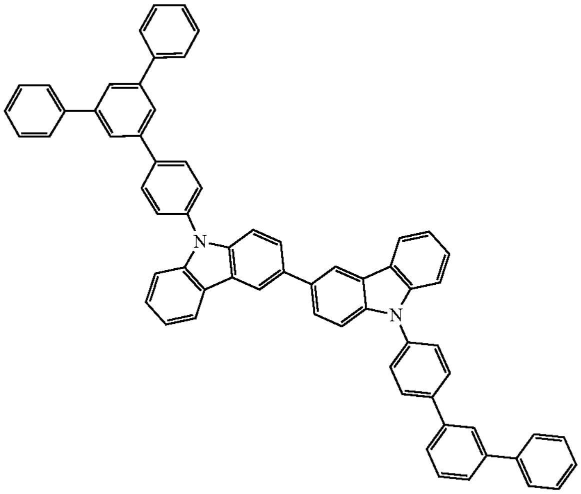
[B-123]
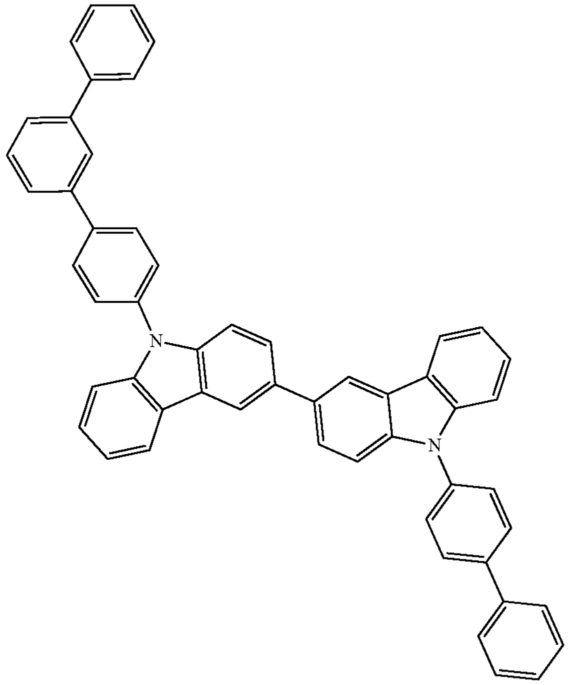
[B-124]
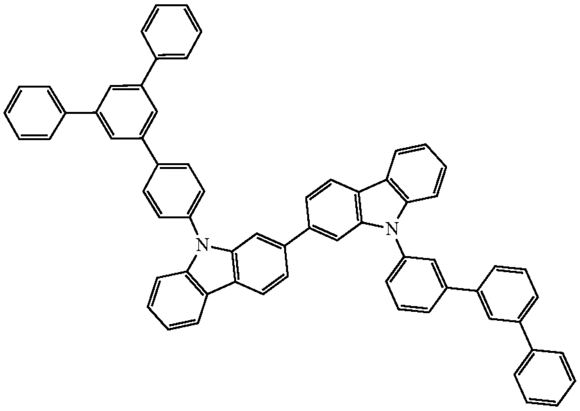
-continued
[B-125]
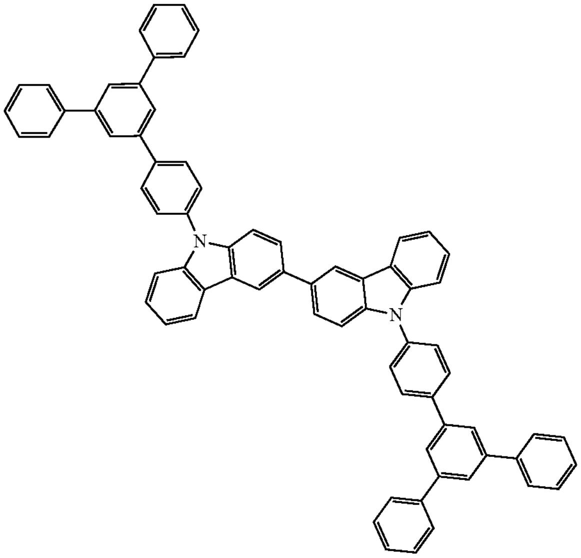
[B-126]
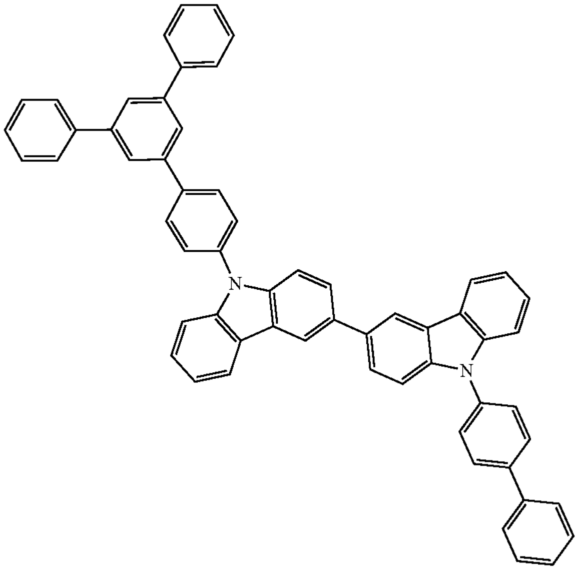

[B-127]
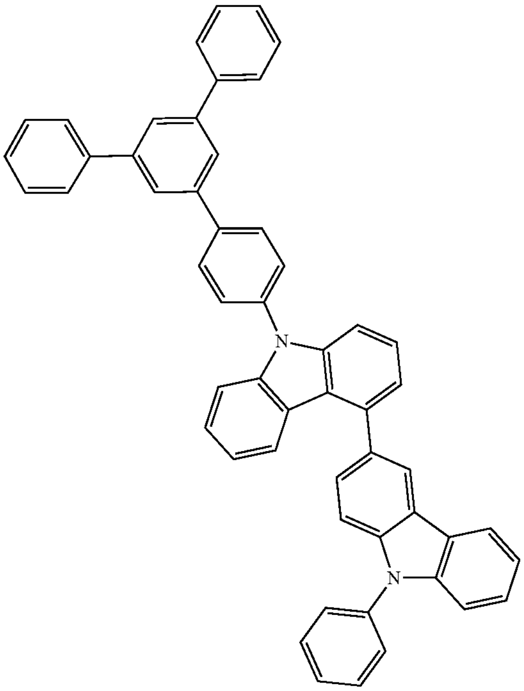
[B-128]
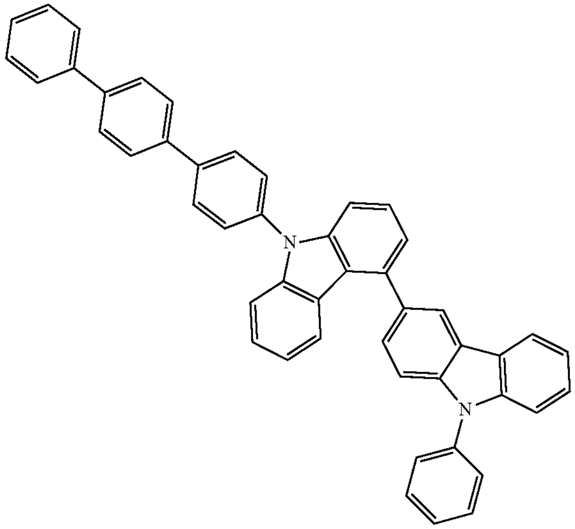
[B-129]
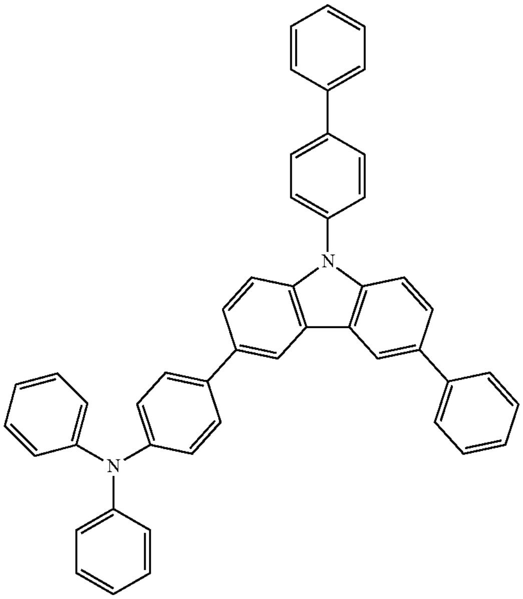
[B-130]
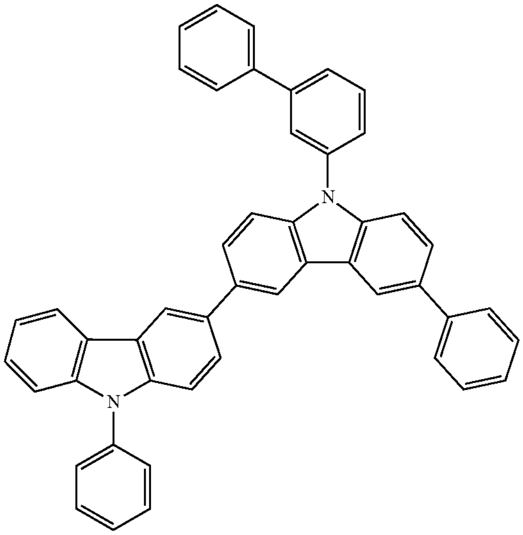

-continued
[B-131]
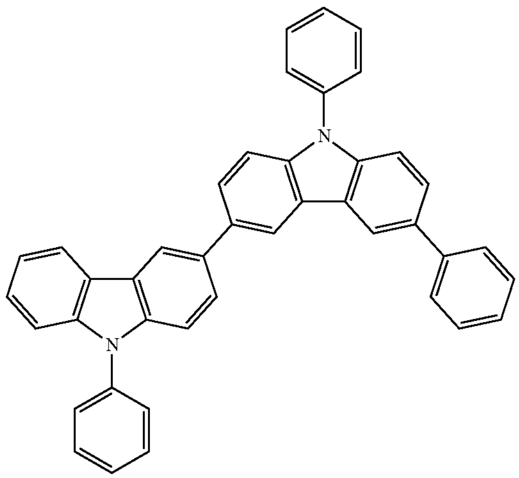
[B-132]
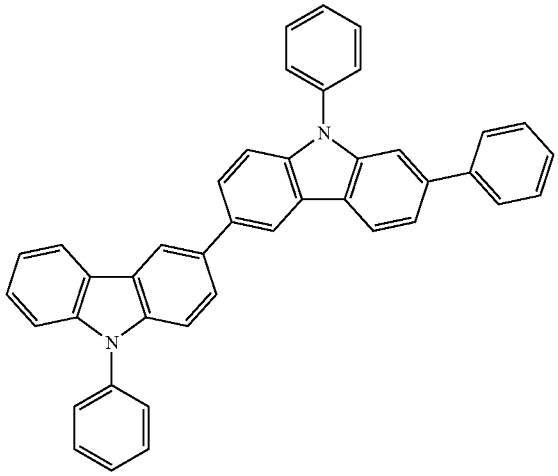
[B-133]
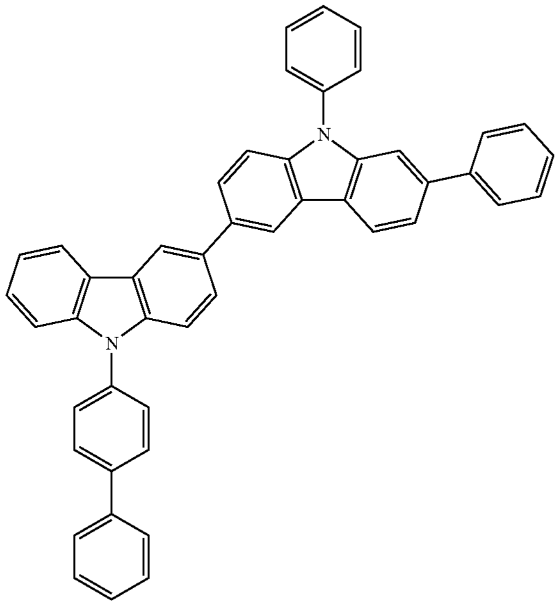
-continued
[B-134]
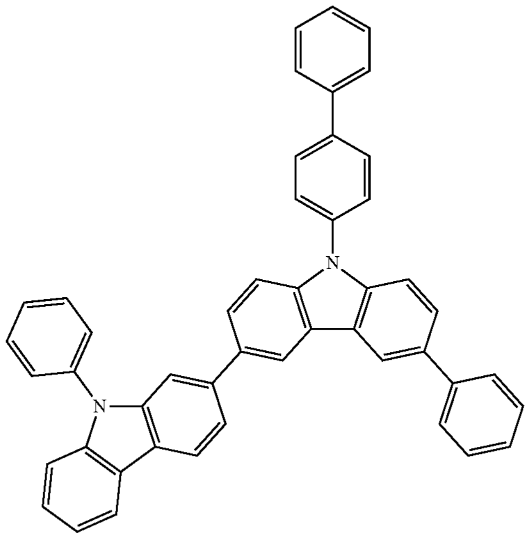
[B-135]
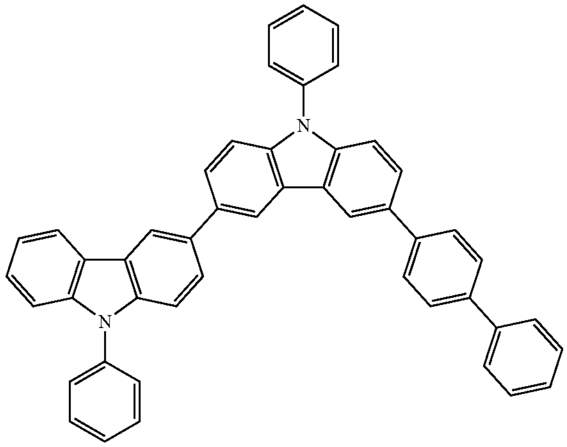
[B-136]
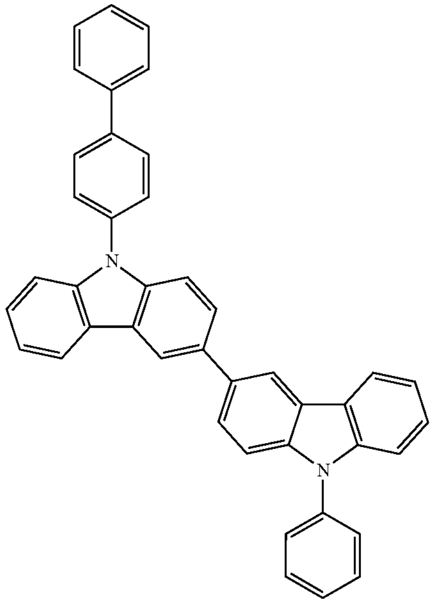

-continued
[B-137]
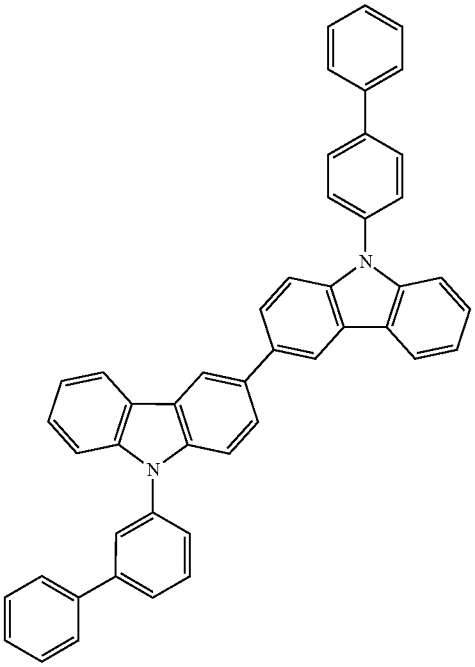
[B-138]
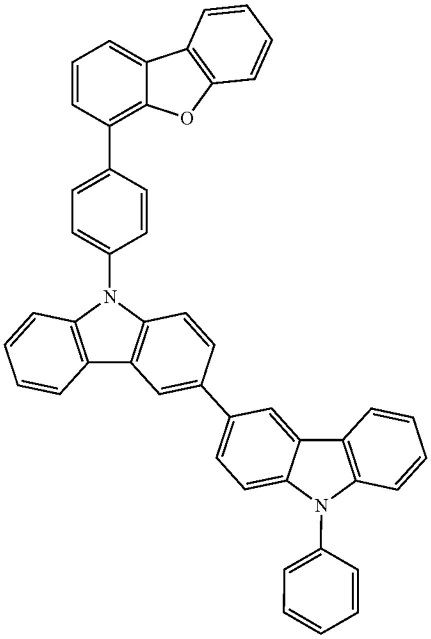
-continued
[B-139]
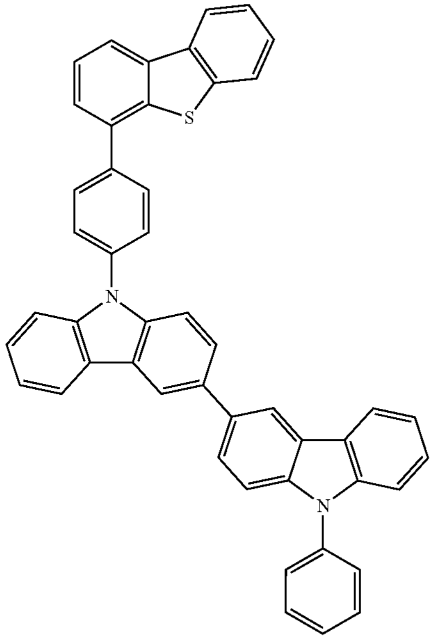
In an embodiment of the present invention, the second compound for the organic optoelectronic diode composed of a moiety represented by Chemical Formula 3 and a moiety represented by Chemical Formula 4 may be represented by at least one of Chemical Formulae 3-I to 3-V.
[Chemical Formula 3-I]
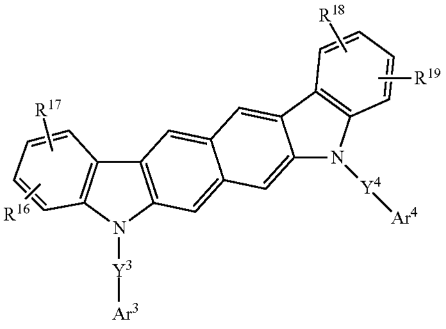
[Chemical Formula 3-II]
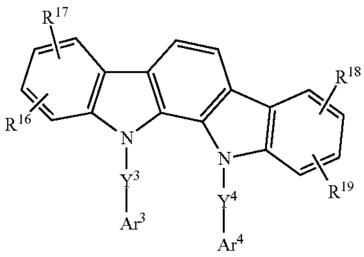

-continued

[Chemical Formula 3-III]

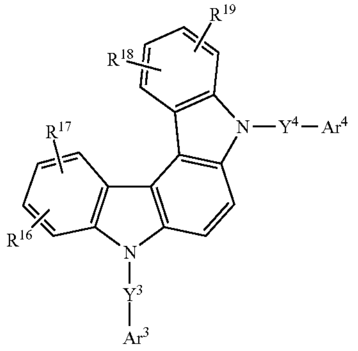

[Chemical Formula 3-IV]

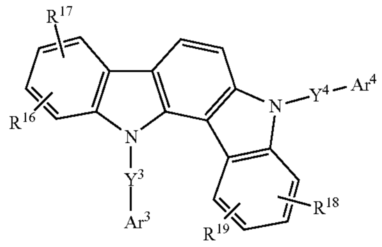

[Chemical Formula 3-V]

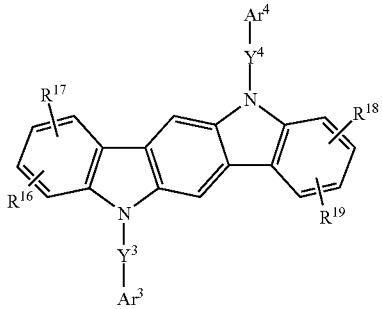

In Chemical Formulae 3-I to 3-V, $Y^3$, $Y^4$, $Ar^3$, $Ar^4$, and $R^{16}$ to $R^{19}$ are the same as described above.

In an embodiment of the present invention, $Y^3$ and Y of Chemical Formula 3-1 to 3-V may be a single bond, a phenylene group, a biphenylene group, a pyridylene group, or a pyrimidinylene group.

In an embodiment of the present invention, $Ar^3$ and $Ar^4$ of Chemical Formulae 3-I to 3-V may be a substituted or unsubstituted phenyl group, a substituted or unsubstituted biphenyl group, a substituted or unsubstituted pyridyl group, a substituted or unsubstituted pyrimidinyl group, or a substituted or unsubstituted triazinyl group.

In an embodiment of the present invention, $R^{16}$ to $R^{19}$ of Chemical Formulae 3-I to 3-V may be hydrogen.

The second compound for the organic optoelectronic diode composed of a moiety represented by Chemical Formula 3 and a moiety represented by Chemical Formula 4 may be for example compounds of Group 3, but is not limited thereto.

[Group 3]

[E-1]

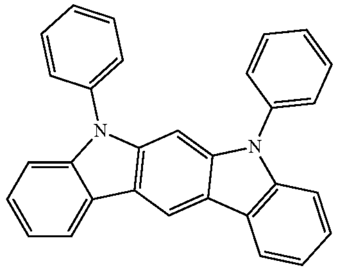

[E-2]

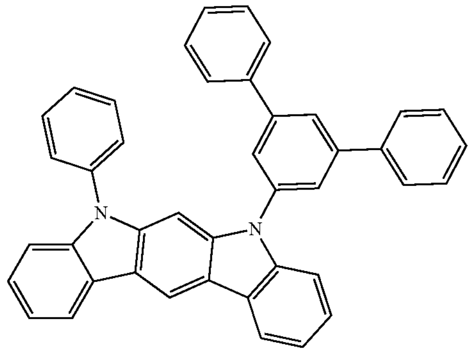

[E-3]

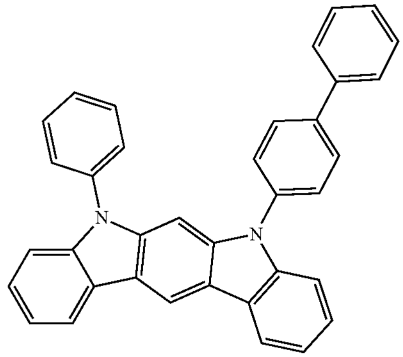

[E-4]

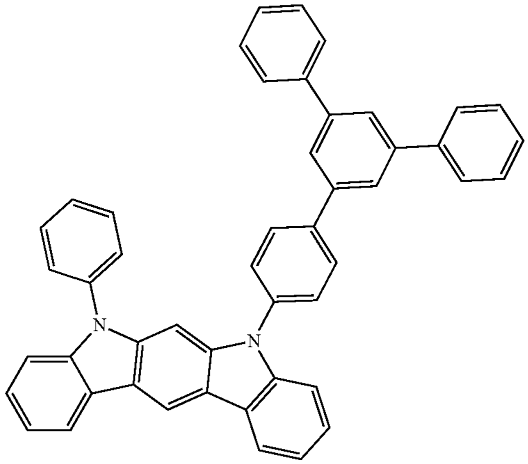

-continued
[E-5]
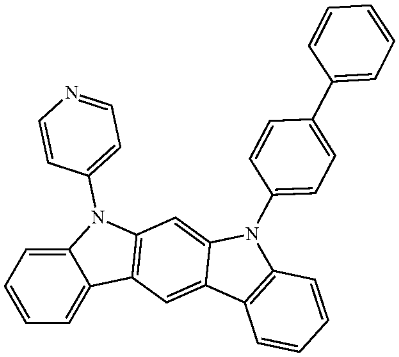
[E-6]
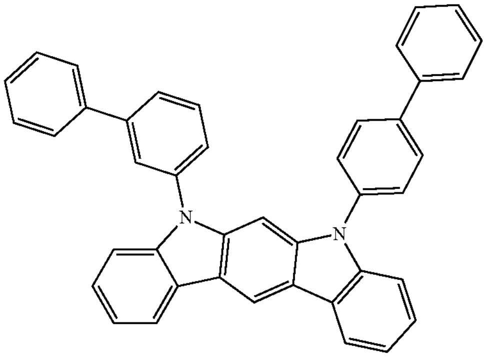
[E-7]
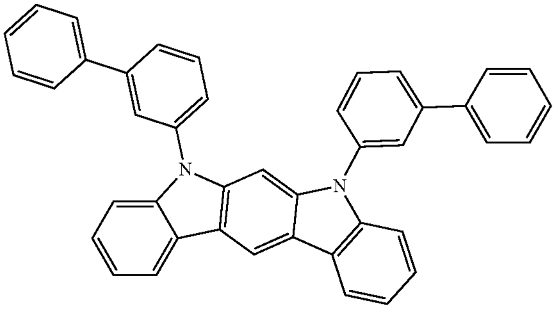
[E-8]
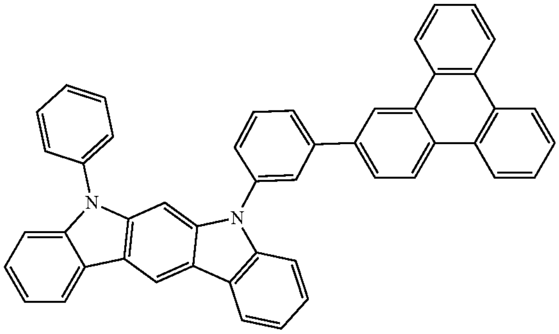
-continued
[E-9]
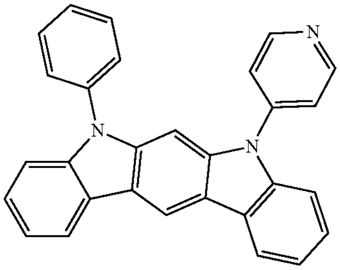
[E-10]
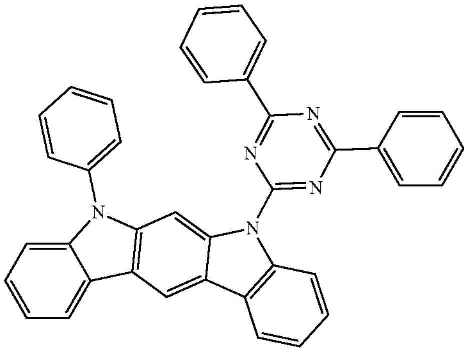
[E-11]
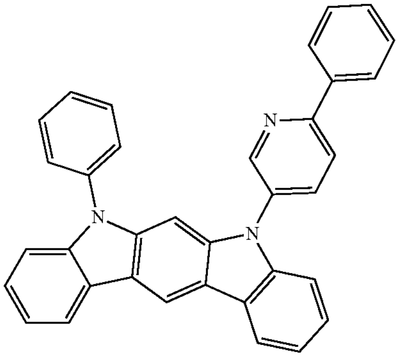
[E-12]
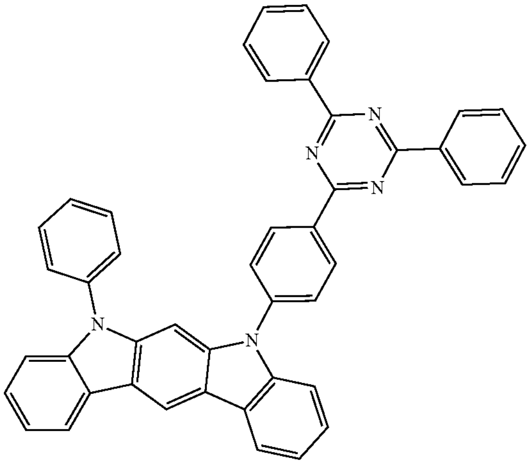

-continued
[E-13]
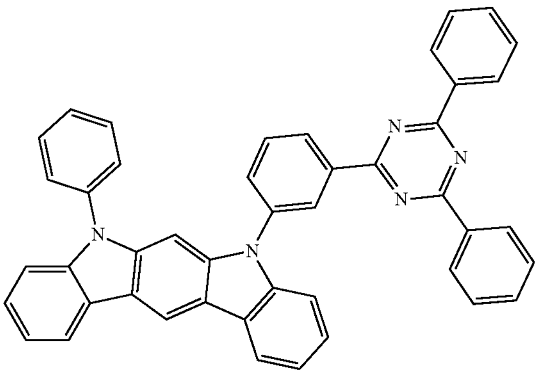
[E-14]
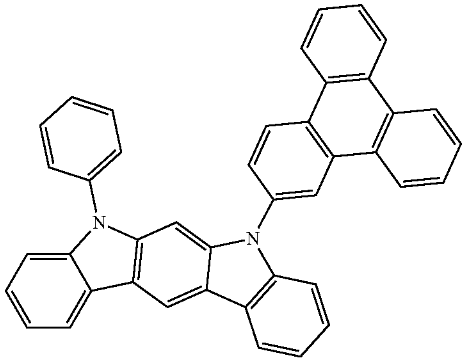
[E-15]
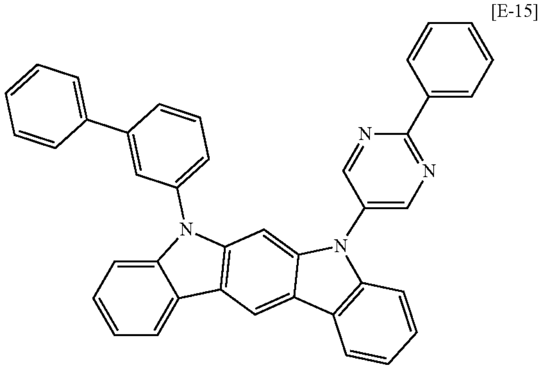
[E-16]
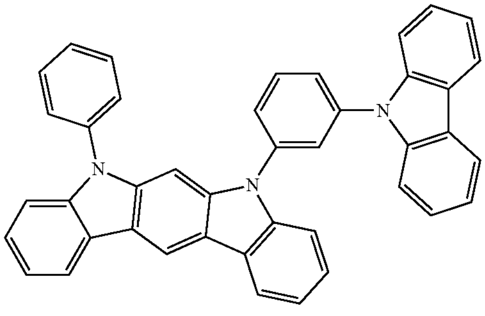
-continued
[E-17]
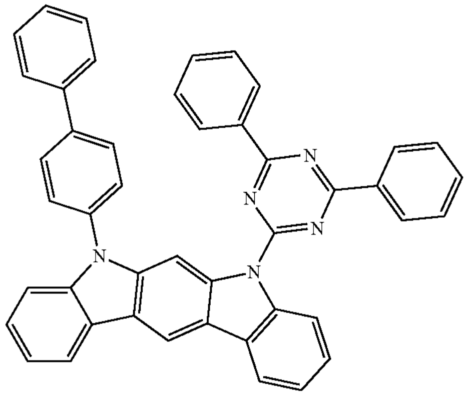
[E-18]
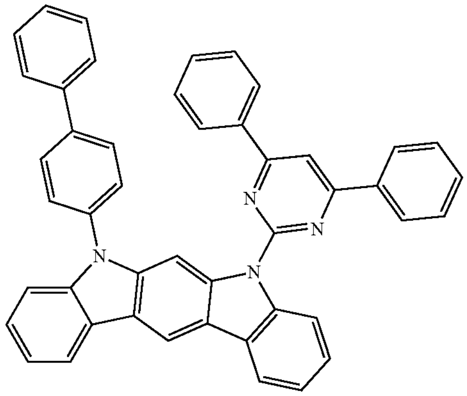
[E-19]
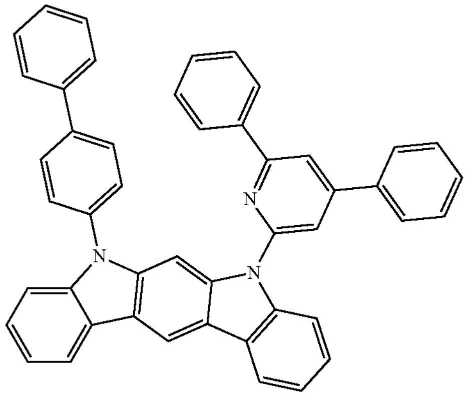
[E-20]
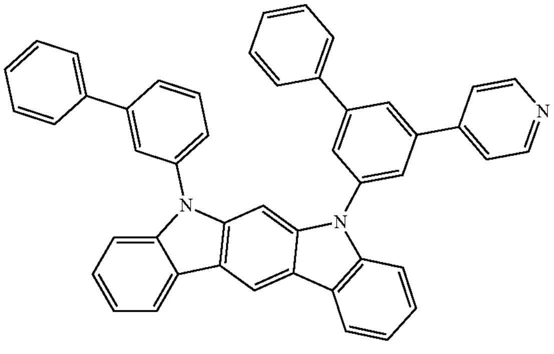

-continued
[E-21]
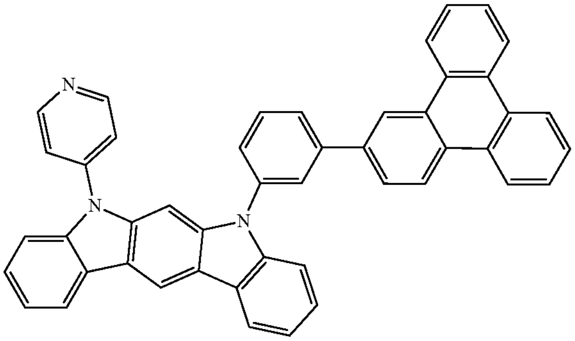
[E-22]
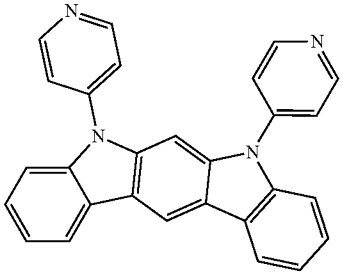
[E-23]
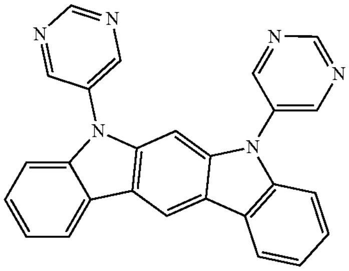
[E-24]
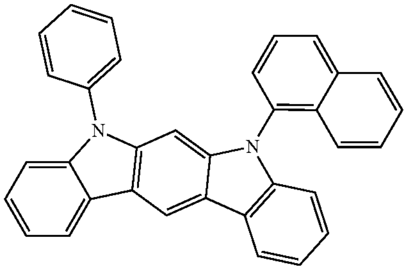
[E-25]
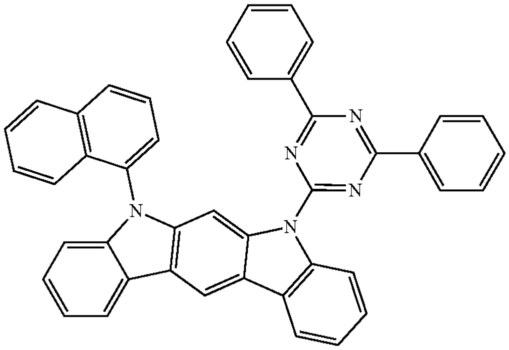
-continued
[E-26]
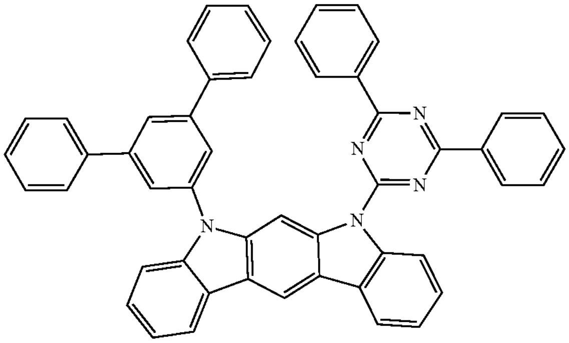
[E-27]
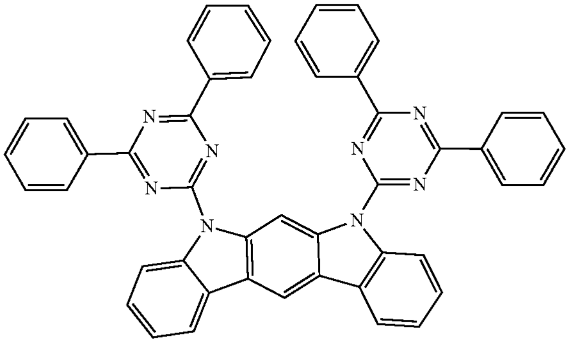
[E-28]
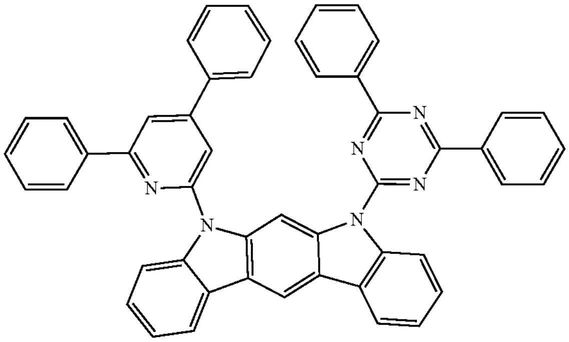
[E-29]
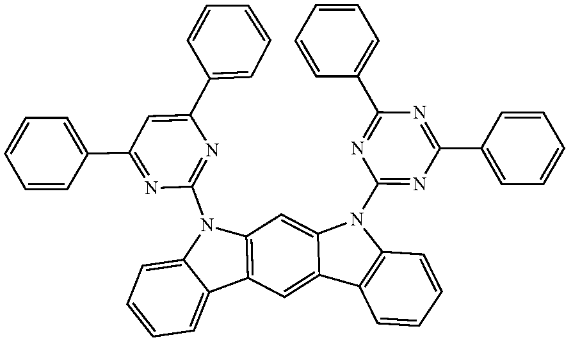

-continued
[E-30]
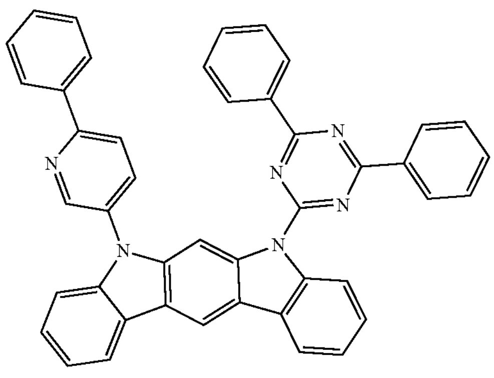
[E-31]
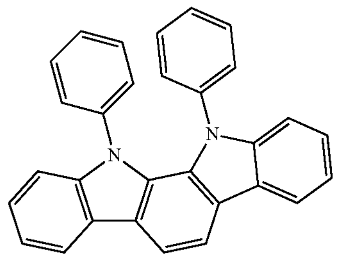
[E-32]
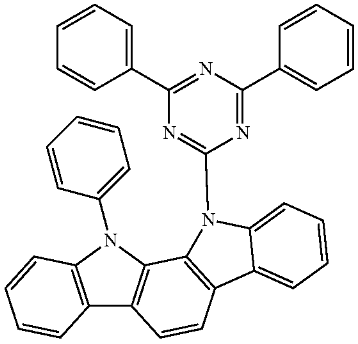
[E-33]
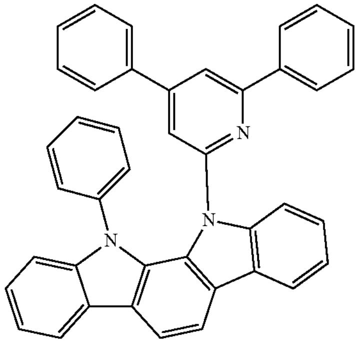
-continued
[E-34]
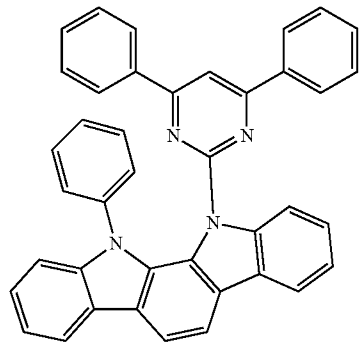
[E-35]
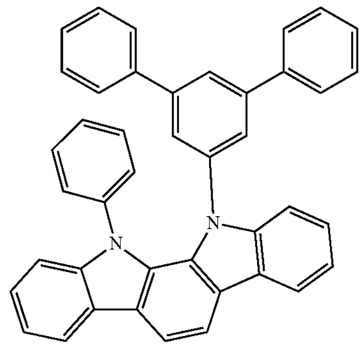
[E-36]
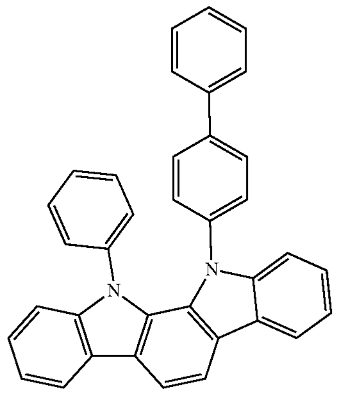
[E-37]
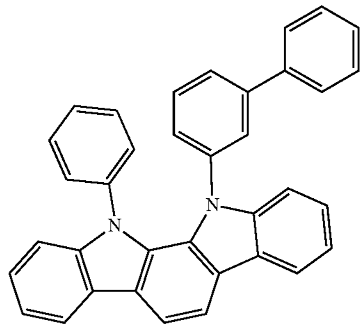

-continued
[E-38]
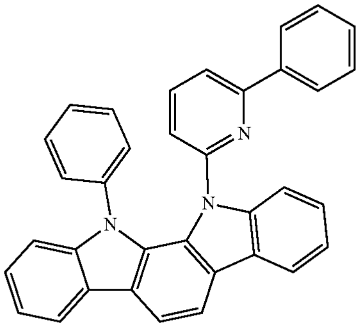
[E-39]
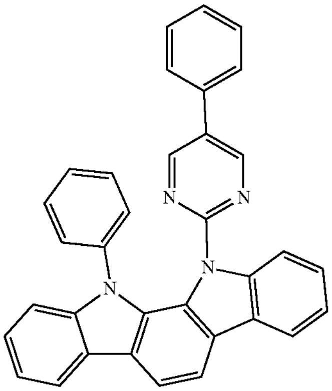
[E-40]
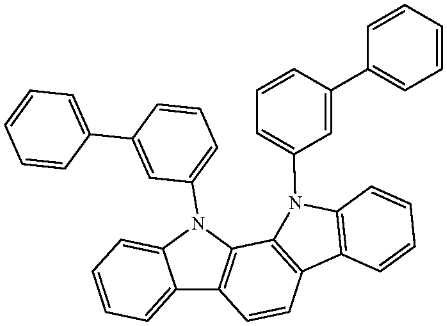
[E-41]
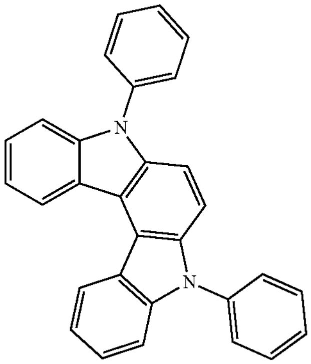
-continued
[E-42]
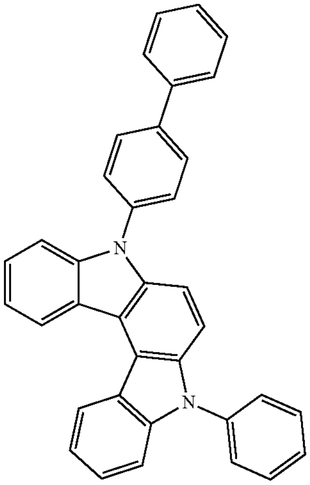
[E-43]
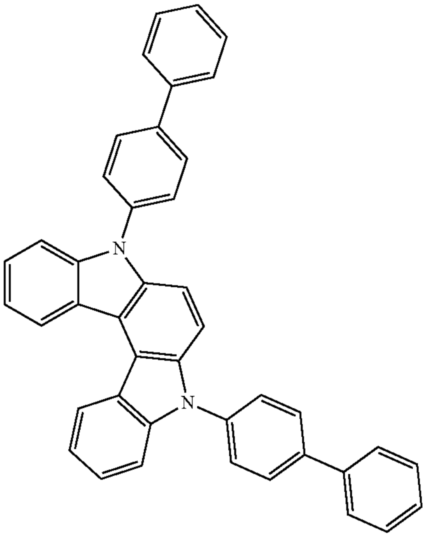
[E-44]
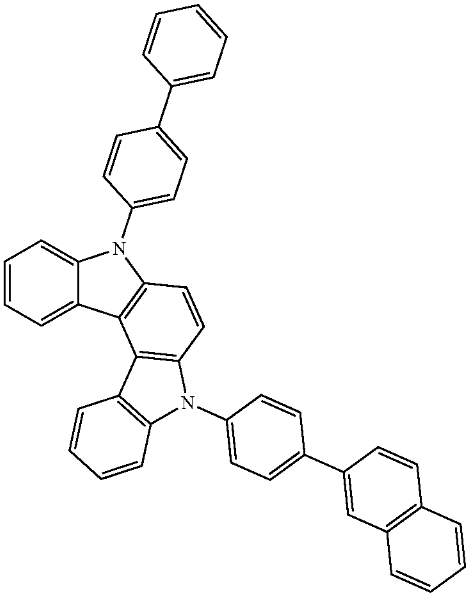

-continued

[E-45]

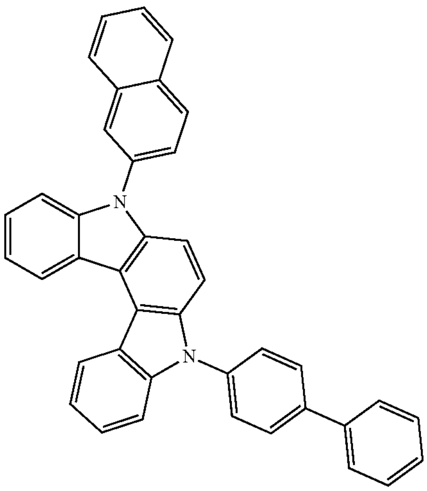

[E-46]

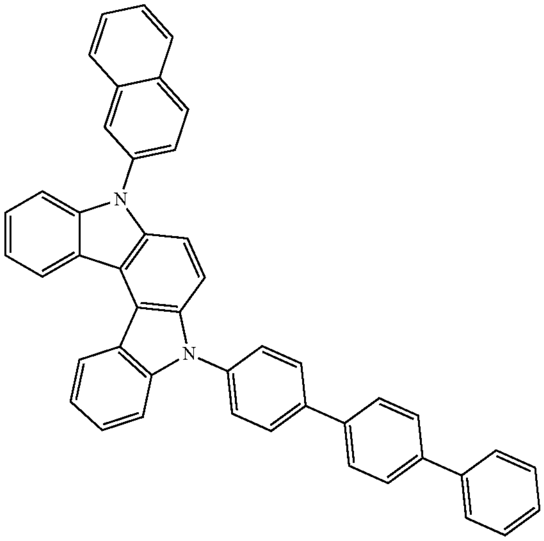

[E-47]

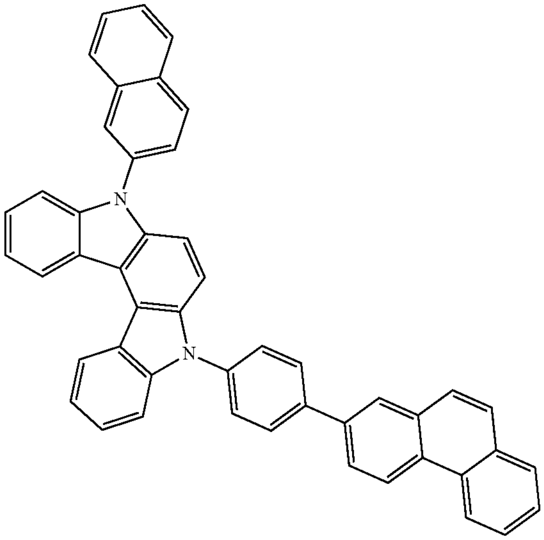

-continued

[E-48]

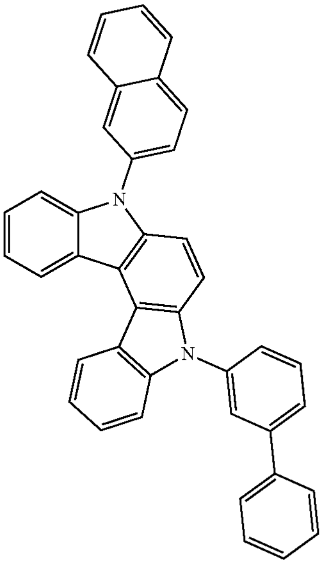

[E-49]

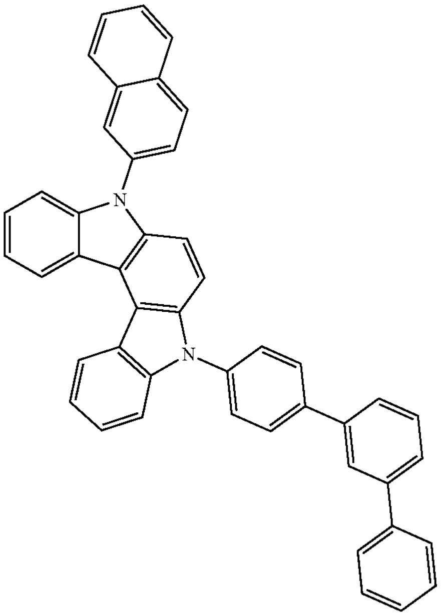

The second compound for an organic optoelectronic diode is used with the first compound for an organic optoelectronic diode in a light emitting layer, and thereby charge mobility and stability are increased and luminous efficiency and life-span characteristics are improved. In addition, a ratio between the second compound for an organic optoelectronic diode and the first compound for an organic optoelectronic diode is controlled and thereby charge mobility may be controlled.

In addition, the first compound for the organic optoelectronic diode and the second compound for the organic optoelectronic diode may be for example included in a weight ratio of about 1:9 to 9:1, 2:8 to 8:2, 3:7 to 7:3, 4:6 to 6:4 and 5:5, specifically a weight ratio of 1:9 to 8:2, 1:9 to 7:3, 1:9 to 6:4, 1:9 to 5:5, and more specifically, a weight ratio of 2:8 to 7:3, 2:8 to 6:4, and 2:8 to 5:5. In addition, they may be included in a weight ratio of 3:7 to 6:4 and 3:7 to 5:5, and more specifically a weight ratio of 3:7 to 4:6, or 5:5.

The composition for the organic optoelectronic diode may be used as a host of a green or red organic light emitting diode.

The compound or composition for the organic optoelectronic diode may further include at least one organic compound.

The compound or composition for the organic optoelectronic diode may further include a dopant. The dopant may be a red, green, or blue dopant.

The dopant is a material in small amount to cause light emission and may be generally a material such as a metal complex that emits light by multiple excitation into a triplet or more. The dopant may be for example an inorganic, organic, or organic/inorganic compound, and one or more types thereof may be used.

One example of the dopant may be a phosphorescent dopant and examples of the phosphorescent dopant may be an organometal compound including Ir, Pt, Os, Ti, Zr, Hf, Eu, Tb, Tm, Fe, Co, Ni, Ru, Rh, Pd, or a combination thereof. The phosphorescent dopant may be, for example a compound represented by Chemical Formula Z, but is not limited thereto.

$L_2MX$ [Chemical Formula Z]

In Chemical Formula Z, M is a metal, and L and X are the same or different, and are a ligand to form a complex compound with M.

The M may be for example, Ir, Pt, Os, Ti, Zr, Hf, Eu, Tb, Tm, Fe, Co, Ni, Ru, Rh, Pd, or a combination thereof and L and X may be for example a bidendate ligand.

Hereinafter, an organic optoelectronic diode including the compound for the organic optoelectronic diode is described.

An organic optoelectronic diode according to another embodiment includes an anode and a cathode facing each other and at least one organic layer disposed between the anode and the cathode, wherein the organic layer includes the aforementioned compound for the organic optoelectronic diode.

For example, the organic layer may include a light emitting layer and the light emitting layer may include the compound for the organic optoelectronic diode of the present invention.

Specifically, the compound for the organic optoelectronic diode may be included as a host, for example a green host or a red host of the light emitting layer.

In addition, the organic layer may include a light emitting layer; and at least one auxiliary layer selected from an electron transport layer, an electron injection layer, and a hole blocking layer, and the auxiliary layer may include the compound for the organic optoelectronic diode.

The organic optoelectronic diode may be any diode to convert electrical energy into photoenergy and vice versa without particular limitation, and may be for example an organic photoelectric device, an organic light emitting diode, an organic solar cell, and an organic photo conductor drum.

Herein, an organic light emitting diode as one example of an organic optoelectronic diode is described referring to drawings.

FIGS. 1 and 2 are cross-sectional views showing organic light emitting diodes according to embodiments.

Referring to FIG. 1, an organic optoelectronic diode 100 according to an embodiment includes an anode 120 and a cathode 110 and facing each other and an organic layer 105 disposed between the anode 120 and the cathode 110.

The anode 120 may be made of a conductor having a large work function to help hole injection, and may be for example a metal, a metal oxide and/or a conductive polymer. The anode 120 may be, for example a metal such as nickel, platinum, vanadium, chromium, copper, zinc, gold, and the like or an alloy thereof; a metal oxide such as zinc oxide, indium oxide, indium tin oxide (ITO), indium zinc oxide (IZO), and the like; a combination of a metal and an oxide such as ZnO and Al or $SnO_2$ and Sb; a conductive polymer such as poly(3-methylthiophene), poly(3,4-(ethylene-1,2-dioxy)thiophene) (PEDT), polypyrrole, and polyaniline, but is not limited thereto.

The cathode 110 may be made of a conductor having a small work function to help electron injection, and may be for example a metal, a metal oxide and/or a conductive polymer. The cathode 110 may be for example a metal such as magnesium, calcium, sodium, potassium, titanium, indium, yttrium, lithium, gadolinium, aluminum silver, tin, lead, cesium, barium, and the like or an alloy thereof; a multi-layer structure material such as LiF/Al, $LiO_2$/Al, LiF/Ca, LiF/Al, and $BaF_2$/Ca, but is not limited thereto.

The organic layer 105 includes a light emitting layer 130 that includes the aforementioned compound for the organic optoelectronic diode.

FIG. 2 is a cross-sectional view showing an organic light emitting diode according to another embodiment.

Referring to FIG. 2, an organic light emitting diode 200 further includes a hole auxiliary layer 140 in addition to the light emitting layer 130. The hole auxiliary layer 140 may further increase hole injection and/or hole mobility while blocking electrons between the anode 120 and the light emitting layer 130. The hole auxiliary layer 140 may include for example at least one of a hole transport layer, a hole injection layer, and/or an electron blocking layer.

The organic layer 105 of FIG. 1 or 2 may further include an electron injection layer, an electron transport layer, an electron transport auxiliary layer, a hole transport layer, a hole transport auxiliary layer, a hole injection layer, or a combination thereof even if they are not shown. The compound for the organic optoelectronic diode of the present invention may be included in these organic layers. The organic light emitting diodes 100 and 200 may be manufactured by forming an anode or a cathode on a substrate, forming an organic layer using a dry film formation method such as a vacuum deposition method (evaporation), sputtering, plasma plating, and ion plating or a wet coating method such as spin coating, dipping, and flow coating, and forming a cathode or an anode thereon.

The organic light emitting diode may be applied to an organic light emitting diode display.

Hereinafter, the embodiments are illustrated in more detail with reference to examples. These examples, however, are not in any sense to be interpreted as limiting the scope of the invention.

Hereinafter, starting materials and reactants used in Examples and Synthesis Examples were purchased from Sigma-Aldrich Co., Ltd. or TCI Inc. as far as there in no particular comment or were synthesized by known methods.

(Preparation of Compound for Organic Optoelectronic Diode)

The compound as one specific examples of the present invention was synthesized through the following steps.

First Compound for Organic Optoelectronic Diode

Synthesis Example 1: Synthesis of Compound 71

[Reaction Scheme 1]

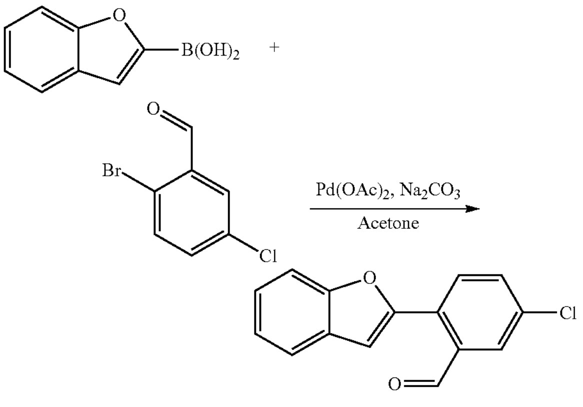

A 21.95 g (135.53 mmol) of 2-benzofuranylboronic acid, 26.77 g (121.98 mmol) of 2-bromo-5-chlorobenzaldehyde, 2.74 g (12.20 mmol) of $Pd(OAc)_2$, and 25.86 g (243.96 mmol) of $Na_2CO_3$ were suspend in 200 ml of acetone and 220 ml of distilled water in a round-bottomed flask and then stirred at room temperature for 12 hours. When a reaction was complete, the resultant was concentrated and extracted with methylene chloride, and an organic layer therefrom was silica gel columned to obtain 21.4 g (Yield=68%) of Compound A as a target compound.

[Reaction Scheme 2]

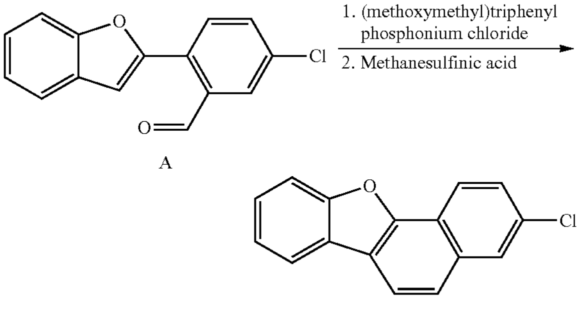

A

B 20.4 g (79.47 mmol) of Compound A synthesized in Reaction Scheme 1 and 29.97 g (87.42 mmol) of (methoxymethyl)triphenyl phosphonium chloride were suspended in 400 ml of THF, and 10.70 g (95.37 mmol) of potassium tert-butoxide was added thereto and then, stirred at room temperature for 12 hours. When a reaction was complete, 400 ml of distilled water was added thereto and then, extracted, an organic layer therefrom was concentrated and reextracted with methylene chloride, and after adding magnesium sulfate, the mixture was stirred for 30 minutes and then, filtered and then, concentrated. 100 ml of methylene chloride was added to the concentrated filtered solution, and 10 ml of methanesulfonic acid was added thereto and then, stirred for one hour.

When a reaction was complete, a solid produced therein was filtered, dried with distilled water and methyl alcohol to obtain 21.4 g (Yield=65%) of Compound B as a target compound.

[Reaction Scheme 3]

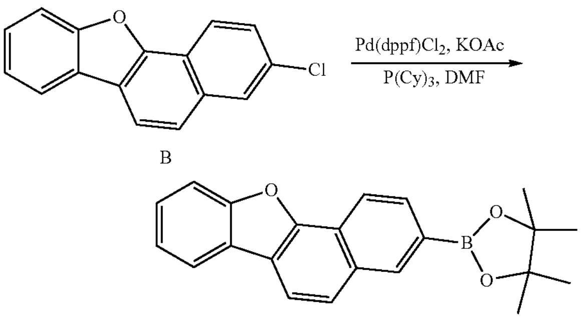

B

C 12.55 g (49.66 mmol) of Compound B synthesized according to Reaction Scheme 2, 2.43 g (2.98 mmol) of $Pd(dppf)Cl_2$, 15.13 g (59.60 mmol) of bis(pinacolato)diboron, 14.62 g (148.99 mmol) of KOAc, and 3.34 g (11.92 mmol) of $P(Cy)_3$ were suspended in 200 ml of DMF and then, refluxed and stirred for 12 hours. When a reaction was complete, a solid generated by adding 200 ml of distilled water thereto was filtered, and an organic layer was extracted with methylene chloride and columned with Hexane:EA=4:1 (v/v) to obtain 13 g (Yield=76%) of Compound C as a target compound.

[Reaction Scheme 4]

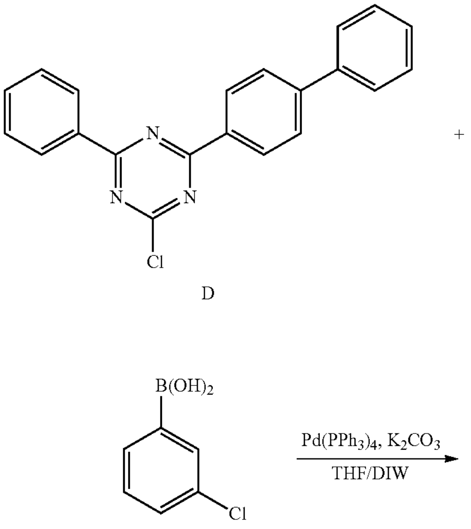

D

-continued

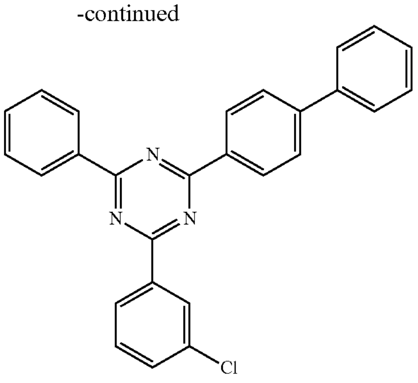

E 22.09 g (64.27 mmol) of Compound D, 10.05 g (64.27 mmol) of 3-chlorophenylboronic acid, 0.74 g (0.64 mmol) of $Pd(PPh_3)_4$, and 17.77 g (128.54 mmol) of $K_2CO_3$ were suspended in 400 ml of THF and 200 ml of distilled water in a round-bottomed flask and then, refluxed and stirred for 12 hours. When a reaction was complete, the resultant was cooled down to room temperature, 300 ml of methyl alcohol was added thereto, and a solid generated therein was filtered and washed with distilled water and methyl alcohol. The solid was added to 400 ml of toluene and then, heated and dissolved therein, the filtered solution obtained through a silica gel filter was concentrated, and a solid therefrom was stirred with 100 ml of acetone for 30 minutes and filtered to obtain 23.98 g (Yield=89%) of Compound E as a target compound.

[Reaction Scheme 5]

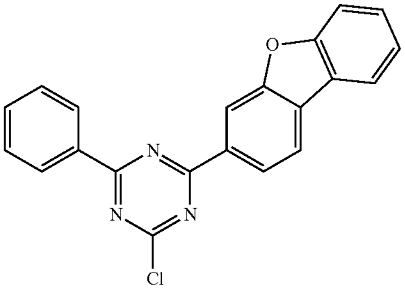

F

+

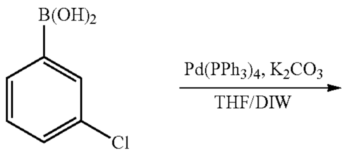

-continued

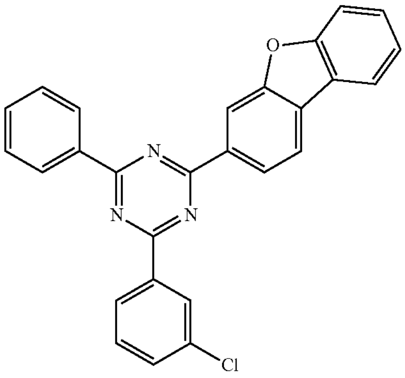

G 14 g (39.21 mmol) of Compound F, 6.74 g (43.13 mmol) of 3-chlorophenylboronic acid, 1.36 g (1.18 mmol) of $Pd(PPh_3)_4$, and 10.84 g (78.42 mmol) of $K_2CO_3$ were suspended in 400 ml of THF and 200 ml of distilled water in a round-bottomed flask and 15.5 g of Compound G as a target compound was synthesized in the same method as Reaction Scheme 4 (Yield=91%).

[Reaction Scheme 6]

Synthesis of Compound 71

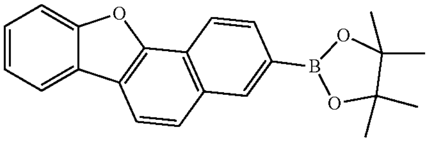

C

+

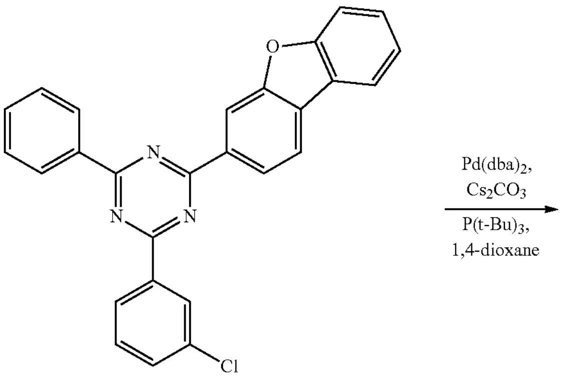

G

-continued

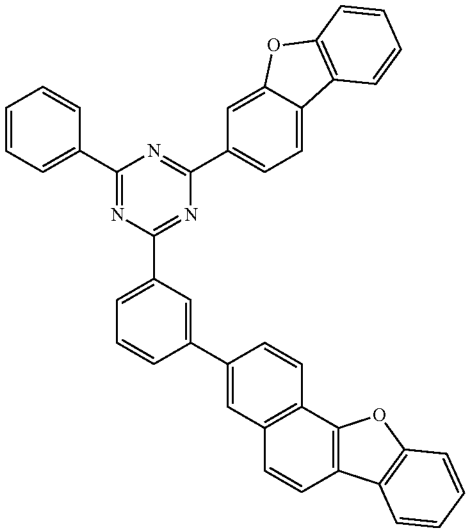

5.24 g (15.21 mmol) of Compound C synthesized in Reaction Scheme 3, 7.78 g (17.94 mmol) of Compound G synthesized in Reaction Scheme 5, 0.24 g (0.41 mmol) of $Pd(dba)_2$, 9.01 g (27.66 mmol) of $Cs_2CO_3$, and 0.28 g (1.38 mmol) of $P(t\text{-}Bu)_3$ were suspended in 100 ml of 1,4-dioxane and refluxed for 12 hours and then, 5.57 g of Compound 71 as a target compound was synthesized in the same method as Reaction Scheme 5 (Yield=50%).

LC-Mass (theoretical value: 615.68 g/mol, measured value: M+=616.4 g/mol)

Synthesis Example 2: Synthesis of Compound 73

[Reaction Scheme 7]

Synthesis of Compound 73

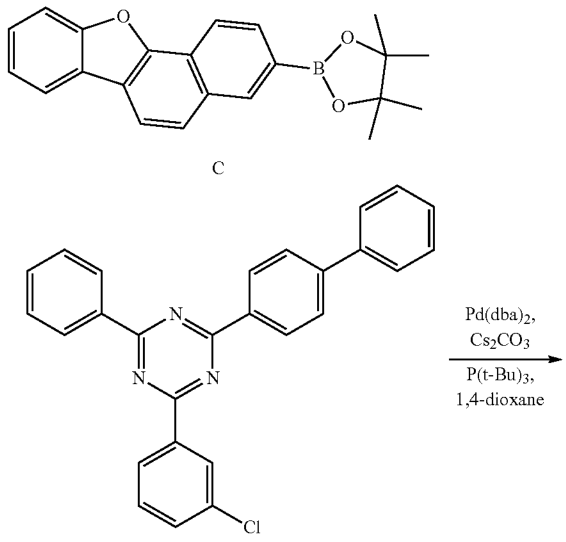

C

E

-continued

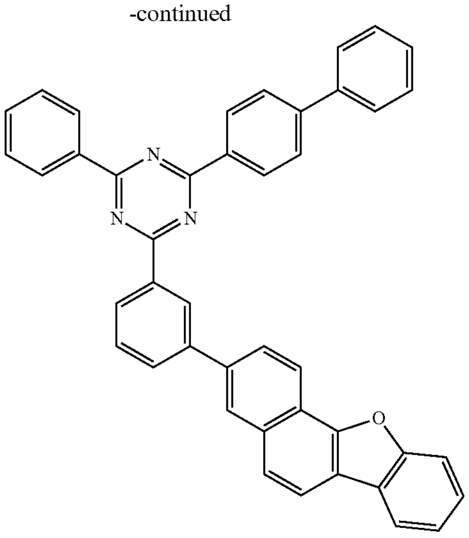

6.11 g (17.75 mmol) of Compound C synthesized in Reaction Scheme 3, 7 g (16.13 mmol) of Compound E synthesized in Reaction Scheme 4, 0.28 g (0.48 mmol) of $Pd(dba)_2$, 10.51 g (32.27 mmol) of $Cs_2CO_3$, and 0.33 g (1.61 mmol) of $P(t\text{-}Bu)_3$ were suspended in 100 ml of 1,4-dioxane and refluxed for 12 hours and then, 6.1 g of Compound 73 as a target compound was synthesized in the same method as Reaction Scheme 5 (Yield=63%).

LC-Mass (theoretical value: 601.69 g/mol, measured value: M+=602.5 g/mol)

Synthesis Example 3: Synthesis of Compound 78

[Reaction Scheme 8]

Synthesis of Compound 78

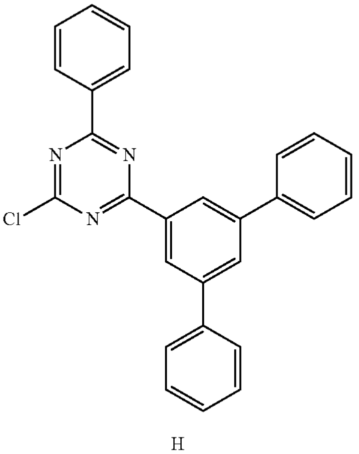

+

H

-continued

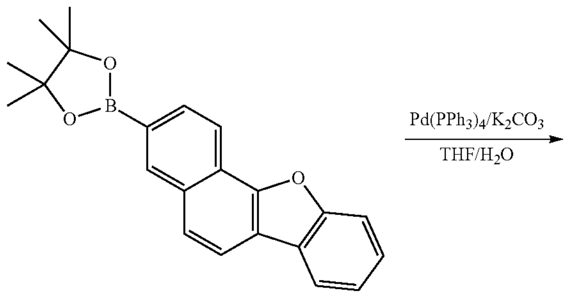

C

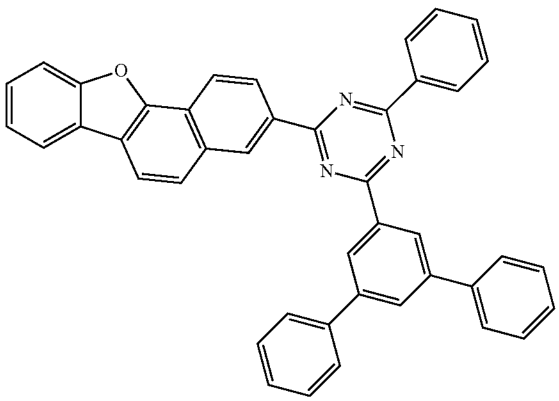

4.68 g (13.60 mmol) of Compound C synthesized in Reaction Scheme 3, 4.76 g (11.34 mmol) of Compound H, 0.39 g (0.34 mmol) of $Pd(PPh_3)_4$, and 3.13 g (22.67 mmol) of $K_2CO_3$ were suspended in 60 ml of THF and 30 ml of distilled water and then, 6.0 g of Compound 78 as a target compound was synthesized in the same method as Reaction Scheme 5 (Yield=88%).

LC-Mass (theoretical value: 601.69 g/mol, measured value: M+=602.4 g/mol)

Synthesis Example 4: Synthesis of Compound 113

[Reaction Scheme 9]

Synthesis of Compound 113

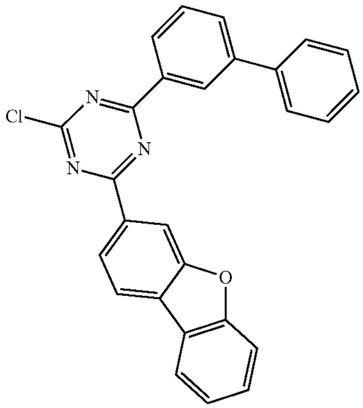

I

+

-continued

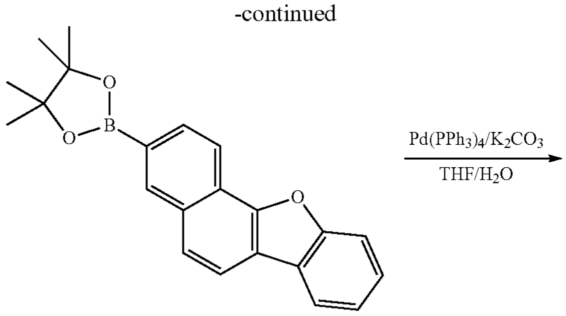

C

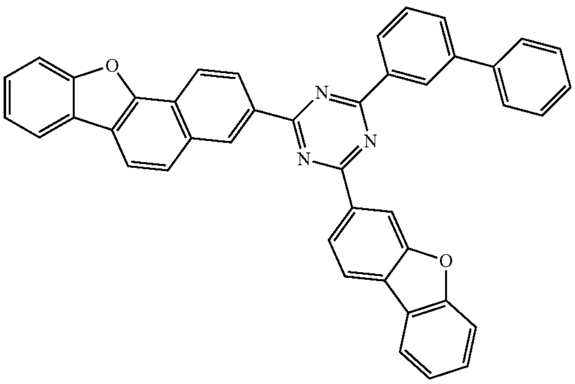

11.42 g (33.19 mmol) of Compound C synthesized in Reaction Scheme 3, 12 g (27.66 mmol) of Compound I, 0.96 g (0.83 mmol) of $Pd(PPh_3)_4$, and 7.64 g (55.31 mmol) of $K_2CO_3$ were suspended in 140 ml of THF and 70 ml of distilled water and then, 14 g of Compound 113 as a target compound was synthesized in the same method as Reaction Scheme 5 (Yield=82%).

LC-Mass (theoretical value: 615.68 g/mol, measured value: M+=616.2 g/mol)

Synthesis Example 5: Synthesis of Compound 116

[Reaction Scheme 10]

Synthesis of Compound 116

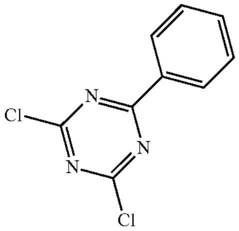

J

+

-continued

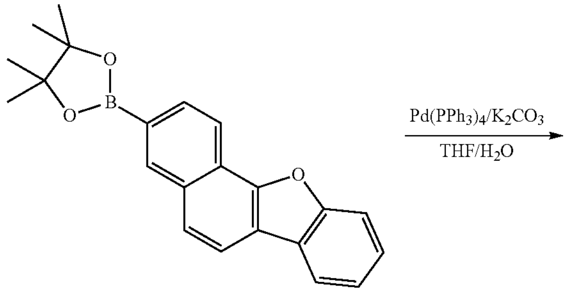

C

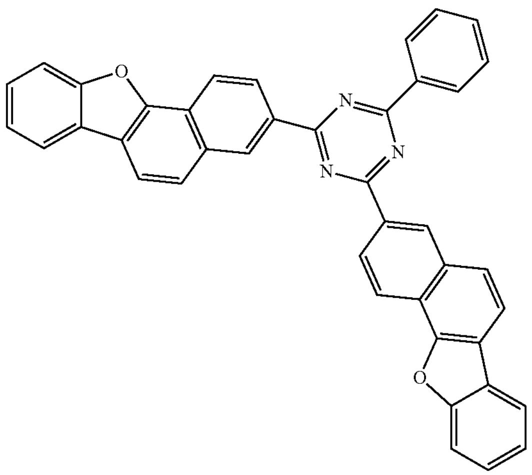

15.23 g (44.24 mmol) of Compound C synthesized in Reaction Scheme 3, 5.0 g (22.12 mmol) of Compound J, 1.28 g (1.1 mmol) of $Pd(PPh_3)_4$, and 12.23 g (88.47 mmol) of $K_2CO_3$ were suspended in 110 ml of THF and 55 ml of distilled water and then, 10 g of Compound 116 as a target compound was synthesized in the same method as Reaction Scheme 5 (Yield=77%).

LC-Mass (theoretical value: 589.64 g/mol, measured value: M+=590.6 g/mol)

Synthesis Example 6: Synthesis of Compound 20

[Reaction Scheme 11]

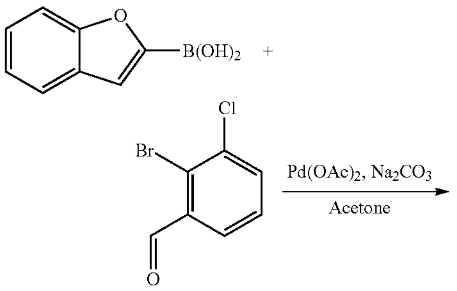

-continued

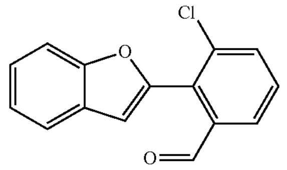

N 23.25 g (143.53 mmol) of 2-benzofuranylboronic acid, 30 g (136.70 mmol) of 2-bromo-3-chlorobenzaldehyde, 3.07 g (13.67 mmol) of $Pd(OAc)_2$, and 28.98 g (273.40 mmol) of $Na_2CO_3$ were put in a round-bottomed flask and then, suspended in 200 ml of acetone and 220 ml of distilled water and stirred at room temperature for 12 hours. When a reaction was complete, the resultant was concentrated and extracted with methylene chloride, and an organic layer therefrom was silica gel columned to obtain 11.3 g (Yield=32%) of Compound N as a target compound.

[Reaction Scheme 12]

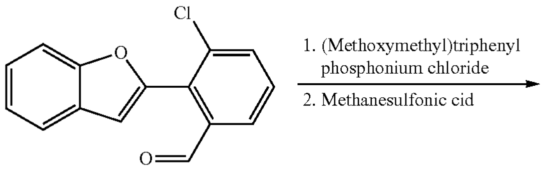

N

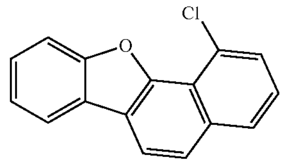

O 8.16 g (Yield=81.6%) of Compound 0 as a target compound was obtained according to the same method as Reaction Scheme 2 except that 11.3 g (39.68 mmol) of Compound N was used.

[Reaction Scheme 13]

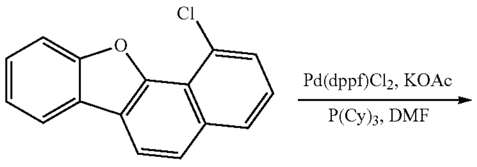

O

-continued

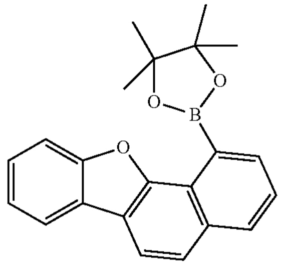

P 7.3 g (Yield=66.8%) of Compound P as a target compound was obtained according to the same method as Reaction Scheme 3 except that 8.16 g (31.73 mmol) of Compound O was used.

[Reaction Scheme 14]

Synthesis of Compound 20

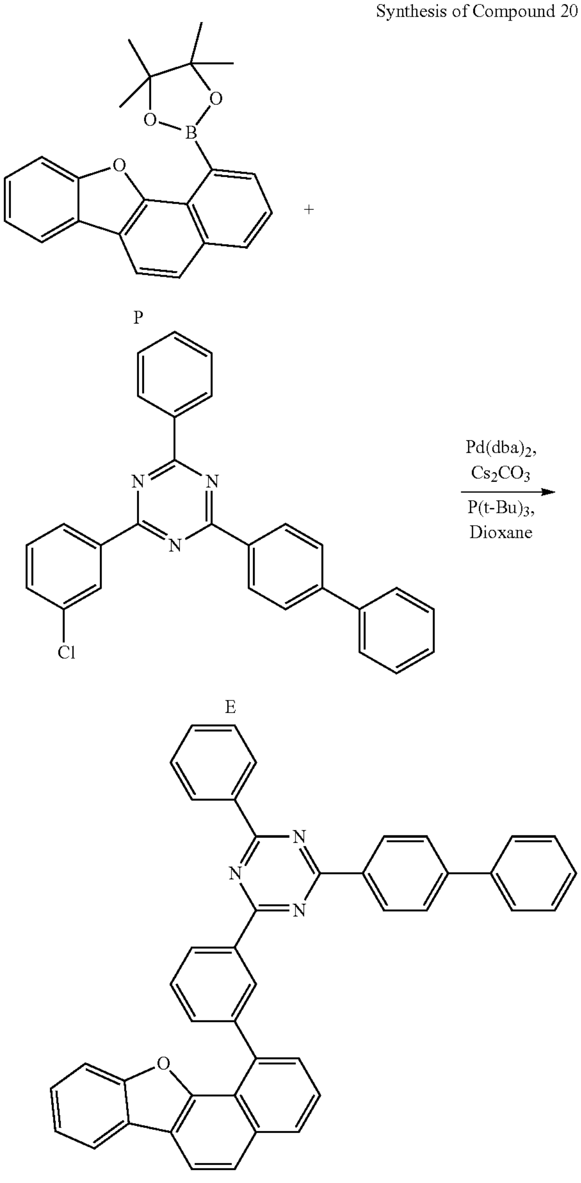

P
E 6.2 g (Yield=60.7%) of Compound 20 as a target compound was obtained according to the same method as Reaction Scheme 5 except that 6.03 g (17.80 mmol) of Compound P was used.

LC-Mass (theoretical value: 601.69 g/mol, measured value: M+=602.52 g/mol)

Synthesis Example 7: Synthesis of Compound 57

[Reaction Scheme 15]

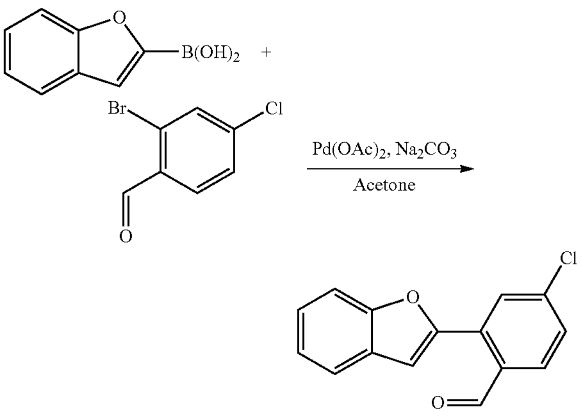

Q 23.25 g (143.53 mmol) of 2-benzofuranylboronic acid, 30 g (136.70 mmol) of 2-bromo-4-chlorobenzaldehyde, 3.07 g (13.67 mmol) of $Pd(OAc)_2$, and 28.98 g (273.40 mmol) of $Na_2CO_3$ were suspended in 200 ml of acetone and 220 ml of distilled water in a round-bottomed flask and then, stirred at room temperature for 12 hours. When a reaction was complete, the resultant was concentrated and extracted with methylene chloride, and an organic layer therefrom was silica gel columned to obtain 20.87 g (Yield=57%) of Compound Q as a target compound.

[Reaction Scheme 16]

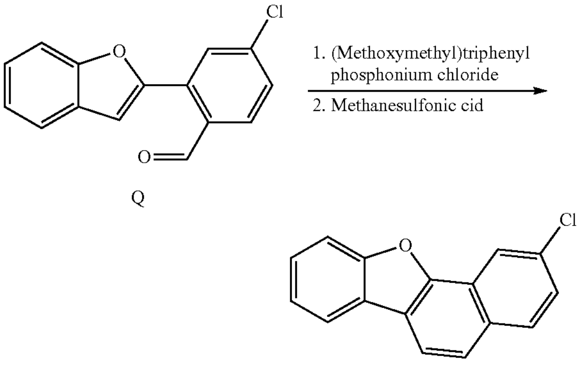

Q
R 11.3 g (Yield=54%) of Compound R as a target compound was obtained according to the same method as Reaction Scheme 2 except that 20.87 g (81.31 mmol) of Compound Q was used.

[Reaction Scheme 17]

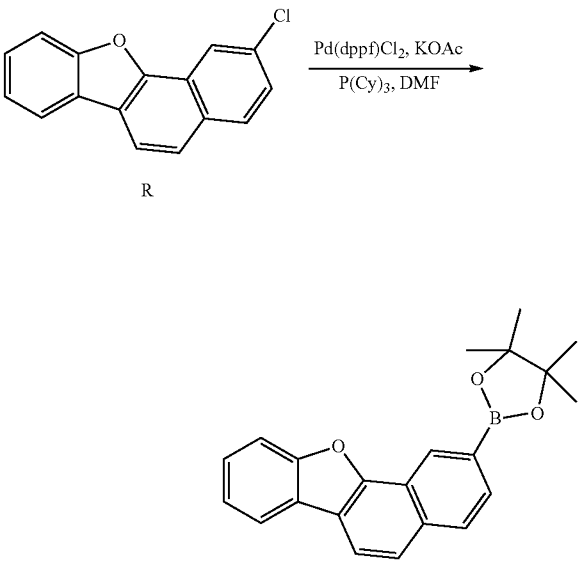

R

S 9.7 g (Yield=64.7%) of Compound S as a target compound was obtained according to the same method as Reaction Scheme 3 except that 11.3 g (43.93 mmol) of Compound R was used.

[Reaction Scheme 18]

Synthesis of Compound 57

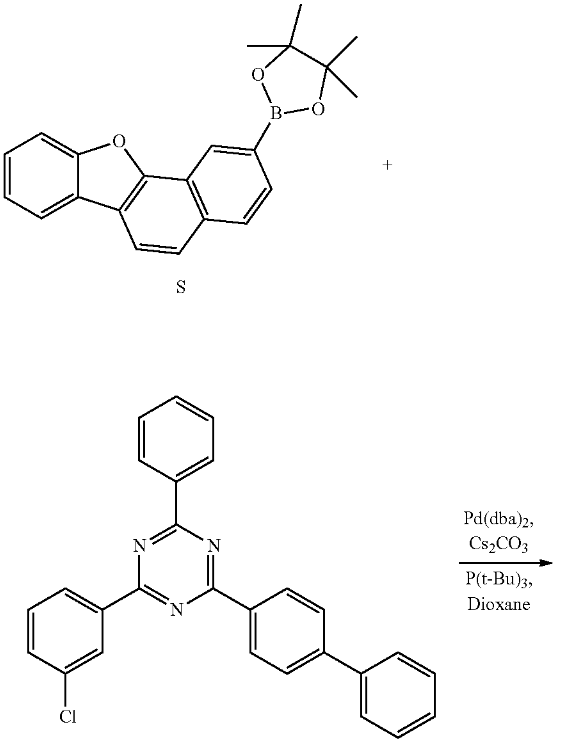

S

E

-continued

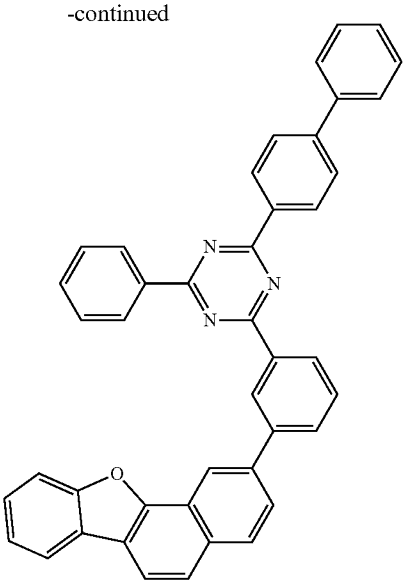

7.01 g of Compound 57 (Yield=66.6%) as a target compound was obtained according to the same method as Reaction Scheme 5 except that 6.03 g (17.50 mmol) of Compound S was used.

LC-Mass (theoretical value: 601.69 g/mol, measured value: M+=602.53 g/mol)

Comparative Synthesis Example 1: Synthesis of Comparative Compound 1

[Reaction Scheme 19]

Synthesis of Comparative Compound 1

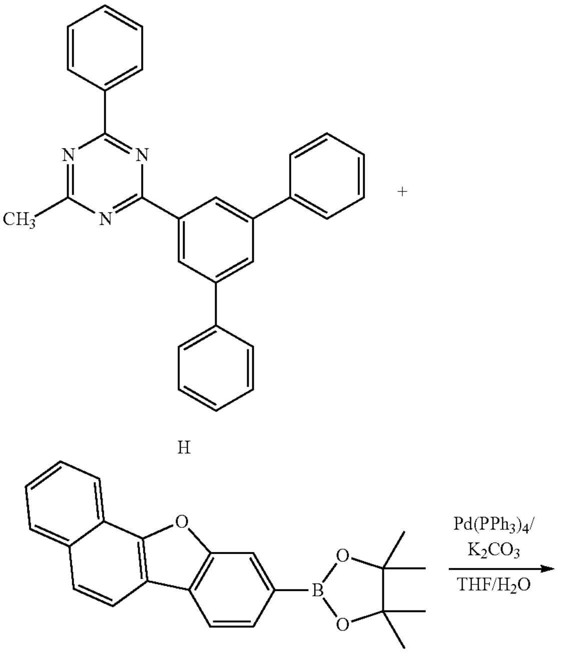

H

K

-continued

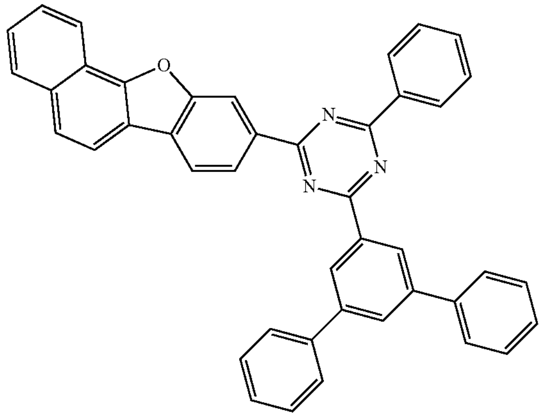

5.00 g (14.53 mmol) of Compound K, 6.10 g (14.53 mmol) of Compound H, 0.50 g (0.44 mmol) of $Pd(PPh_3)_4$, and 4.02 g (29.05 mmol) of $K_2CO_3$ were suspended in 100 ml of THF and 50 ml of distilled water and then, 8.0 g of Comparative Compound 1 as a target compound was synthesized according to the same method as Reaction Scheme 5 (Yield=80%).

LC-Mass (theoretical value: 601.69 g/mol, measured value: M+=602.4 g/mol)

Comparative Synthesis Example 2: Synthesis of Comparative Compound 2

[Reaction Scheme 20]

Synthesis of Comparative Compound 2

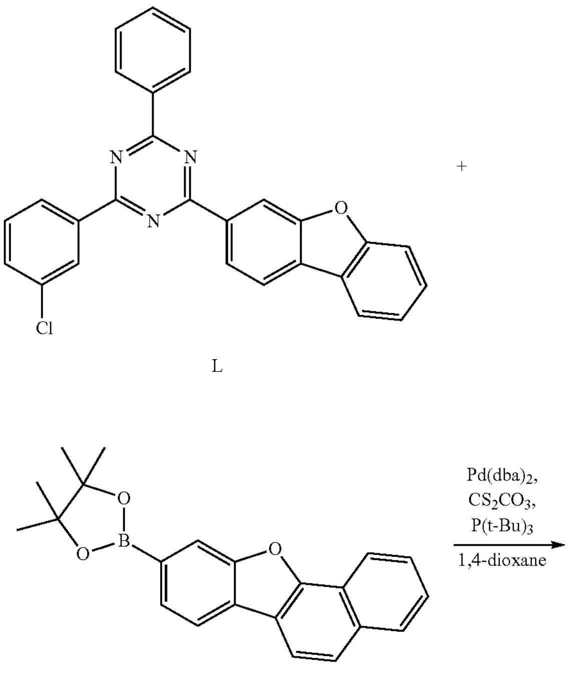

L

K

-continued

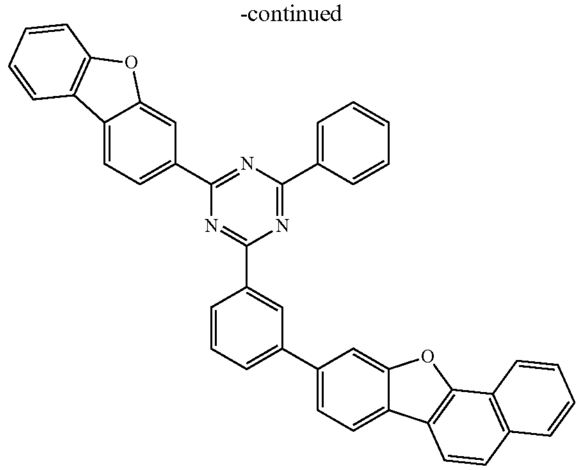

7.0 g (20.33 mmol) of Intermediate K, 8.40 g (19.37 mmol) of Intermediate L, 0.33 g (0.58 mmol) of $Pd(dba)_2$, 12.62 g (38.74 mmol) of $Cs_2CO_3$, and 0.39 g (1.93 mmol) of $P(t\text{-}Bu)_3$ were suspended in 100 ml of 1,4-dioxane and then, 4.51 g of Comparative Compound 2 as a target compound was synthesized according to the same method as Reaction Scheme 5 (Yield=38%).

LC-Mass (theoretical value: 615.68 g/mol, measured value: M+=616.5 g/mol)

Manufacture of Organic Light Emitting Diode

Green Light Emitting Diode

Example 1

A glass substrate coated with ITO (indium tin oxide) as a 1500 Å-thick thin film was washed with distilled water. After washed with distilled water, the glass substrate was ultrasonic wave-washed with a solvent such as isopropyl alcohol, acetone, methanol, and the like and dried, moved to a plasma cleaner, cleaned with oxygen plasma for 10 minutes, and moved to a vacuum depositor. This obtained ITO transparent electrode was used as an anode, Compound A was vacuum-deposited on the ITO substrate to form a 700 Å-thick hole injection layer, Compound B was deposited to be 50 Å thick on the injection layer, and Compound C was deposited to be 1020 Å thick to form a hole transport layer. A 400 Å-thick light emitting layer was formed on the hole transport layer by vacuum-depositing Compound 71 of Synthesis Example 1 and Compound B-99 simultaneously as a host and 10 wt % of tris(2-phenylpyridine)iridium(III) [$Ir(ppy)_3$] as a dopant. Herein, Compound 71 and Compound B-99 were used at a weight ratio of 3:7 and in the following examples, the ratios are separately described. Subsequently, Compound D and Liq were vacuum-deposited simultaneously at a 1:1 ratio on the light-emitting layer to form a 300 Å-thick electron transport layer and a cathode was formed by sequentially vacuum-depositing Liq to be 15 Å thick and Al to be 1200 Å thick on the electron transport layer, manufacturing an organic light emitting diode.

The organic light emitting diode had a five-layered organic thin layer, and specifically ITO/Compound A (700 Å)/Compound B (50 Å)/Compound C (1020 Å)/EML [Compound 71:Compound B-99: $Ir(ppy)_3$](400 Å)/Compound D:Liq (300 Å)/Liq (15 Å)/Al (1200 Å).

Compound A: N4,N4'-diphenyl-N4,N4'-bis(9-phenyl-9H-carbazol-3-yl)biphenyl-4,4'-diamine Compound B: 1,4,5,8,9,11-hexaazatriphenylene-hexacarbonitrile (HAT-CN), Compound C: N-(biphenyl-4-yl)-9,9-dimethyl-N-(4-(9-phenyl-9H-carbazol-3-yl)phenyl)-9H-fluoren-2-amine Compound D: 8-(4-(4,6-di(naphthalen-2-yl)-1,3,5-triazin-2-yl)phenyl)quinolone Example 2

An organic light emitting diode was manufactured according to the same method as Example 1 except that Compound 73 was used instead of Compound 71 as the compound of the light emitting layer.

Example 3

An organic light emitting diode was manufactured according to the same method as Example 1 except that Compound 20 was used instead of Compound 71 as the compound of the light emitting layer.

Example 4

An organic light emitting diode was manufactured according to the same method as Example 1 except that Compound 57 was used instead of Compound 71 as the compound of the light emitting layer.

Comparative Examples 1 to 2

Each organic light emitting diode of Comparative Example 1 and Comparative Example 2 was manufactured according to the same method as Example 1 except that each of Comparative Compound 1 and Comparative Compound 2 was used instead of Compound 71 as the compound of the light emitting layer.

Red Light Emitting Diode

Example 5

A glass substrate coated with ITO (indium tin oxide) as a 1500 Å-thick thin film was washed with distilled water. After washed with distilled water, the glass substrate was ultrasonic wave-washed with a solvent such as isopropyl alcohol, acetone, methanol, and the like and dried, moved to a plasma cleaner, cleaned with oxygen plasma for 10 minutes, and moved to a vacuum depositor. This obtained ITO transparent electrode was used as an anode, Compound A was vacuum-deposited on the ITO substrate to form a 700 Å-thick hole injection layer, Compound B was deposited to be 50 Å thick on the injection layer, and Compound C was deposited to be 1020 Å thick to form a hole transport layer. A 400 Å-thick light emitting layer was formed on the hole transport layer by vacuum-depositing Compound 71 of Synthesis Example 1 and Compound B-99 as a host and 5 wt % of [Ir(piq)$_2$acac] as a dopant. Compound 71 and Compound B-99 were used in a weight ratio of 3:7, and subsequently Compound D and Liq were vacuum-deposited simultaneously in a 1:1 ratio on the light emitting layer to form a 300 Å-thick electron transport layer and a cathode was formed by sequentially vacuum-depositing Liq to be 15 Å thick and Al to be 1200 Å thick on the electron transport layer, manufacturing an organic light emitting diode.

The organic light emitting diode had a five-layered organic thin layer, and specifically as follows.

Compound A: N4,N4'-diphenyl-N4,N4'-bis(9-phenyl-9H-carbazol-3-yl)biphenyl-4,4'-diamine Compound B: 1,4,5,8,9,11-hexaazatriphenylene-hexacarbonitrile (HAT-CN), Compound C: N-(biphenyl-4-yl)-9,9-dimethyl-N-(4-(9-phenyl-9H-carbazol-3-yl)phenyl)-9H-fluoren-2-amine Compound D: 8-(4-(4,6-di(naphthalen-2-yl)-1,3,5-triazin-2-yl)phenyl)quinoline Examples 6 to 11

Each organic light emitting diode of Examples 6 to 11 was manufactured according to the same method as Example 5 by respectively using the hosts shown in Table 2 instead of Compound 71 as the compound of the light emitting layer.

Example 12

An organic light emitting diode was manufactured according to the same method as Example 5 except that Compound 71 and Compound E-46 were used instead of Compound 71 as the compound of the light emitting layer.

Comparative Example 3

An organic light emitting diode was manufactured according to the same method as Example 5 except that Comparative Compound 1 was used instead of Compound 71 as the compound of the light emitting layer.

Comparative Example 4

An organic light emitting diode was manufactured according to the same method as Example 5 except that Comparative Compound 1 and Compound E-46 were used instead of Compound 71 as the compound of the light emitting layer.

Evaluation

Luminous efficiency and life-span characteristics of each organic light emitting diode according to Examples 1 to 12 and Comparative Examples 1 to 4 were evaluated. Specific measurement methods are as follows, and the results are shown in Table 1 and Table 2.

(1) Measurement of Current Density Change Depending on Voltage Change

The obtained organic light emitting diodes were measured regarding a current value flowing in the unit device, while increasing the voltage from 0 V to 10 V using a current-voltage meter (Keithley 2400), and the measured current value was divided by area to provide the results.

(2) Measurement of Luminance Change Depending on Voltage Change

Luminance was measured by using a luminance meter (Minolta Cs-1000A), while the voltage of the organic light emitting diodes was increased from 0 V to 10 V.

(3) Measurement of Luminous Efficiency

Current efficiency (cd/A) at the same current density (10 mA/cm$^2$) were calculated by using the luminance, current density, and voltages (V) from the items (1) and (2).

(4) Measurement of Life-Span

T97 life-spans of the organic light emitting diodes according to Examples 1 to 12 and Comparative Examples 1 to 4 were measured as a time when their luminance decreased to 97% relative to the initial luminance (cd/m$^2$) after emitting light with 18000 cd/m$^2$ as the initial luminance (cd/m$^2$) and measuring their luminance decrease depending on a time with a Polanonix life-span measurement system.

(5) Measurement of Driving Voltage

A driving voltage of each diode was measured using a current-voltage meter (Keithley 2400) at 15 mA/cm$^2$ to obtain the results.

TABLE 1

| Green diode | | | | | |
|---|---|---|---|---|---|
| | First host | Second host | Efficiency Cd/A | Life-span (T97, h) | Driving voltage (V) |
| Example 1 | Compound 71 | Compound B-99 | 67.1 | 40 | 3.92 |
| Example 2 | Compound 73 | Compound B-99 | 68.3 | 30 | 3.89 |
| Example 3 | Compound 20 | Compound B-99 | 68.7 | 35 | 3.91 |
| Example 4 | Compound 57 | Compound B-99 | 66.1 | 43 | 3.82 |
| Comparative Example 1 | Comparative Compound 1 | Compound B-99 | 65.4 | 15 | 3.93 |
| Comparative Example 2 | Comparative Compound 2 | Compound B-99 | 65.8 | 20 | 4.0 |

Referring to Table 1, the organic light emitting diodes according to Example 1 to Example 4 exhibited improved luminous efficiency and life-span characteristics simultaneously, particularly improvement in life-span and efficiency compared with the organic light emitting diodes according to Comparative Example 1 and Comparative Example 2.

TABLE 2

| Red diode | | | | | |
|---|---|---|---|---|---|
| | First host | Second host | Efficiency Cd/A | Life-span (T97, h) | Driving voltage (V) |
| Example 5 | Compound 71 | Compound B-99 | 21.0 | 97 | 4.04 |
| Example 6 | Compound 73 | Compound B-99 | 21.1 | 90 | 3.92 |
| Example 7 | Compound 78 | Compound B-99 | 21.4 | 105 | 3.96 |
| Example 8 | Compound 113 | Compound B-99 | 21.5 | 110 | 3.87 |
| Example 9 | Compound 116 | Compound B-99 | 21.7 | 106 | 3.85 |
| Example 10 | Compound 20 | Compound B-99 | 21.4 | 120 | 3.87 |
| Example 11 | Compound 57 | Compound B-99 | 21.0 | 114 | 3.93 |
| Example 12 | Compound 71 | Compound E-46 | 22.5 | 105 | 3.98 |
| Comparative Example 3 | Comparative Compound 1 | Compound B-99 | 20.5 | 42 | 4.05 |
| Comparative Example 4 | Comparative Compound 1 | Compound E-46 | 19.5 | 43 | 4.04 |

Referring to Table 2, the organic light emitting diodes according to Example 5 to Example 12 exhibited improved luminous efficiency and life-span characteristics simultaneously, particularly improvement in life-span compared with the organic light emitting diodes according to Comparative Example 3 and Comparative Example 4.

While this invention has been described in connection with what is presently considered to be practical embodiments, it is to be understood that the invention is not limited to the disclosed embodiments, but, on the contrary, is intended to cover various modifications and equivalent arrangements included within the spirit and scope of the appended claims. Therefore, the aforementioned embodiments should be understood to be exemplary but not limiting the present invention in any way.

DESCRIPTION OF SYMBOLS

100, 200: organic light emitting diode
105: organic layer
110: cathode
120: anode
130: light emitting layer
140: hole auxiliary layer

The invention claimed is:

1. A compound for an organic optoelectronic diode represented by Chemical Formula 1A:

[Chemical Formula 1A]

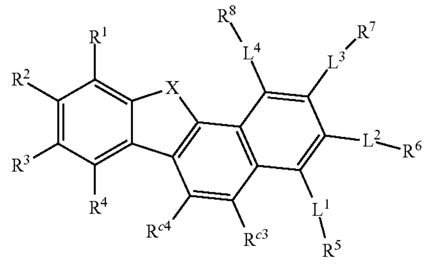

wherein, in Chemical Formula 1A,

X is O or S, $R^1$ to $R^4$, $R^{c3}$, and $R^{c4}$ are independently hydrogen, deuterium, a cyano group, a substituted or unsubstituted C1 to C30 silyl group, a substituted or unsubstituted C1 to C30 alkyl group, or a substituted or unsubstituted C6 to C30 aryl group, $L^1$ to $L^4$ are independently a single bond, a substituted or unsubstituted phenylene group, or a substituted or unsubstituted biphenylene group, $R^5$ to $R^8$ are independently hydrogen, deuterium, a cyano group, a substituted or unsubstituted C1 to C30 silyl group, a substituted or unsubstituted C1 to C30 alkyl group, a substituted or unsubstituted C6 to C30 aryl group, or a substituted or unsubstituted C2 to C30 heterocyclic group, at least one of $R^5$ to $R^8$ is a substituted or unsubstituted pyridinyl group, a substituted or unsubstituted pyrimidinyl group, or a substituted or unsubstituted triazinyl group, and the "substituted" refers to replacement of at least one hydrogen by deuterium, a C1 to C10 alkyl group, a C6 to C30 aryl group, or a C2 to C20 heterocyclic group.

2. The compound of claim 1, which is represented by one of Chemical Formula 1A-a, Chemical Formula 1A-b, Chemical Formula 1A-c, and Chemical Formula 1A-d:

[Chemical Formula 1A-a]

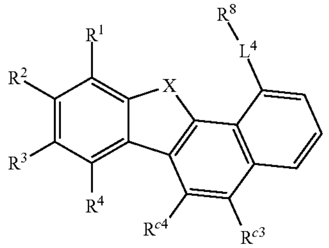

[Chemical Formula 1A-b]

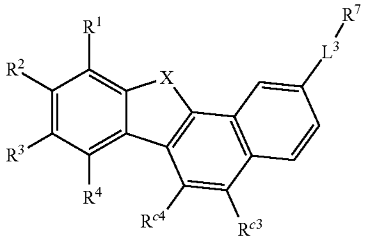

[Chemical Formula 1A-c]

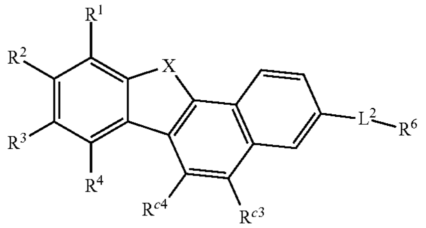

-continued

[Chemical Formula 1A-d]

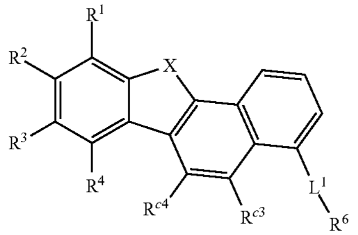

wherein, in Chemical Formula 1A-a, Chemical Formula 1A-b, Chemical Formula 1A-c, and Chemical Formula 1A-d, X is O or S, $R^1$ to $R^4$, $R^{c3}$, and $R^{c4}$ are independently hydrogen, deuterium, or a substituted or unsubstituted C1 to C30 alkyl group, $L^1$ to $L^4$ are independently a single bond, a substituted or unsubstituted phenylene group, or a substituted or unsubstituted biphenylene group, and $R^5$ to $R^8$ are independently a substituted or unsubstituted pyridinyl group, a substituted or unsubstituted pyrimidinyl group, or a substituted or unsubstituted triazinyl group.

3. The compound of claim 1, wherein at least one of $R^5$ to $R^8$ is a substituted or unsubstituted pyridinyl group, a substituted or unsubstituted pyrimidinyl group, or a substituted or unsubstituted triazinyl group, wherein "substituted" refers to replacement of at least one hydrogen by deuterium, a C1 to C4 alkyl group, a phenyl group, a naphthyl group, a biphenyl group, a terphenyl group, a fluorenyl group, a fluorenephenyl group, a 9-methylfluoren-9-yl group, a 9,9'-spirofluorenyl group, a 9-phenylfluorene-9-phenylene group, a carbazolyl group, a dibenzofuranyl group, a dibenzothiophenyl group, a benzonaphthofuranyl group, or a benzonaphthothiophenyl group.

4. The compound of claim 1, which is selected from compounds of Group 1:

[Group 1]

Inv-001

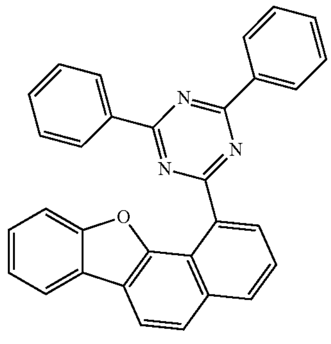

Inv-002

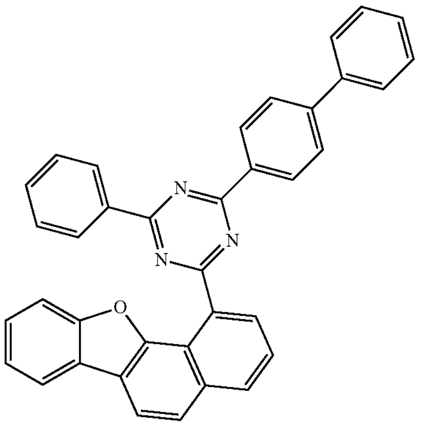

-continued
Inv-003
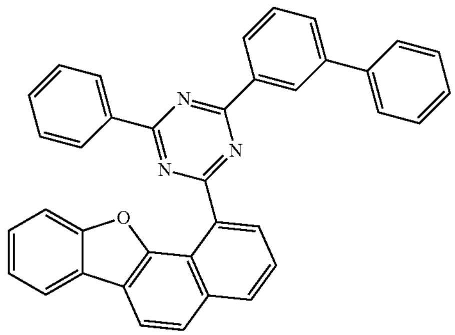
Inv-004
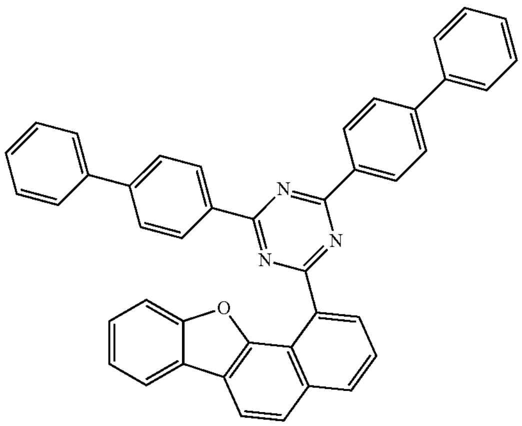
Inv-005
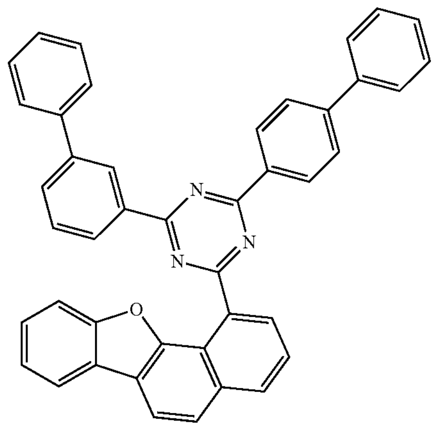
Inv-006
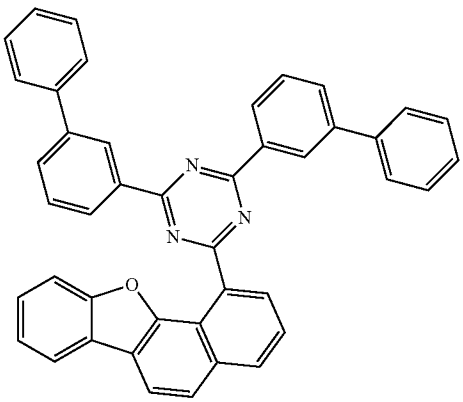
Inv-007
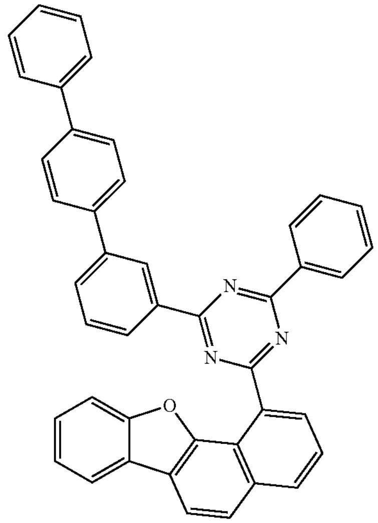
Inv-008
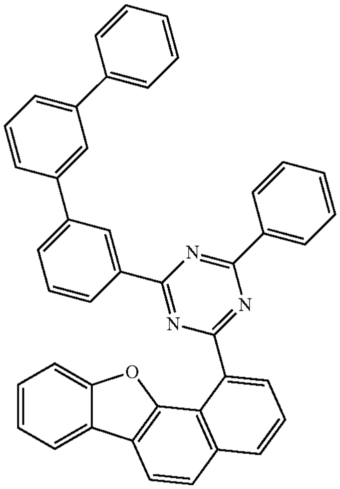

-continued
Inv-009
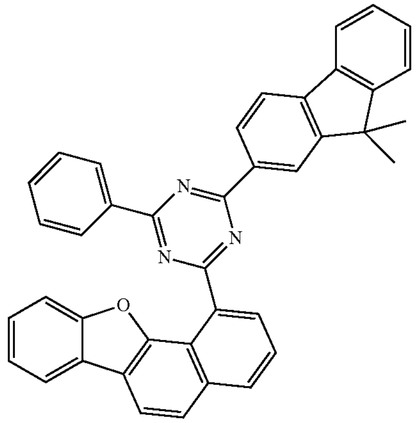
Inv-010
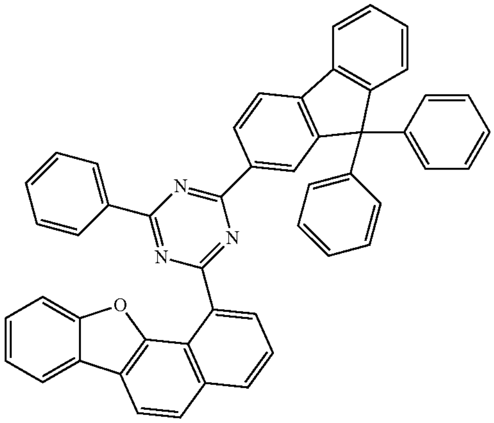
Inv-011
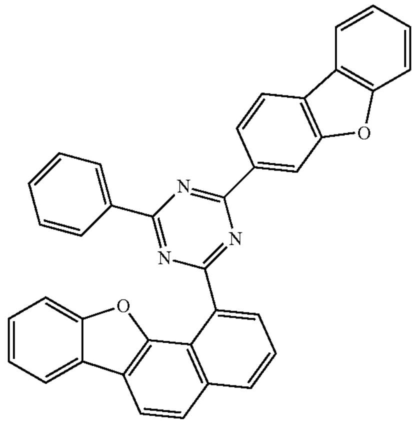
Inv-012
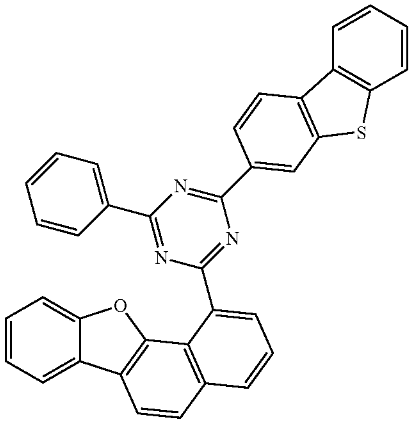
Inv-013
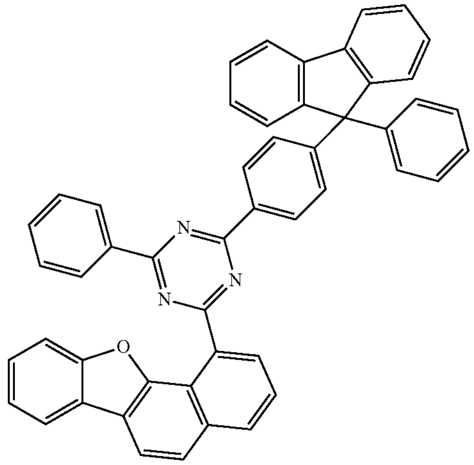
Inv-014
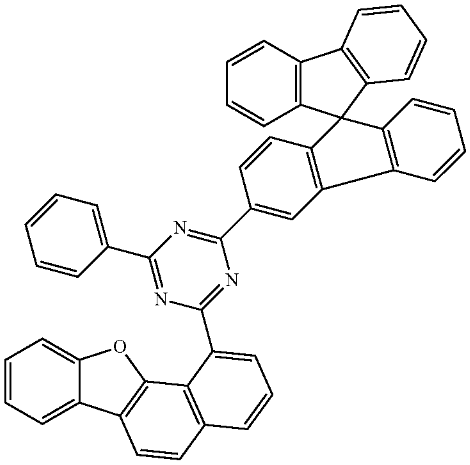

-continued
Inv-015
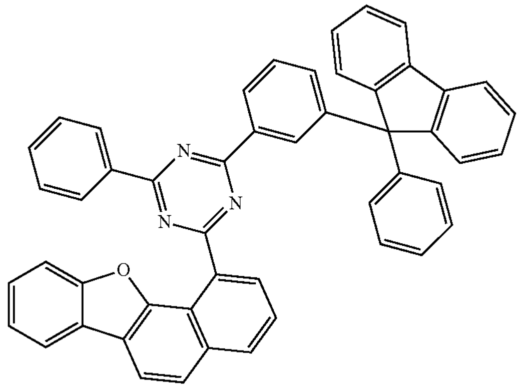
Inv-016
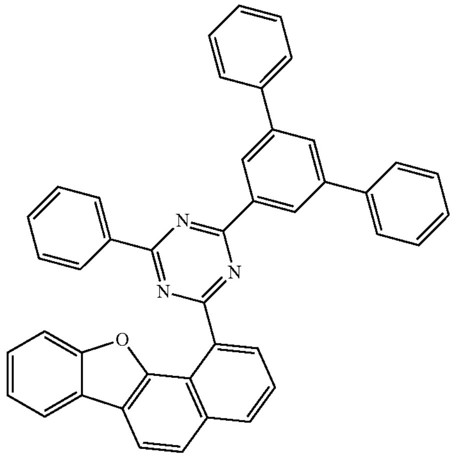
Inv-017
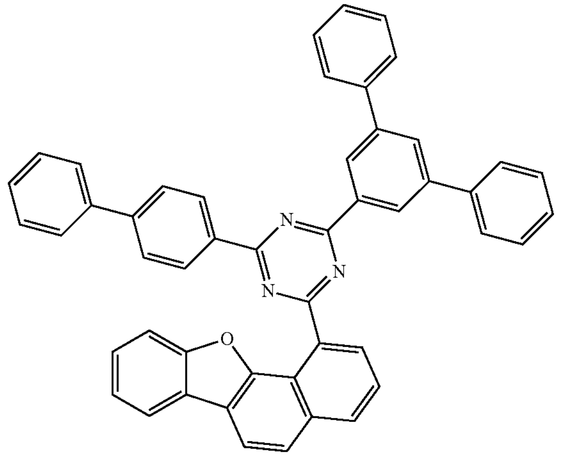
Inv-018
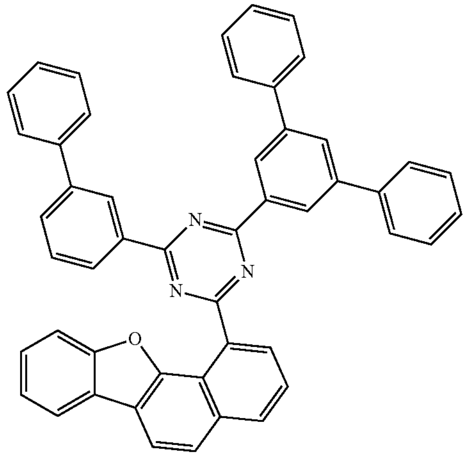
Inv-019
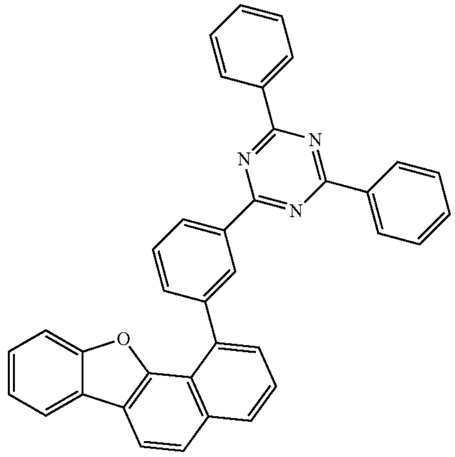
Inv-020
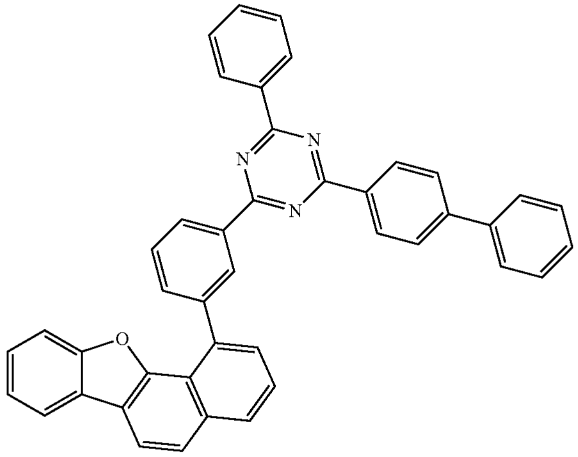

-continued
Inv-021
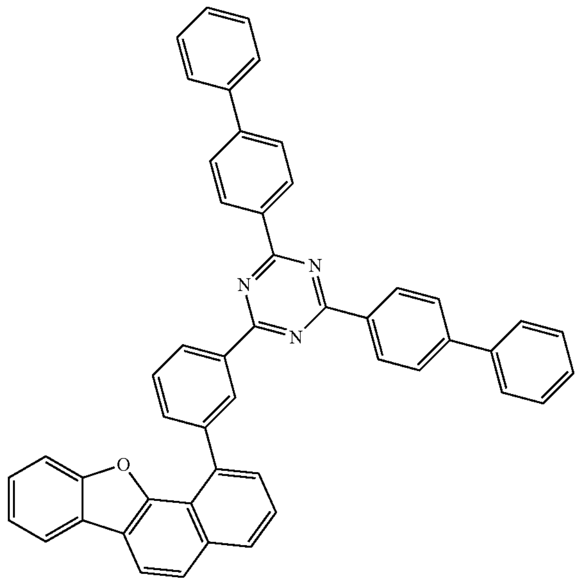
Inv-022
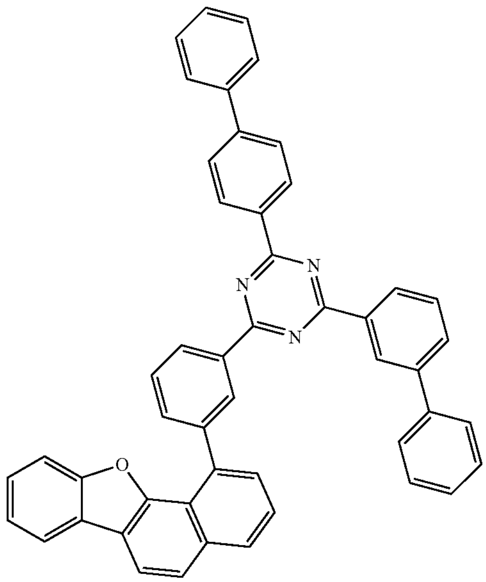
Inv-023
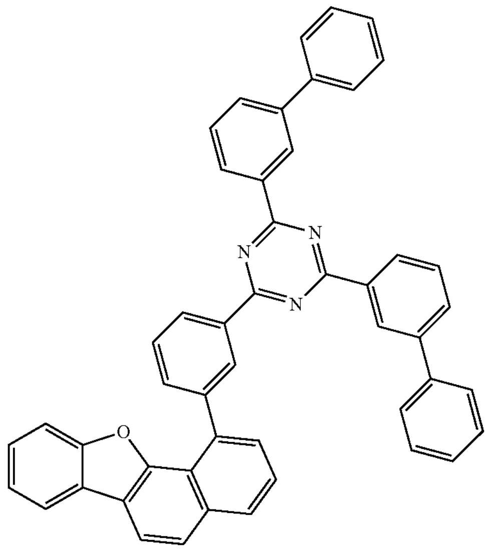
Inv-024
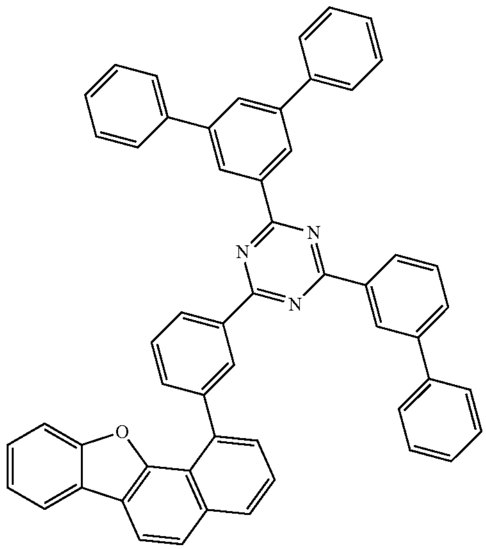

-continued
Inv-025
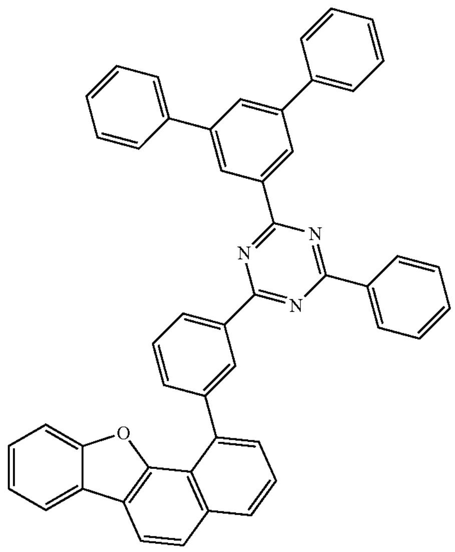
Inv-026
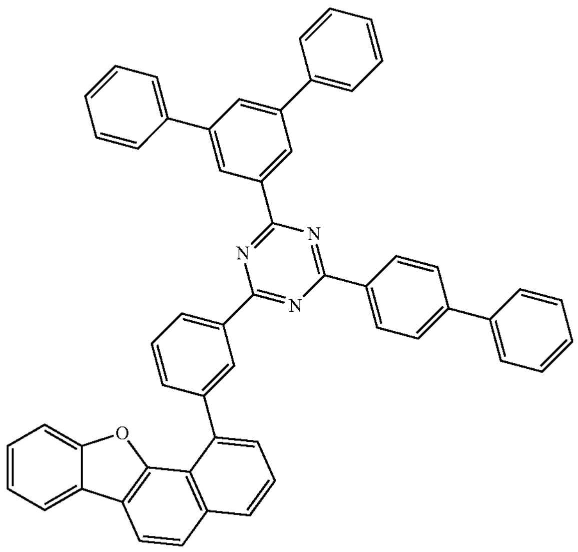
Inv-027
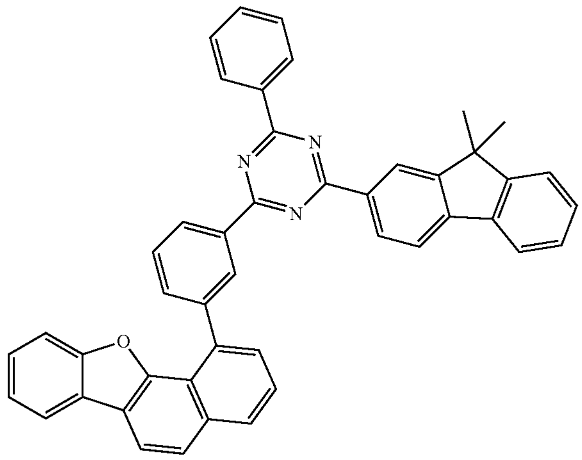
Inv-028
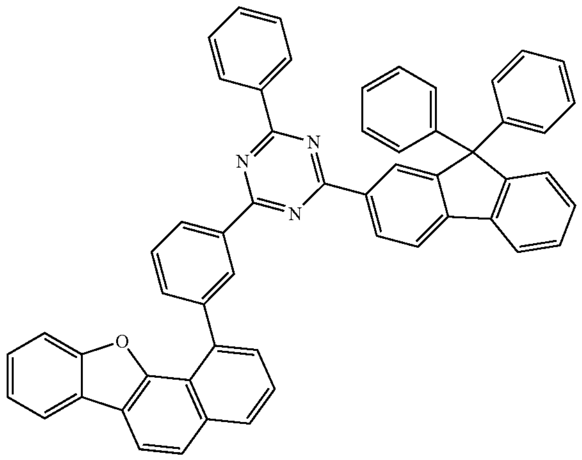
Inv-029
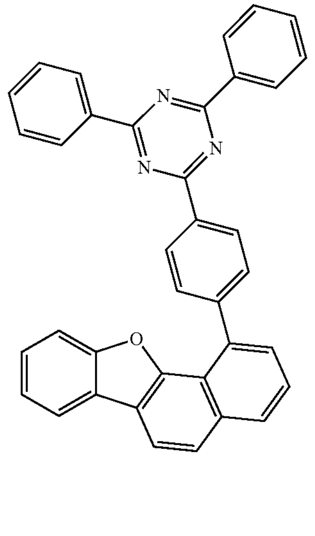
Inv-030
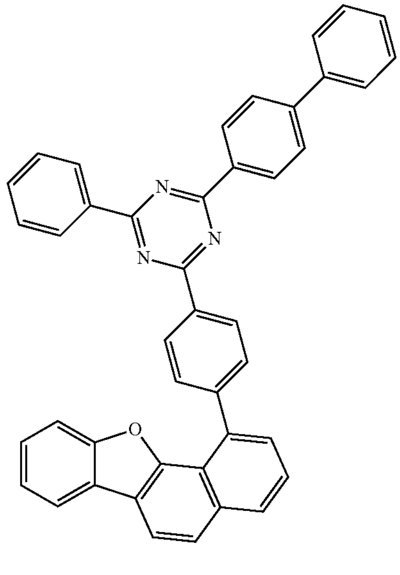

-continued
Inv-031
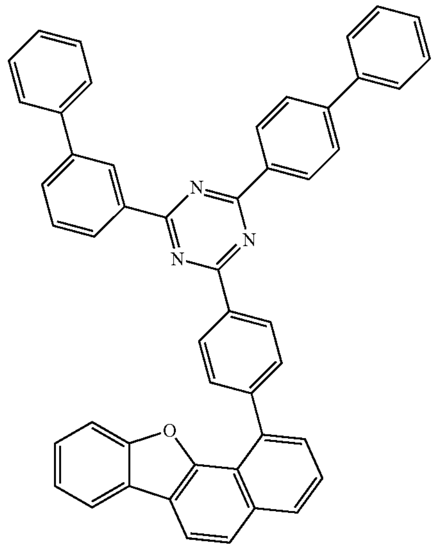
Inv-032
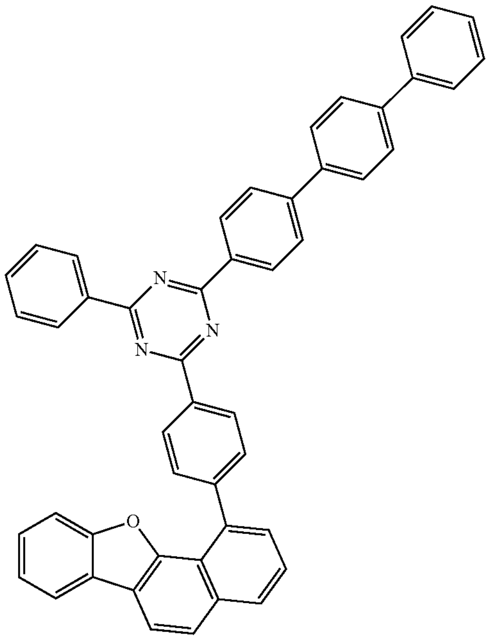
Inv-033
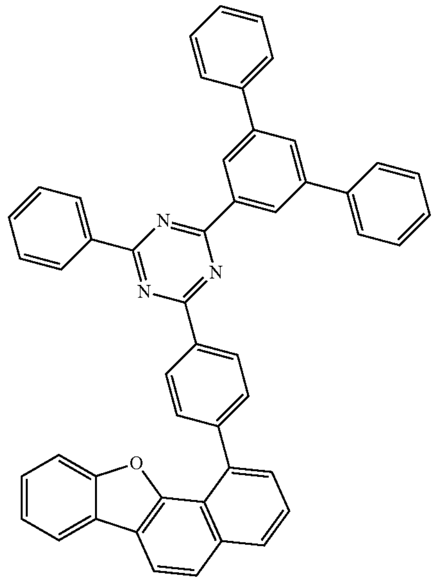
Inv-034
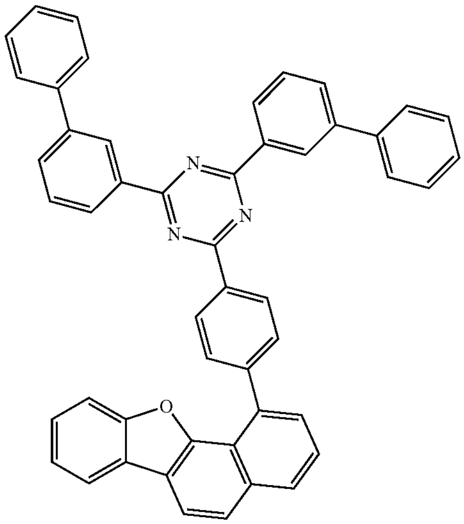

-continued
Inv-035
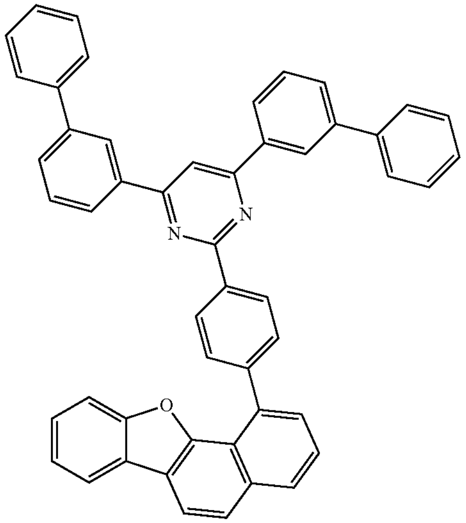
Inv-036
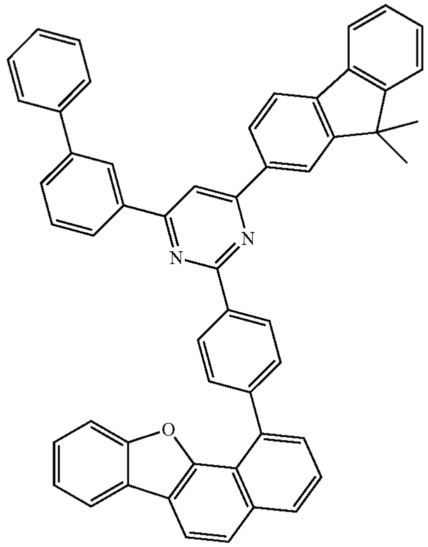
Inv-037
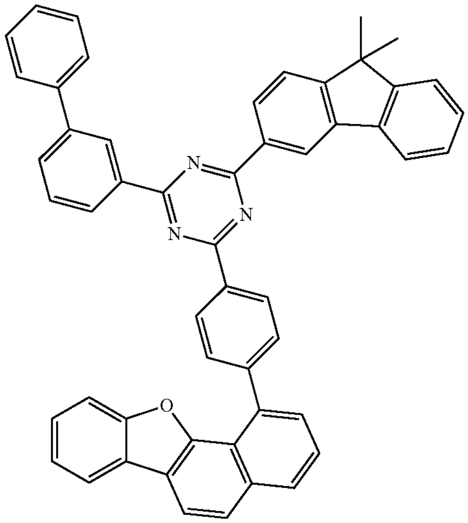
Inv-038
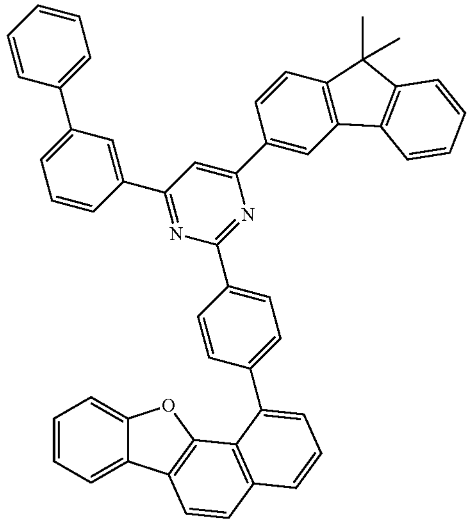
Inv-039
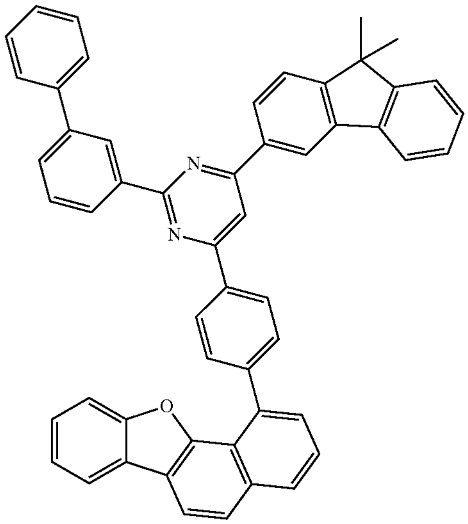
Inv-040
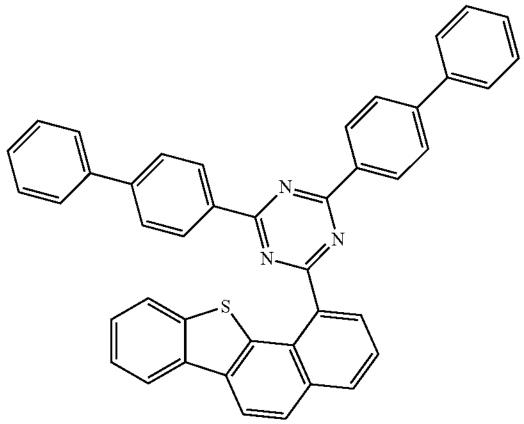

-continued
Inv-041
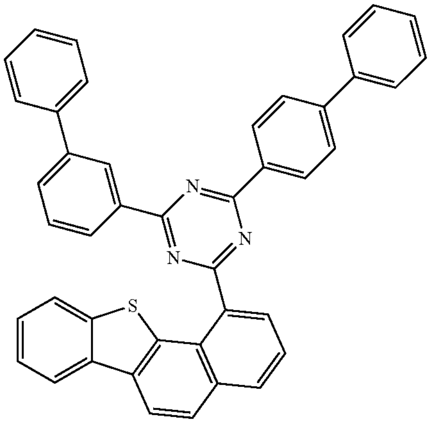
Inv-042
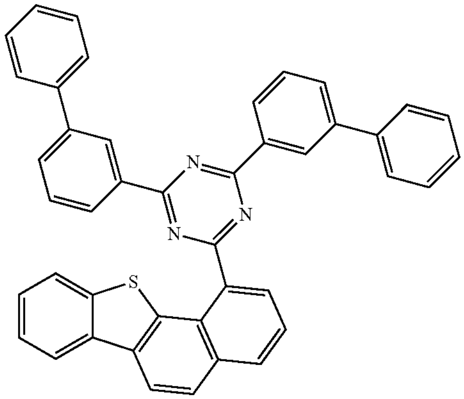
Inv-046
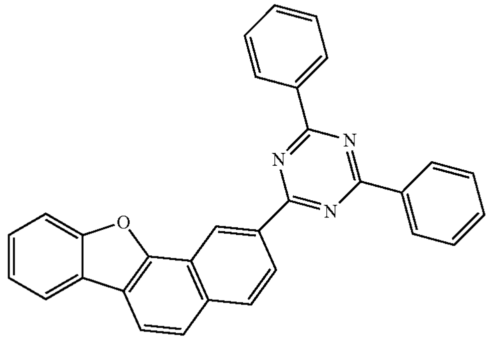
Inv-047
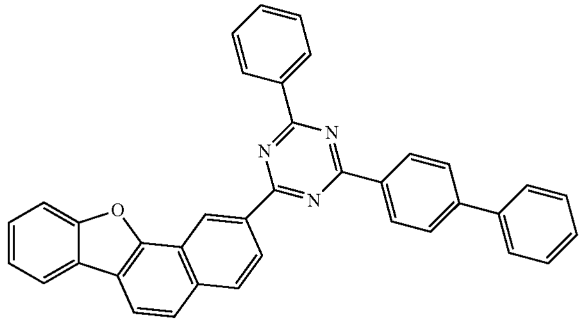
Inv-048
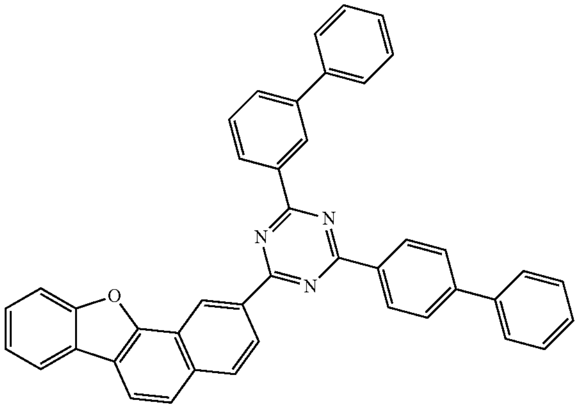

-continued
Inv-049
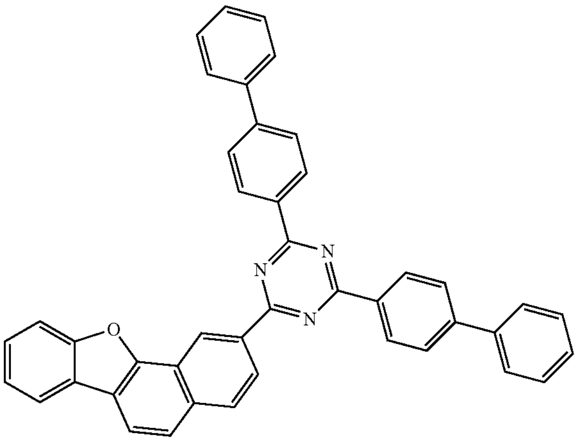
Inv-050
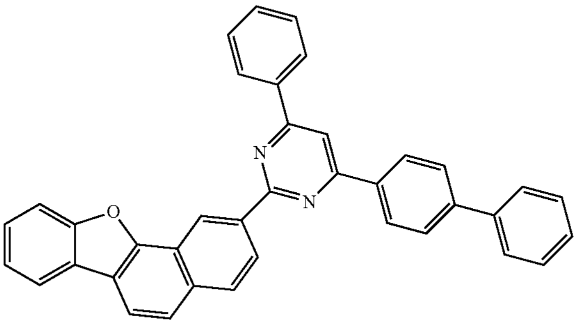
Inv-051
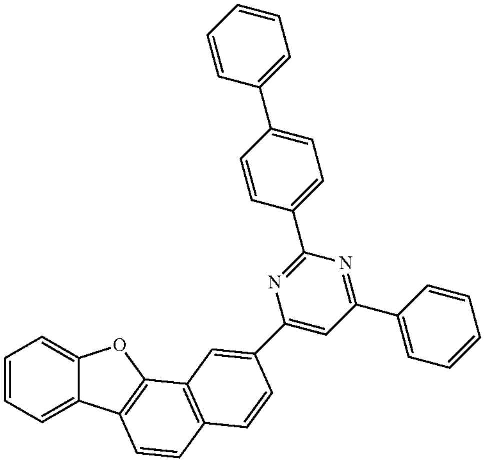
Inv-052
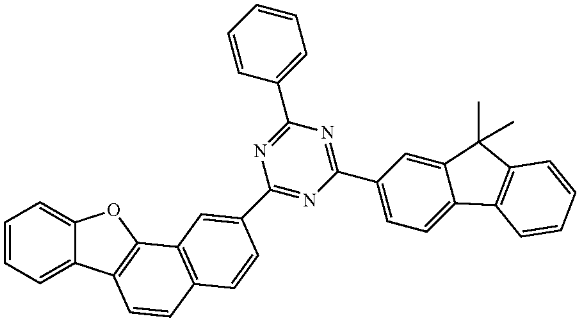
Inv-053
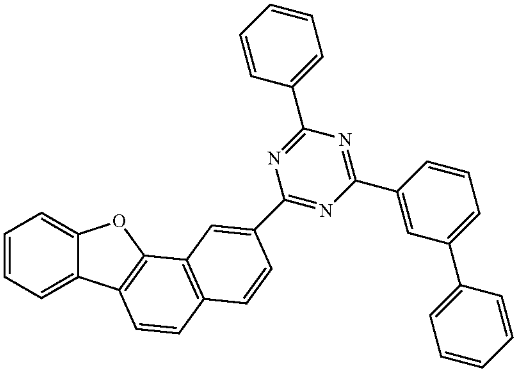
Inv-054
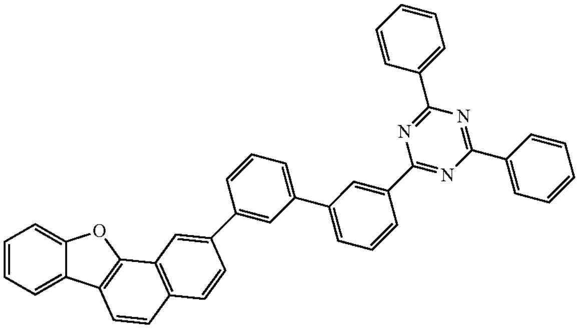

-continued
Inv-055
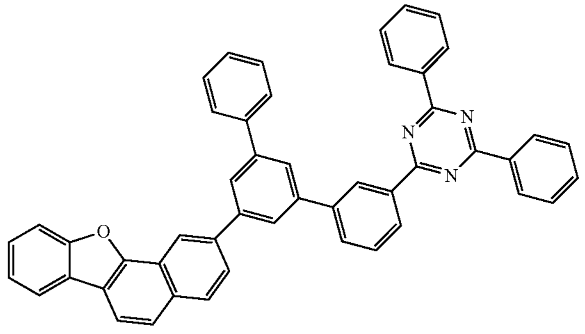
Inv-056
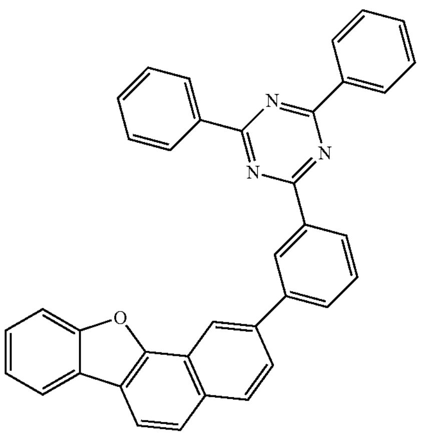
Inv-057
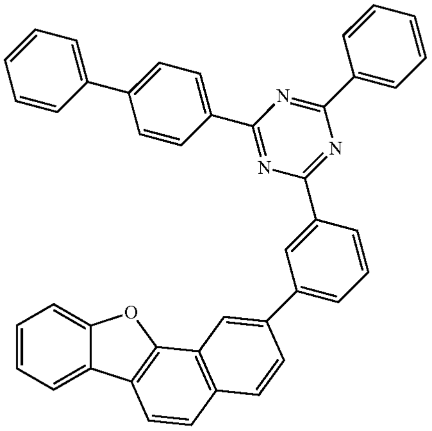
Inv-058
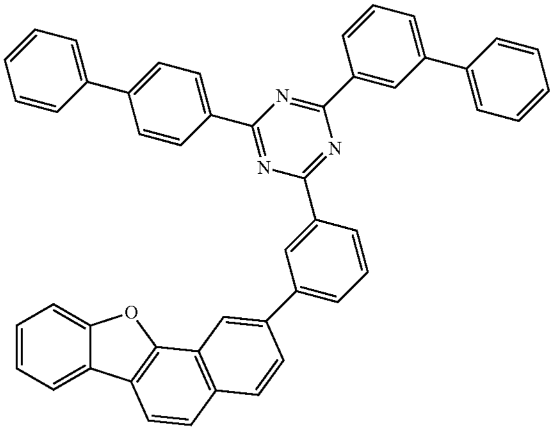
Inv-059
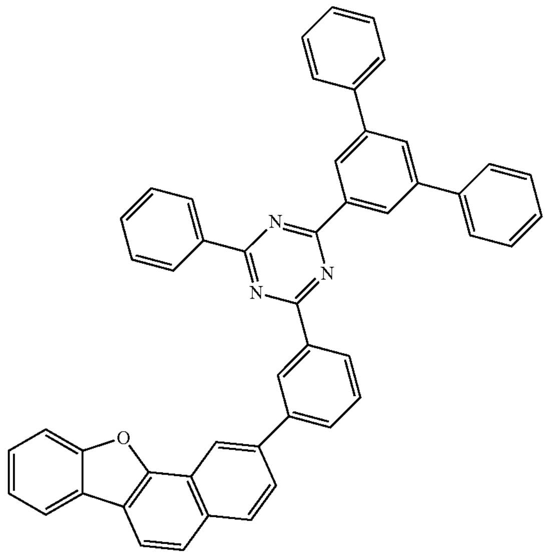
Inv-060
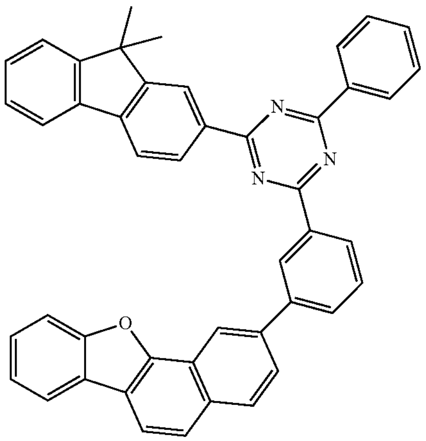

-continued
Inv-061
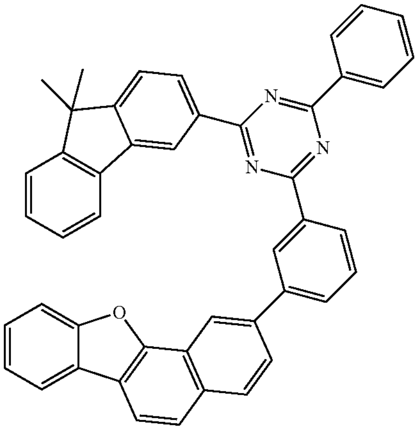
Inv-062
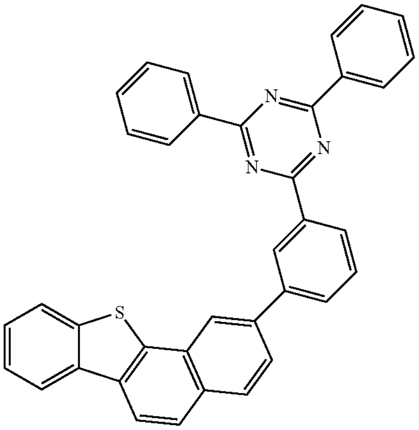
Inv-063
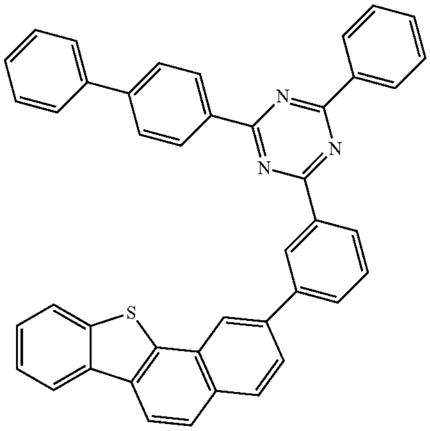
Inv-064
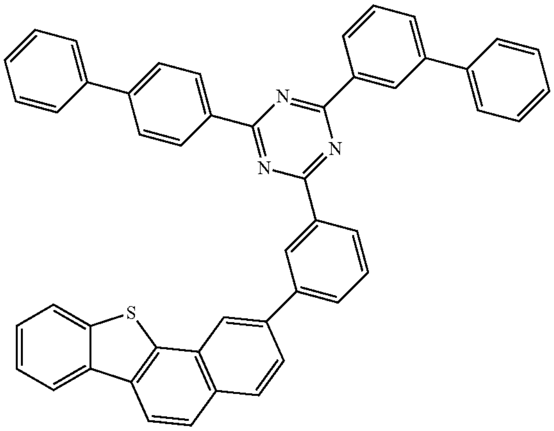
Inv-065
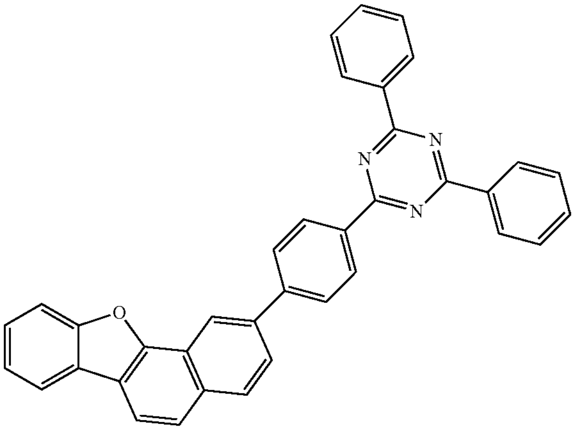
Inv-066
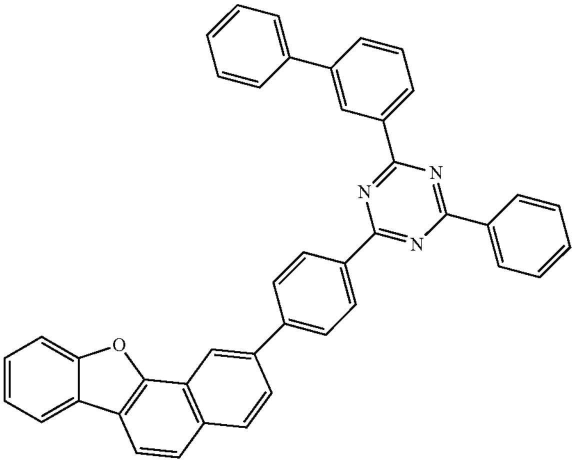

-continued
Inv-067
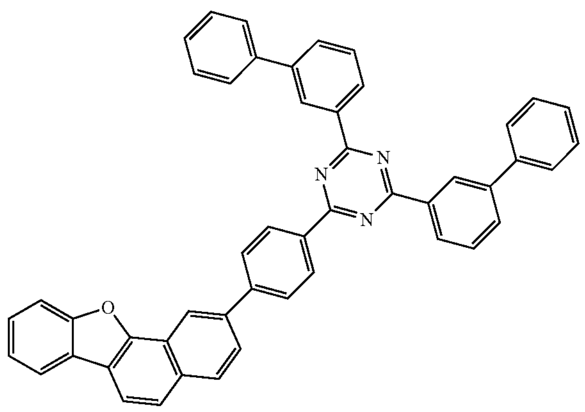
Inv-068
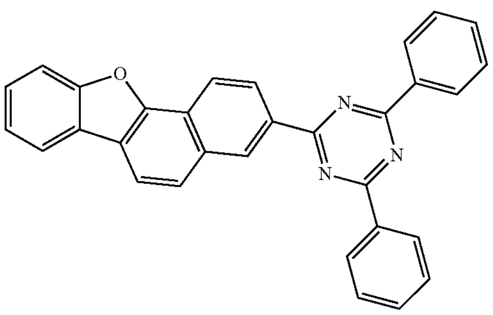
Inv-069
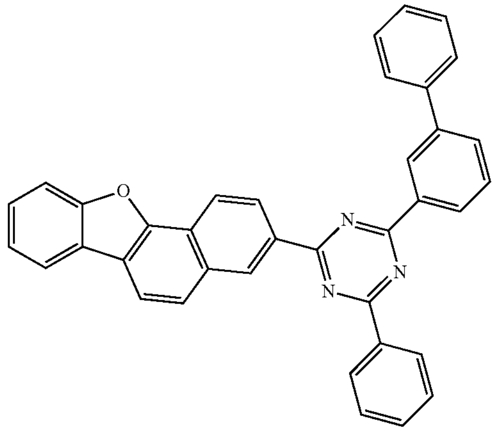
Inv-070
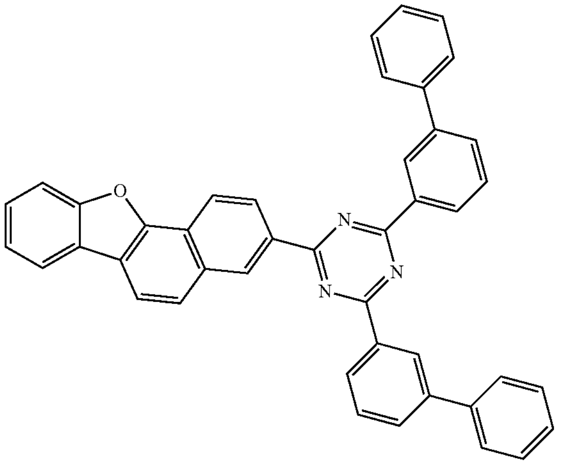
Inv-071
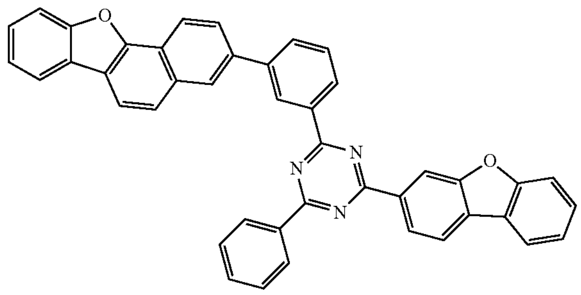
Inv-072
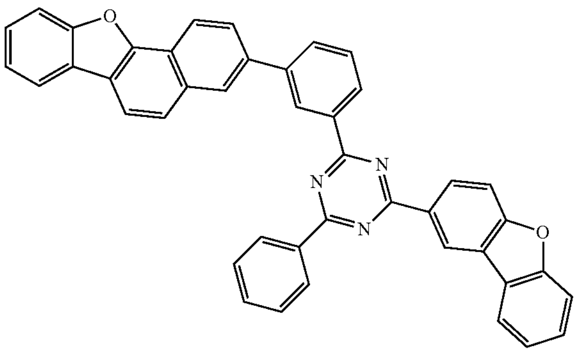

-continued
Inv-073
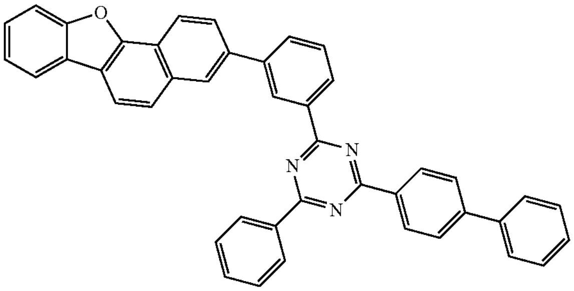
Inv-074
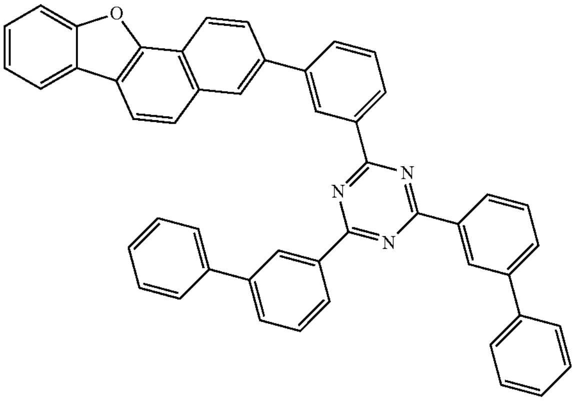
Inv-075
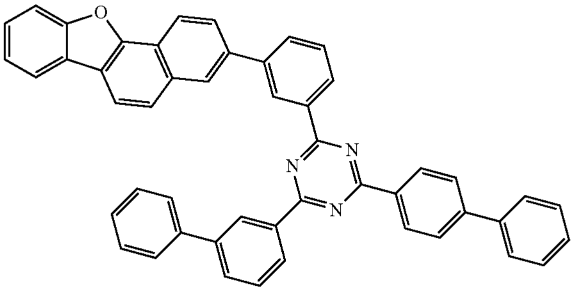
Inv-076
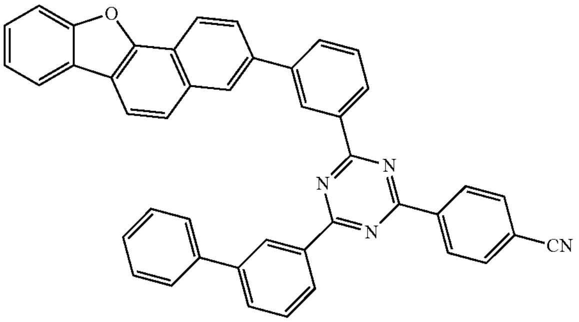
Inv-077
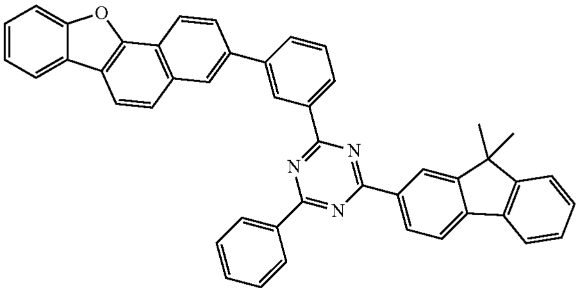
Inv-078
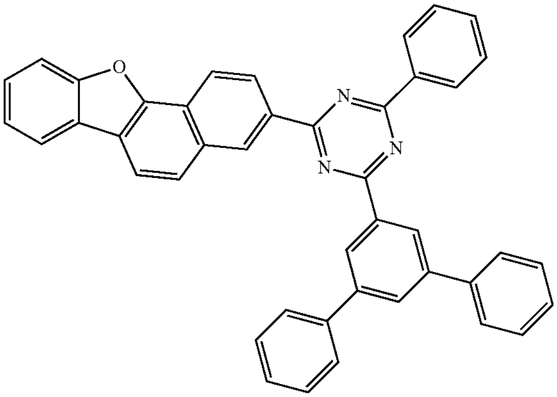
Inv-079
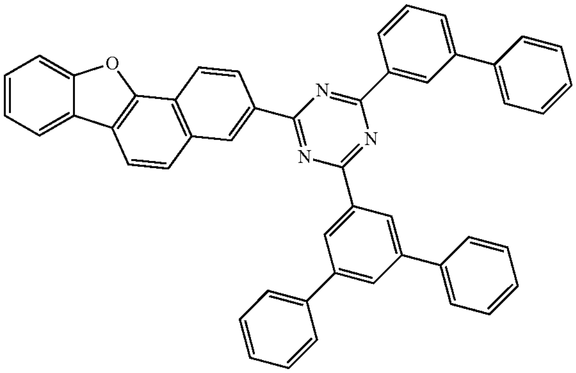
Inv-080
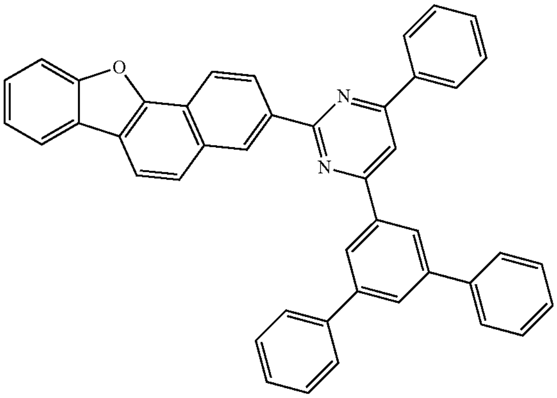

-continued
Inv-081
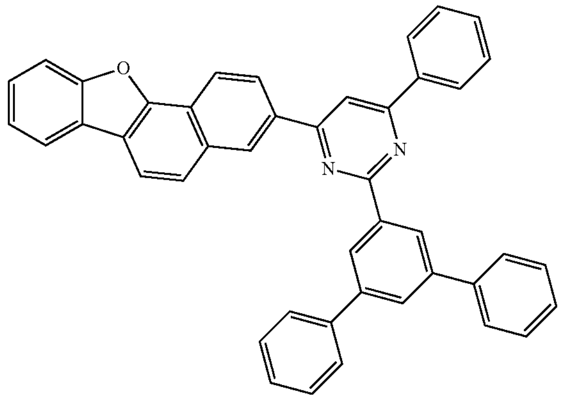
Inv-082
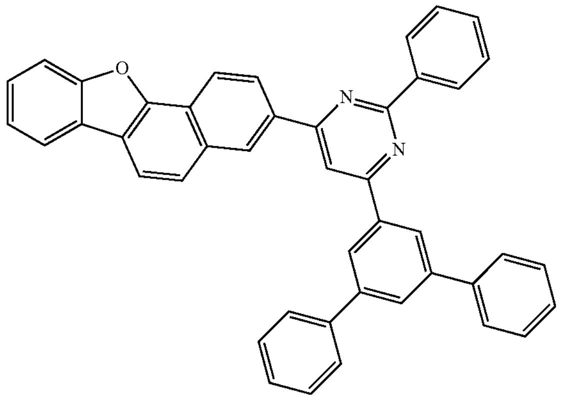
Inv-083
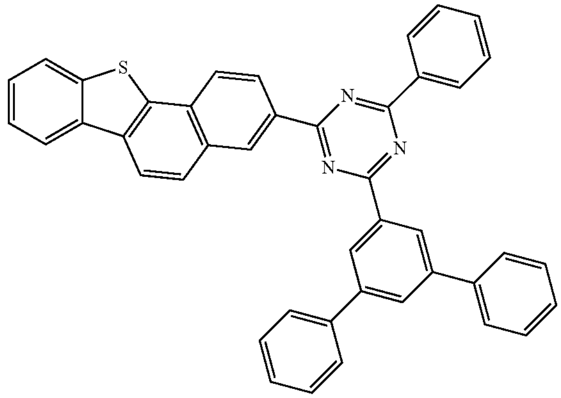
Inv-084
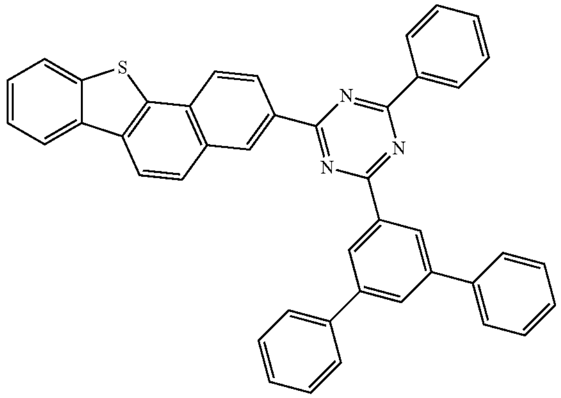
Inv-085
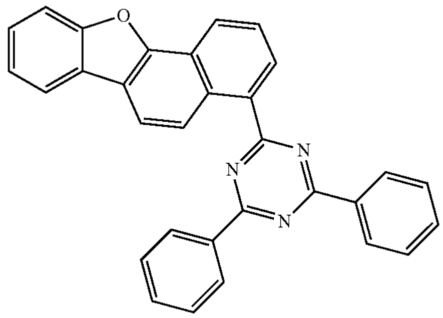
Inv-086
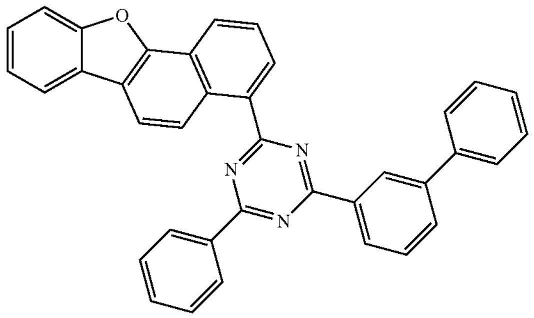
Inv-087
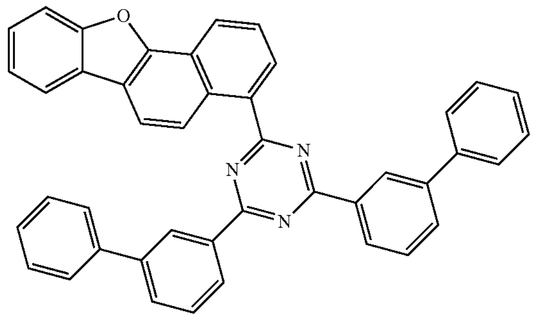
Inv-088
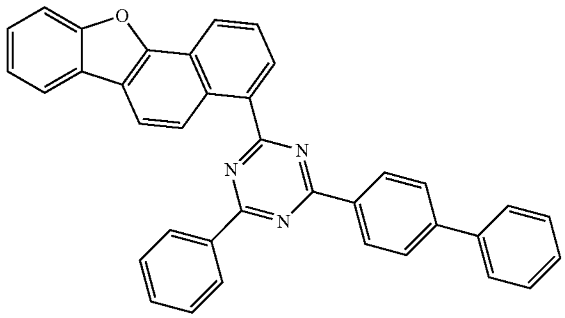

-continued
Inv-089
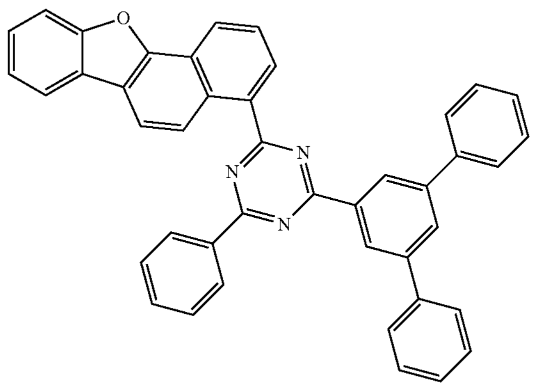
Inv-090
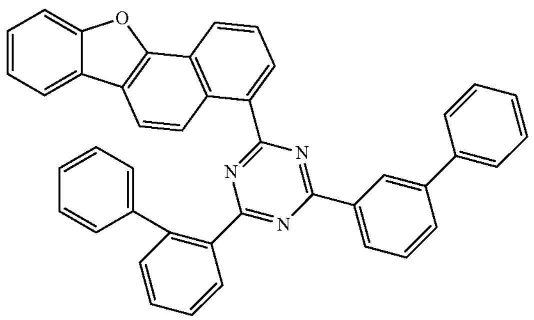
Inv-091
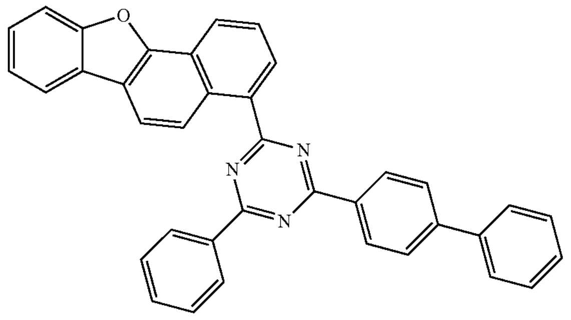
Inv-092
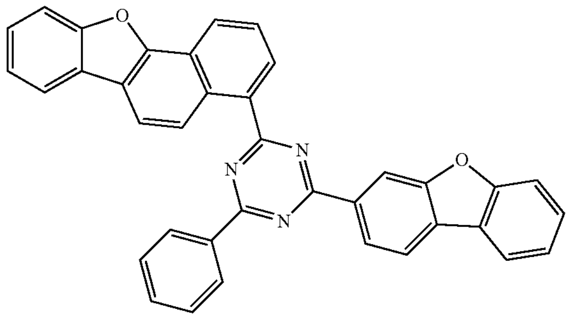
Inv-093
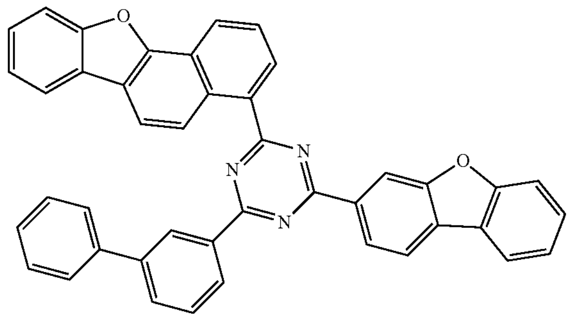
Inv-094
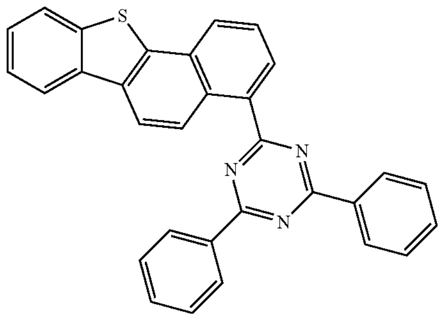
Inv-095
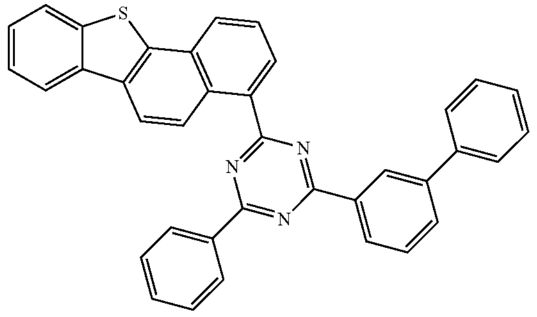
Inv-096
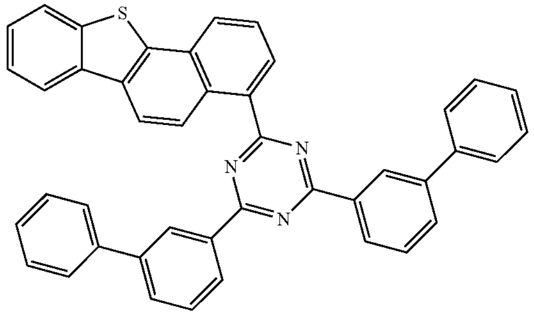

-continued
Inv-097
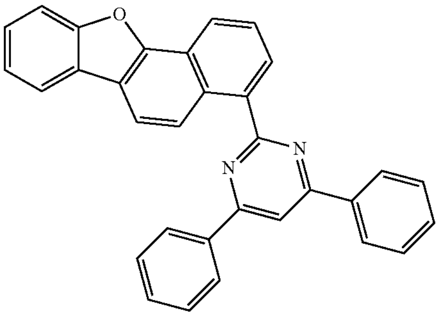
Inv-098
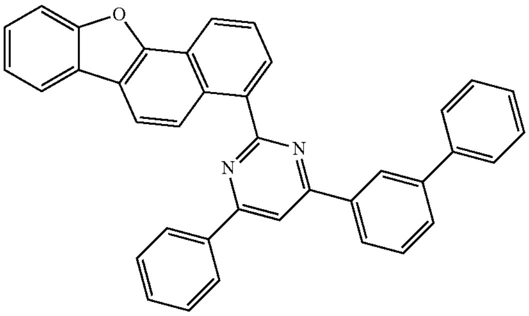
Inv-099
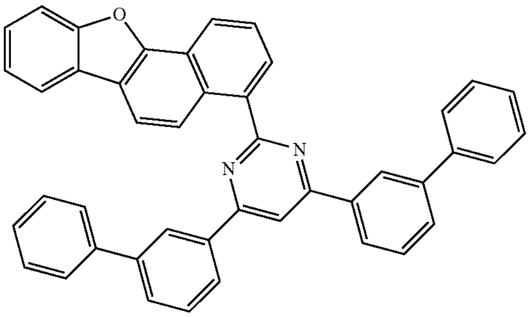
Inv-100
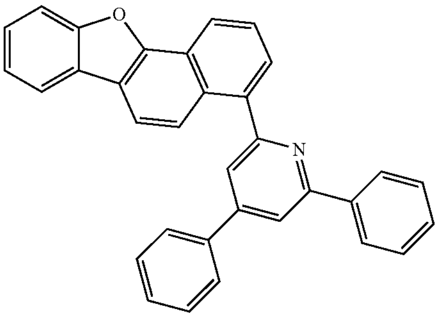
Inv-101
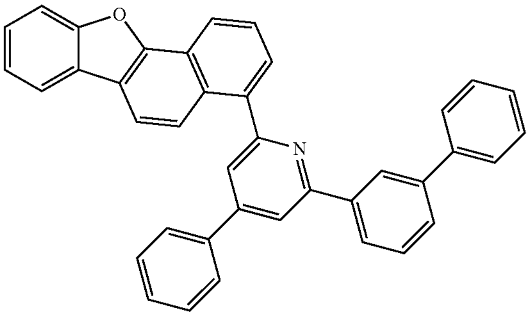
Inv-102
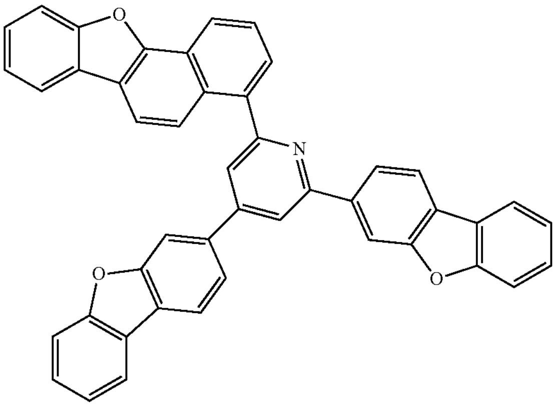
Inv-103
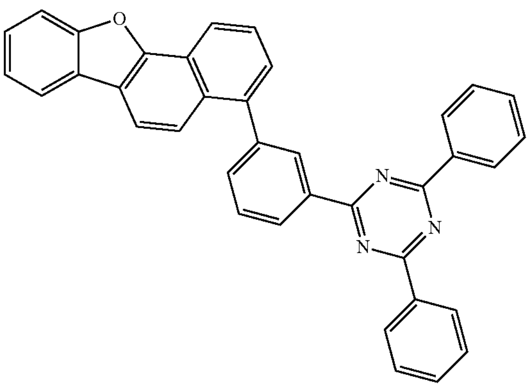
Inv-104
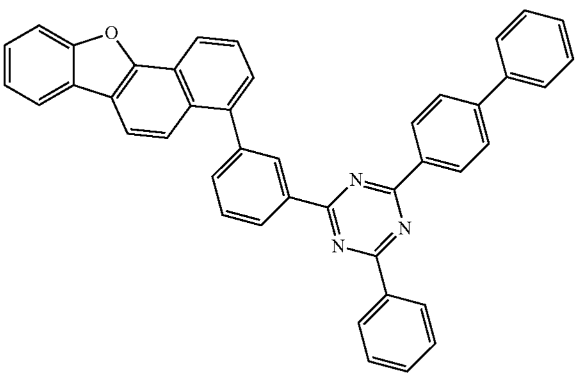

-continued
Inv-105
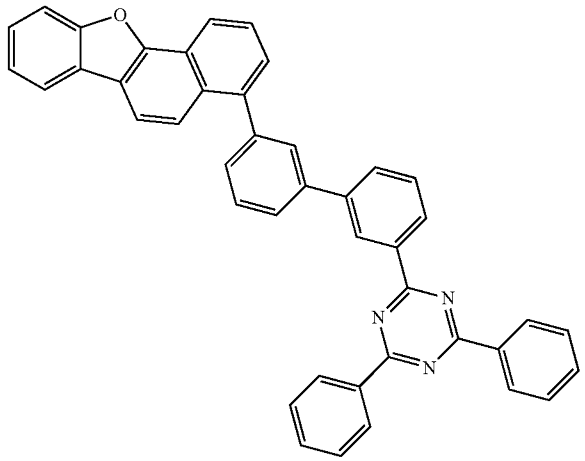
Inv-106
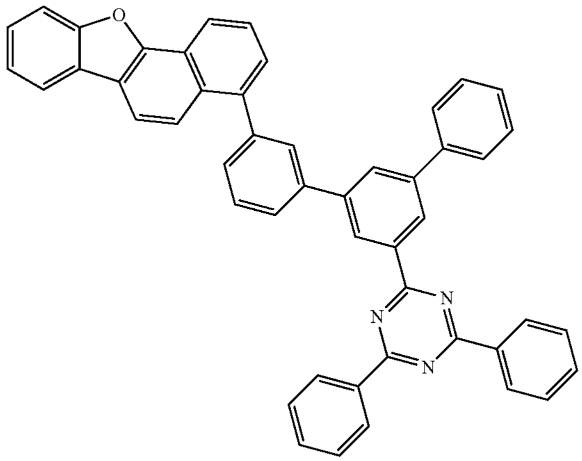
Inv-107
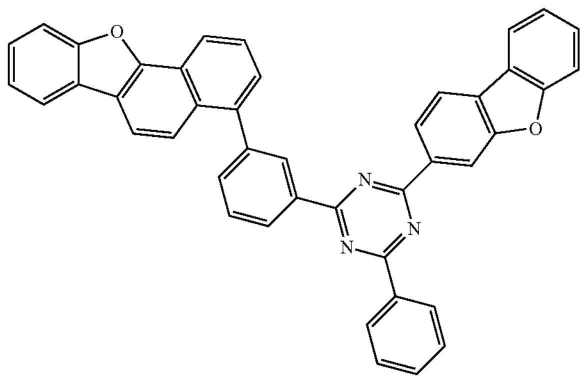
Inv-108
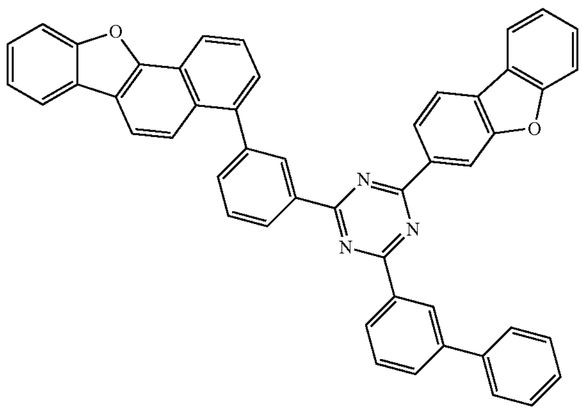
Inv-109
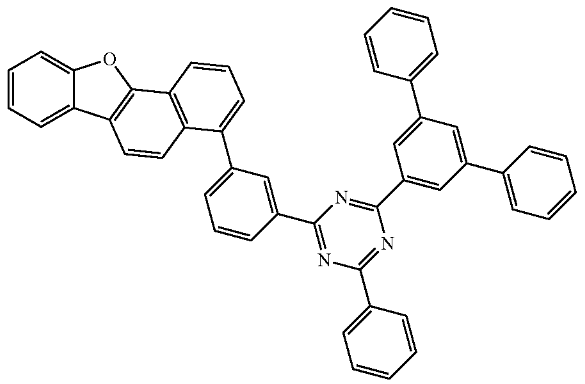
Inv-110
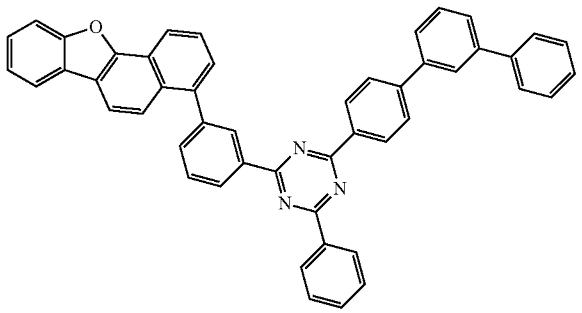

-continued
Inv-111
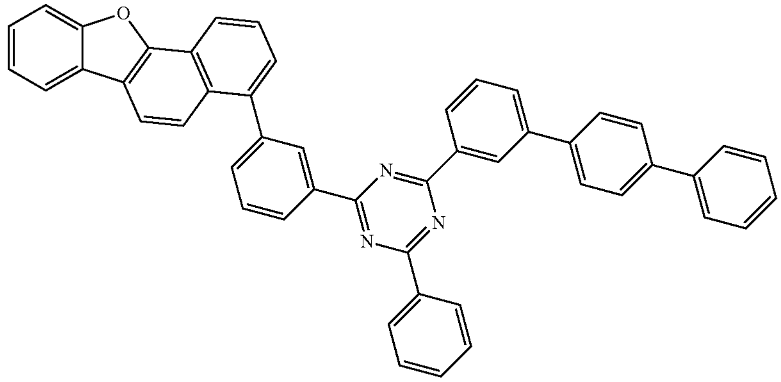
Inv-112
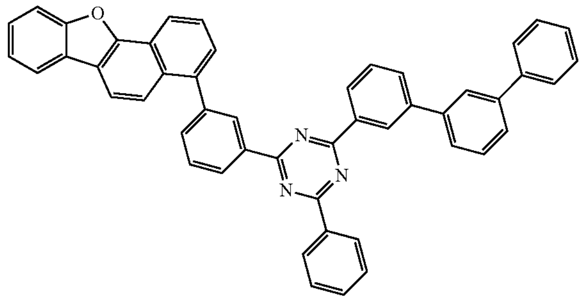
Inv-113
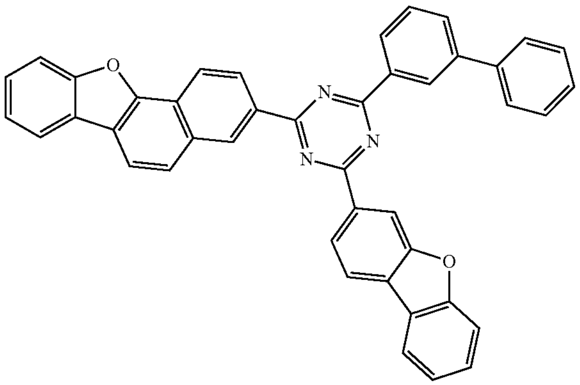
Inv-114
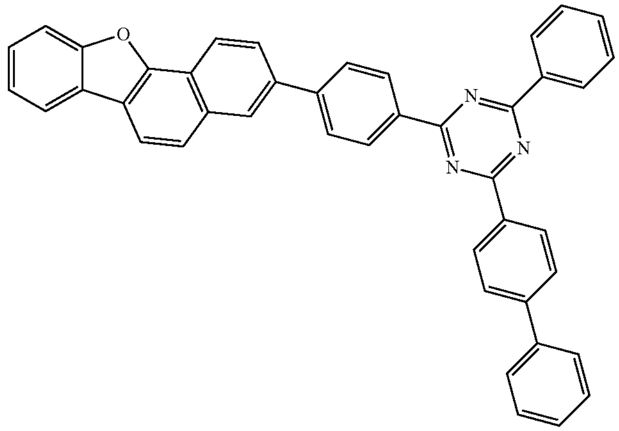
Inv-115
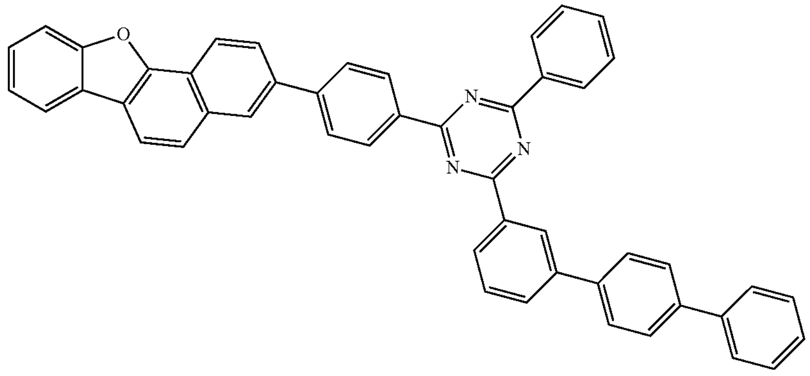

-continued
Inv-116
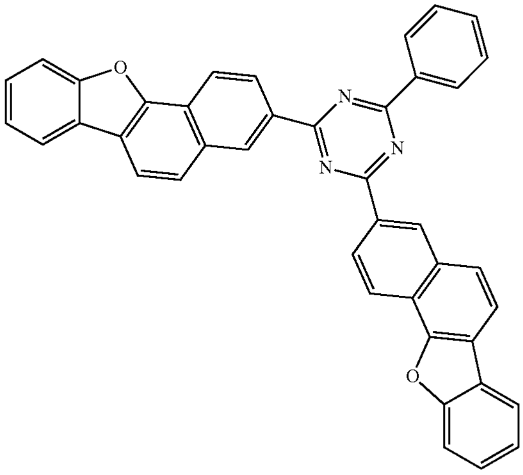
Inv-117
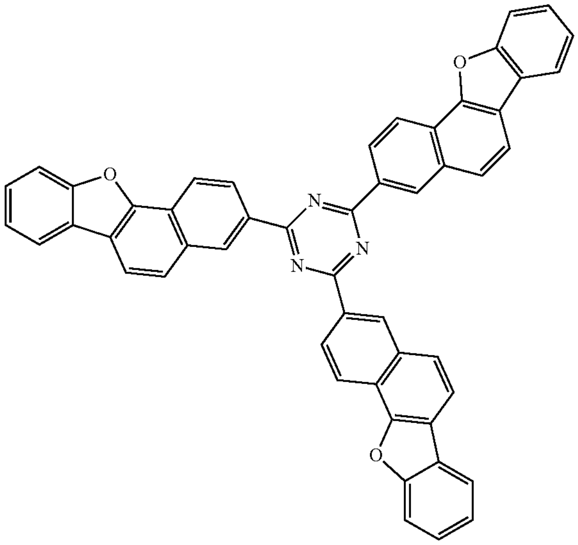
Inv-118
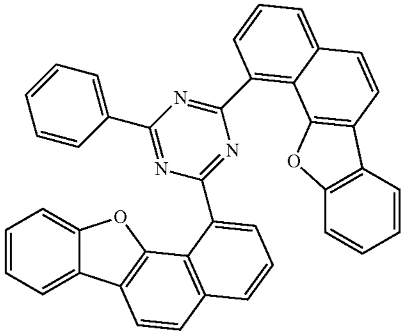
Inv-119
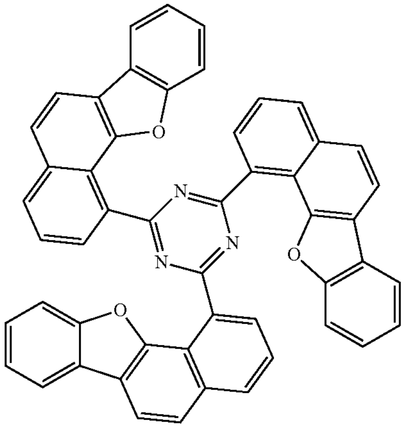
Inv-120
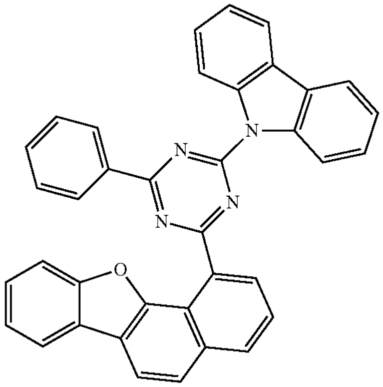
Inv-121
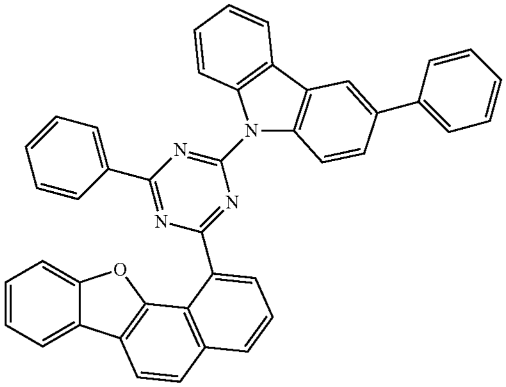

-continued
Inv-122
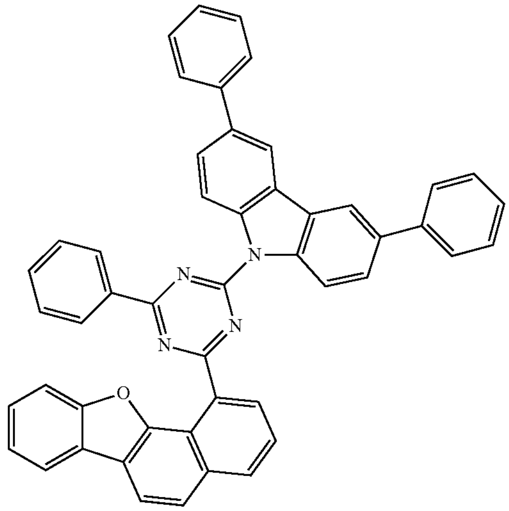
Inv-123
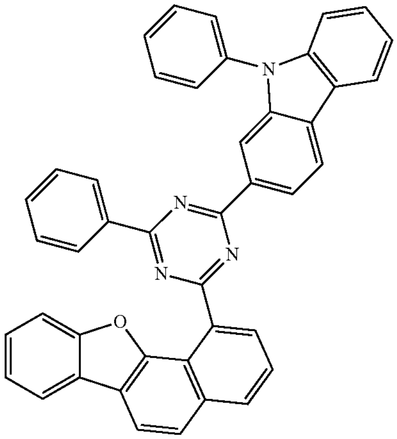
Inv-124
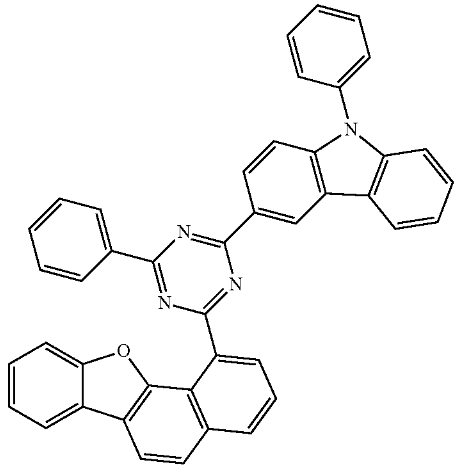
Inv-125
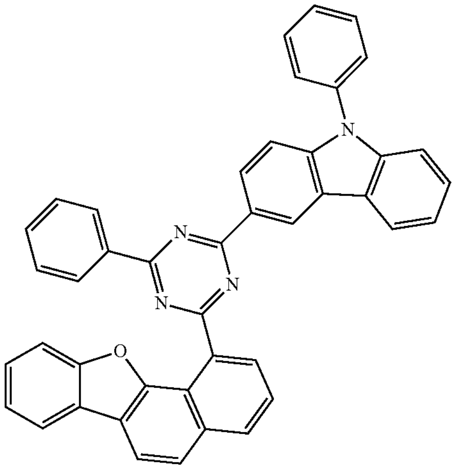
Inv-126
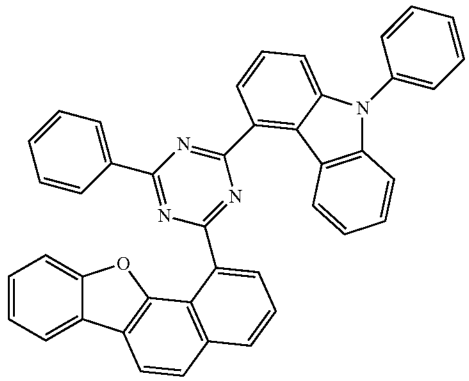
Inv-127
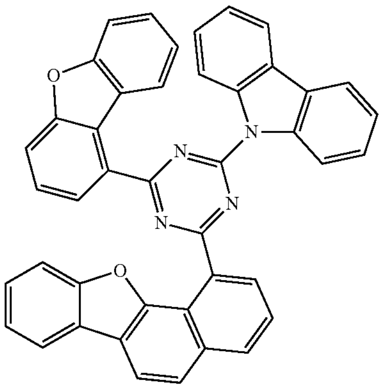

-continued
Inv-128
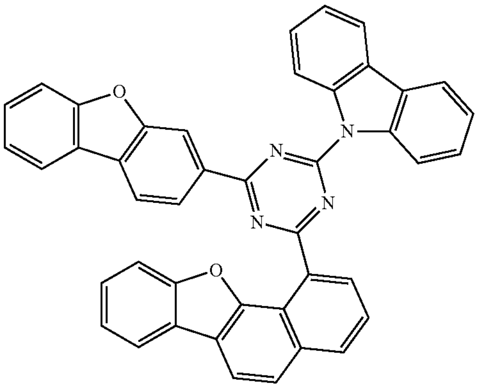
Inv-129
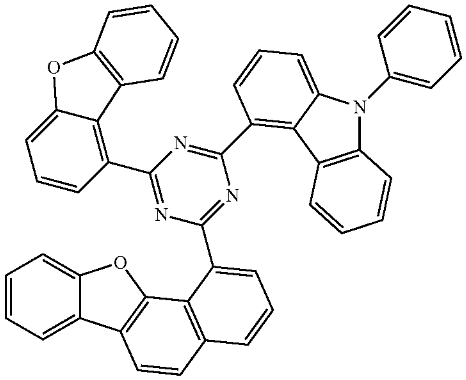
Inv-130
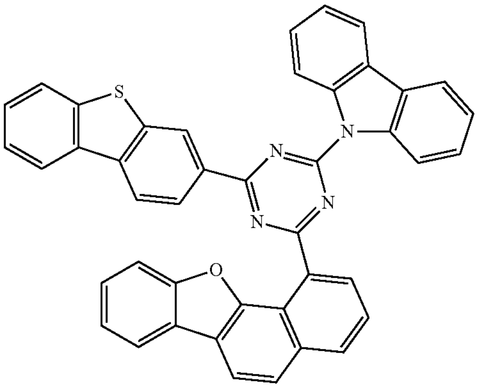
Inv-131
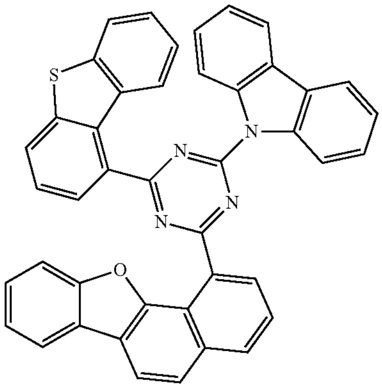
Inv-132
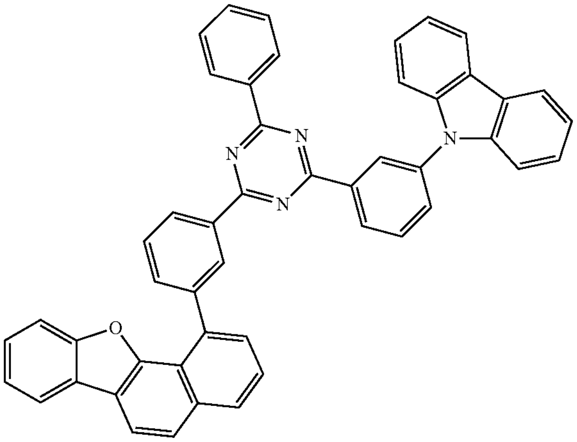
Inv-133
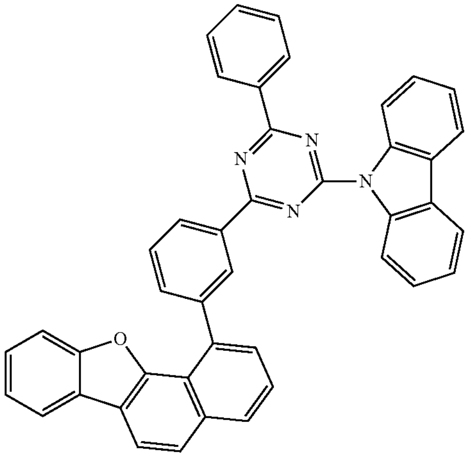

-continued
Inv-134
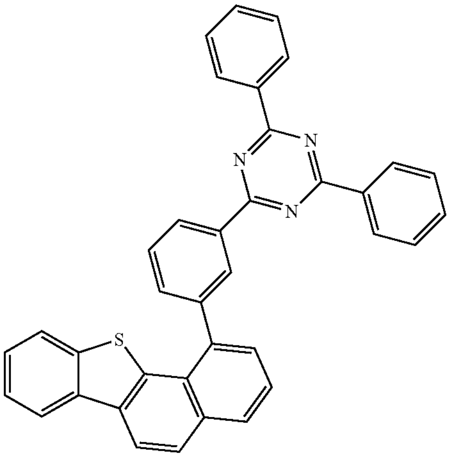
Inv-135
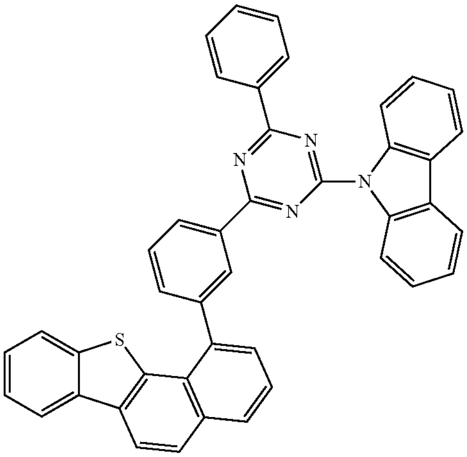
Inv-136
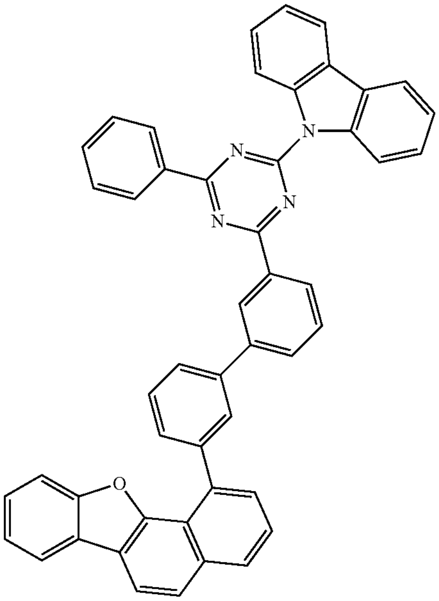
Inv-137
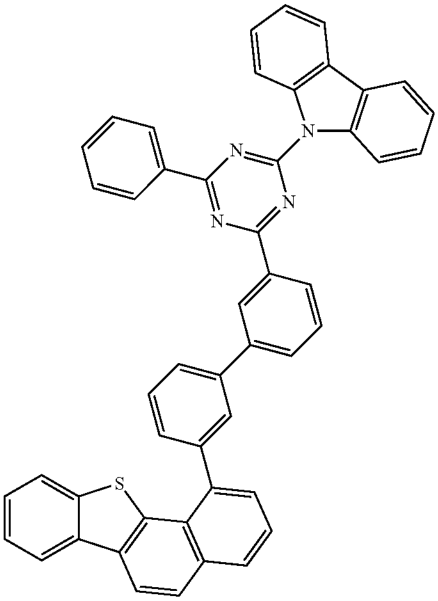
Inv-138
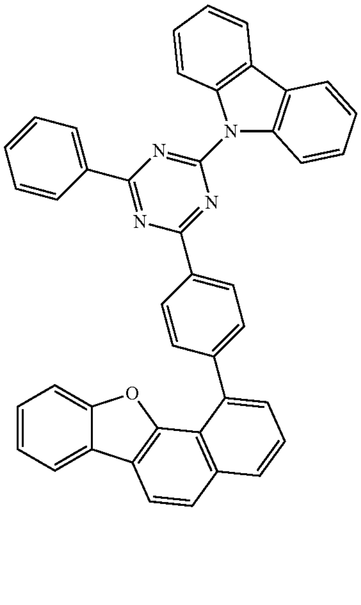
Inv-139
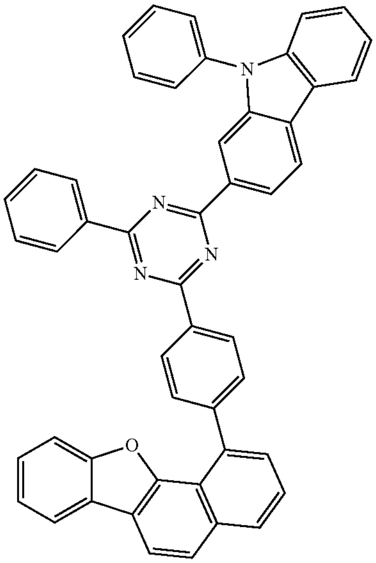

-continued
Inv-140
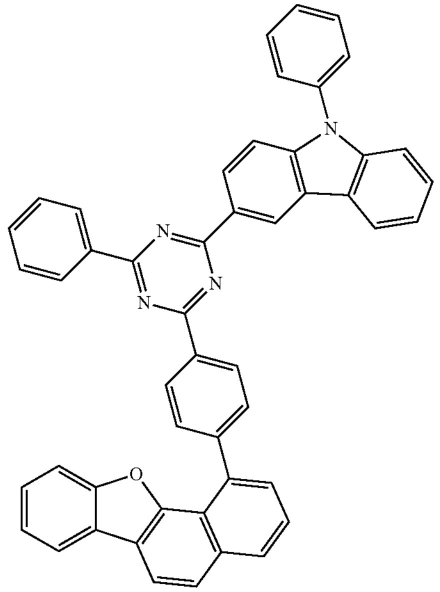
Inv-141
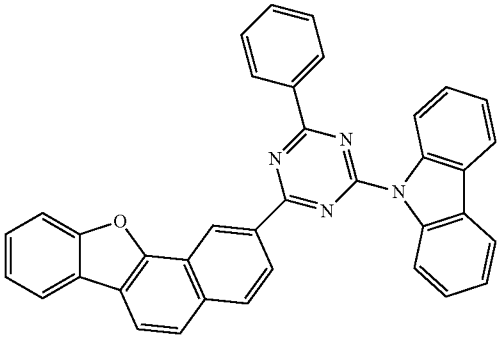
Inv-142
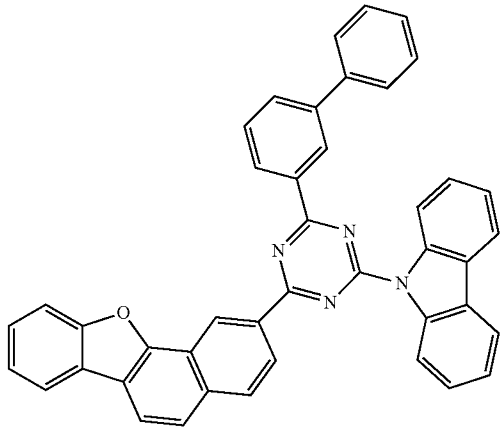
Inv-143
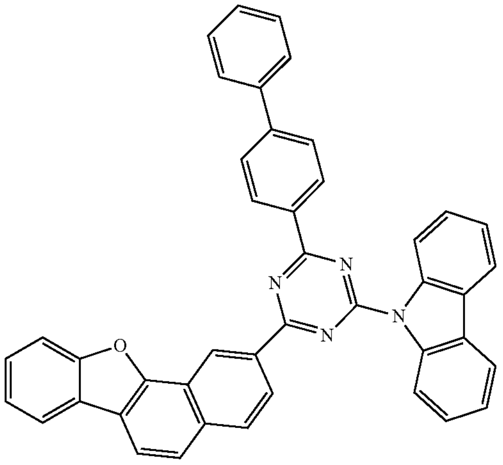
Inv-144
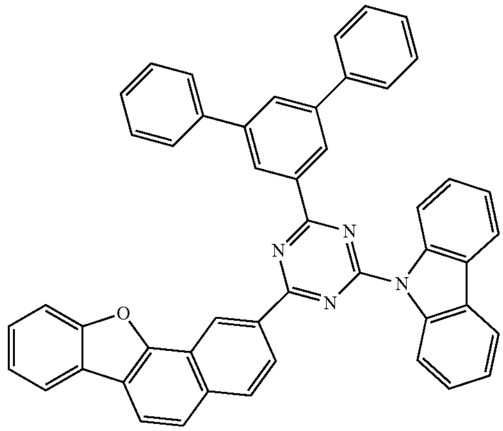
Inv-145
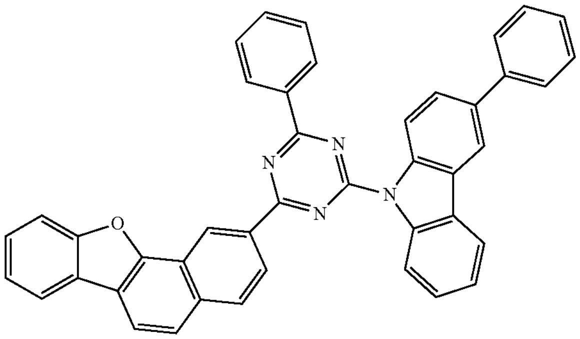

-continued
Inv-146
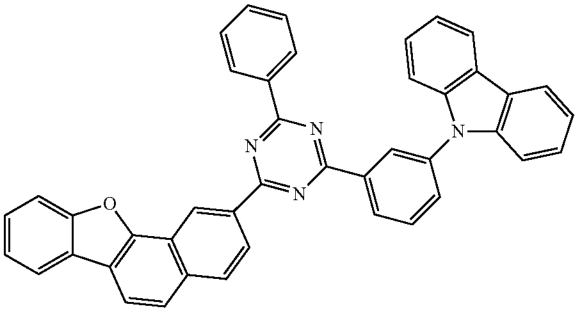
Inv-147
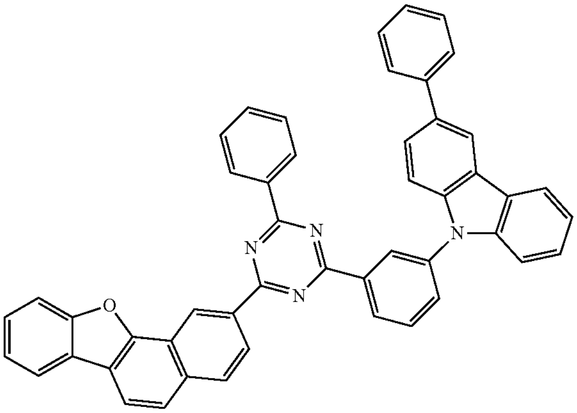
Inv-148
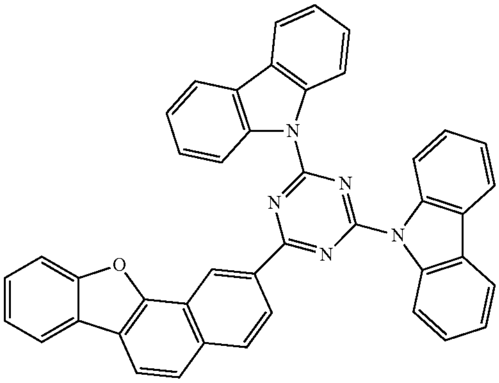
Inv-149
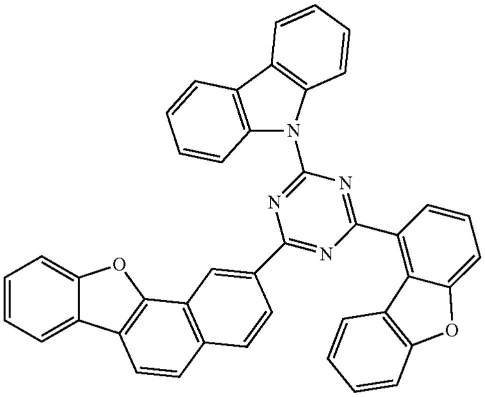
Inv-150
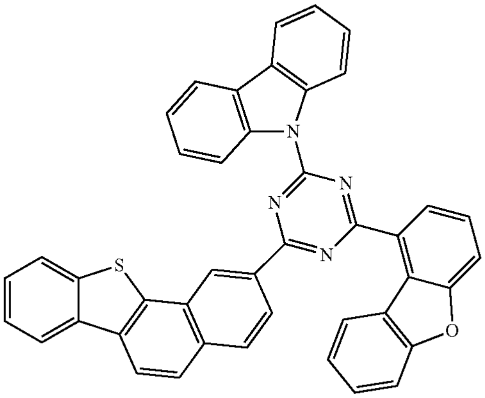
Inv-151
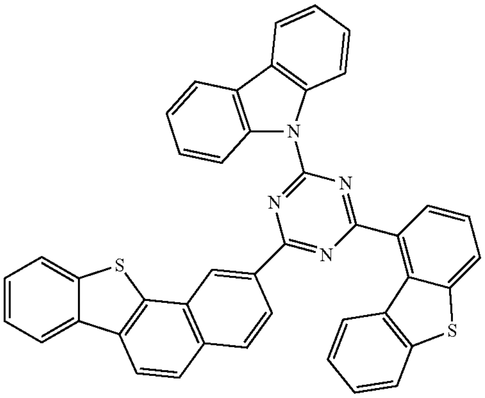

-continued
Inv-152
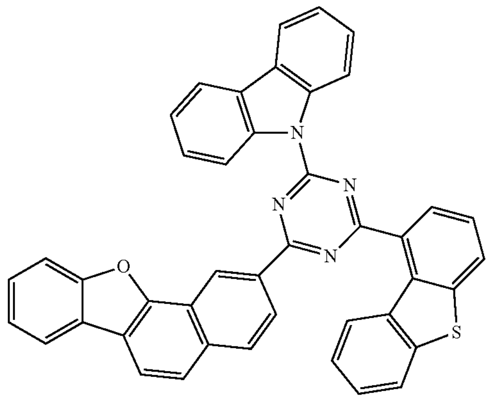
Inv-153
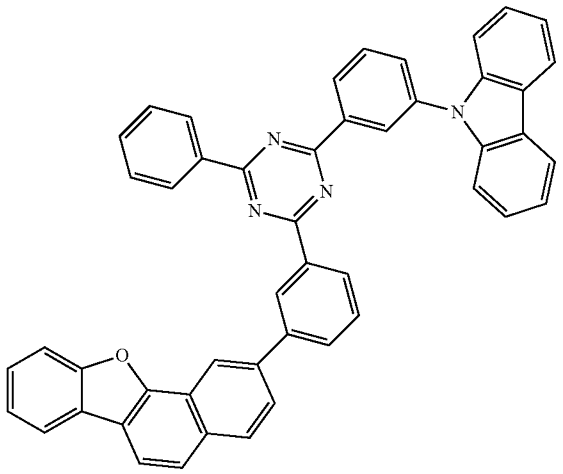
Inv-154
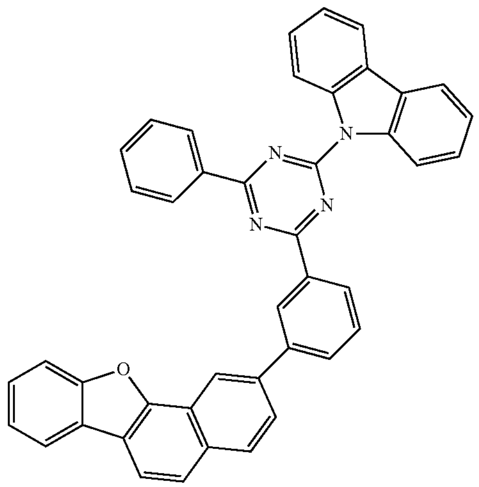
Inv-155
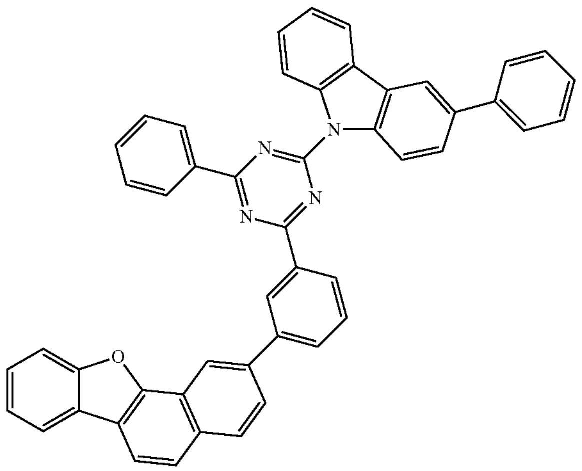
Inv-156
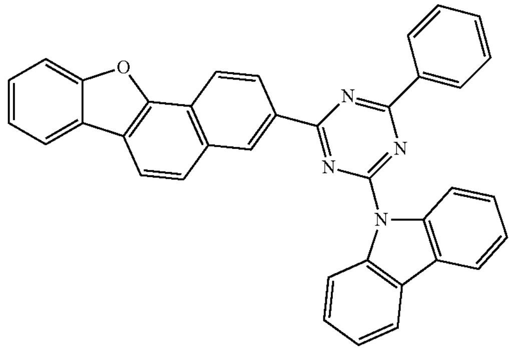
Inv-157
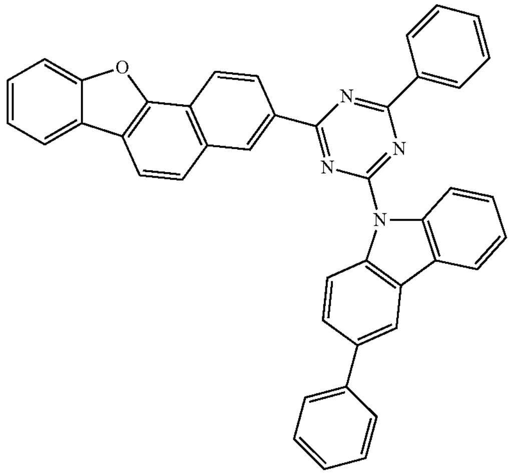

-continued
Inv-158
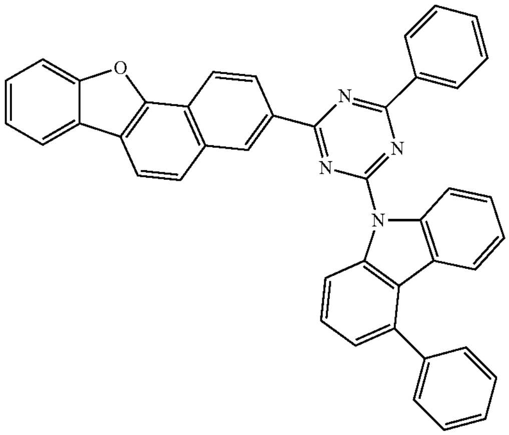
Inv-159
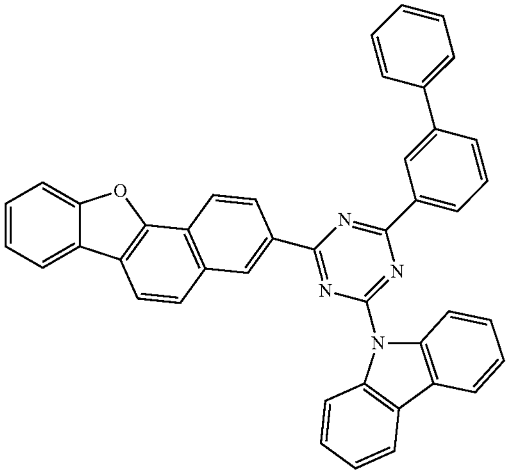
Inv-160
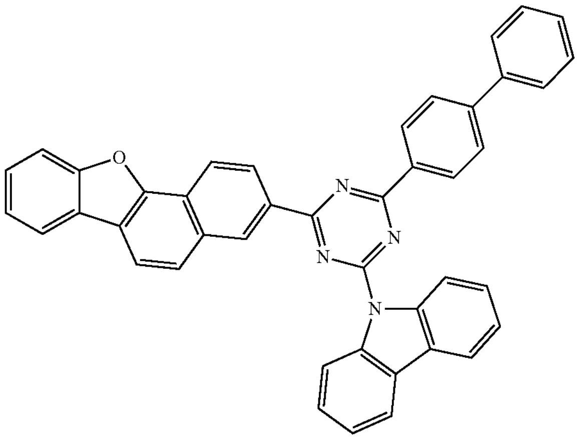
Inv-161
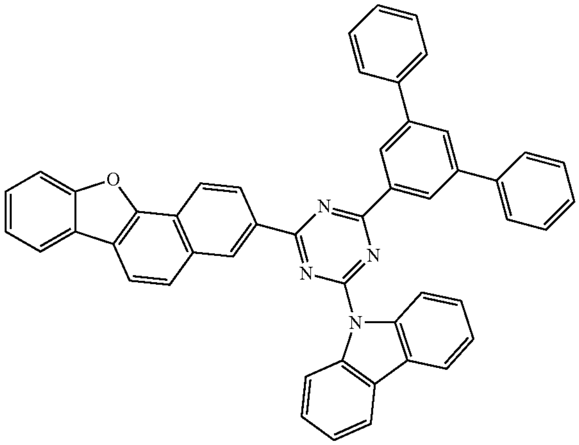
Inv-162
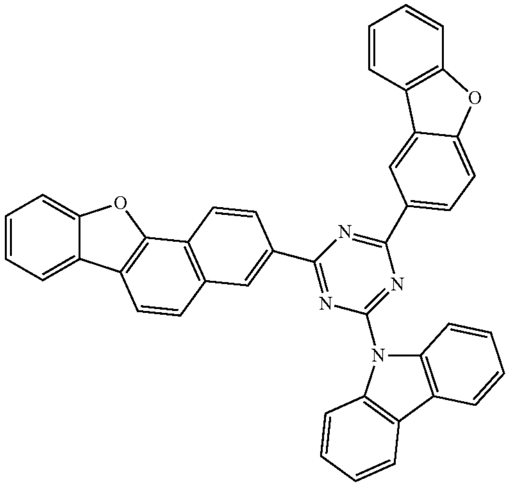
Inv-163
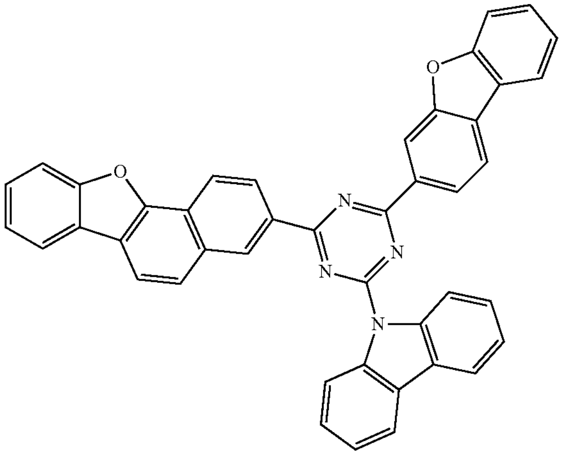

-continued
Inv-164
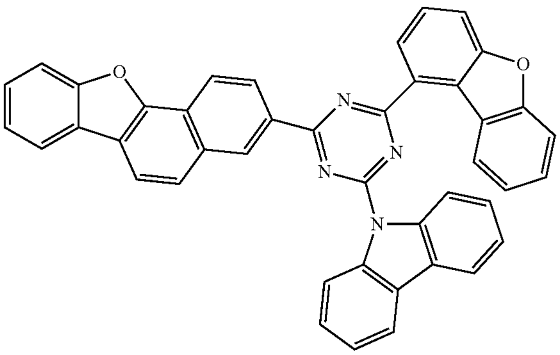
Inv-165
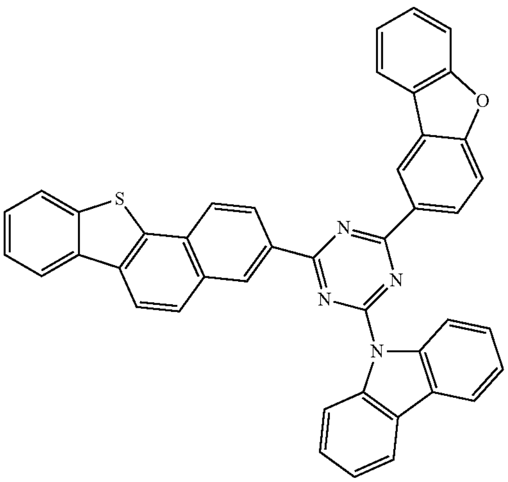
Inv-166
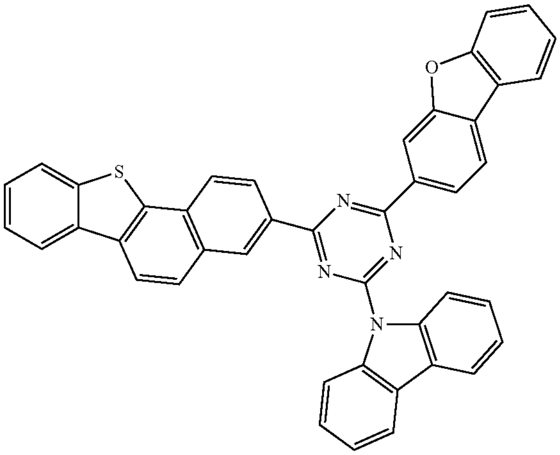
Inv-167
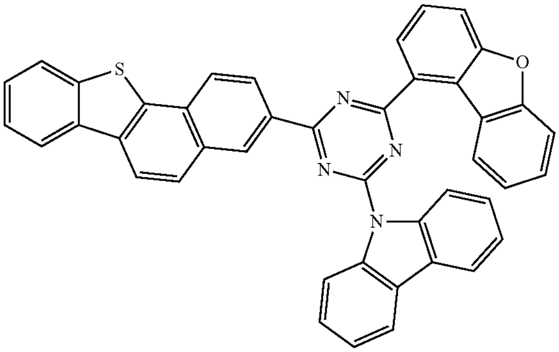
Inv-168
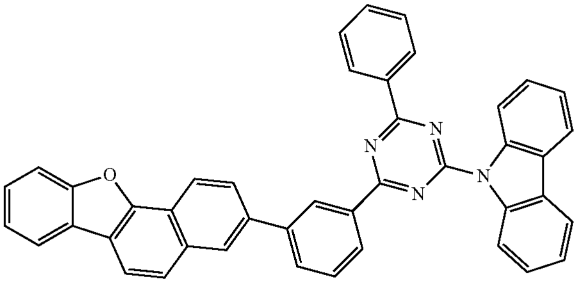
Inv-169
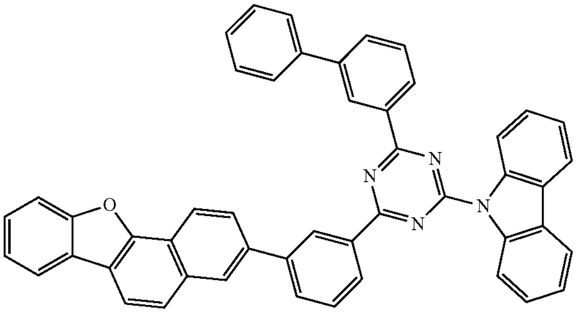

-continued
Inv-170
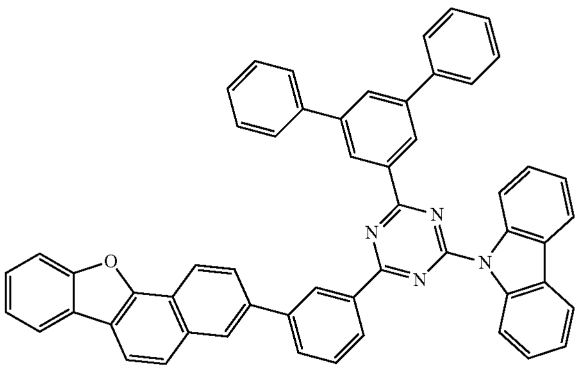
Inv-171
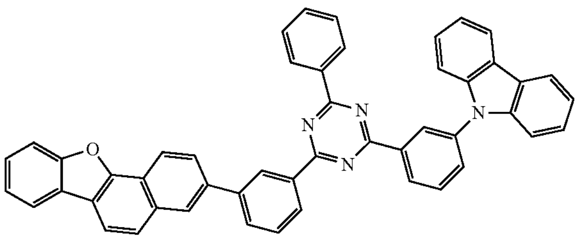
Inv-172
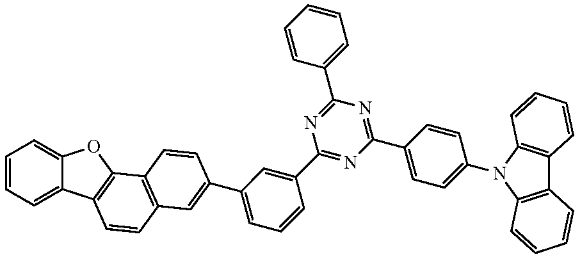
Inv-173
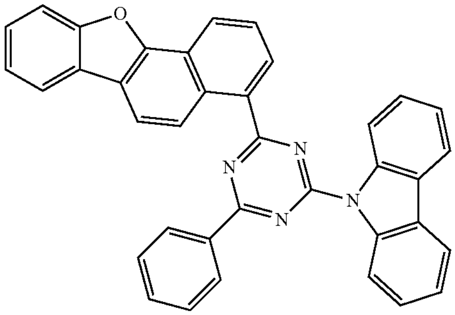
Inv-174
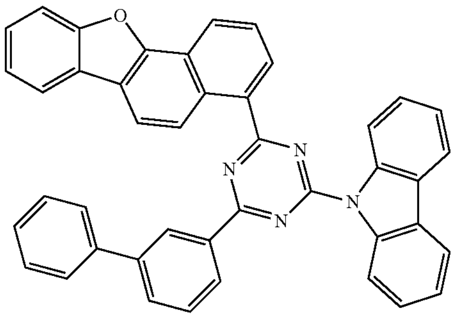
Inv-175
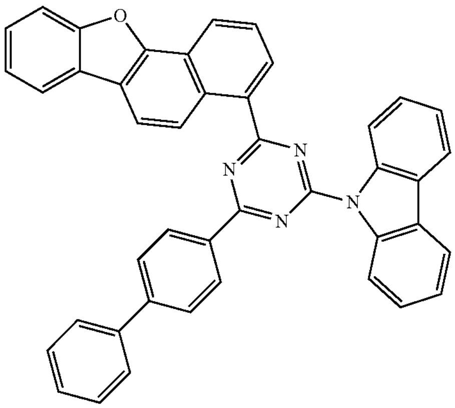
Inv-176
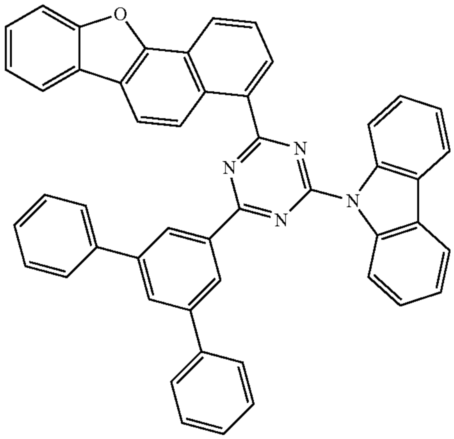
Inv-177
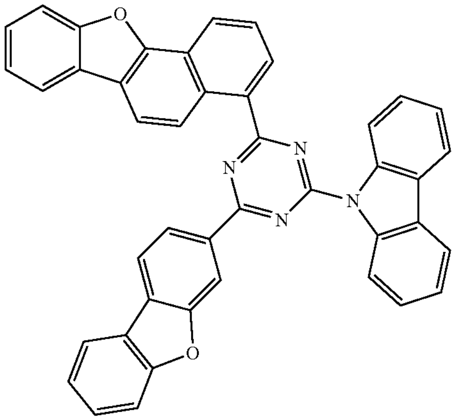

-continued
Inv-178
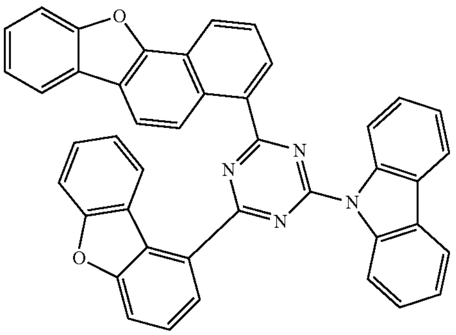
Inv-179
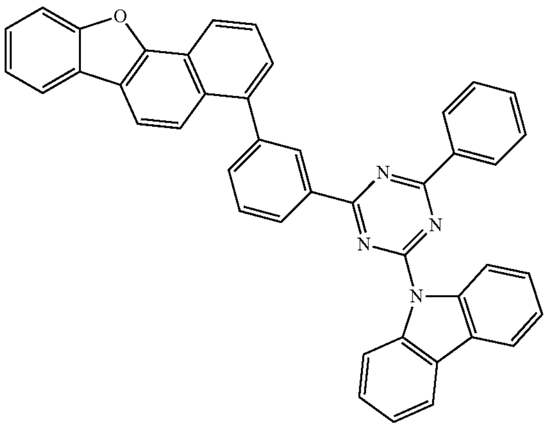
Inv-180
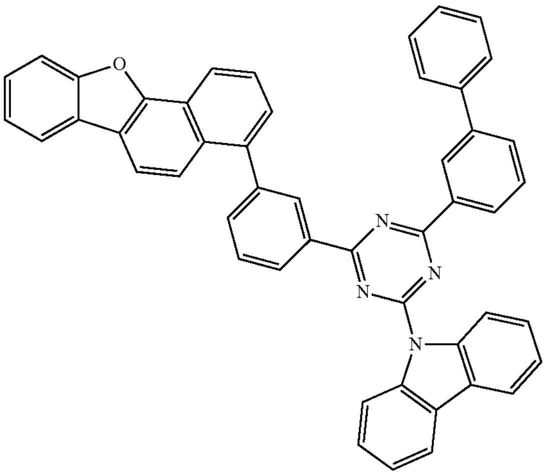
Inv-181
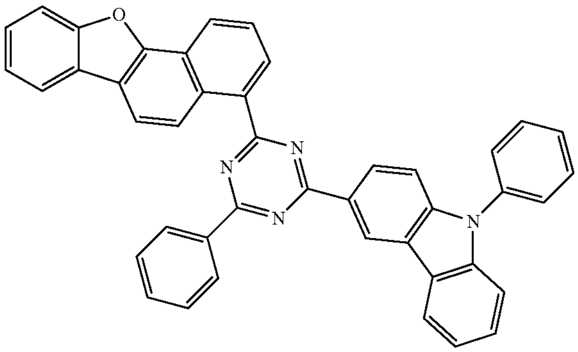
Inv-182
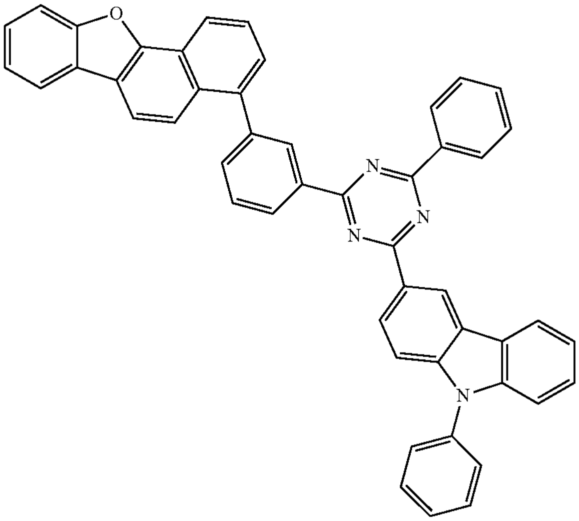
Inv-183
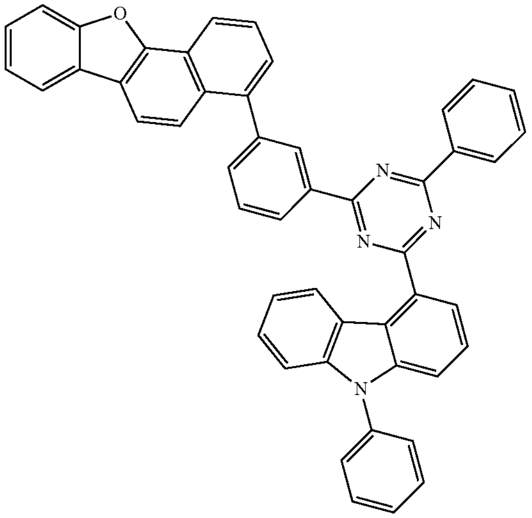

-continued

Inv-184

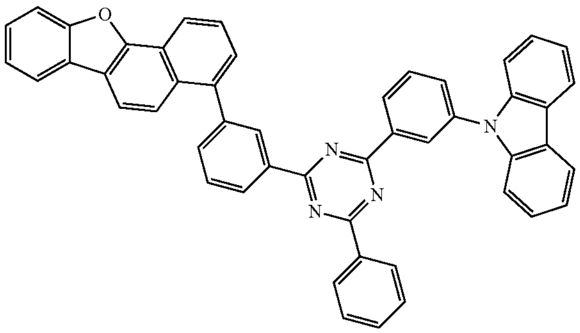

Inv-185

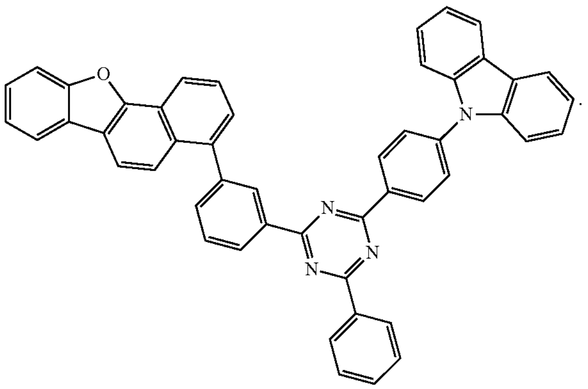

5. A composition for an organic optoelectronic diode, comprising a first compound, the first compound being represented by Chemical Formula 1A, and a second compound comprising a compound represented by Chemical Formula 2 or a compound composed of a moiety represented by Chemical Formula 3 and a moiety represented by Chemical Formula 4:

[Chemical Formula 1A]

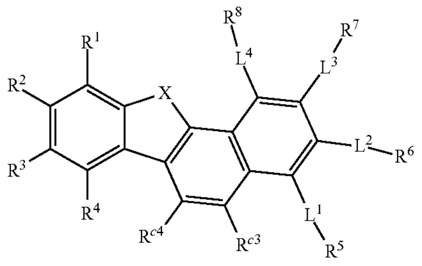

wherein, in Chemical Formula 1A,

X is O, S, or $CR^aR^b$, $R^1$ to $R^4$, $R^a$, $R^b$, $R^{c3}$, and $R^{c4}$ are independently hydrogen, deuterium, a cyano group, a substituted or unsubstituted C1 to C30 silyl group, a substituted or unsubstituted C1 to C30 alkyl group, or a substituted or unsubstituted C6 to C30 aryl group, $L^1$ to $L^4$ are independently a single bond, a substituted or unsubstituted phenylene group, or a substituted or unsubstituted biphenylene group, $R^5$ to $R^8$ are independently hydrogen, deuterium, a cyano group, a substituted or unsubstituted C1 to C30 silyl group, a substituted or unsubstituted C1 to C30 alkyl group, a substituted or unsubstituted C6 to C30 aryl group, or a substituted or unsubstituted C2 to C30 heterocyclic group, at least one of $R^5$ to $R^8$ is a substituted or unsubstituted pyridinyl group, a substituted or unsubstituted pyrimidinyl group, or a substituted or unsubstituted triazinyl group, and the “substituted” of Chemical Formula 1A refers to replacement of at least one hydrogen by deuterium, a C1 to C10 alkyl group, a C6 to C30 aryl group, or a C2 to C20 heterocyclic group,

[Chemical Formula 2]

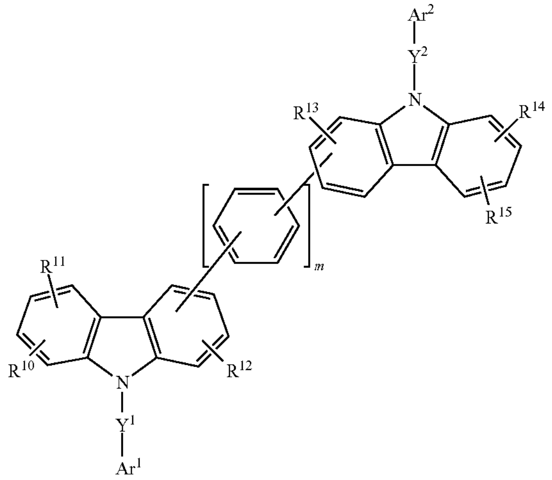

wherein, in Chemical Formula 2, $Y^1$ and $Y^2$ are independently a single bond, a substituted or unsubstituted C6 to C30 arylene group, a substituted or unsubstituted C2 to C30 heteroarylene group, or a combination thereof, $Ar^1$ and $Ar^2$ are independently a substituted or unsubstituted C6 to C30 aryl group, a substituted or unsubstituted C2 to C30 heterocyclic group, or a combination thereof, $R^{10}$ to $R^{15}$ are independently hydrogen, deuterium, a substituted or unsubstituted C1 to C20 alkyl group, a substituted or unsubstituted C6 to C30 aryl group, a substituted or unsubstituted C2 to C50 heterocyclic group, or a combination thereof, and m is one of integers of 0 to 2;

[Chemical Formula 3]

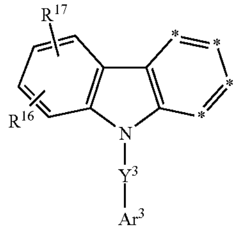

[Chemical Formula 4]

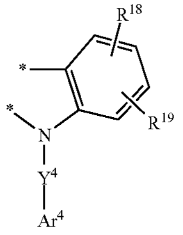

wherein, in Chemical Formulae 3 and 4, $Y^3$ and $Y^4$ are independently a single bond, a substituted or unsubstituted C6 to C30 arylene group, a substituted or unsubstituted C2 to C30 heteroarylene group, or a combination thereof, $Ar^3$ and $Ar^4$ are independently a substituted or unsubstituted C6 to C30 aryl group, a substituted or unsubstituted C2 to C30 heterocyclic group, or a combination thereof, $R^{16}$ to $R^{19}$ are independently hydrogen, deuterium, a substituted or unsubstituted C1 to C20 alkyl group, a substituted or unsubstituted C6 to C50 aryl group, a substituted or unsubstituted C2 to C50 heterocyclic group, or a combination thereof, adjacent two *'s of Chemical Formula 3 are linked with two *'s of Chemical Formula 4 to form a fused ring and *'s which do not form a fused ring in Chemical Formula 3 are independently $CR^d$, and $R^d$ is hydrogen, deuterium, a substituted or unsubstituted C1 to C10 alkyl group, a substituted or unsubstituted C6 to C12 aryl group, a substituted or unsubstituted C2 to C12 heterocyclic group, or a combination thereof;

wherein the "substituted" of Chemical Formulae 2 to 4 refers to replacement of at least one hydrogen by deuterium, a C1 to C4 alkyl group, a C6 to C18 aryl group, or a C2 to C18 heteroaryl group.

6. The composition of claim 5, wherein $Ar^1$ and $Ar^2$ of Chemical Formula 2 are independently a substituted or unsubstituted phenyl group, a substituted or unsubstituted biphenyl group, a substituted or unsubstituted terphenyl group, a substituted or unsubstituted naphthyl group, a substituted or unsubstituted anthracenyl group, a substituted or unsubstituted triphenylenyl group, a substituted or unsubstituted pyridinyl group, a substituted or unsubstituted pyrimidinyl group, a substituted or unsubstituted quinazolyl group, a substituted or unsubstituted isoquinazolyl group, a substituted or unsubstituted dibenzothiophenyl group, a substituted or unsubstituted dibenzofuranyl group, a substituted or unsubstituted carbazolyl group, a substituted or unsubstituted fluorenyl group, or a combination thereof.

7. The composition of claim 5, wherein Chemical Formula 2 is one of the structures of Group III, and $*—Y^1—Ar^1$ and $*—Y^2—Ar^2$ are one of the substituents of Group IV:

[Group III]

C-1

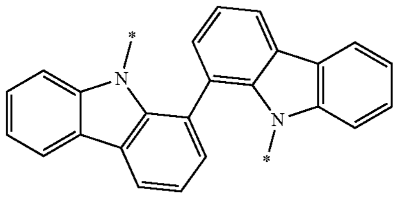

C-2

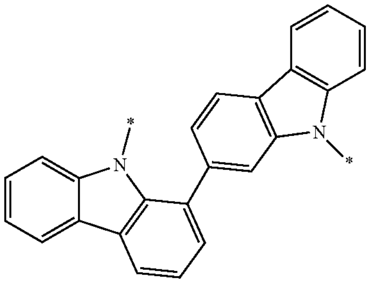

C-3

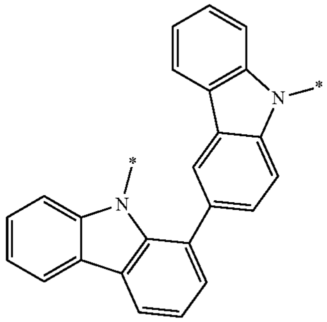

C-4

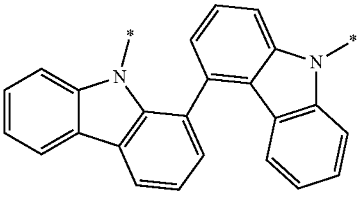

C-5

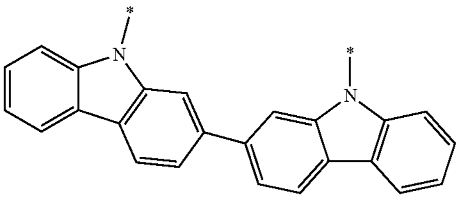

C-6

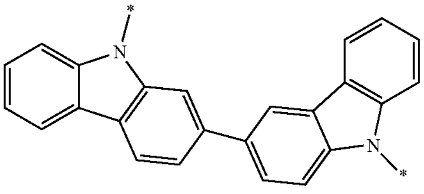

-continued
C-7
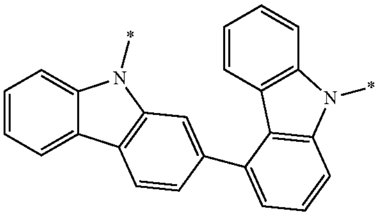
C-8
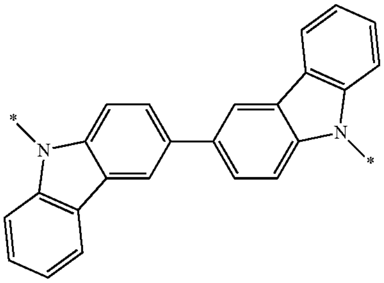
C-9
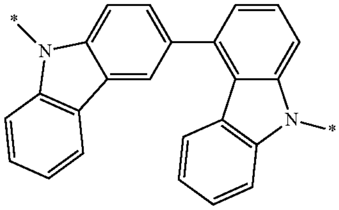
C-10
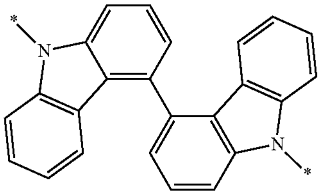
C-11
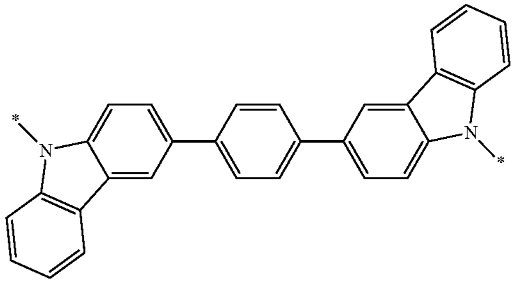
C-12
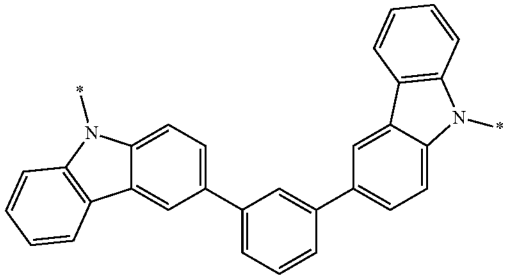
-continued
C-13
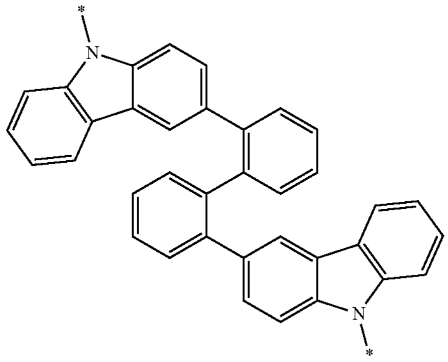
C-14
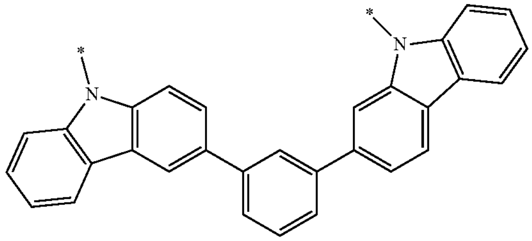
C-15
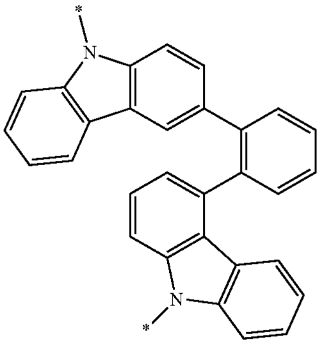
C-16
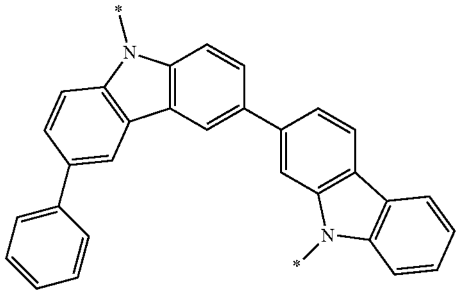
C-17
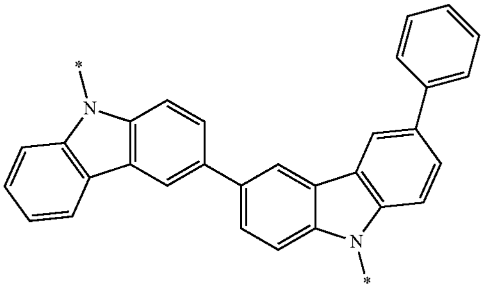

-continued
C-18
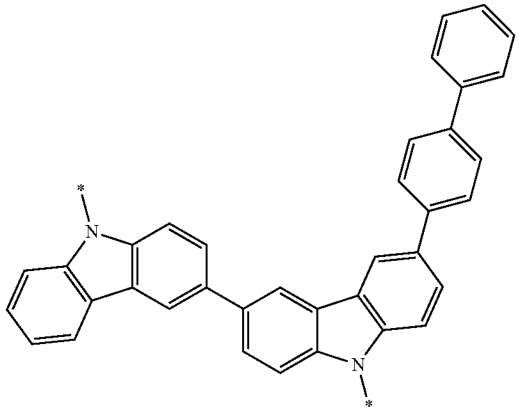
[Group IV]
B-1
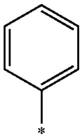
B-2
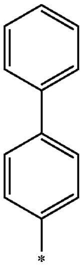
B-3
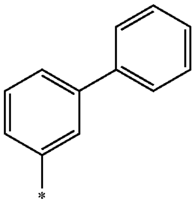
B-4
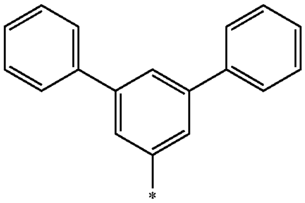
B-5
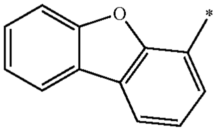
B-6
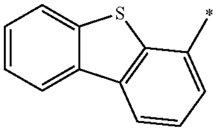
-continued
B-7
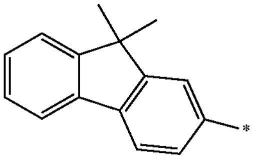
B-8
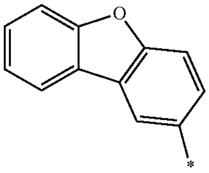
B-9
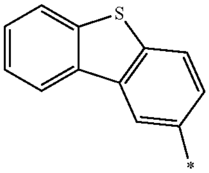
B-10
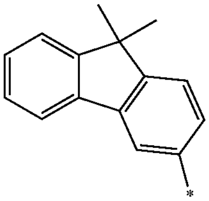
B-11
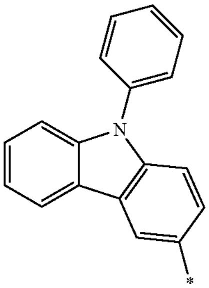
B-12
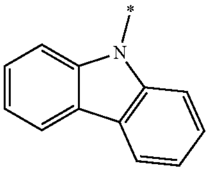
B-13
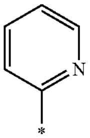
B-14
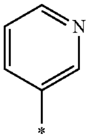

-continued
B-15
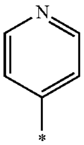
B-16
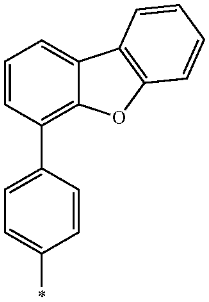
B-17
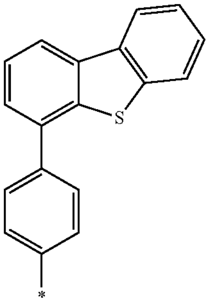
B-18
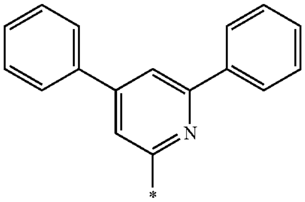
B-19
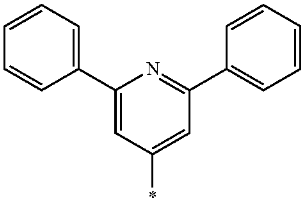
B-20
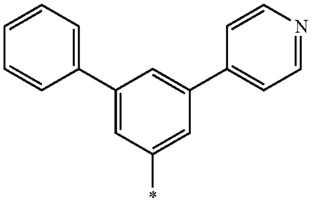
B-21
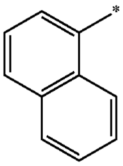
-continued
B-22
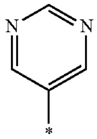
B-23
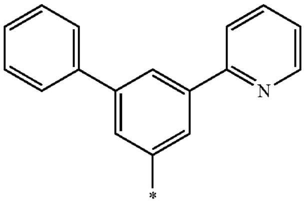
B-24
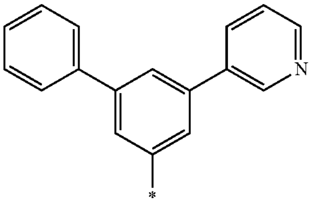
B_25
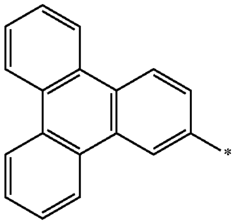
B-26
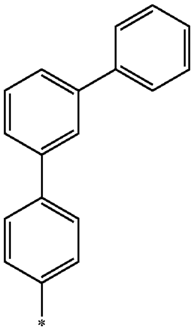
B-27
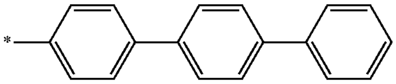
B-28
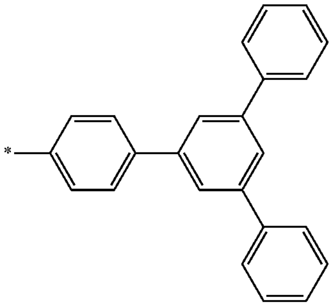
wherein, in Group III and Group IV, * is a linking point.

8. The composition of claim 7, wherein Chemical Formula 2 is represented by C-8 of Group III, and *—$Y^1$—$Ar^1$ and *—$Y^2$—$Ar^2$ are represented by one of B-1 to B-4 of Group IV.

9. The composition of claim 5, wherein the compound composed of a moiety represented by Chemical Formula 3 and a moiety represented by Chemical Formula 4 is represented by at least one of Chemical Formulae 3-I to 3-V:

[Chemical Formula 3-I]

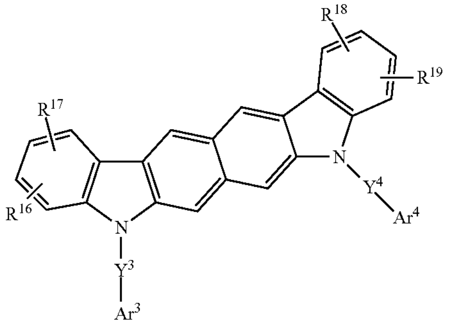

[Chemical Formula 3-II]

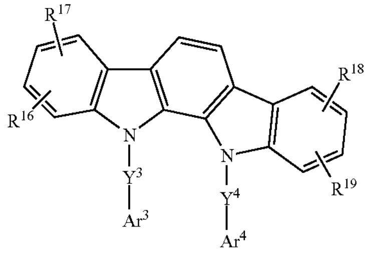

[Chemical Formula 3-III]

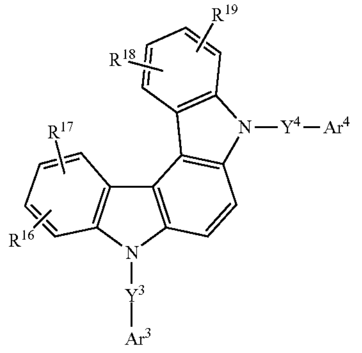

[Chemical Formula 3-IV]

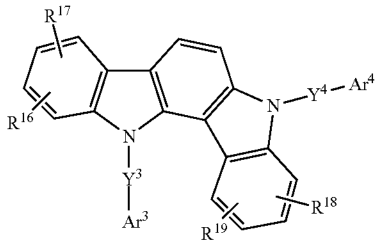

-continued

[Chemical Formula 3-V]

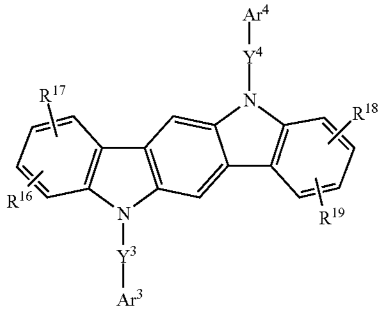

wherein, in Chemical Formulae 3-I to 3-V, $Y^3$ and $Y^4$ are a single bond, a phenylene group, a biphenylene group, a pyridylene group, or a pyrimidinylene group, $Ar^3$ and $Ar^4$ are a substituted or unsubstituted phenyl group, a substituted or unsubstituted biphenyl group, a substituted or unsubstituted pyridyl group, a substituted or unsubstituted pyrimidinyl group, or a substituted or unsubstituted triazinyl group, and $R^{16}$ to $R^{19}$ is hydrogen.

10. An organic optoelectronic diode, comprising an anode and a cathode facing each other, and at least one organic layer disposed between the anode and the cathode, wherein the organic layer comprises the compound for the organic optoelectronic diode of claim 1.

11. The organic optoelectronic diode of claim 10, wherein the organic layer comprises a light emitting layer, and the light emitting layer comprises the compound for the organic optoelectronic diode.

12. The organic optoelectronic diode of claim 11, wherein the compound for the organic optoelectronic diode is a host of the light emitting layer.

13. The organic optoelectronic diode of claim 11, wherein the organic layer comprises a light emitting layer; and at least one auxiliary layer selected from an electron transport layer, an electron injection layer, and a hole blocking layer, and the auxiliary layer wherein the auxiliary layer comprises the compound for the organic optoelectronic diode.

14. A display device comprising the organic optoelectronic diode of claim 10.

15. An organic optoelectronic diode, comprising an anode and a cathode facing each other, and at least one organic layer disposed between the anode and the cathode, wherein the organic layer comprises the composition for the organic optoelectronic diode of claim 5.

16. The organic optoelectronic diode of claim 15, wherein the organic layer comprises a light emitting layer, and the light emitting layer comprises the composition for the organic optoelectronic diode.

17. The organic optoelectronic diode of claim 16, wherein the composition for the organic optoelectronic diode is a host of the light emitting layer.

18. The organic optoelectronic diode of claim 16, wherein the organic layer comprises a light emitting layer; and at least one auxiliary layer selected from an electron transport layer, an electron injection layer, and a hole blocking layer, and the auxiliary layer wherein the auxiliary layer comprises the composition for the organic optoelectronic diode.

19. A display device comprising the organic optoelectronic diode of claim 15.

20. The compound of claim 1, wherein at least one of $R^5$ to $R^8$ is a substituted or unsubstituted pyrimidinyl group or a substituted or unsubstituted triazinyl group.

* * * * *